(12) United States Patent
Job et al.

(10) Patent No.: US 10,464,960 B2
(45) Date of Patent: *Nov. 5, 2019

(54) SALEN COMPLEXES WITH DIANIONIC COUNTERIONS

(71) Applicant: Saudi Aramco Technologies Company, Dhahran (SA)

(72) Inventors: Gabriel E. Job, Ithaca, NY (US); Jay J. Farmer, Ithaca, NY (US); Anna E. Cherian, Ithaca, NY (US)

(73) Assignee: Saudi Aramco Technologies Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/222,502

(22) Filed: Jul. 28, 2016

(65) Prior Publication Data

US 2017/0107241 A1  Apr. 20, 2017

Related U.S. Application Data

(62) Division of application No. 14/364,349, filed as application No. PCT/US2012/068985 on Dec. 11, 2012, now Pat. No. 9,403,861.

(60) Provisional application No. 61/570,974, filed on Dec. 15, 2011, provisional application No. 61/569,286, filed on Dec. 11, 2011.

(51) Int. Cl.
| | |
|---|---|
| *C07F 11/00* | (2006.01) |
| *C07F 15/06* | (2006.01) |
| *C08G 64/02* | (2006.01) |
| *C08G 64/34* | (2006.01) |
| *C08G 65/26* | (2006.01) |

(52) U.S. Cl.
CPC .......... *C07F 15/065* (2013.01); *C07F 11/005* (2013.01); *C08G 64/0208* (2013.01); *C08G 64/34* (2013.01); *C08G 65/266* (2013.01)

(58) Field of Classification Search
CPC ..... C07F 15/065; C07F 11/005; C08G 65/266
USPC ................................................ 570/183, 187
See application file for complete search history.

(56) References Cited

U.S. PATENT DOCUMENTS

| | | | |
|---|---|---|---|
| 5,637,739 A | 6/1997 | Jacobsen et al. | |
| 5,663,393 A | 9/1997 | Jacobsen et al. | |
| 5,665,890 A | 9/1997 | Jacobsen et al. | |
| 5,929,232 A | 7/1999 | Jacobsen et al. | |
| 6,130,340 A | 10/2000 | Jacobsen et al. | |

(Continued)

FOREIGN PATENT DOCUMENTS

| | | |
|---|---|---|
| EP | 2146977 B1 | 11/2012 |
| EP | 2257559 B1 | 10/2014 |

(Continued)

OTHER PUBLICATIONS

International Search Report for PCT/US2012/068985, 2 pages (dated Feb. 21, 2013).

(Continued)

*Primary Examiner* — Shane Fang
(74) *Attorney, Agent, or Firm* — Choate, Hall & Stewart LLP; Charles E. Lyon; Michael A. Shinall

(57) ABSTRACT

The present invention describes metal salen complexes having dianionic counterions. Such complexes can be readily precipitated and provide an economical method for the purification and isolation of the complexes, and are useful to prepare novel polymer compositions.

13 Claims, 13 Drawing Sheets

(56) References Cited

U.S. PATENT DOCUMENTS

| | | |
|---|---|---|
| 6,309,997 B1 | 10/2001 | Fujita et al. |
| 6,639,087 B2 | 10/2003 | Larrow et al. |
| 6,844,448 B2 | 1/2005 | Jacobsen et al. |
| 6,884,750 B2 | 4/2005 | Kim et al. |
| 6,903,043 B2 | 6/2005 | Kim et al. |
| 7,145,022 B2 | 12/2006 | Luinstra et al. |
| 7,244,805 B2 | 7/2007 | Park et al. |
| 8,163,867 B2 | 4/2012 | Lee et al. |
| 8,207,365 B2 | 6/2012 | Zheng et al. |
| 8,232,267 B2 | 7/2012 | Groves |
| 8,247,520 B2 | 8/2012 | Allen et al. |
| 8,252,955 B2 | 8/2012 | Gao et al. |
| 8,461,290 B2 | 6/2013 | Carpentier et al. |
| 8,470,956 B2 | 6/2013 | Allen et al. |
| 8,507,733 B2 | 8/2013 | Ok et al. |
| 8,598,309 B2 | 12/2013 | Jeong et al. |
| 8,604,155 B2 | 12/2013 | Allen et al. |
| 8,633,123 B2 | 1/2014 | Allen et al. |
| 8,642,721 B2 | 2/2014 | Ok et al. |
| 8,791,274 B2 | 7/2014 | Ok et al. |
| 8,921,508 B2 | 12/2014 | Allen et al. |
| 8,946,109 B2 | 2/2015 | Allen et al. |
| 8,951,930 B2 | 2/2015 | Allen et al. |
| 8,956,989 B2 | 2/2015 | Allen et al. |
| 9,156,803 B2 * | 10/2015 | Allen .................... C07D 307/60 |
| 9,327,280 B2 * | 5/2016 | Lee ........................ C07F 15/065 |
| 9,403,861 B2 | 8/2016 | Job et al. |
| 9,593,203 B2 * | 3/2017 | Allen .................... C08G 64/34 |
| 2010/0256329 A1 | 10/2010 | Nozaki et al. |
| 2011/0152497 A1 | 6/2011 | Allen et al. |
| 2011/0230580 A1 | 9/2011 | Allen et al. |
| 2011/0245424 A1 | 10/2011 | Jeong et al. |
| 2014/0228538 A1 | 8/2014 | Allen et al. |
| 2014/0249279 A1 | 9/2014 | Williams et al. |
| 2014/0296522 A1 | 10/2014 | Lee et al. |
| 2014/0336354 A1 | 11/2014 | Job et al. |
| 2014/0343246 A1 | 11/2014 | Allen et al. |
| 2015/0232496 A1 | 8/2015 | Job et al. |
| 2015/0252145 A1 | 9/2015 | Allen et al. |

FOREIGN PATENT DOCUMENTS

| | | |
|---|---|---|
| KR | 10-2014-0054079 A | 5/2014 |
| WO | WO-1993/003838 A1 | 3/1993 |
| WO | WO-98/04538 A1 | 2/1998 |
| WO | WO-2005/108406 A1 | 11/2005 |
| WO | WO-2008/136591 A1 | 11/2008 |
| WO | WO-2010/022388 A2 | 2/2010 |
| WO | WO-2010/028362 A1 | 3/2010 |
| WO | WO-2011/163133 A1 | 12/2011 |
| WO | WO-2012/158573 A1 | 11/2012 |
| WO | WO-2013/012895 A1 | 1/2013 |
| WO | WO-2013/067460 A1 | 5/2013 |
| WO | WO-2013/090276 A1 | 6/2013 |
| WO | WO-2014/031811 A1 | 2/2014 |

OTHER PUBLICATIONS

Noh, E. K. et al., Two Components in a Molecule: Highly Efficient and Thermally Robust Catalytic System for $CO_2$/Epoxide Copolymerization, J. Am. Chem. Soc., 129:8082-8083 (2007) with Supporting Information 21 pages.

Ren, W. et al., Highly Active, Bifunctional Co(III)-Salen Catalyst for Alternating Copolymerization of $CO_2$ with Cyclohexene Oxide and Terpolymerization with Aliphatic Epoxides, Macromolecules, 43:1396-1402 (2010) with Supporting Information, 18 pages.

Aimoto, Y. et al., Catalytic Function of Cobalt(III) Complexes with N,N'-Disalicylideneethylenediamine on Oxygenation of tert-Butylphenols, Bulletin of the Chemical Society of Japan, 58(2): 646 (1985).

* cited by examiner

SALEN COMPLEXES WITH DIANIONIC COUNTERIONS

CROSS REFERENCE TO RELATED APPLICATIONS

The present application claims priority to U.S. provisional application Ser. No. 61/569,286 filed Dec. 11, 2011, and to U.S. provisional application Ser. No. 61/570,974 filed Dec. 15, 2011; the entire contents of each of which are hereby incorporated herein by reference.

GOVERNMENT SUPPORT

The invention was made in part with United States Government support under grants DE-FE0002474 awarded by the Department of Energy. The United States Government has certain rights in the invention.

FIELD OF THE INVENTION

The invention pertains to the field of chemical synthesis. More particularly, the invention pertains to metal salen complexes with a counterion selected to allow isolation and purification of such complexes by precipitation.

BACKGROUND

Members of the class of ligands made by condensation of a diamine with two molar equivalents of optionally functionalized salicylaldehyde molecules are commonly referred to as salen ligands or "salens" after the simplest member of the class, N,N'-ethylenebis(salicylimine). The salen ligand may be either symmetric (containing two identical optionally functionalized salicylaldehyde moieties) or non-symmetric (containing two different optionally functionalized salicylaldehyde moieties).

This class of ligands may be generalized further to include compounds formed by condensation of a diamine with two molar equivalents of optionally functionalized β-hydroxy carbonyl compounds. As noted earlier, the ligands may be either symmetric or non-symmetric. These tetradentate ligands form Co(III) and Cr(III) complexes when the two oxygen atoms and the two nitrogen atoms of the ligand form bonds with metal atom. The remaining +1 charge on the metal is balanced by an anionic counterion. Cr(III) and Co(III) salen complexes have been shown to catalyze epoxide hydrolysis, epoxide-$CO_2$ copolymerization, and phenol oxidation, among other reactions. In some cases, isolation of the desired salen complexes comprising monoanionic counterions (nitrate, chloride, acetate, trifluoroacetate, and other monocarboxylic acids for example) is difficult owing to poor precipitation. Often, when attempts are made to precipitate such compounds, a viscous oil or sticky solid that cannot be easily handled until exhaustively dried is formed. This is not an efficient or economical method for isolation on manufacturing scale; furthermore, isolation in this manner does not provide any means for purification, which is desirable for a catalytic species. Alternatively, it would be desirable to precipitate a Cr(III) or Co(III) salen complex directly from a crude reaction mixture by the addition of a co-solvent or the removal of a solvent which dissolves the complex.

SUMMARY OF THE INVENTION

The present invention encompasses the recognition that dianionic counterions in Cr(III) and Co(III) salen complexes can allow efficient precipitation of the complexes from solution and thereby provide an effective means for the convenient isolation and purification of the salen complexes. The present invention provides, among other things, such Cr(III) and Co(III) salen complexes with dianionic counterions. The present invention also provides solvent systems useful for the precipitation of the metal salen complexes containing dianionic counterions as well as methods for purifying the complexes.

In certain embodiments, provided compounds are of Formula I:

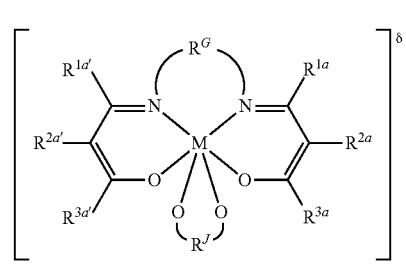

Wherein, $R^{1a}$, $R^{2a}$, $R^{3a}$, $R^{1a'}$, $R^{2a'}$, $R^{3a'}$, $R^{J}$, $R^{G}$, M and δ are as defined below and in the specific embodiments and examples herein.

In certain embodiments, the present invention also provides methods for the purification of metal salen complexes. Such methods include a step of converting the metal salen complex to a compound having a dianionic counterion and then precipitating the complex.

In certain embodiments, the present invention provides novel aliphatic polycarbonate compositions characterized in that they have a unimodal molecular weight distribution.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain embodiments, mixtures of enantiomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of enantiomers.

As used herein, the term "isomers" includes any and all geometric isomers and stereoisomers—both those arising from connectivity among carbon atoms and those arising from arrangement of coordinating heteroatoms around chromium. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a stereoisomer may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of an enantiomer. In other embodiments the compound is made up of at least about 95%, 98%, 99%, 99.5%, 99.6%, 99.7%, 99.8%, 99.9%, or 99.99% by weight of an enantiomer. Enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

When substituents are described herein, the term "radical" or "optionally substituted radical" is sometimes used. In this context, "radical" means a moiety or functional group having an available position for attachment to the structure on which the substituent is bound. In general, the point of attachment would bear a hydrogen atom if the substituent were an independent neutral molecule rather than a substituent. The terms "radical" or "optionally-substituted radical" in this context are thus interchangeable with "group" or "optionally-substituted group".

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms. In some embodiments, aliphatic groups contain 1-4 carbon atoms. In some embodiments, aliphatic groups contain 1-3 carbon atoms. In some embodiments, aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic or bicyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In certain embodiments, the term "3- to 8-membered carbocycle" refers to a 3- to 8-membered saturated or partially unsaturated monocyclic carbocyclic ring. In certain embodiments, the terms "3- to 14-membered carbocycle" and "$C_{3-14}$ carbocycle" refer to a 3- to 8-membered saturated or partially unsaturated monocyclic carbocyclic ring, or a 7- to 14-membered saturated or partially unsaturated polycyclic carbocyclic ring. In certain embodiments, the term "$C_{3-20}$ carbocycle" refers to a 3- to 8-membered saturated or partially unsaturated monocyclic carbocyclic ring, or a 7- to 20-membered saturated or partially unsaturated polycyclic carbocyclic ring.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms. In some embodiments, alkyl groups contain 1-4 carbon atoms. In certain embodiments, alkyl groups contain 1-3 carbon atoms. In some embodiments, alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms. In some embodiments, alkenyl groups contain 2-4 carbon atoms. In some embodiments, alkenyl groups contain 2-3 carbon atoms. In some embodiments, alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms. In some embodiments, alkynyl groups contain 2-4 carbon atoms. In some embodiments, alkynyl groups contain 2-3 carbon atoms. In some embodiments, alkynyl groups contain 2 carbon atoms. Representative alkynyl groups include, but are not limited to, ethynyl, 2-propynyl (propargyl), 1-propynyl, and the like.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like. In certain embodiments, the terms "6- to 10-membered aryl" and "$C_{6-10}$ aryl" refer to a phenyl or an 8- to 10-membered polycyclic aryl ring. In certain embodiments, the term "6- to 12-membered aryl" refers to a phenyl or an 8- to 12-membered polycyclic aryl ring. In certain embodiments, the term "$C_{6-14}$ aryl" refers to a phenyl or an 8- to 14-membered polycyclic aryl ring.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. In certain embodiments, the term "5- to 10-membered heteroaryl" refers to a 5- to 6-membered heteroaryl ring having 1 to 3 heteroatoms independently selected from nitrogen, oxygen, or sulfur, or an 8- to 10-membered bicyclic heteroaryl ring having 1 to 4 heteroatoms independently selected from nitrogen, oxygen, or sulfur. In certain embodiments, the term "5- to 12-membered heteroaryl" refers to a 5- to 6-membered heteroaryl ring having 1 to 3 heteroatoms independently selected from nitrogen, oxygen, or sulfur, or an 8- to 12-membered bicyclic heteroaryl ring having 1 to 4 heteroatoms independently selected from nitrogen, oxygen, or sulfur.

As used herein, the terms "heterocycle", "heterocyclyl", "heterocyclic radical", and "heterocyclic ring" are used interchangeably and refer to a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). In some embodiments, the term "3- to 7-membered heterocyclic" refers to a 3- to 7-membered saturated or partially unsaturated monocyclic heterocyclic ring having 1 to 2 heteroatoms independently selected from nitrogen, oxygen, or sulfur. In some embodiments, the term "3- to 8-membered heterocycle" refers to a 3- to 8-membered saturated or partially unsaturated monocyclic heterocyclic ring having 1 to 2 heteroatoms independently selected from nitrogen, oxygen, or sulfur. In some embodiments, the term "3- to 12-membered heterocyclic" refers to a 3- to 8-membered saturated or partially unsaturated monocyclic heterocyclic ring having 1 to 2 heteroatoms independently selected from nitrogen, oxygen, or sulfur, or a 7- to 12-membered saturated or partially unsaturated polycyclic heterocyclic ring having 1-3 heteroatoms independently selected from nitrogen, oxygen, or sulfur. In some embodiments, the term "3- to 14-membered heterocycle" refers to a 3- to 8-membered saturated or partially unsaturated monocyclic heterocyclic ring having 1 to 2 heteroatoms independently selected from nitrogen, oxygen, or sulfur, or a 7- to 14-membered saturated or partially unsaturated polycyclic heterocyclic ring having 1-3 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

One of ordinary skill in the art will appreciate that the synthetic methods, as described herein, may utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In some embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. By way of non-limiting example, hydroxyl protecting groups include methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxy ethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). Exemplary protecting groups are detailed herein, however, it will be appreciated that the present disclosure is not intended to be limited to these protecting groups; rather, a variety of additional equivalent protecting groups can be readily identified using the above criteria and utilized in the method of the present disclosure. Additionally, a variety of protecting groups are described in *Protecting Groups in Organic Synthesis*, T. W. Greene and P. G. M. Wuts, $3^{rd}$ edition, John Wiley & Sons, 1999, the entirety of which is incorporated herein by reference.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)$ —NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)N(R°)$_2$; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O) NR°$_2$; —C(O)N(OR°)R°; —C(O)C(O)R°; —C(O)CH$_2$C(O) R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP (O)R°$_2$; —OP(O)(OR°)$_2$; SiR°$_3$; —(C$_{1-4}$ straight or branched alkylene)O—N(R°)$_2$; or —(C$_{1-4}$ straight or branched)alkylene)C(O)O—N(R°)$_2$, wherein each R° may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3- to 12-membered saturated, partially unsaturated, or aryl mono- or polycyclic ring having 0-4 heteroatoms independently selected from nitrogen, oxygen, or sulfur, which may be substituted as defined below.

Suitable monovalent substituents on R°(or the ring formed by taking two independent occurrences of R° together with their intervening atoms), are independently halogen, —(CH$_2$)$_{0-2}$R●, -(haloR●), —(CH$_2$)$_{0-2}$OH, —(CH$_2$)$_{0-2}$OR●, —(CH$_2$)$_{0-2}$CH(OR●)$_2$; —O(haloR●), —CN, —N$_3$, —(CH$_2$)$_{0-2}$C(O)R●, —(CH$_2$)$_{0-2}$C(O)OH, —(CH$_2$)$_{0-2}$C(O) OR●, —(CH$_2$)$_{0-4}$C(O)N(R°)$_2$; —(CH$_2$)$_{0-2}$SR●, —(CH$_2$)$_{0-2}$SH, —(CH$_2$)$_{0-2}$NH$_2$, —(CH$_2$)$_{0-2}$NHR●, —(CH$_2$)$_{0-2}$NR●$_2$, —NO$_2$, —SiR●$_3$, —OSiR●$_3$, —C(O) SR●, —(C$_{1-4}$ straight or branched alkylene)C(O)OR●, or —SSR● wherein each R● is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5- to 6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O) R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5- to 6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur. A substitutable nitrogen may be substituted with three R† substituents to provide a charged ammonium moiety —N$^+$(R†)$_3$, wherein the ammonium moiety is further complexed with a suitable counterion.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

As used herein, the term "catalyst" refers to a substance the presence of which increases the rate and/or extent of a chemical reaction, while not being consumed or undergoing a permanent chemical change itself.

In some chemical structures herein, substituents are shown attached to a bond which crosses another bond of a depicted molecule. This means that one or more of the substituents may be attached to the molecule at any available position (usually in place of a hydrogen atom of the parent structure). In cases where an atom of a molecule so substituted has two substitutable positions, two groups may be present on the same ring atom. When more than one substituent is present, each is defined independently of the others, and each may have a different structure. In cases where the substituent shown crossing a bond of the molecule is —R, this has the same meaning as if the ring were said to be "optionally substituted" as described in the preceding paragraph.

Any tetradentate ligand capable of complexing a metal atom which is formed from a diamine condensed with two molar equivalents of a β-hydroxy carbonyl compound herein is included in the class of salens and defined as a "salen" or "salen ligand." A salen ligand may be symmetrical meaning that the diamine is condensed with two identical β-hydroxy carbonyl compounds or a salen ligand may be nonsymmetrical meaning that the diamine is condensed with two different β-hydroxy carbonyl compounds. In some embodiments, the terms "salen" and "salen ligand" refer to the structural elements of N,N'-ethylenebis(salicylimine) (CAS 94-93-9), or an analog thereof, that are necessary to form a tetradentate ligand capable of complexing metals. The term "salen complex" refers to the complex formed between a "salen" or "salen ligand" and a metal.

In salen complexes having dianionic counterions, the counterion may be bound in a bidentate manner to a metal. As a result, the tetradentate salen ligand which is often planar and occupies the equatorial sites of an octagonal metal complex, will have one of its heteroatoms out of plane and occupying an apical coordination site on a metal. Therefore, certain compounds of the present invention can exist in various isomeric forms, wherein the metal atom is a stereocenter, for example:

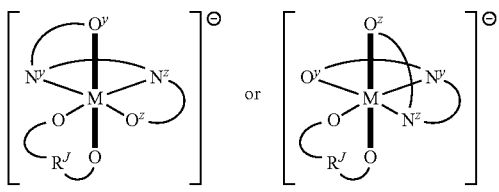

where each

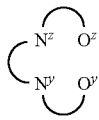

represents a salen ligand:

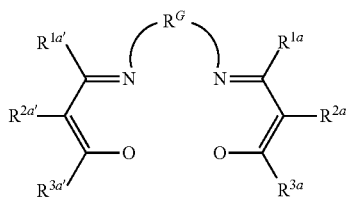

and where M, $R^G$ and $R^J$ are as defined herein

Thus, inventive compounds and compositions thereof may be in the form of an individual enantiomer, diastereomer or geometric isomer, or may be in the form of a mixture of these isomers.

The term "TBD" refers to 1,4,9-triazabicyclo[4.4.0]dec-9-ene.

The term "MeTBD" refers to 1-methyl-1,4,9-triazabicyclo[4.4.0]dec-9-ene.

The term "TBO" refers to 1,4,6-triazabicyclo[3.3.0]oct-4-ene.

The term "molecular weight population" refers to a distinct elution peak observable in a gel permeation chromatogram; monomodal polymer samples have substantially one such peak, while bimodal polymer samples have two distinctly observable peaks.

BRIEF DESCRIPTION OF THE DRAWINGS

FIGS. 8a and 8b are reproduced from JACS. 2007, 129, 8082-8083, supporting info. FIG. 8c is reproduced from Macromolecules, 2010, 43 (3), pp 1396-1402 supporting info.

DETAILED DESCRIPTION OF THE INVENTION

Figure 1:
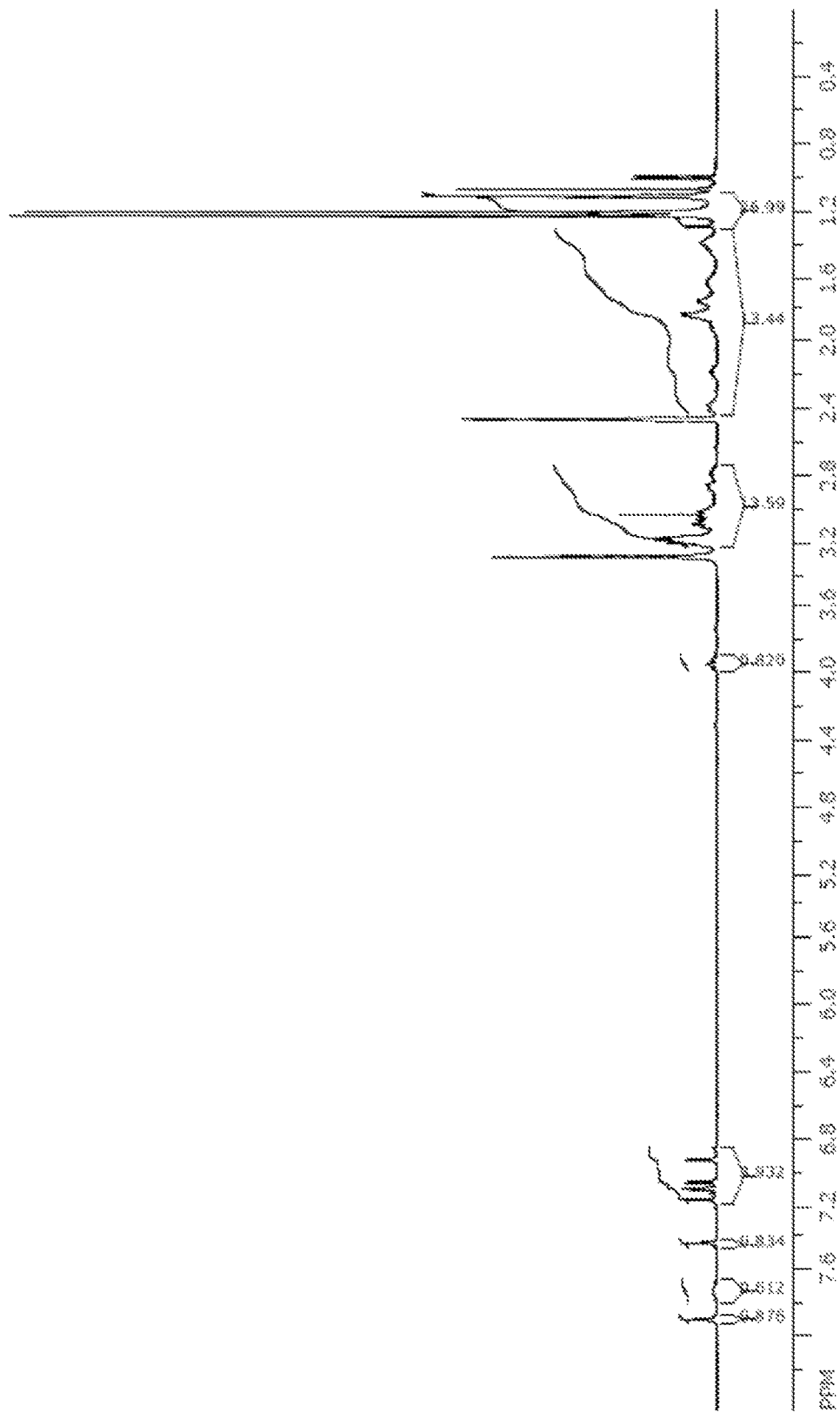
FIG. 1 depicts an NMR spectrum of compound N, a cobalt(III)salen complex with an oxalate counterion.
Figure 2:
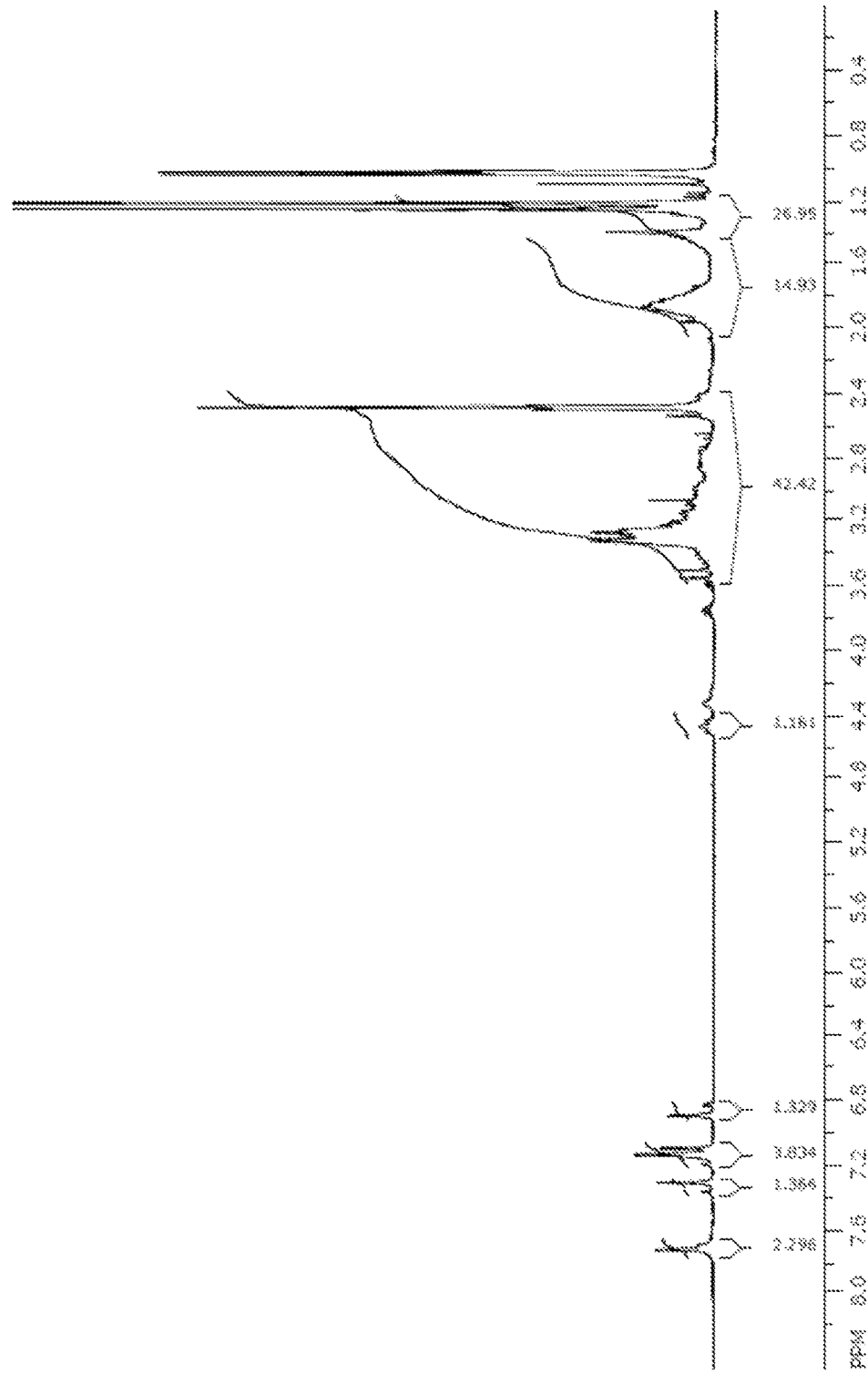
FIG. 2 depicts an NMR spectrum of compound O, a cobalt(III)salen complex with a malonate counterion.
Figure 3:
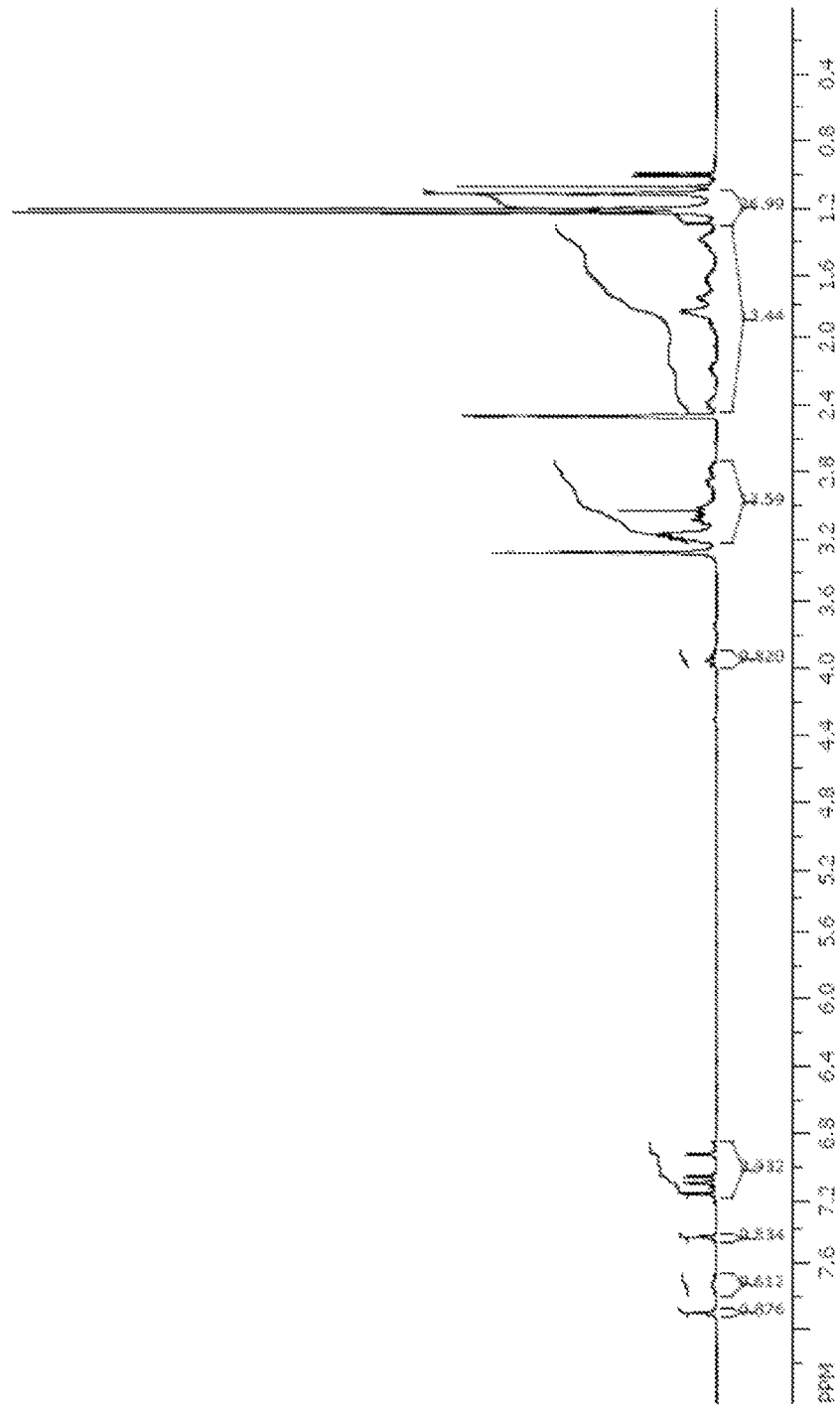
FIG. 3 depicts an NMR spectrum of compound Q, a cobalt(III)salen complex with a carbonate counterion.
Figure 4:
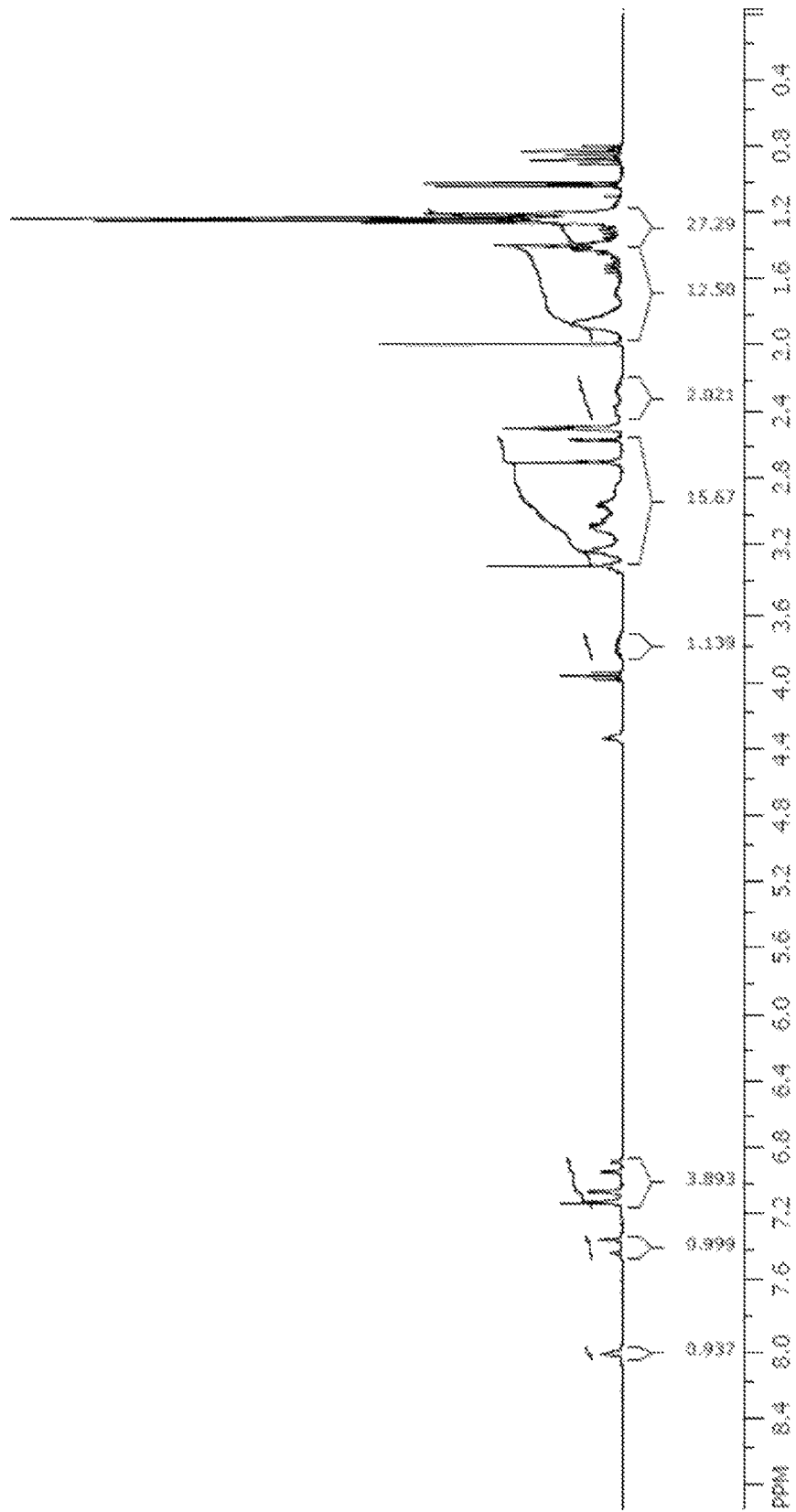
FIG. 4 depicts an NMR spectrum of compound R, a cobalt(III)salen complex with a carbonate counterion.
Figure 5:
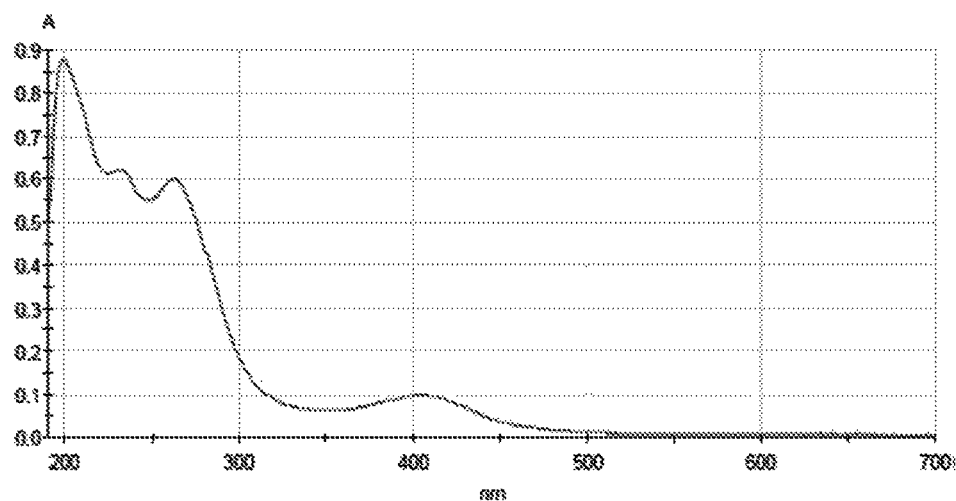
FIG. 5 depicts UV spectra. Top panel: UV-Vis spectrum of compound N, a cobalt(III)salen complex with an oxalate counterion. Bottom panel: UV-Vis spectrum of compound O, a cobalt(III)salen complex with a malonate counterion.
Figure 5:
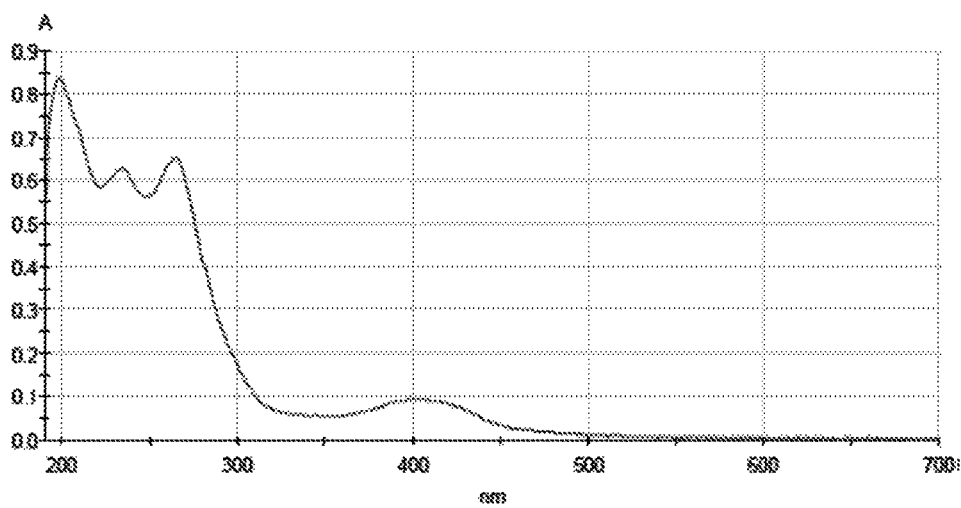
Figure 6:
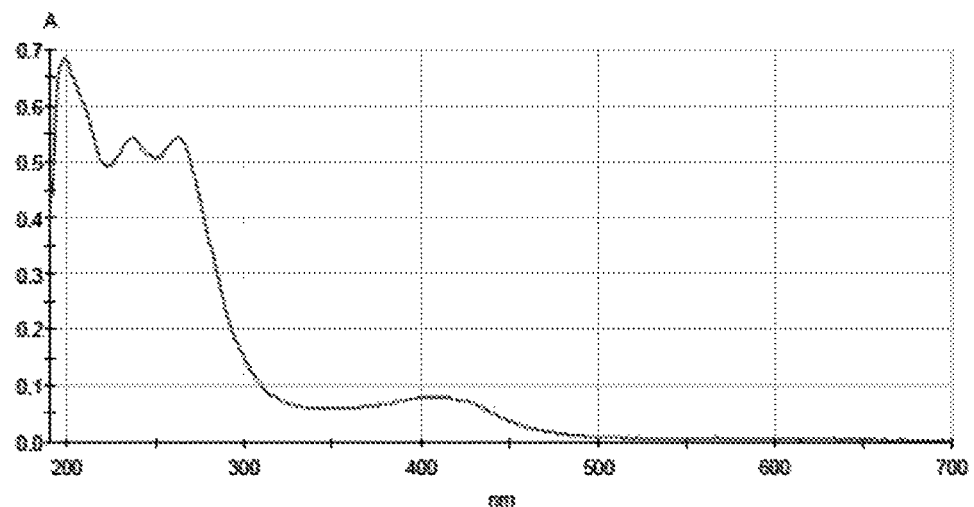
FIG. 6 depicts UV spectra. Top panel: UV-Vis spectrum of compound Q, a cobalt(III)salen complex with a carbonate counterion. Bottom panel: UV-Vis spectrum of compound R, a cobalt(III)salen complex with a carbonate counterion.
Figure 6:
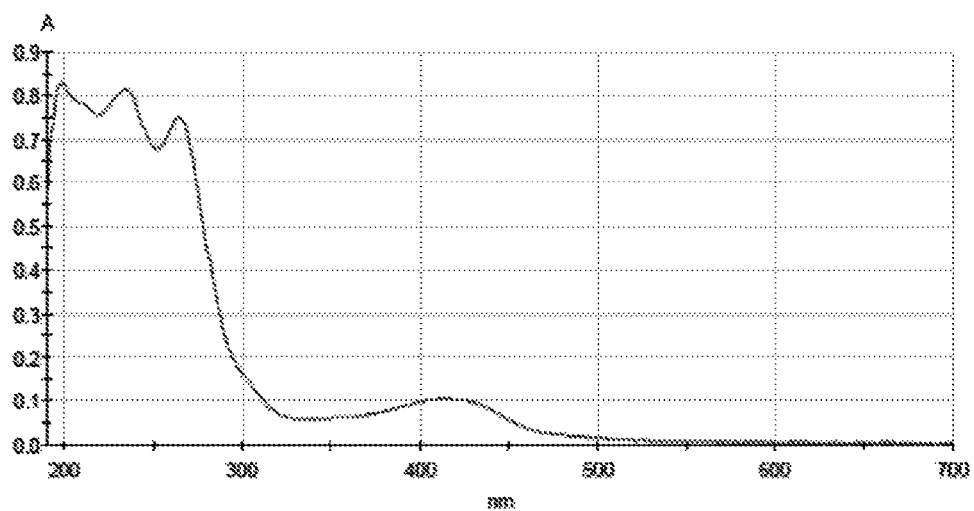
Figure 7:
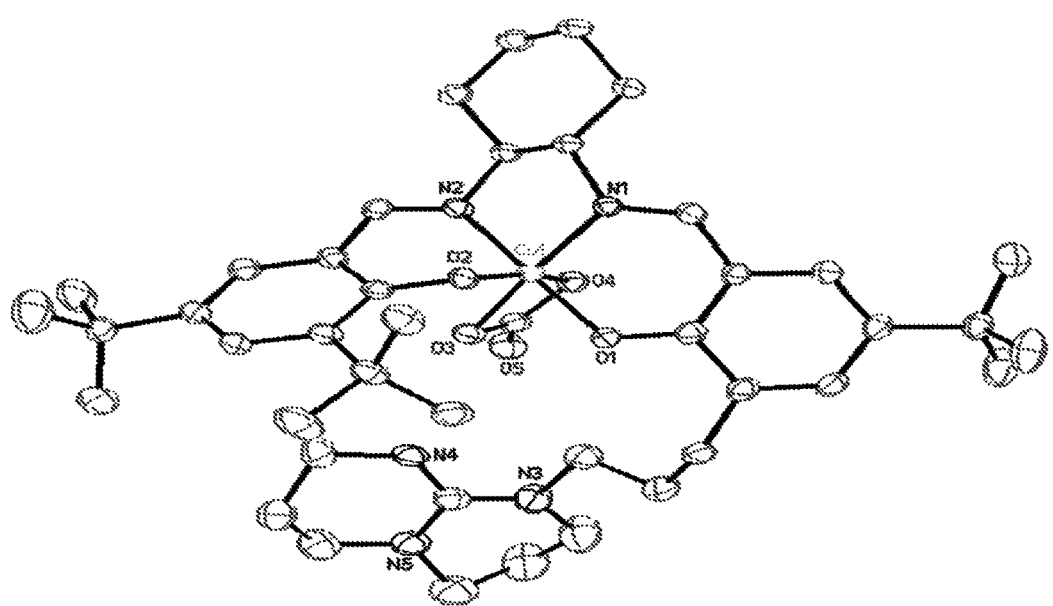
FIG. 7 depicts an x-Ray structure of compound Q, a Co(III) salen complex with a carbonate counterion.

The present invention provides, among other things, the recognition that a dianionic counterion can facilitate economical isolation and purification of Cr(III) and Co(III) salen complexes by causing precipitation of the complex directly from a reaction mixture. The present invention further provides, among other things, a method for the precipitation of tetradentate salen metal complexes by the use of a dianionic counterion for the complex.

In certain embodiments, the present invention provides salen Cr(III) or Co(III) complexes characterized in that they comprise a dianionic couterion. In certain embodiments, such complexes are further characterized in that they comprise one or more nitrogen-, phosphorous-, or arsenic-containing functional groups covalently tethered to the salen ligand (for example such as those disclosed in published PCT applications WO/2010/022388 and WO 2008/136591 each of which is incorporated herein by reference). In certain embodiments, such nitrogen-, phosphorous-, or arsenic-containing functional groups comprise cationic groups (or moieties that can be protonated to form cationic groups). In certain embodiments, such tethered cationic or protonated groups balance a negative charge from the dianion-coordinated to the complex. In certain embodiments, the negative charge thus balanced resides on the metal atom. In other embodiments, the negative charge thus balanced may reside on an atom other than the metal atom, including an atom of the dianion.

In certain embodiments, where a tethered group comprises a nitrogen-containing functional group, the group comprises a quaternary nitrogen atom. In other embodiments, covalently tethered cationic groups comprise a protonated nitrogen atom. In certain embodiments, covalently tethered cationic groups comprise ammonium salts. In certain embodiments, covalently tethered cationic groups comprise guanidinium salts. In certain embodiments, covalently tethered cationic groups comprise amidinium salts. In certain embodiments, covalently tethered cationic groups comprise arsonium salts.

In certain embodiments, the metal complexes encompassed by the present invention comprise complexes described in WO 2010/022388 and/or WO 2008/136591 wherein one or more mono-anionic counterions of the catalysts disclosed therein are replaced by a dianion as described herein. The entire content of each of these documents is incorporated herein by reference.

Metal Complexes

In certain embodiments, provided compounds are of Formula I:

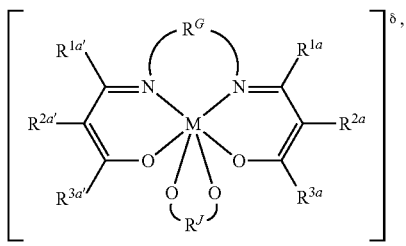

wherein:
M is Co or Cr;
$R^{1a}$, $R^{1a'}$, $R^{2a}$, $R^{2a'}$, $R^{3a}$, and $R^{3a'}$ are independently a $\sim\!\!\!\sim (Z)_m$ group, hydrogen, R, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$, —C(O)R, —NRC(O)R, —OC(O)R, —CO$_2$R, —OC(O)N(R)$_2$, —C(O)NR$_2$, —NRC(O)NR—, —NRC(O)OR; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7- to 14-membered saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered monocyclic saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where each R is independently hydrogen, an optionally substituted radical selected the group consisting of acyl; carbamoyl; arylalkyl; phenyl; C$_{1-12}$ aliphatic; C$_{1-12}$ heteroaliphatic; a 3- to 8-membered saturated or partially unsaturated monocyclic carbocycle, a 7- to 14-membered saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered monocyclic saturated or partially unsaturated heterocyclic ring having 1-3 heteroatoms independently selected from nitrogen, oxygen, or sulfur; an 8- to 10-membered bicyclic heteroaryl ring having 1-5 heteroatoms independently selected from nitrogen, oxygen, or sulfur; an oxygen protecting group; and a nitrogen protecting group; or: two R on the same nitrogen atom are taken with the nitrogen to form a 3- to 7-membered heterocyclic ring, and wherein any of [$R^{2a'}$ and $R^{3a'}$], [$R^{2a}$ and $R^{3a}$], [$R^{1a}$ and $R^{2a}$], and [$R^{1a'}$ and $R^{2a'}$] may optionally be taken together with the carbon atoms to which they are attached to form one or more rings which may in turn be optionally substituted as defined above, or substituted with one or more R groups; and
$R^G$ is selected from the group consisting of:

a)

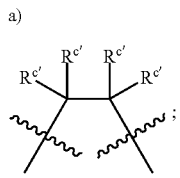

b)

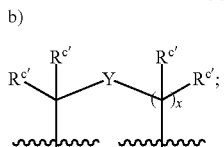

c)

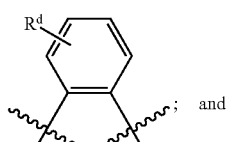
and d)

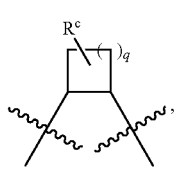

$R^J$ is a bivalent linker selected from the group consisting of: —C(O)—, —C(O)C(O)—, —C(O)—R$^H$—C(O)—, —SO—, —SO$_2$—, —P(O)(OR$^{J1}$)—, —P(O)R$^{J1}$—, —R$^{J1}$C=N—, —C(O)—R$^H$—P(O)(OR$^{J1}$)—, —C(O)—R$^H$—S(O)—, —C(O)—R$^H$—S(O)$_2$—, —SO$_2$—R$^H$—P(O)(OR$^{J1}$)—, —SO—R$^H$—P(O)(OR$^{J1}$)—, —C(O)R$^H$—;

where,
$R^c$ groups are optionally present, and if present are, independently at each occurrence selected from the group consisting of: a $\sim\!\!\!\sim (Z)_m$ group, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$, —C(O)R, —NRC(O)R, —OC(O)R, —CO$_2$R, —OC(O)N(R)$_2$, —C(O)NR$_2$, —NRC(O)NR—, —NRC(O)OR; or an optionally substituted radical selected from the group consisting of arylalkyl; phenyl; C$_{1-20}$ aliphatic; C$_{1-20}$ heteroaliphatic; a 3- to 8-membered saturated or partially unsaturated monocyclic carbocycle, a 7- to 14-membered saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered monocyclic saturated or partially unsaturated heterocyclic ring having 1-3 heteroatoms independently selected from nitrogen, oxygen, or sulfur; an 8- to 10-membered bicyclic heteroaryl ring having 1-5 heteroatoms independently selected from nitrogen, oxygen, or sulfur; where two or more R$^c$ groups may be taken together with the carbon atoms to which they are attached and any intervening atoms to form one or more optionally substituted rings; and where when two R$^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;

$R^d$ groups are optionally present, and if present are, independently at each occurrence selected from the group consisting of: a $\sim\!\!\!\sim (Z)_m$ group, halogen, —R, —OR, —NR₂, —SR, —CN, —NO₂, —SO₂R, —SOR, —SO₂NR₂; —CNO, —NRSO₂R, —NCO, —N₃, —SiR₃, —C(O)R, —NRC(O)R, —OC(O)R, —CO₂R, —OC(O)N(R)₂, —C(O)NR₂, —NRC(O)NR—, —NRC(O)OR; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; where two or more $R^c$ groups may be taken together with the carbon atoms to which they are attached and any intervening atoms to form one or more optionally substituted rings optionally containing one or more heteroatoms;

$R^{c'}$ is, independently at each occurrence, —H, or $R^c$;

Y is a bivalent linker selected from the group consisting of: —$(CR^{c'}_2)_{q'}$—; —NR—, —N(R)C(O)—, —C(O)NR—, —O—, —C(O)—, —OC(O)—, —C(R)₂—, —C(O)O—, —S—, —SO—, —SO₂—, —C(=S)—, —C(=NR)—, or —N=N—; a polyether; $C_{1-6}$ aliphatic; a $C_3$ to $C_8$ substituted or unsubstituted carbocycle; and a 3- to 8-membered substituted or unsubstituted heterocycle;

$R^H$ is selected from the group consisting of $R^G$ and —$(CR^{c'}_2)_{q'}$, $R^{J1}$ is independently at each occurrence selected from the group consisting of: hydrogen, a metal atom, an optionally substituted radical selected from the group consisting of acyl; carbamoyl; arylalkyl; phenyl; $C_{1-12}$ aliphatic; $C_{1-12}$ heteroaliphatic; 4- to 7-membered heterocyclyl; a 5- to 6-membered monocyclic heteroaryl ring having 1-4 heteroatoms independently selected from nitrogen, oxygen, or sulfur; or an oxygen protecting group; and q' is an integer from 1 to 6;

q is from 0 to 5, inclusive;

x is 0, 1, or 2; and

δ represents the net charge of the metal complex exclusive of any non-covalently bound counterions and may be any number between −1 and +5; ⁓ $(Z)_m$ represents one or more activating moieties attached to the multidentate ligand, where ⁓ is a linker moiety covalently coupled to the ligand, each Z is an activating functional group; and m is an integer from 1 to 4 representing the number of Z groups present on an individual linker moiety.

In some embodiments, at least one of [$R^{2a}$ and $R^{3a}$] and [$R^{2a'}$ and $R^{3a'}$] are taken together to form a ring. In some embodiments, both [$R^{2a}$ and $R^{3a}$] and [$R^{2a'}$ and $R^{3a'}$] are taken together to form rings. In some embodiments, the rings formed by [$R^{2a}$ and $R^{3a}$] and/or [$R^{2a'}$ and $R^{3a'}$] are substituted phenyl rings.

In certain embodiments, M is chromium. In certain embodiments, M is Cr(III), in certain embodiments, M is cobalt. In certain embodiments, M is Co(III).

In certain embodiments, one or more of $R^{1a}$, $R^{1a'}$, $R^{2a}$, $R^{2a'}$, $R^{3a}$, and $R^{3a'}$ are independently a ⁓$(Z)_m$ group.

In some embodiments, Y is a bivalent linker selected from $C_{1-6}$ aliphatic or a $C_3$ to $C_8$ substituted or unsubstituted carbocycle. In some embodiments, Y is $C_{1-6}$ alkyl or $C_{1-6}$ alkenyl.

In certain embodiments of provided metal complexes with a dianionic counterion, a salen complex has a structure selected from the group consisting of:

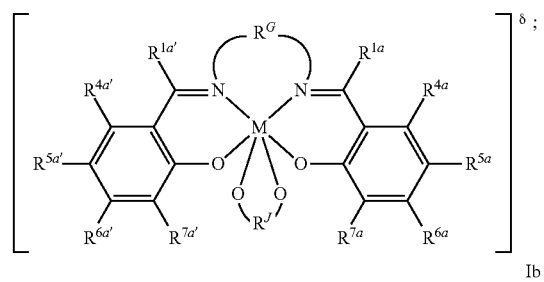

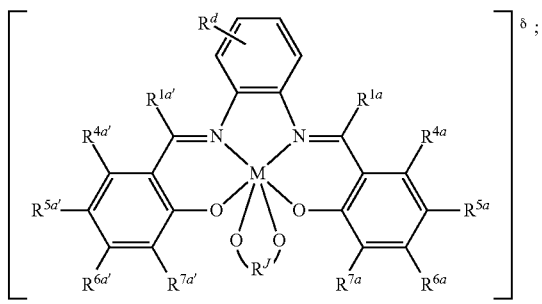

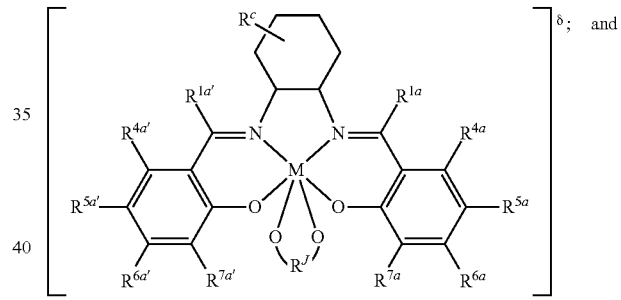

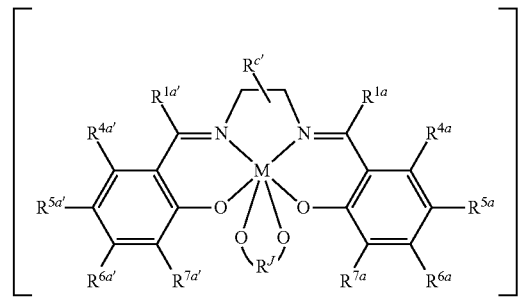

wherein each of M, $R^G$, $R^c$, $R^d$, $R^J$, $R^{1a}$, $R^{1a'}$, and δ is as defined above and described in classes and subclasses herein; and $R^{4a}$, $R^{4a'}$, $R^{5a}$, $R^{5a'}$, $R^{6a}$, $R^{6a'}$, $R^{7a}$, and $R^{7a'}$ are each independently hydrogen, or an $R^d$ group wherein [$R^{1a}$ and $R^{4a}$], [$R^{1a'}$ and $R^{4a'}$] and any two adjacent $R^{4a}$, $R^{4a'}$, $R^{5a}$, $R^{5a'}$, $R^{6a}$, $R^{6a'}$, $R^{7a}$, and $R^{7a'}$ groups can be taken together with intervening atoms to form one or more optionally substituted rings;

In some embodiments of complexes of formulae Ia through Id, $R^{1a}$, $R^{1a'}$, $R^{4a}$, $R^{4a'}$, $R^{6a}$, and $R^{6a'}$ are each —H.

In some embodiments, $R^{5a}$, $R^{5a'}$, $R^{7a}$ and $R^{7a'}$ are each optionally substituted $C_1$-$C_{12}$ aliphatic. In some embodiments, $R^{4a}$, $R^{4a'}$, $R^{5a}$, $R^{5a'}$, $R^{6a}$, $R^{6a'}$, $R^{7a}$, and $R^{7a'}$ are each independently selected from the group consisting of: —H, —SiR$_3$; methyl, ethyl, n-propyl, i-propyl, n-butyl, sec-butyl, t-butyl, isoamyl, t-amyl, thexyl, and trityl. In some embodiments, $R^{1a}$, $R^{1a'}$, $R^{4a}$, $R^{4a'}$, $R^{6a}$, and $R^{6a'}$ are each —H. In some embodiments, $R^{7a}$ is selected from the group consisting of —H; methyl; ethyl; n-propyl; i-propyl; n-butyl; sec-butyl; t-butyl; isoamyl; t-amyl; thexyl; and trityl. In some embodiments, $R^{5a}$ and $R^{7a}$ are independently selected from the group consisting of —H; methyl; ethyl; n-propyl; i-propyl; n-butyl; sec-butyl; t-butyl; isoamyl; t-amyl; thexyl; and trityl. In certain embodiments, one or more of $R^{5a}$, $R^{5a'}$, $R^{7a}$ and $R^{7a'}$ is a —⁓(Z)$_m$ group. In some embodiments, $R^{5a}$ and $R^{5a'}$ are a —⁓(Z)$_m$ group. In some embodiments, one of $R^{5a}$ or $R^{5a'}$ is a —⁓(Z)$_m$ group. In some embodiments, one of $R^{7a}$ or $R^{7a'}$ is a —⁓(Z)$_m$ group.

In certain embodiments of complexes having formulae Ia through Id, at least one of the phenyl rings comprising a salicylaldehyde-derived portion of the salen ligand is independently selected from the group consisting of:

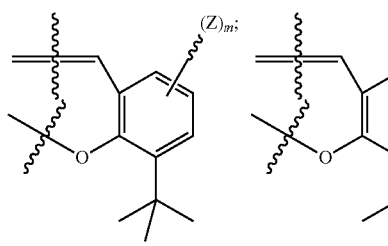
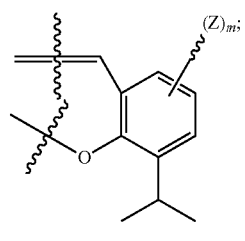

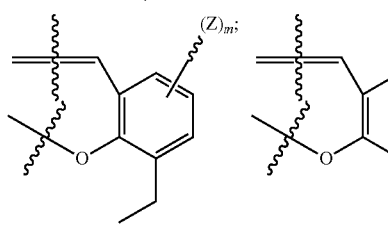
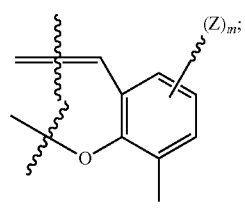

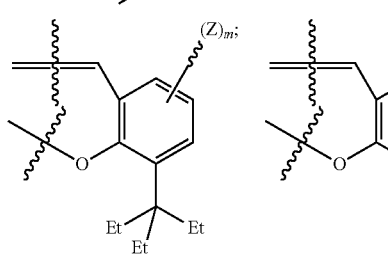
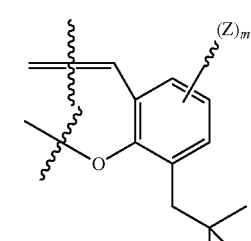

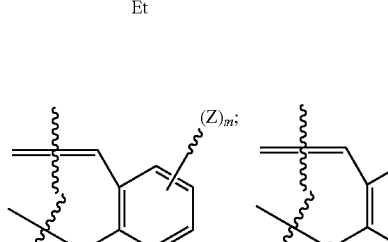
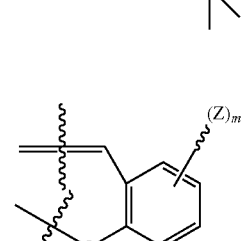

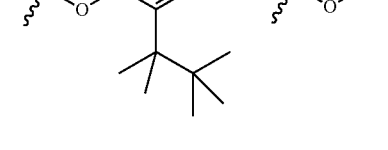
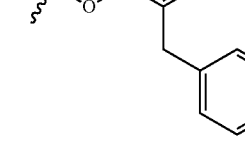

-continued

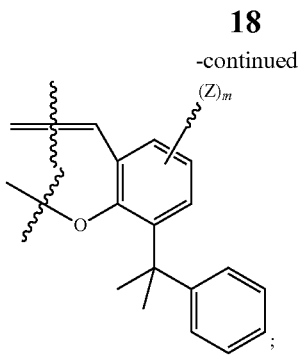

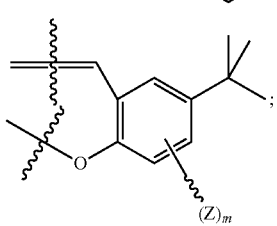

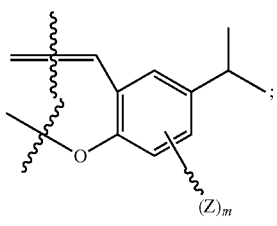

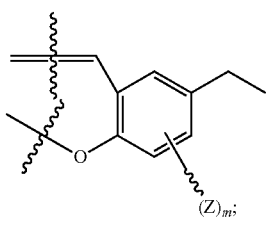

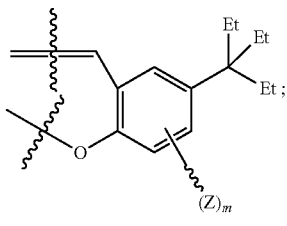

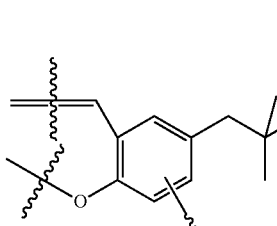

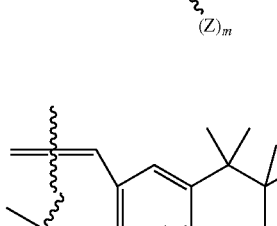

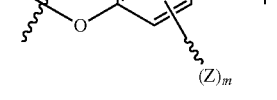

-continued
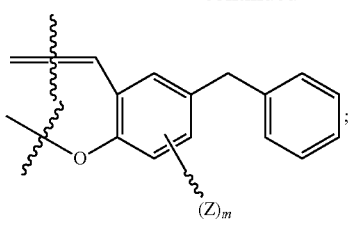
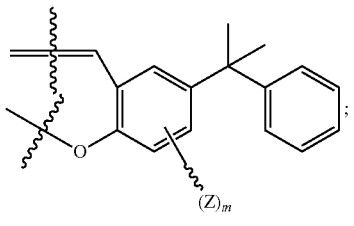
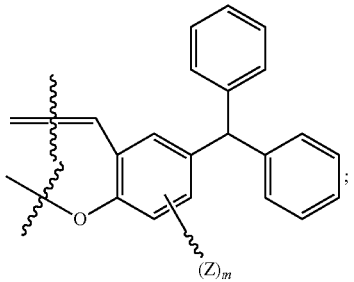
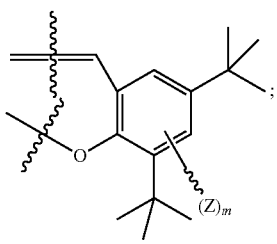
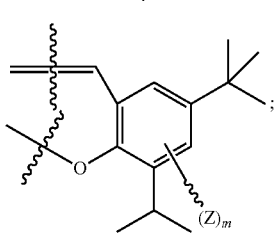
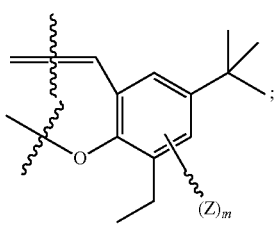
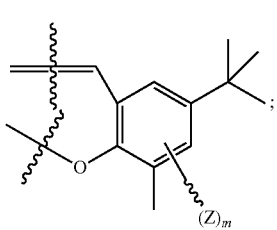
-continued
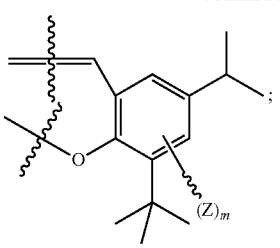
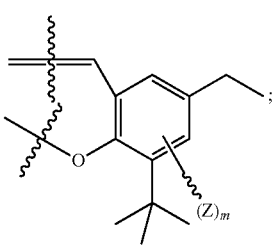
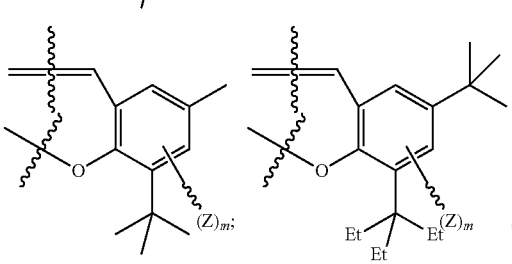
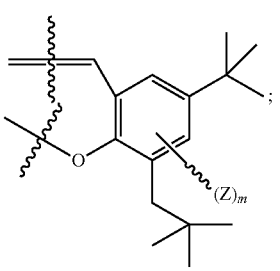
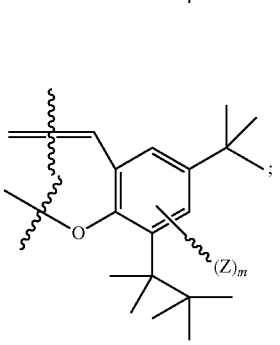
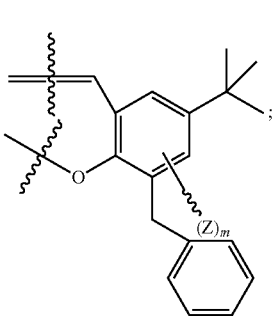

-continued

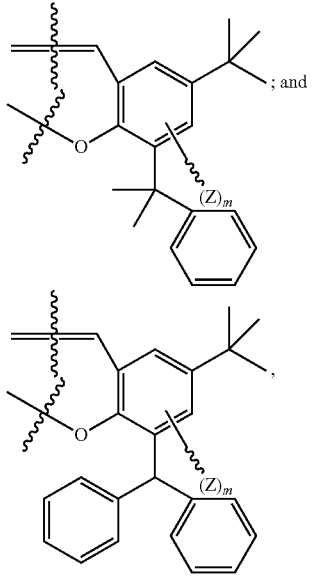

wherein ⸺ $(Z)_m$ is as defined above and described in the embodiments and examples herein.

In certain embodiments, there is an activating moiety tethered to the position ortho to a metal-bound oxygen substituent of one or both of the salicylaldehyde-derived phenyl rings of a salen ligand as in formulae Ia-1 and Ia-2:

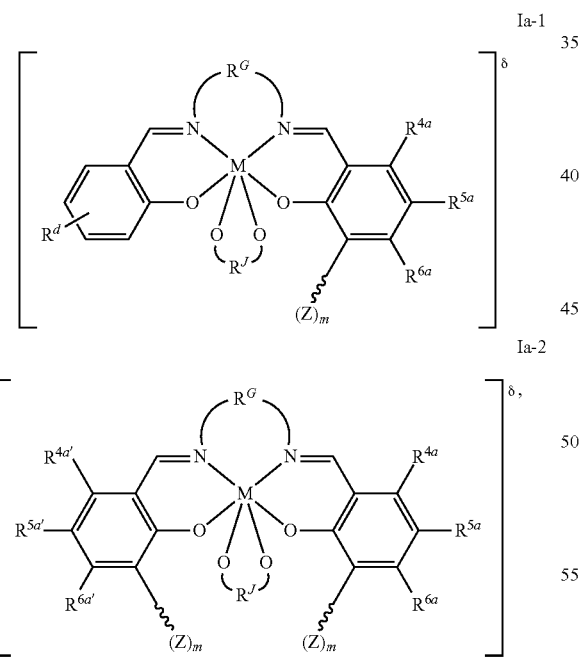

Ia-1

Ia-2 wherein M, $R^d$, $R^{4a}$, $R^{4a'}$, $R^{5a}$, $R^{5a'}$, $R^{6a}$, $R^{6a'}$ $R^G$, $R^J$, $\delta$, and ⸺ $(Z)_m$ are as defined above and described in the embodiments and examples herein.

In certain embodiments of compounds having formulae Ia-1 or Ia-2, $R^{4a}$, $R^{4a'}$, $R^{6a}$, and $R^{6a'}$ are each hydrogen, and $R^{5a}$, $R^{5a'}$ are, independently, optionally substituted $C_1$-$C_{20}$ aliphatic.

In certain embodiments of complexes Ia-1 and Ia-2, at least one of the phenyl rings comprising a salicylaldehyde-derived portion of a catalyst is independently selected from the group consisting of:

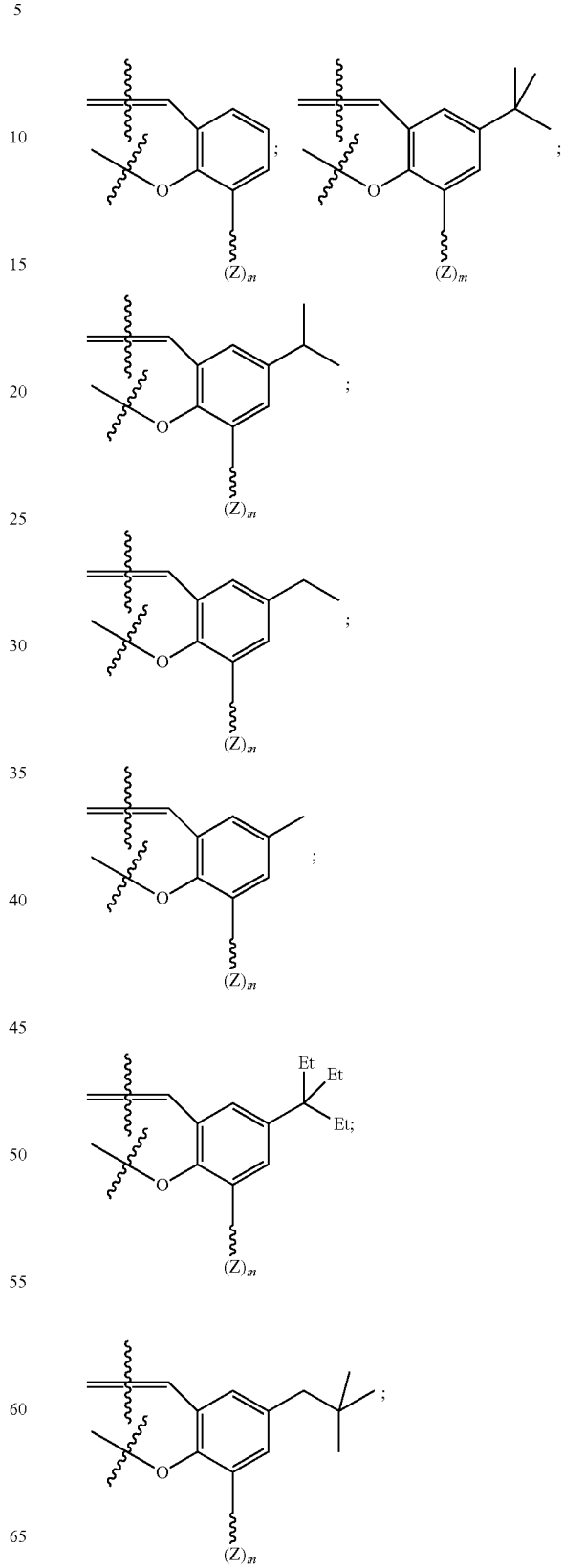

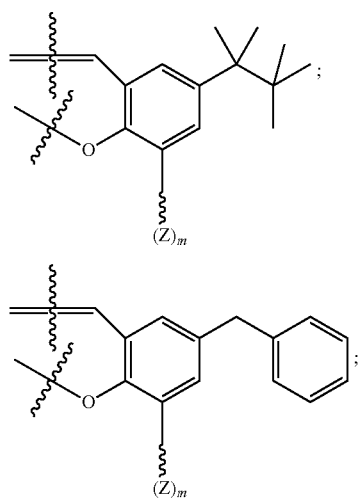

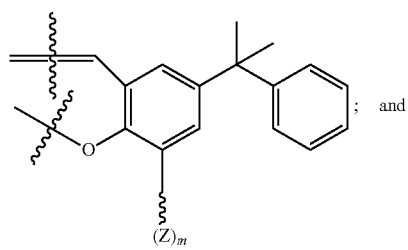

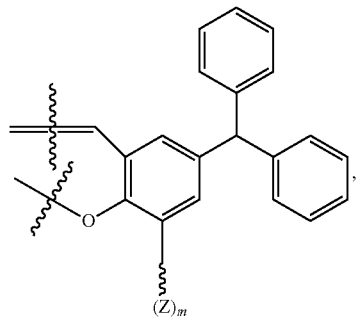

and

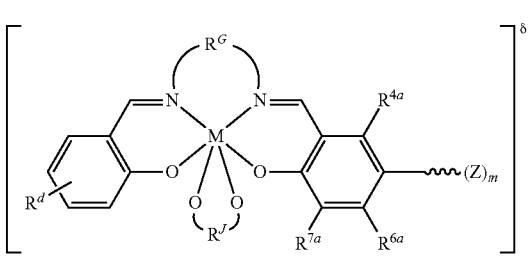

wherein ⟿ $(Z)_m$ is as described herein.

In certain embodiments, there is an activating moiety tethered to the position para to the phenolic oxygen of one or both of a salicylaldehyde-derived phenyl rings of the salen ligand as in structures Ia-3 and Ia-4:

Ia-3

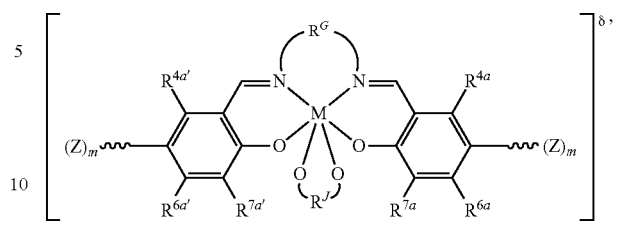

Ia-4

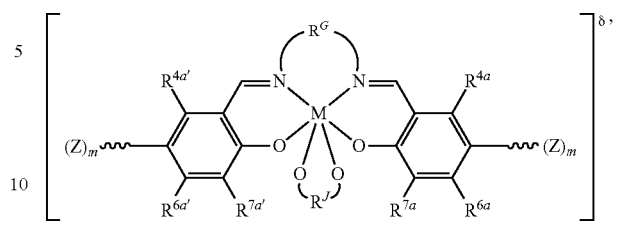

wherein $R^d$, $R^{4a}$, $R^{4a'}$, $R^{6a}$, $R^{6a'}$ $R^{7a}$, $R^{7a'}$, $R^G$, $R^J$, δ, and ⟿ $(Z)_m$ are as defined above and described in the embodiments and examples herein.

In certain embodiments of compounds having formulae Ia-3 or Ia-4, $R^{4a}$, $R^{4a'}$, $R^{6a}$, and $R^{6a'}$ are hydrogen, and each $R^{7a}$, $R^{7a'}$ is, independently, optionally substituted $C_1$-$C_{20}$ aliphatic.

In certain embodiments of catalysts Ia-3 or Ia-4, at least one of the phenyl rings comprising a salicylaldehyde-derived portion of a catalyst is independently selected from the group consisting of:

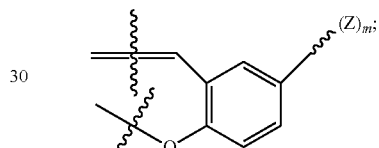

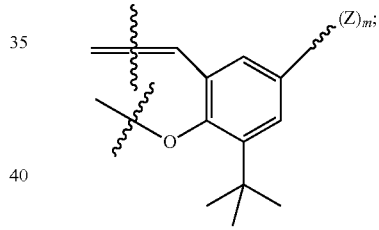

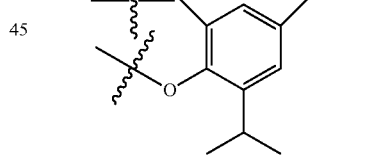

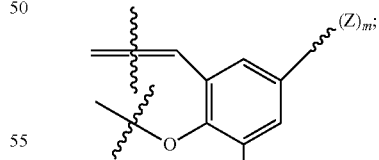

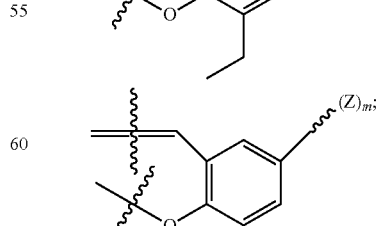

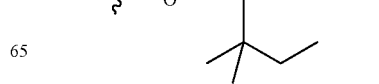

-continued

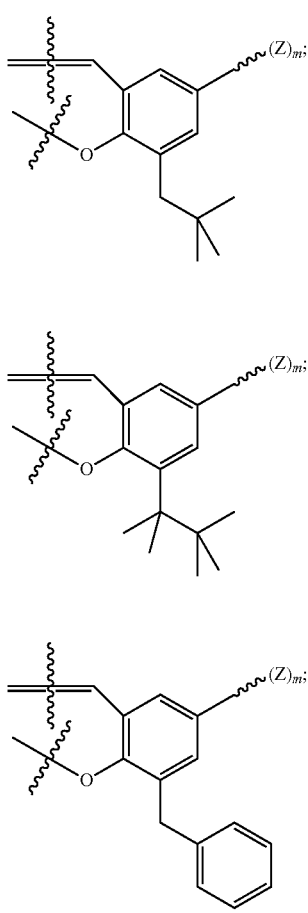

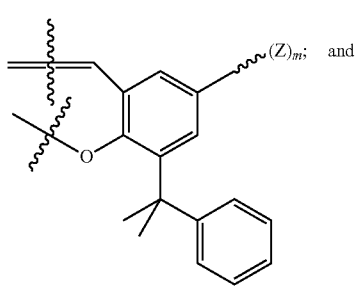 and

-continued

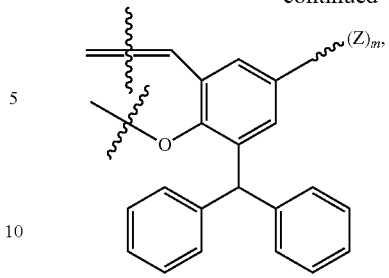

wherein —(Z)$_m$ is as described herein.

In some embodiments, there are activating moieties tethered to the positions ortho and para to the phenolic oxygen of one or both of the salicylaldehyde-derived phenyl rings of a salen ligand as in formulae Ia-5 and Ia-6:

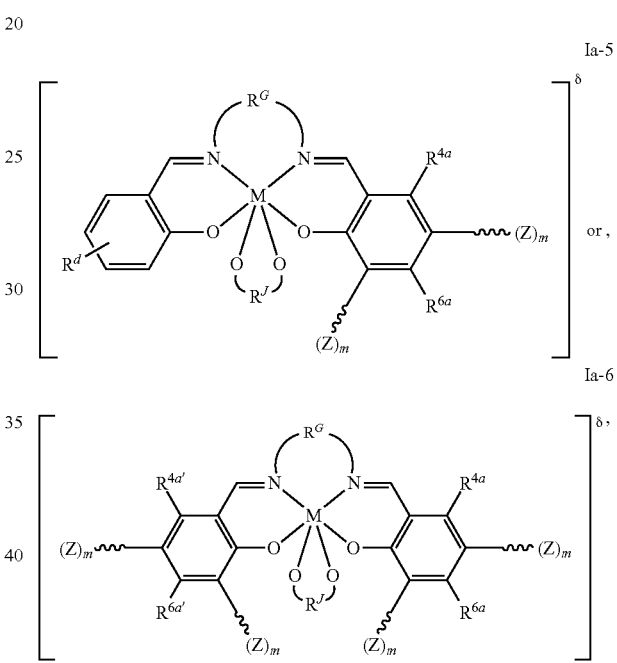

wherein M, $R^d$, $R^{4a}$, $R^{4a'}$, $R^{6a}$, $R^{6a'}$ $R^G$, $R^J$, δ, and —(Z)$_m$ are as defined above and described in the embodiments and examples herein.

In certain embodiments of compounds having formulae Ia-5 and Ia-6, each $R^{6a}$, $R^{6a'}$, $R^{4a}$, and $R^{4a'}$ is, independently, hydrogen or optionally substituted $C_1$-$C_{20}$ aliphatic.

In certain embodiments of compounds having formulae Ia-5 and Ia-6, each $R^{6a}$, $R^{6a'}$, $R^{4a}$, and $R^{4a'}$ is hydrogen.

In certain embodiments, in the salen ligands of catalysts Ia-1 through Ia-6 above, the moiety:

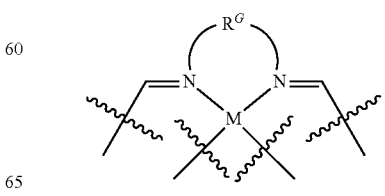

is selected from the group:

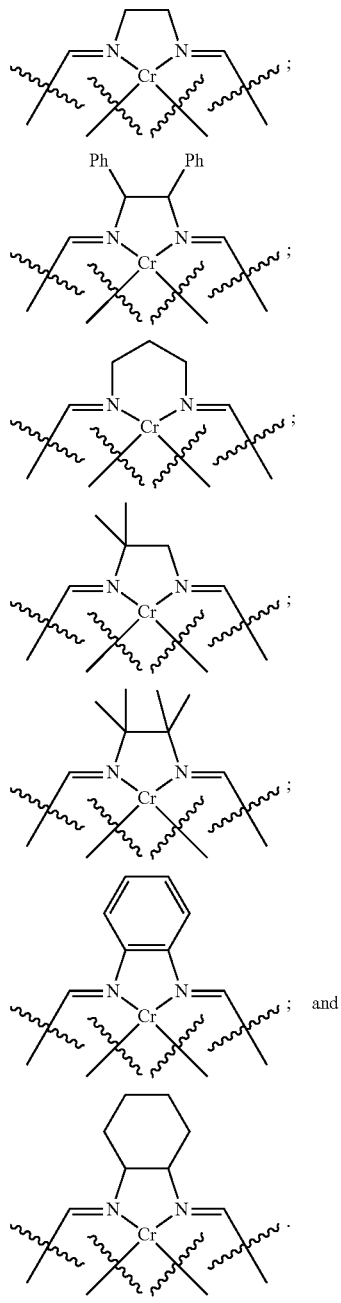

is selected from the group:

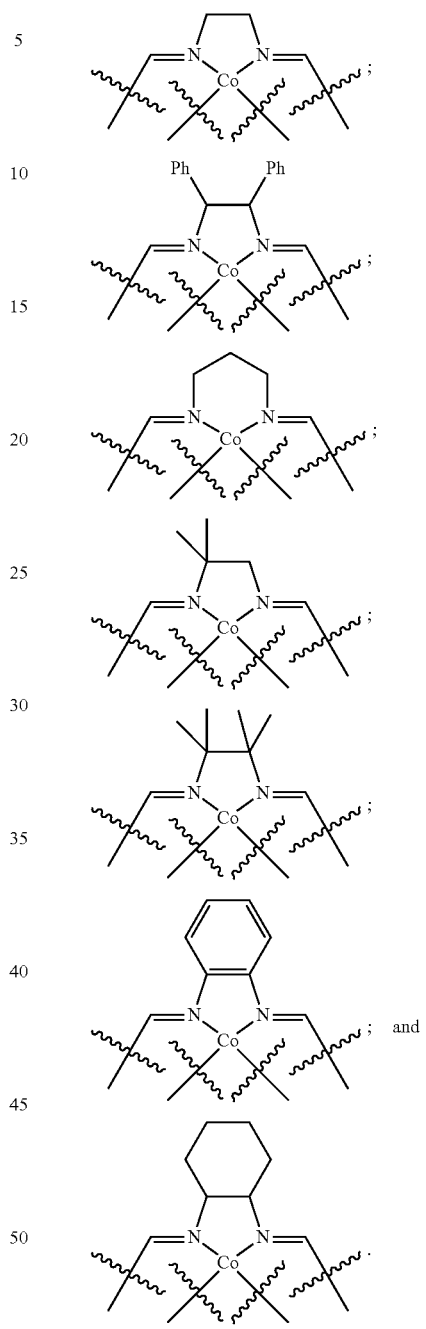

In certain embodiments, in the salen ligands of catalysts Ia-1 through I-a6 above, the moiety:

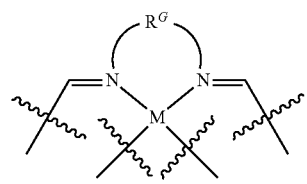

Dianions

As noted above, the chromium and cobalt complexes of the present invention are characterized in that they comprise a dianionic counterion associated with the metal atom, and/or optionally one or more cationic groups that may be covalently tethered to the salen ligand.

In certain embodiments, the dianion comprises one or more groups selected from the group consisting of: carbonate, carboxylate, dicarboxylate, sulfur-containing anions, phosphorous-containing anions, and combinations of two or more of these.

In certain embodiments, a dianion

bound to the metal in a provided compound forms the moiety:

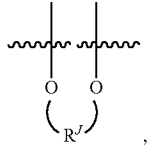

where $R^J$ is as defined above and described in the examples and embodiments herein.

In certain embodiments, in any of the chromium complexes described above including compounds of Formulae Ia through Id and Ia-1 through Ia-6, the moiety

is carbonate. In certain embodiments, the moiety

is oxalate. In certain embodiments, the moiety

is malonate. In certain embodiments, the moiety

is maleate. In certain embodiments, the moiety

is fumarate. In certain embodiments, the moiety

is succinate. In certain embodiments, in compounds of Formulae Ia through Id and Ia-1 through Ia-6, the moiety

is glutarate. In certain embodiments, the moiety

is phthalate.

In some embodiments, $R^J$ in any of the compounds described herein is —C(O)—. In some embodiments, $R^J$ is —C(O)C(O)—. In some embodiments, $R^J$ is —C(O)—$R^H$—C(O)—. In some embodiments, $R^J$ is —SO—. In some embodiments, $R^J$ is —SO$_2$—. In some embodiments, $R^J$ is —P(O)(OR$^{J1}$)—. In some embodiments, $R^J$ is —P(O)R$^{J1}$—. In some embodiments, $R^J$ is —R$^{J1}$C=N—. In some embodiments, $R^J$ is —C(O)—$R^H$—P(O)(OR$^{J1}$)—. In some embodiments, $R^J$ is —C(O)—$R^H$—S(O)—. In some embodiments, $R^J$ is —C(O)—$R^H$—S(O)$_2$—. In some embodiments, $R^J$ is —SO$_2$—$R^H$—P(O)(OR$^{J1}$)—. In some embodiments, $R^J$ is —SO—$R^H$—P(O)(OR$^{J1}$)—. In some embodiments, $R^J$ is —C(O)R$^H$—.

In some embodiments, $R^H$ is

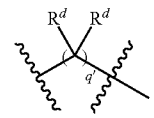

wherein q' is from 1 to 6, wherein $R^d$ is as defined above. In some embodiments, $R^H$ is

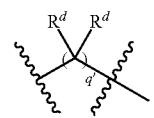

wherein q' is from 1 to 5. In some embodiments, $R^H$ is

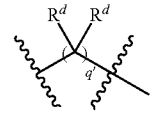

wherein q' is from 1 to 4. In some embodiments, $R^H$ is

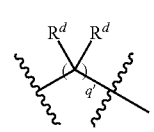

wherein q' is from 1 to 3. In some embodiments, $R^H$ is

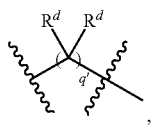

wherein q' is from 1 to 2.
In some embodiments, $R^H$ is

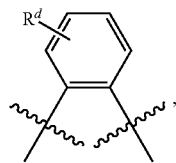

where $R^d$, is as defined above. In some embodiments, $R^H$ is

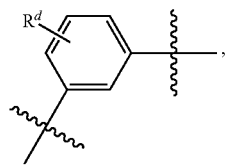

where $R^d$, is as defined above. In some embodiments, $R^H$ is

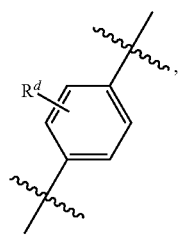

where $R^d$, is as defined above.

In certain embodiments, where a $R^J$ group comprises $R^c$, $R^{c'}$, or $R^d$, the $R^c$, $R^{c'}$, and $R^d$ group(s) are other than —$(Z)_m$.

Tethered Moieties

As noted above, in certain embodiments, metal complexes of the present invention comprise one or more nitrogen- or phosphorous-containing functional groups covalently tethered to the salen ligand. In certain embodiments, these tethered functional groups are defined as —$(Z)_m$ groups, where — represents the covalent tether (also referred to herein as a 'linker,' a 'linker moiety,' or a 'Z-linker'), each Z comprises a nitrogen-, phosphorous-, or arsenic-containing functional group, and m is an integer of one or greater indicating how many such nitrogen-, phosphorous-, or arsenic-containing functional groups are attached to a given linker.

In certain embodiments, —$(Z)_m$ is defined by the embodiments found in Appendix A, infra. It is to be understood that definitions in the appendix are to be read independently. For example, the definitions of R groups in the appendix may differ from correspondingly designated R groups in the body of the specification: in such instances, the definitions are to be regarded to be independent and specific to the appendix. As such, a limitation on an R-group in an appendix is not necessarily intended to limit any definition provided in the specification and vice-versa.

In certain embodiments, —$(Z)_m$ groups that may be present on complexes of the present invention include those disclosed in WO/2010/022388 incorporated herein by reference.

In certain embodiments, each tether (or "Z-linker") moiety — contains 1-30 atoms including at least one carbon atom, and optionally one or more atoms selected from the group consisting of N, O, S, Si, B, and P. Additional embodiments of such linker moieties are described in Appendix A hereafter, and in descriptions of the embodiments, and examples herein.

In certain embodiments, each Z is independently a quaternary amine, a guanadine, a guanidinium, an amidine, an amidinium, a neutral or cationic nitrogen-containing heterocycle or a variant or combination of any of these. In certain embodiments, one or more Z groups comprises a guanidine, or more specifically a cyclic guanidine, or more specifically a bicyclic guanidine. In certain embodiments, one or more Z groups comprises a guanidinium salt, or more specifically a cyclic guanidinium salt, or more specifically a bicyclic guanidinium salt. In certain embodiments, one or more Z groups comprises an amidine, or more specifically a cyclic amidine, or more specifically a bicyclic amidine. In certain embodiments, one or more Z groups comprises a amidinium salt, or more specifically a cyclic amidinium salt, or more specifically a bicyclic amidinium salt. In certain embodiments, one or more Z groups comprises a quaternary ammonium group, or more specifically a trialkyl ammonium group, or more specifically a trimethylammonium group, triethylammonium group, tripropyl ammonium group, tributyl ammonium group, a diethyl isopropyl ammonium group, a dimethylbutyl ammonium group, or similar mixed lower-alkyl ammonium groups.

In certain embodiments, one or Z groups comprises a moiety having a formula selected from:

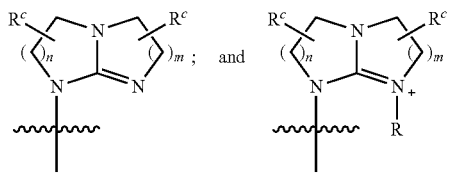

where $R^c$ and R are as defined hereinabove and in the examples and embodiments described herein, and each of n and m is independently an integer from 1 to 4 inclusive. In certain embodiments, one or more Z groups are independently selected from the group consisting of:

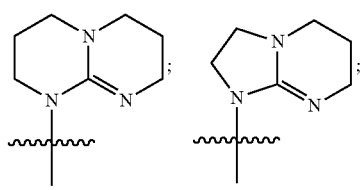

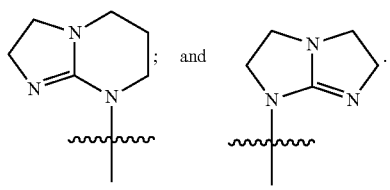

In certain embodiments, one or more Z groups are independently selected from the group consisting of:

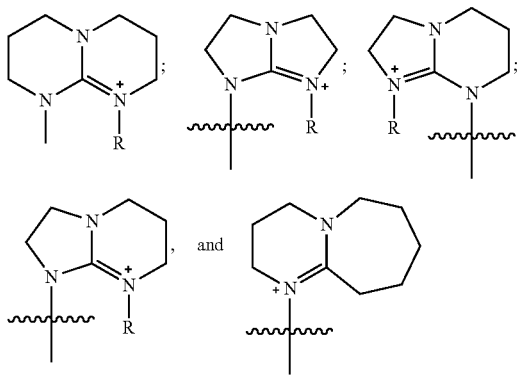

where —R is as defined above.

In certain embodiments, one or more Z groups are independently selected from the group consisting of:

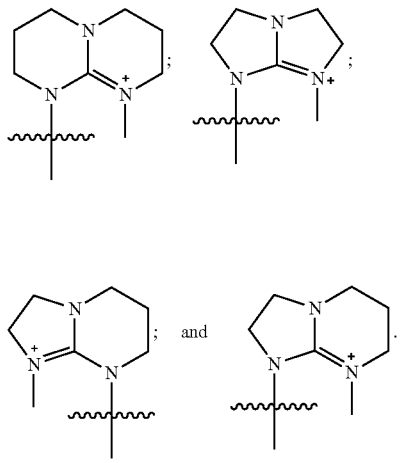

In certain embodiments, one or more Z groups are independently selected from the group consisting of:

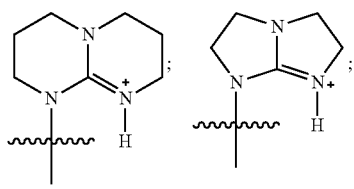

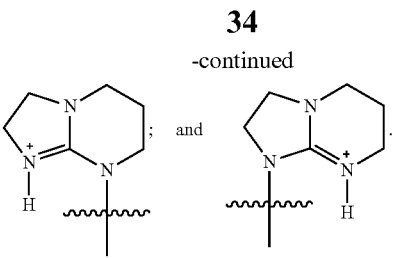

In certain embodiments, —(Z)$_m$ groups present on the metal complexes of the present invention are selected from the group consisting of:

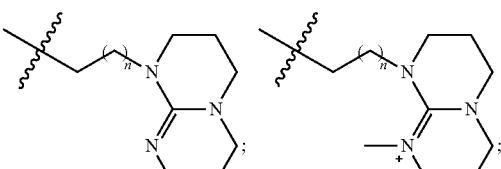
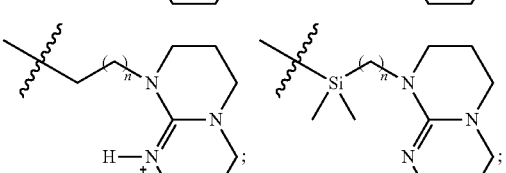
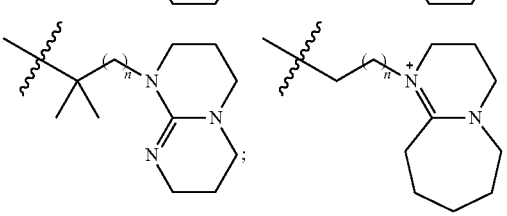
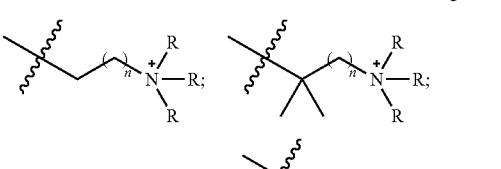
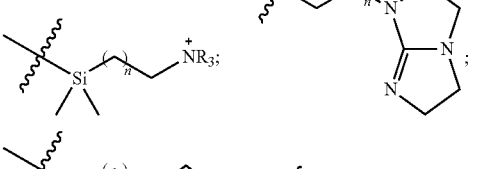
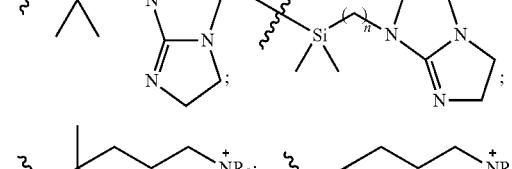
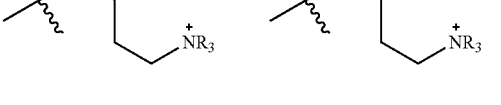

-continued
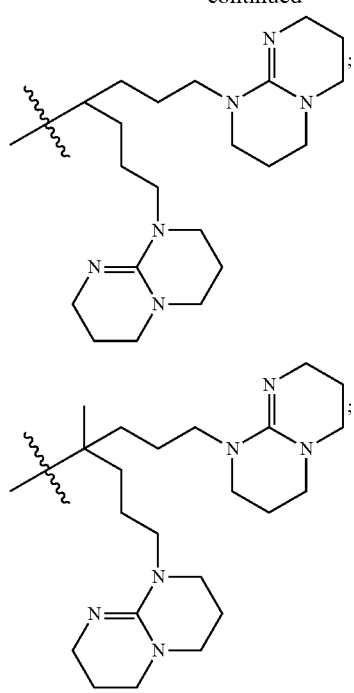
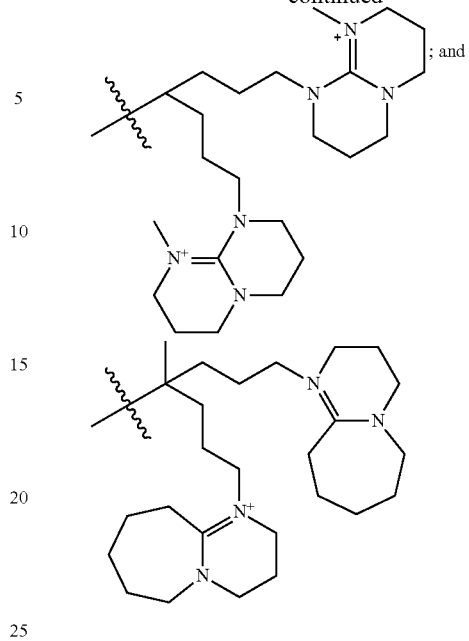
wherein each of R and n is as defined above and in the classes and subclasses herein.
In certain embodiments, metal complexes of the present invention are selected from amongst those shown in Table 1. Many similar variations and related compounds will be apparent to the skilled artisan.
TABLE 1
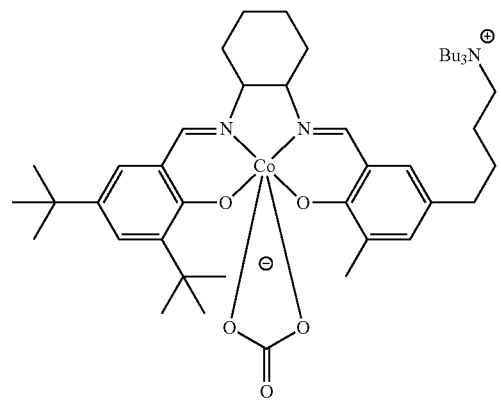
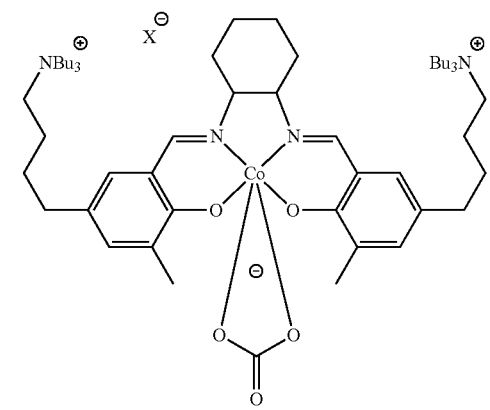

TABLE 1-continued
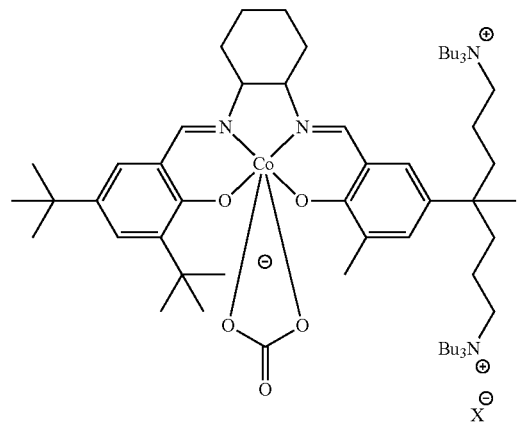
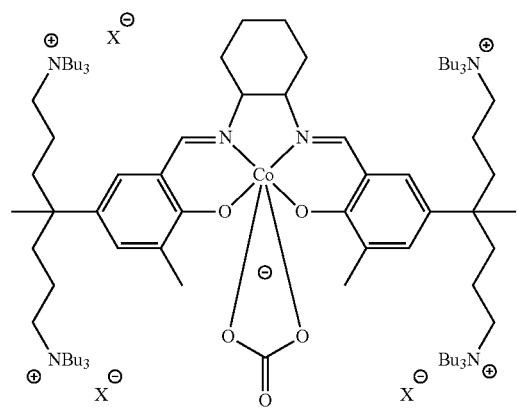
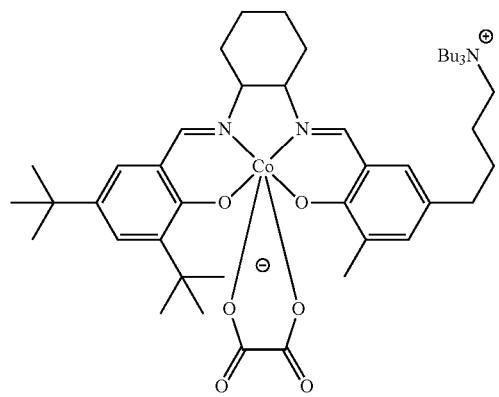
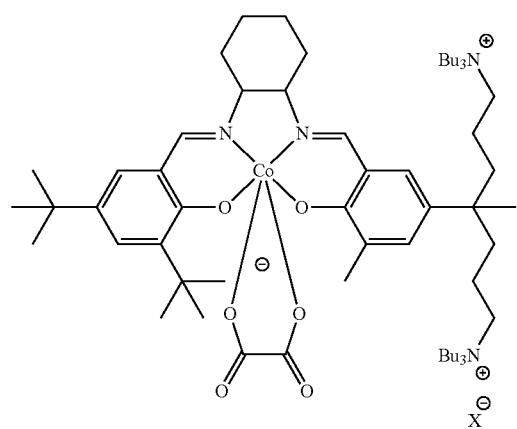

TABLE 1-continued
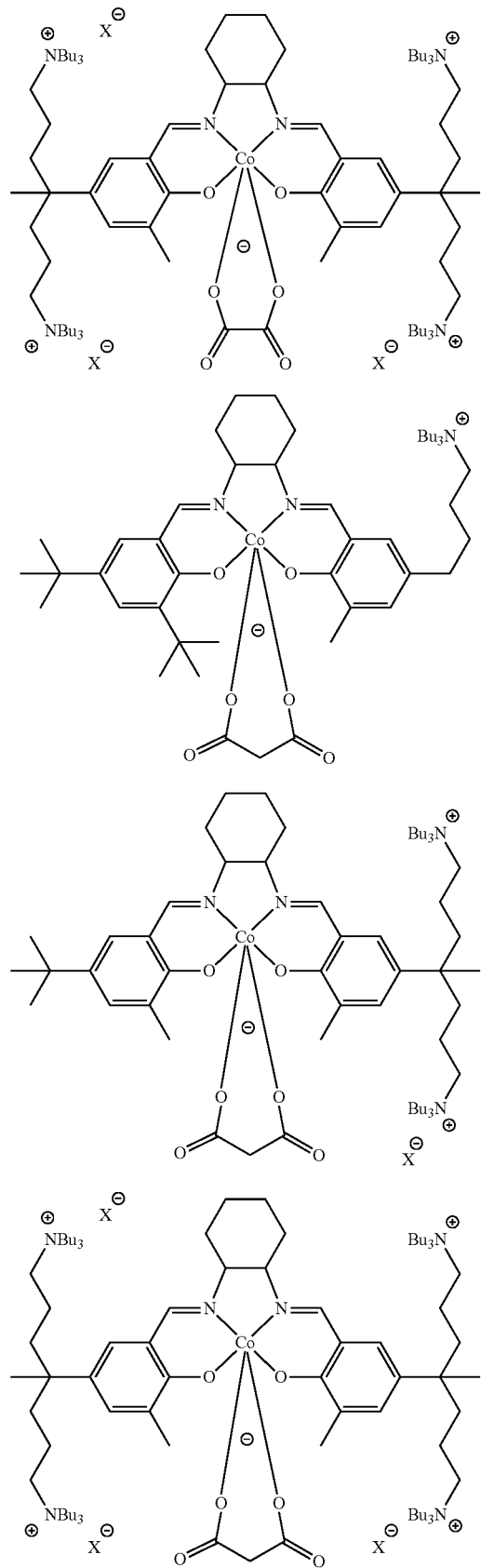

TABLE 1-continued
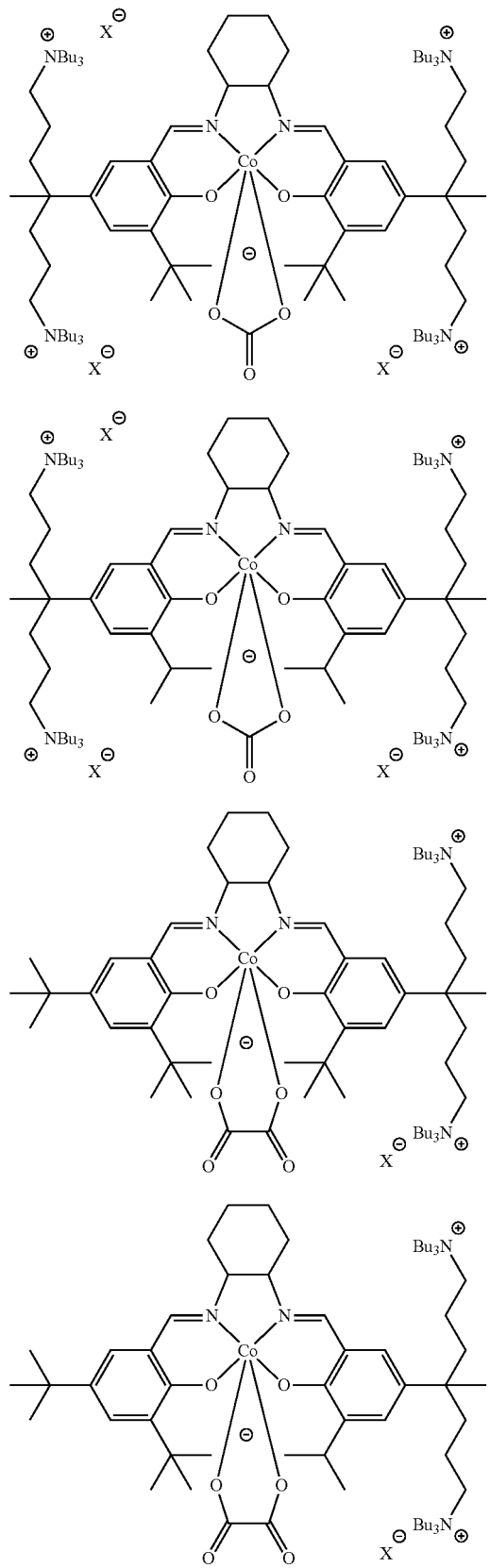

TABLE 1-continued
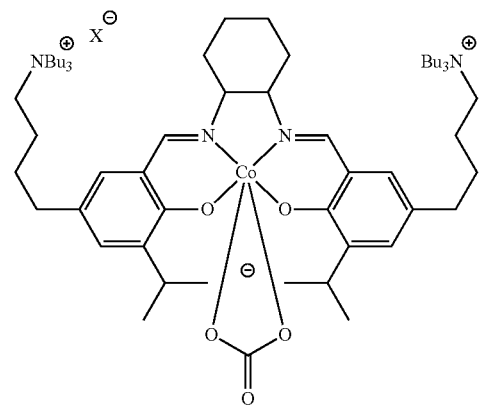
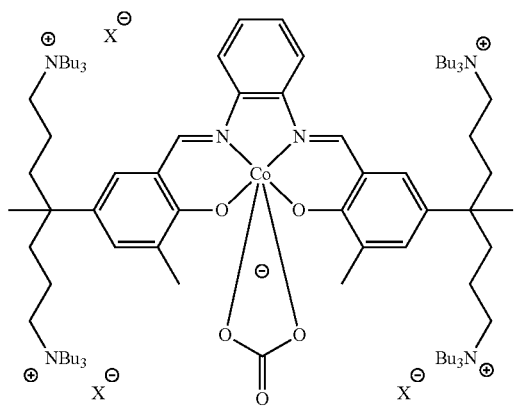
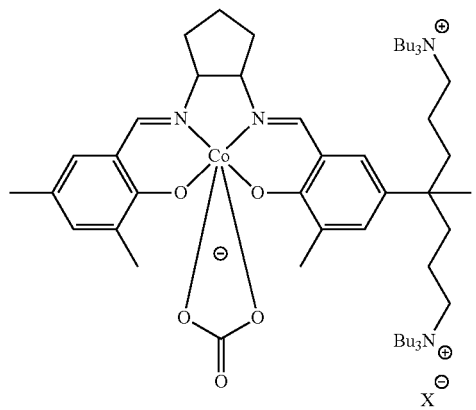
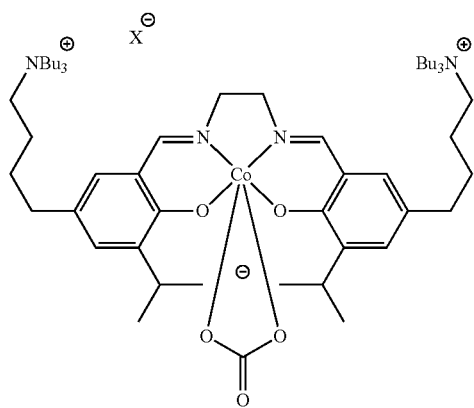

TABLE 1-continued
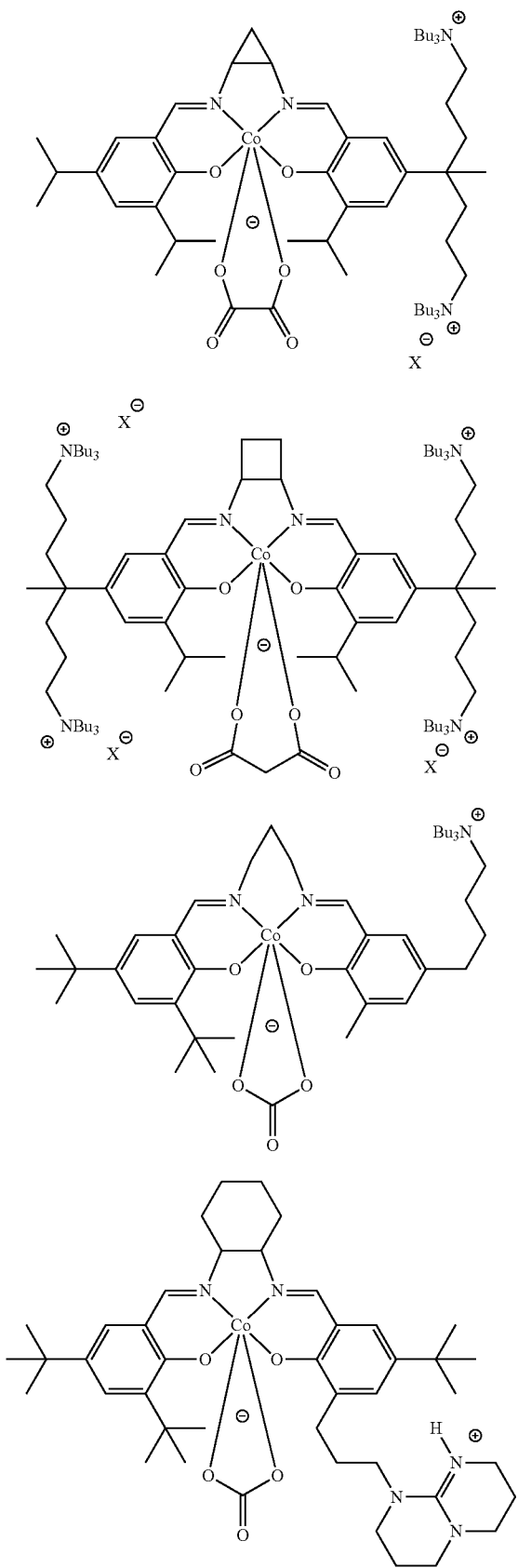

TABLE 1-continued
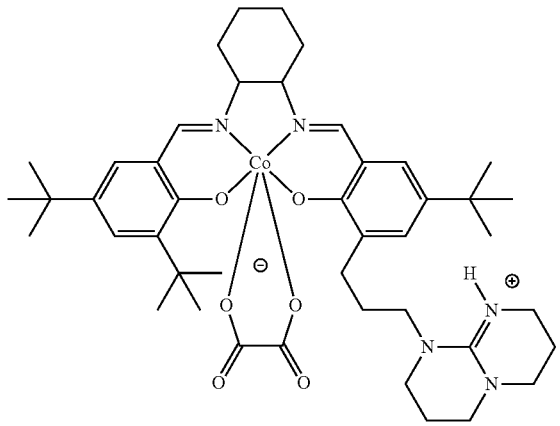
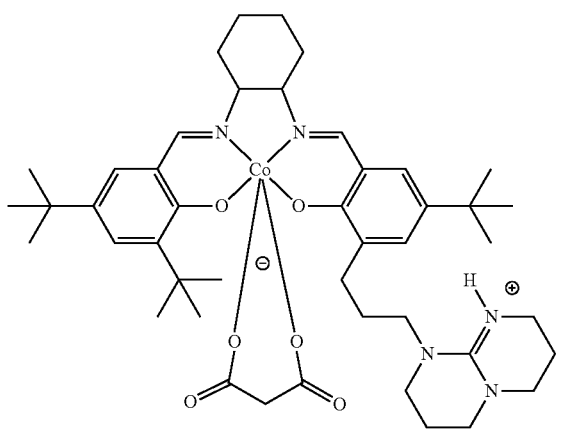
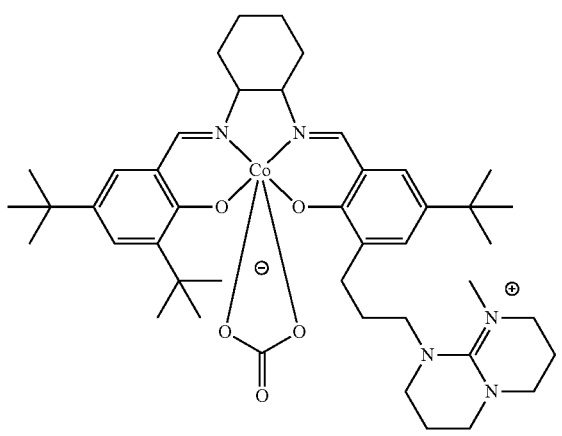

TABLE 1-continued
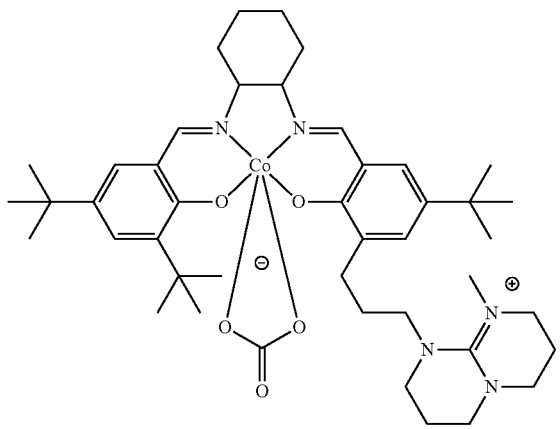
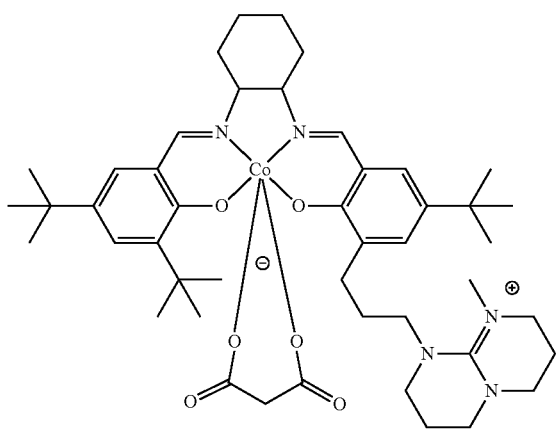
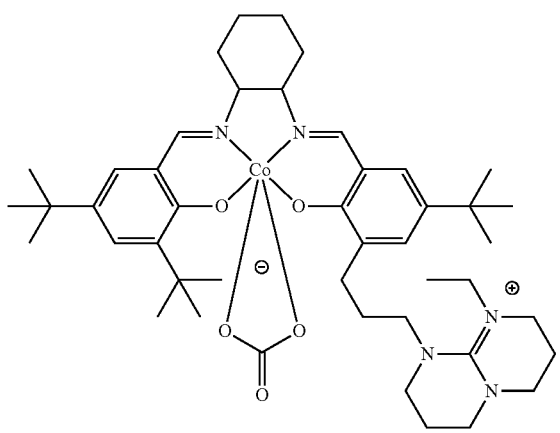

TABLE 1-continued
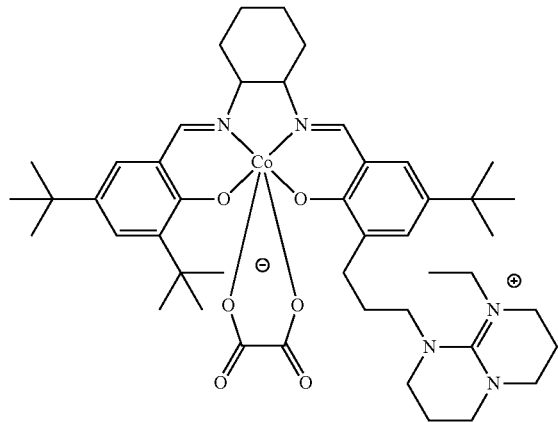
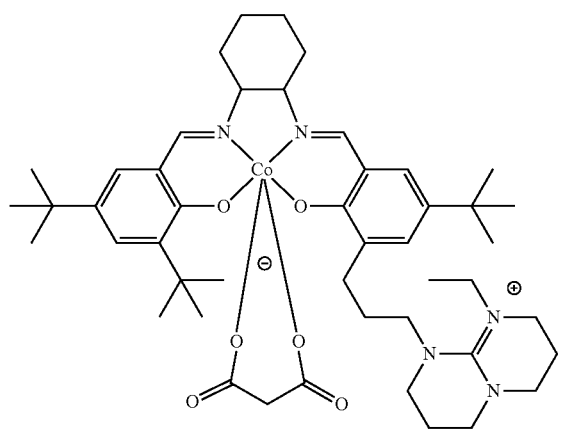
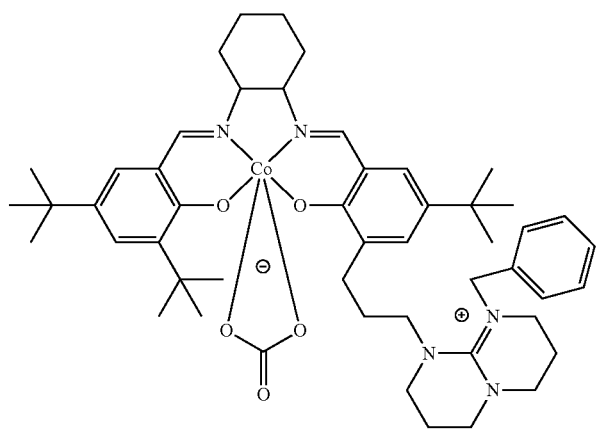

TABLE 1-continued
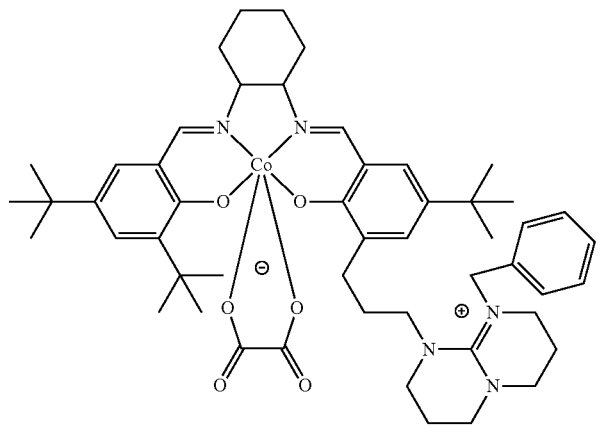
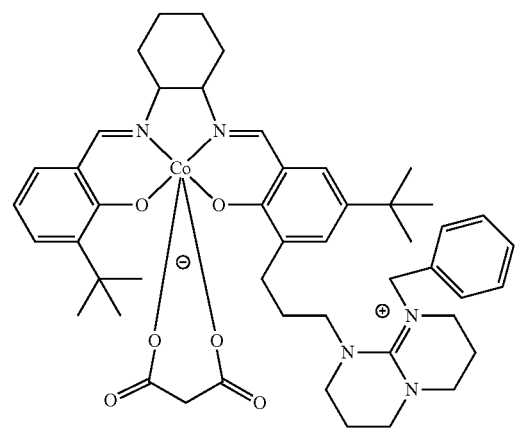
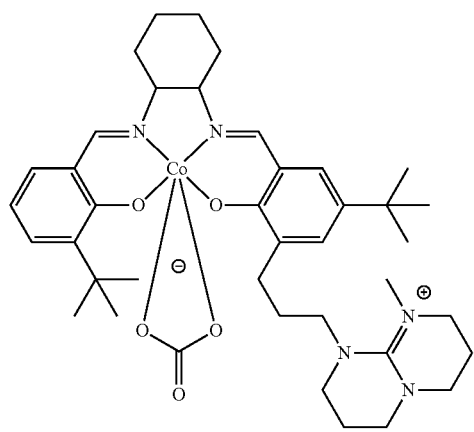

TABLE 1-continued
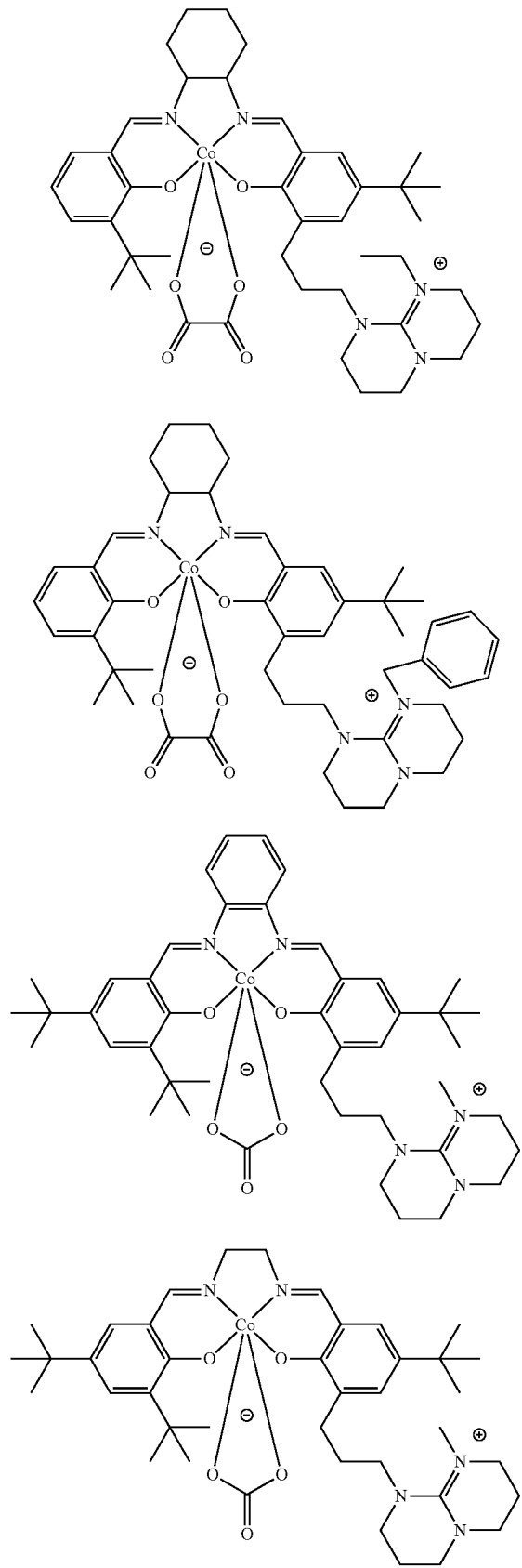

TABLE 1-continued
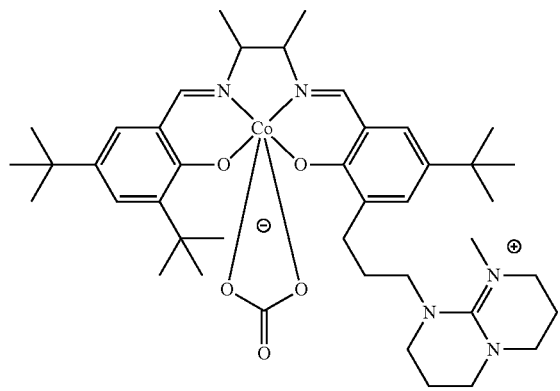
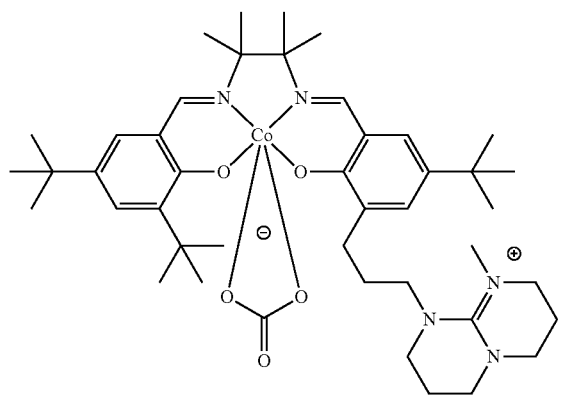
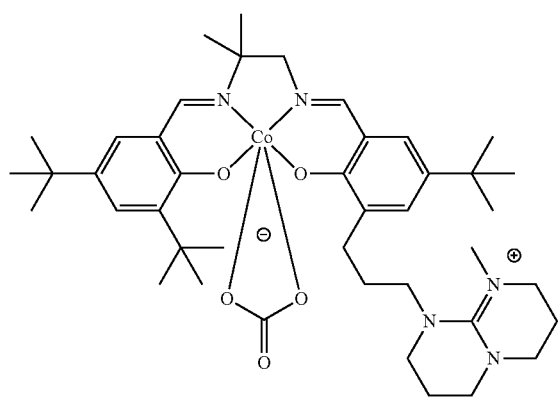
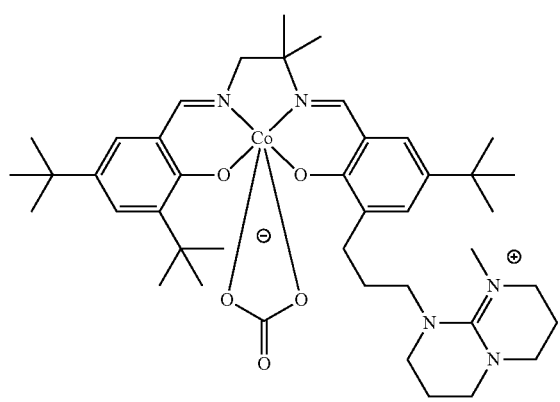

TABLE 1-continued
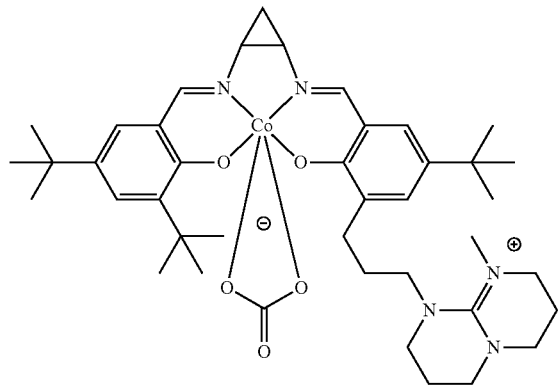
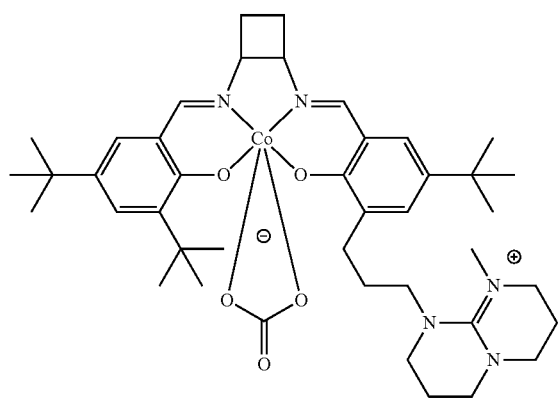
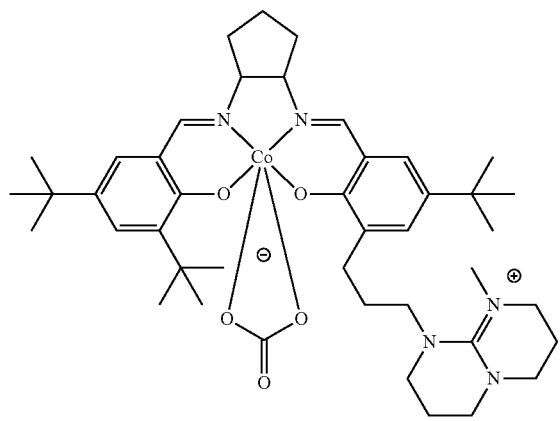
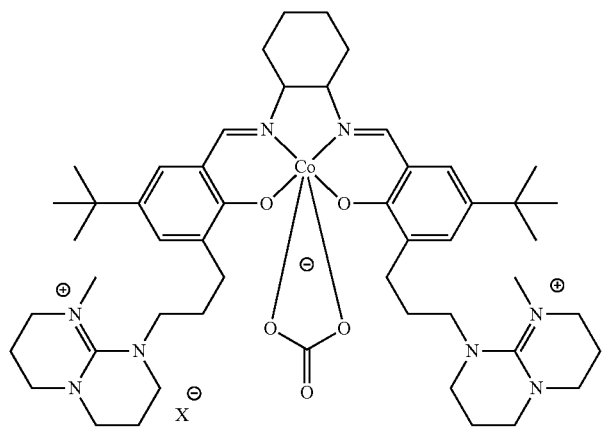

TABLE 1-continued
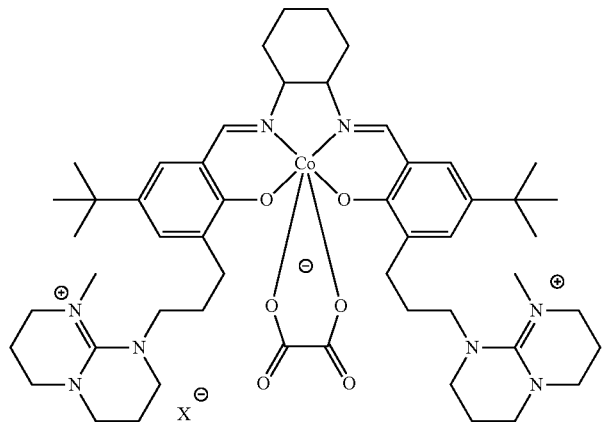
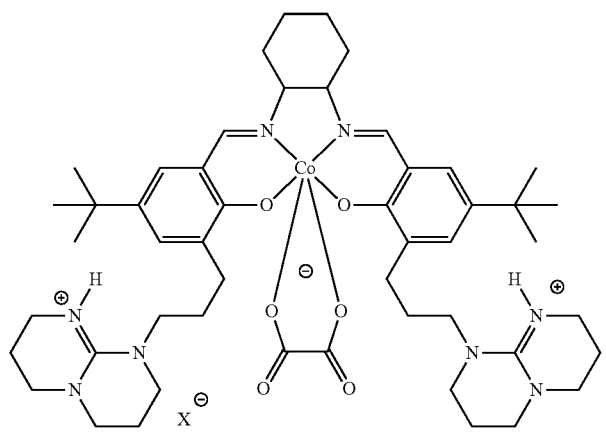
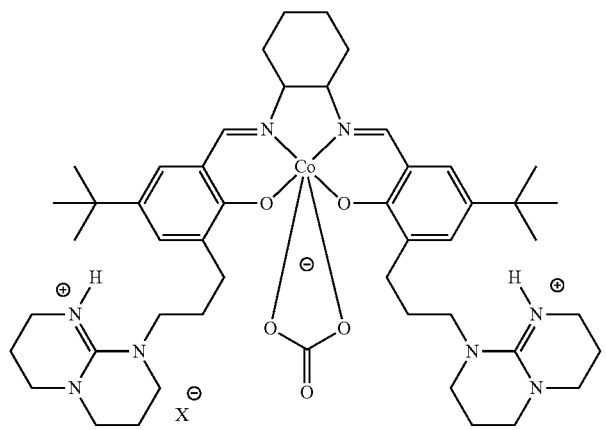

TABLE 1-continued
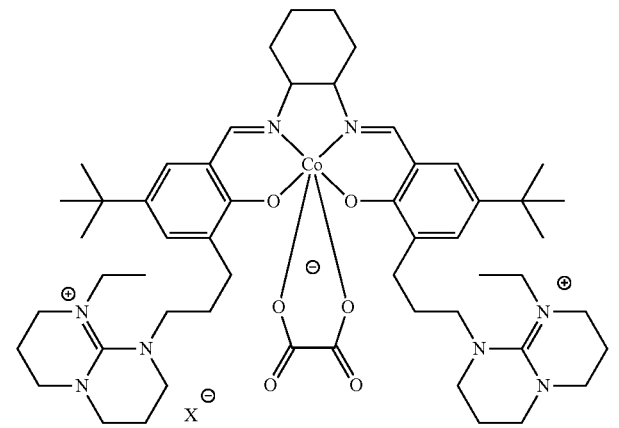
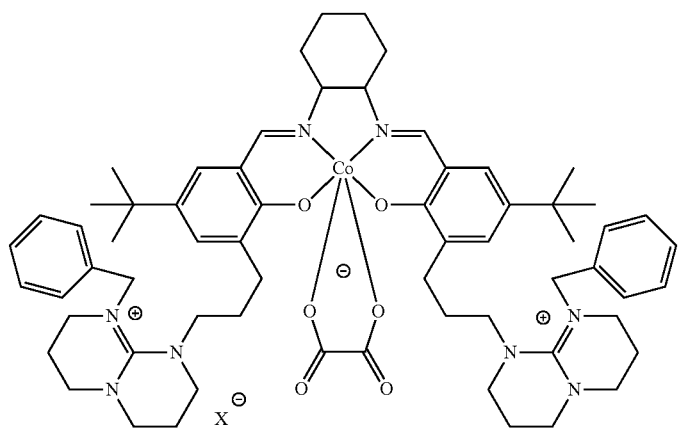
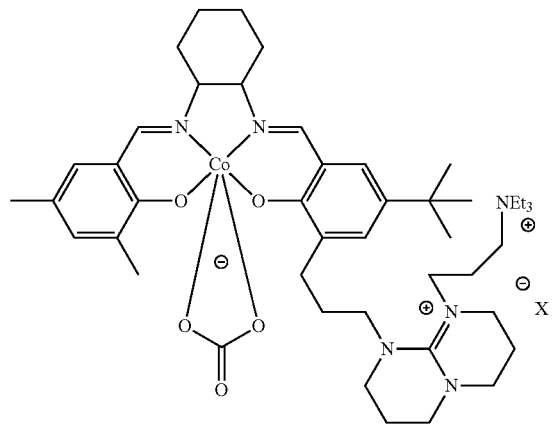
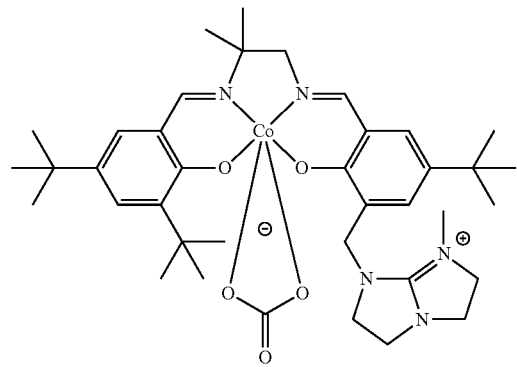

TABLE 1-continued
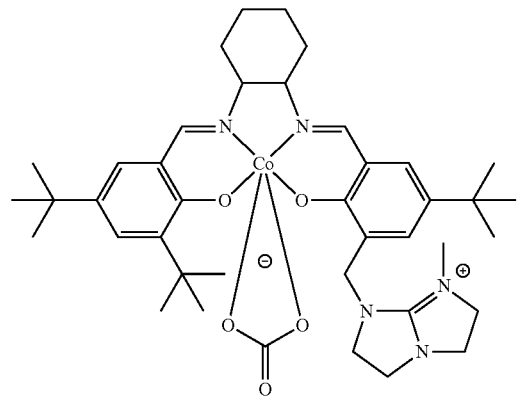
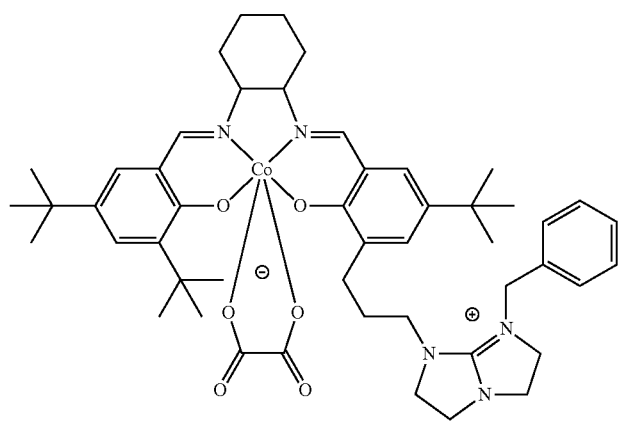
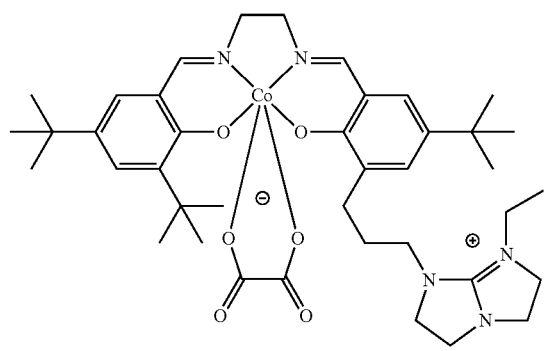
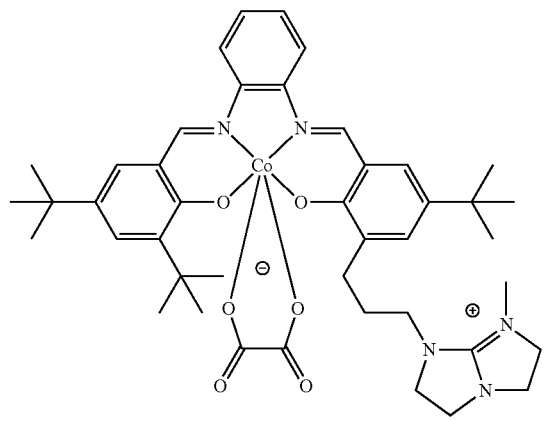

TABLE 1-continued
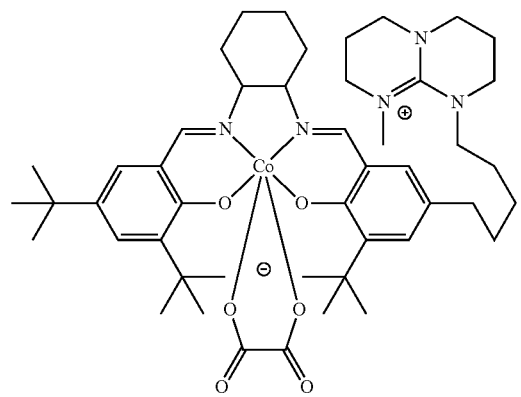
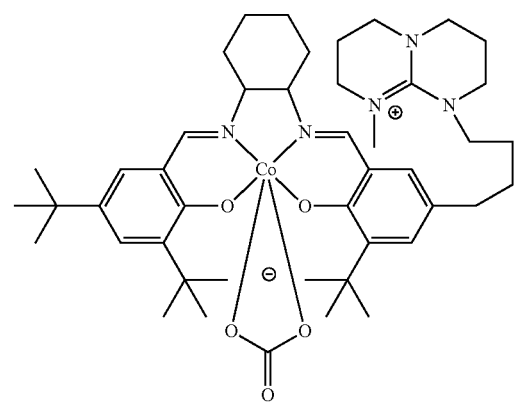
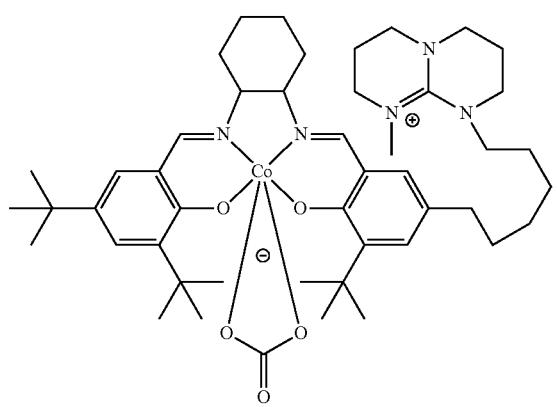
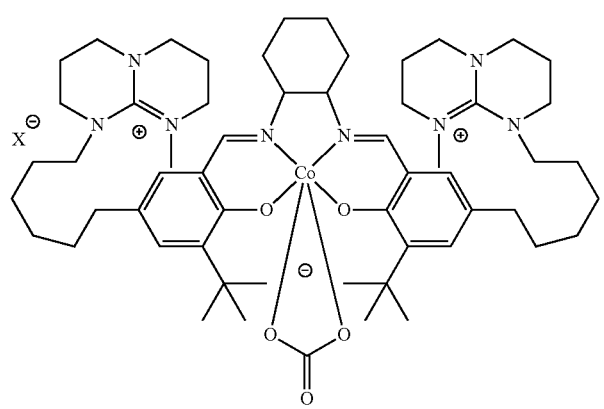

TABLE 1-continued
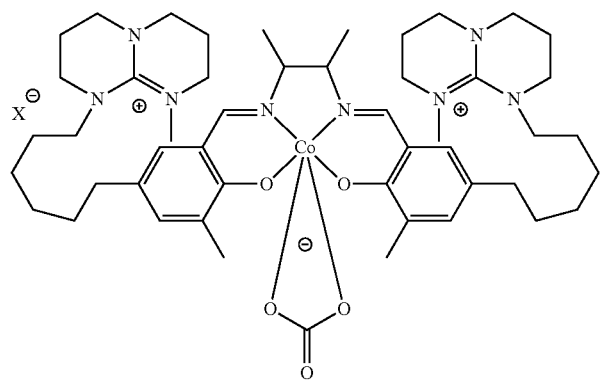
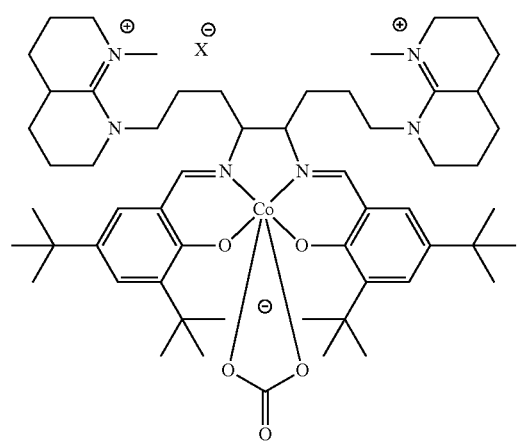
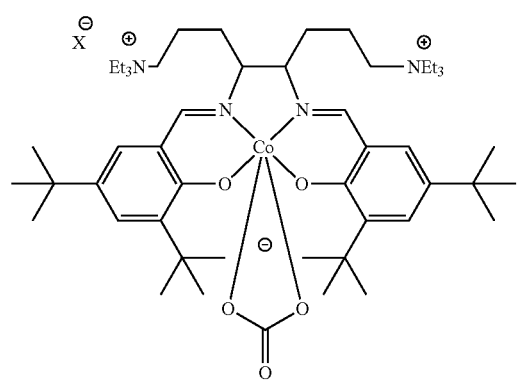
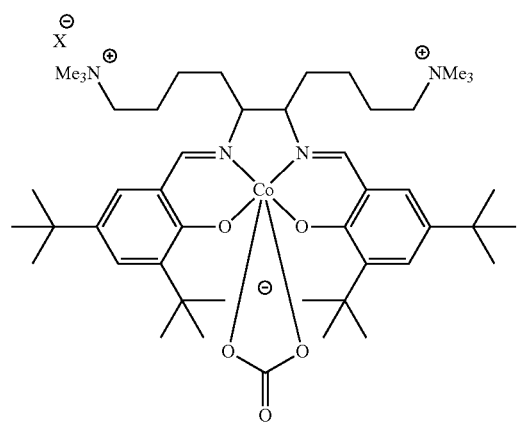

TABLE 1-continued
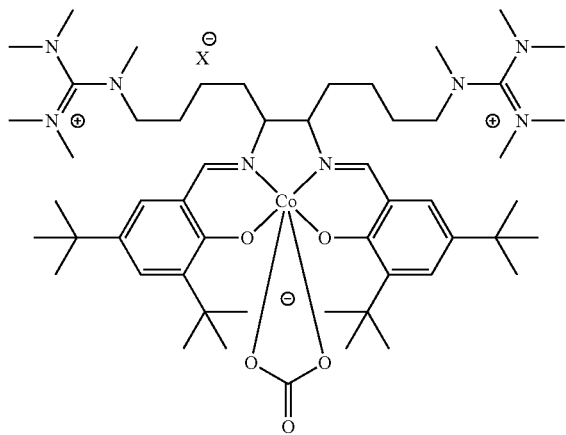
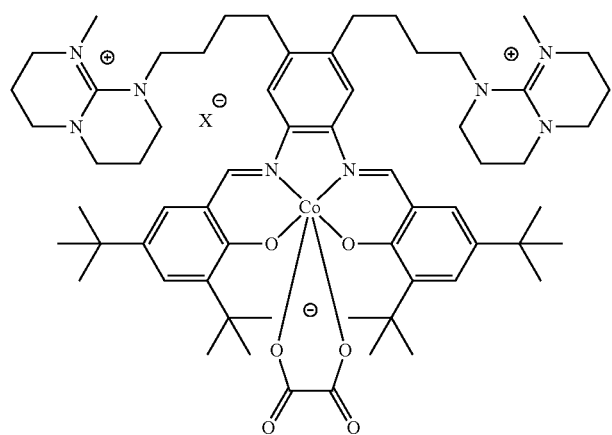
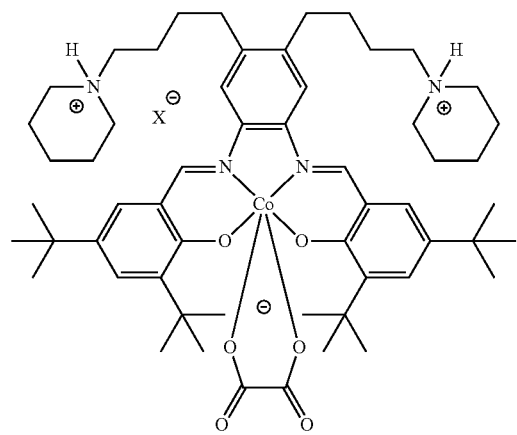

TABLE 1-continued
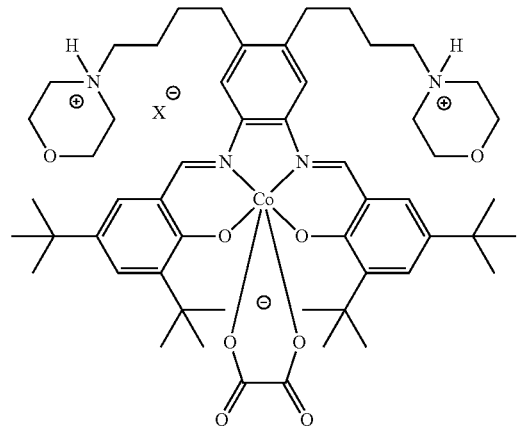
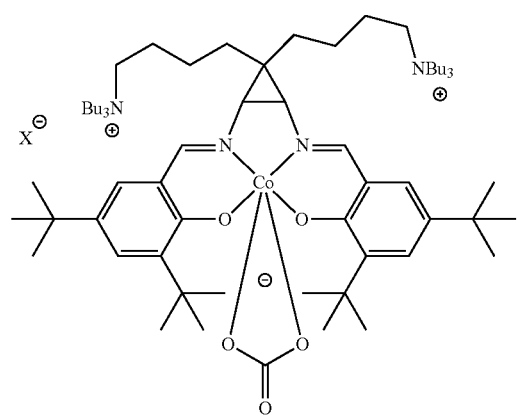
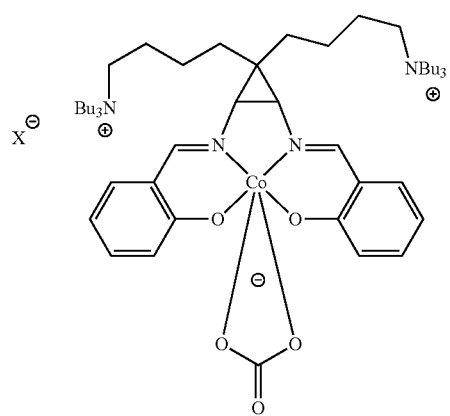

TABLE 1-continued
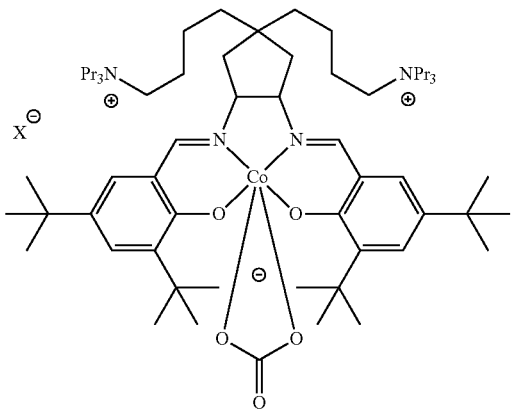
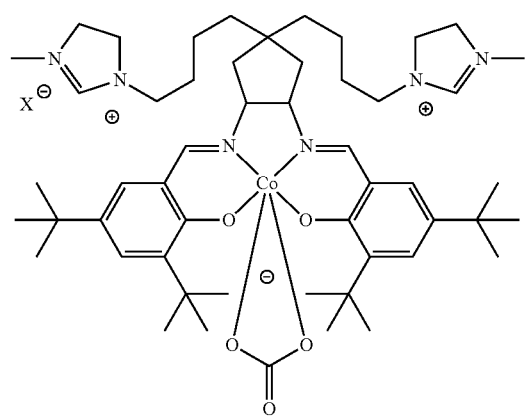
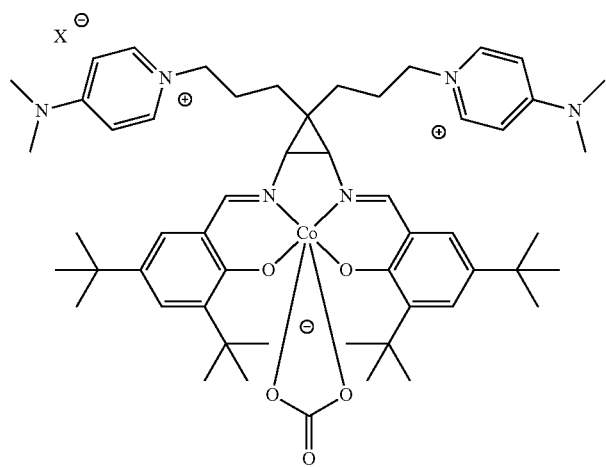

TABLE 1-continued
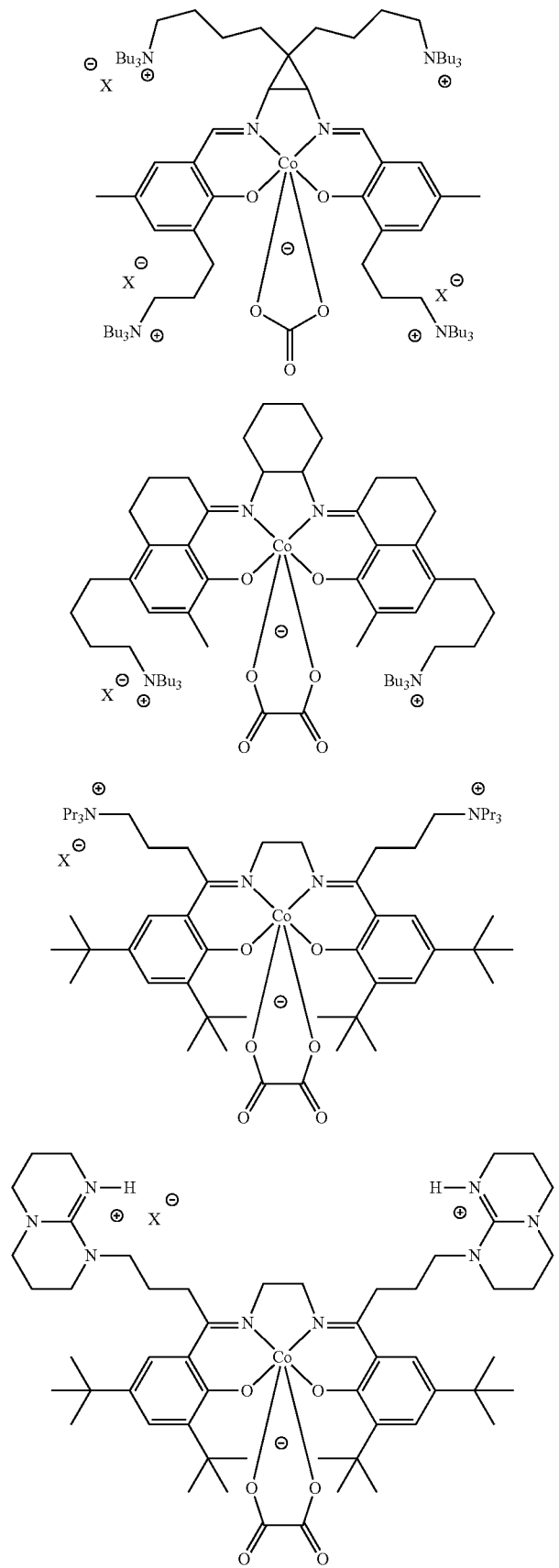

TABLE 1-continued
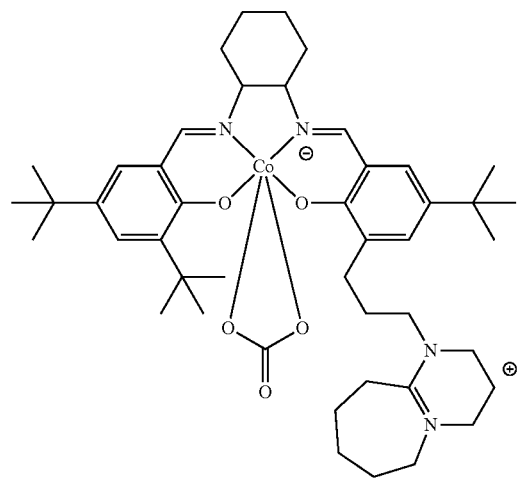
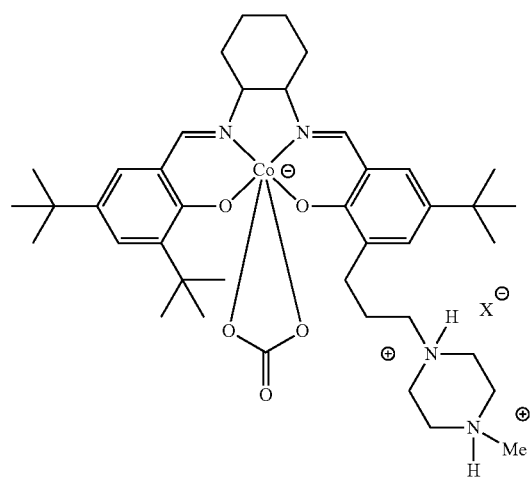
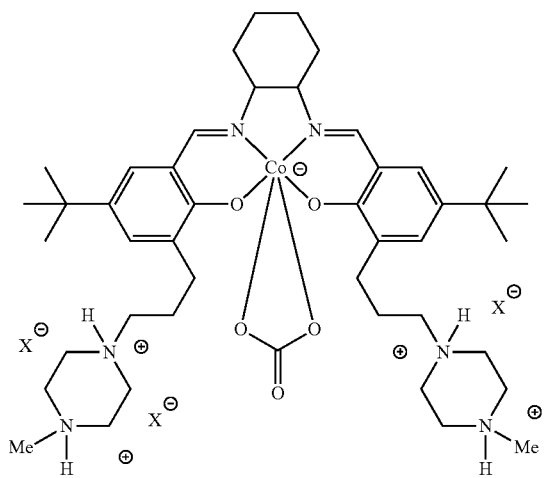

TABLE 1-continued
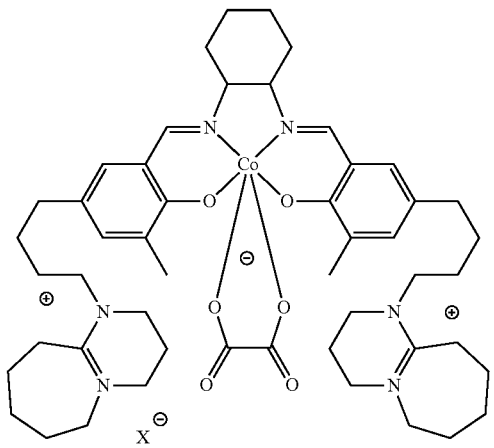
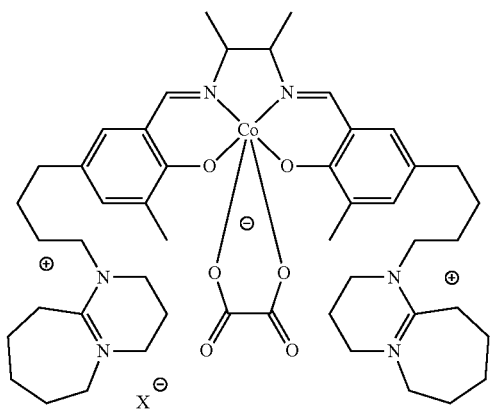
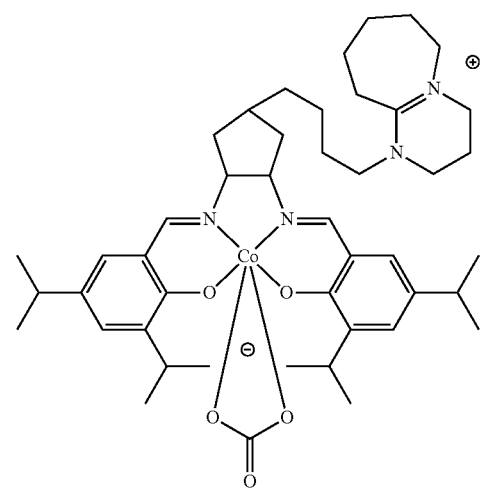

TABLE 1-continued
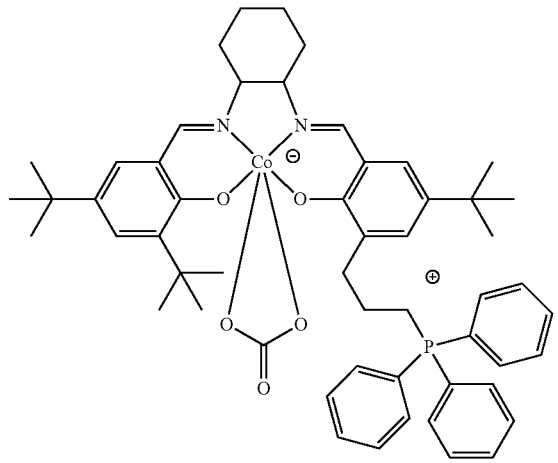
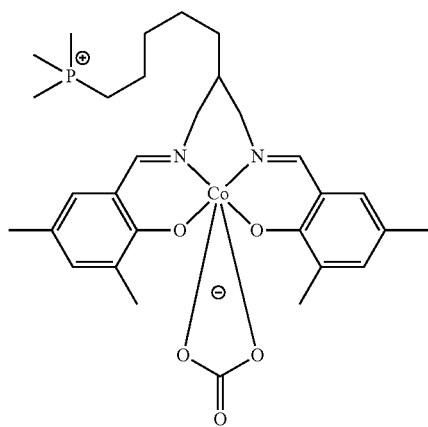
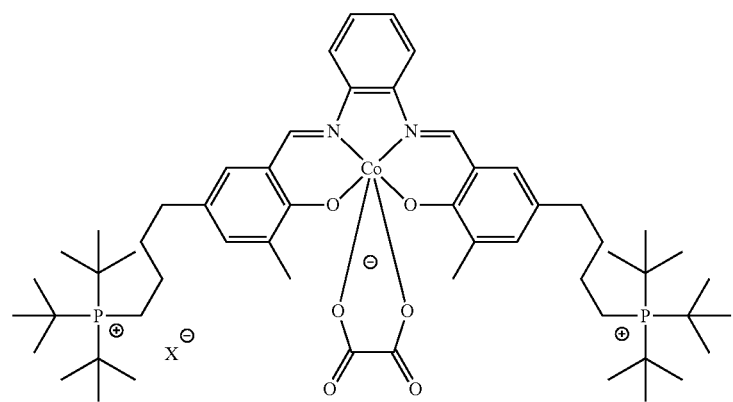

TABLE 1-continued
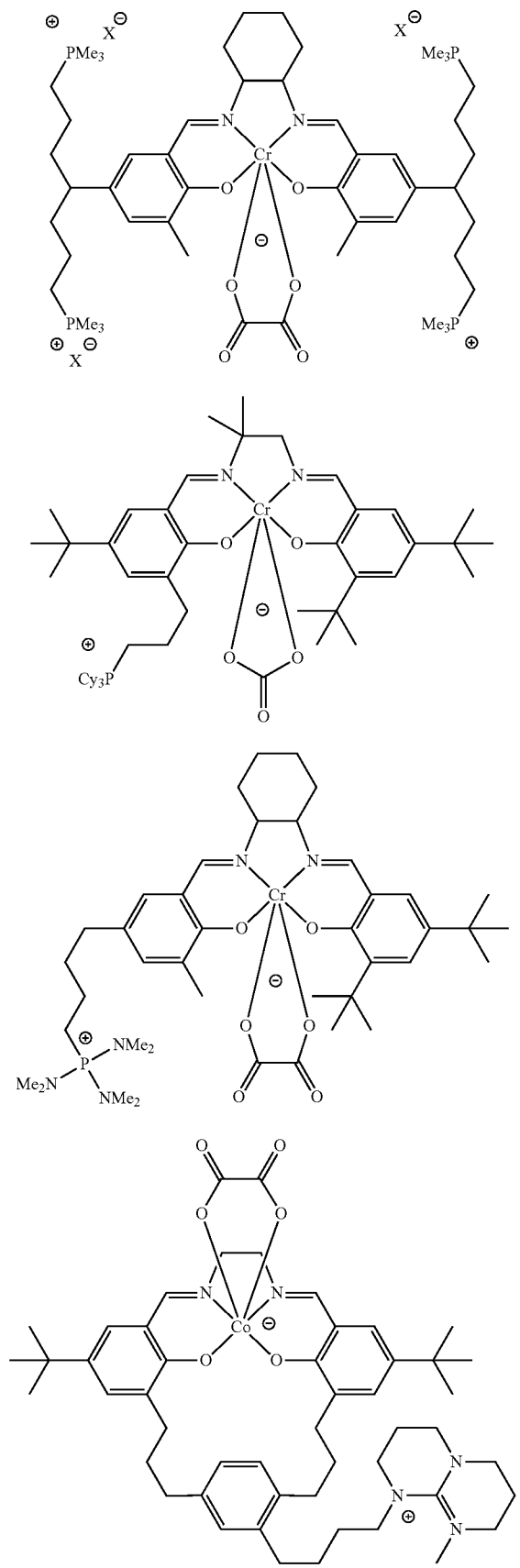

TABLE 1-continued
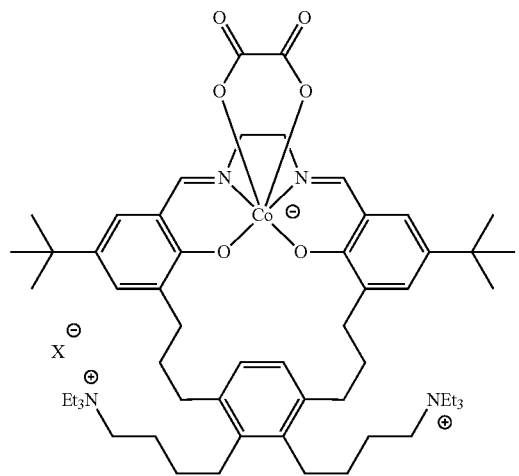
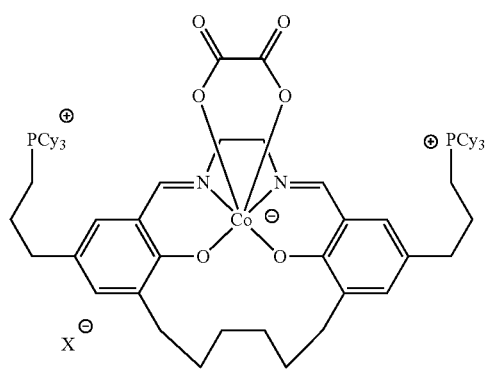
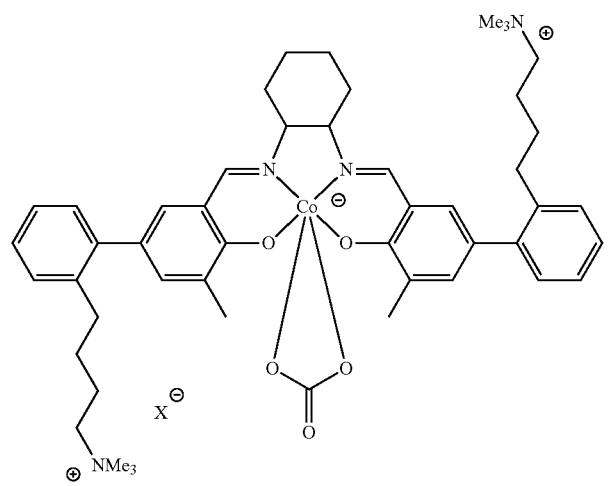

TABLE 1-continued
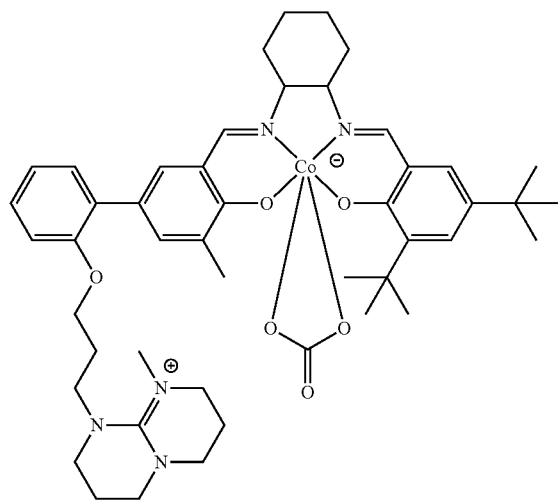
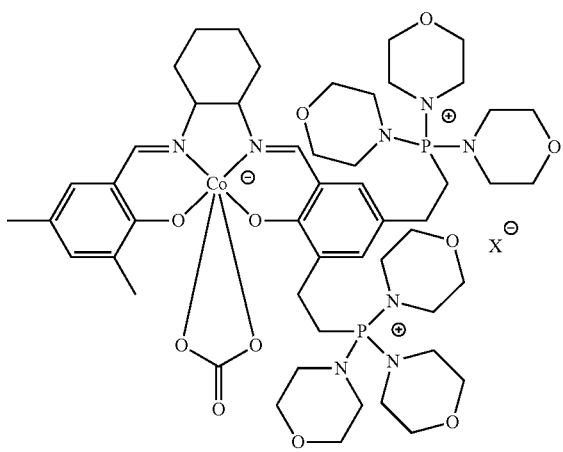
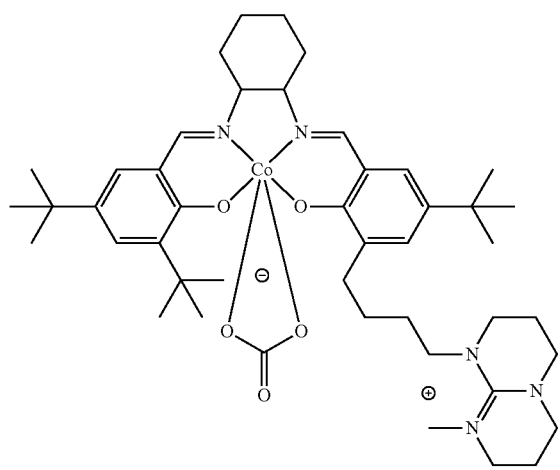

TABLE 1-continued
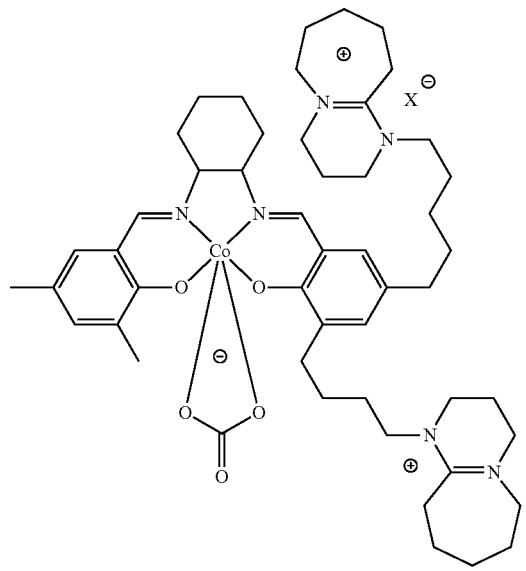
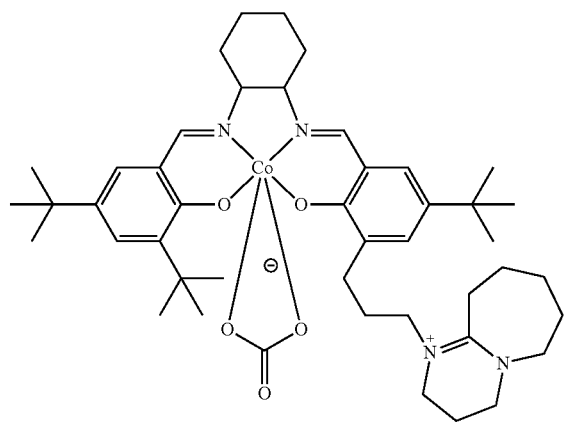
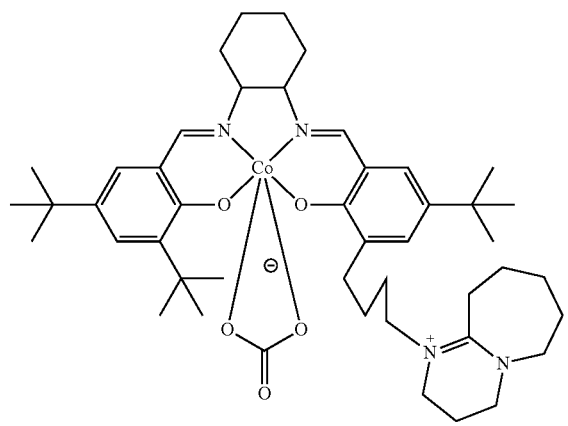

TABLE 1-continued
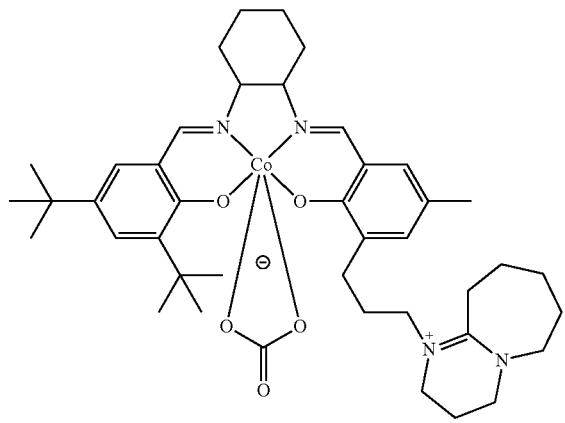
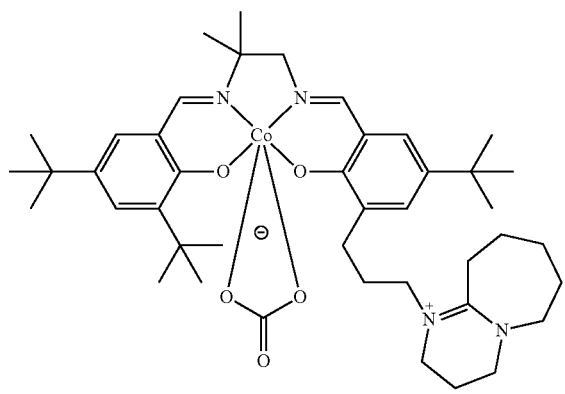
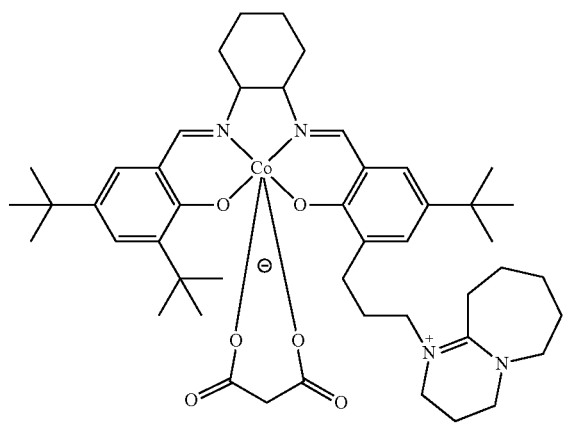
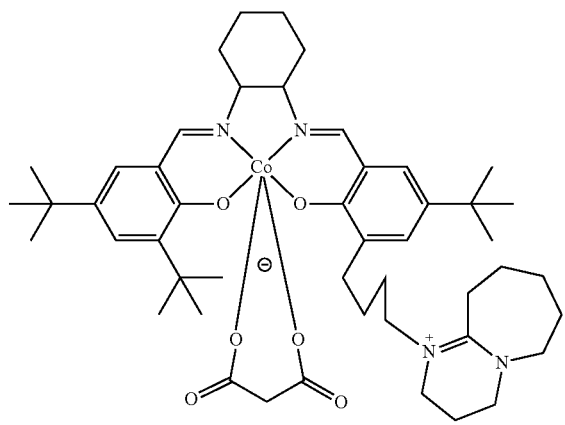

TABLE 1-continued
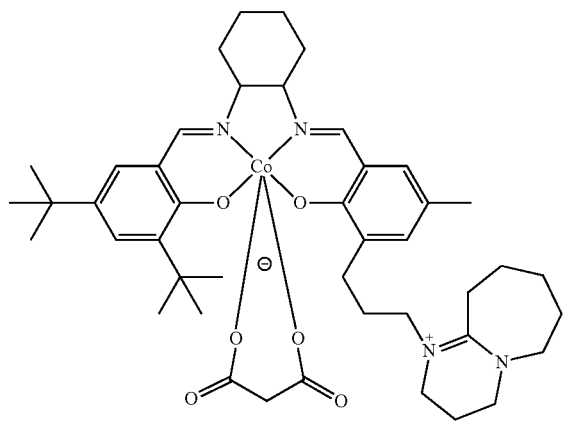
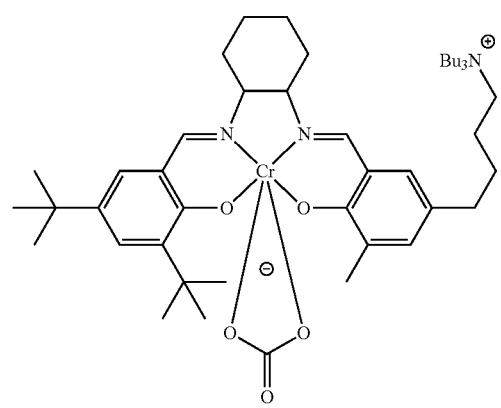
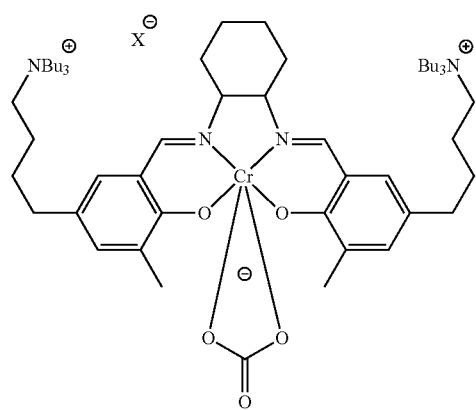

TABLE 1-continued
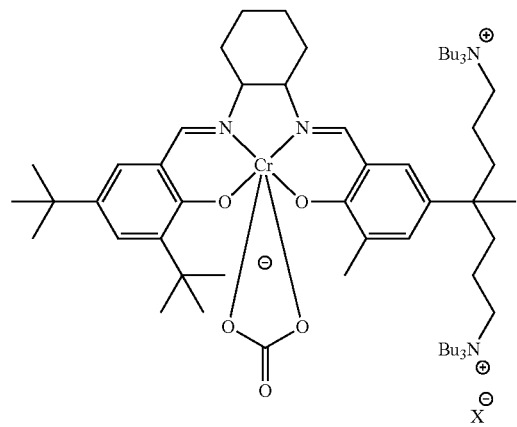
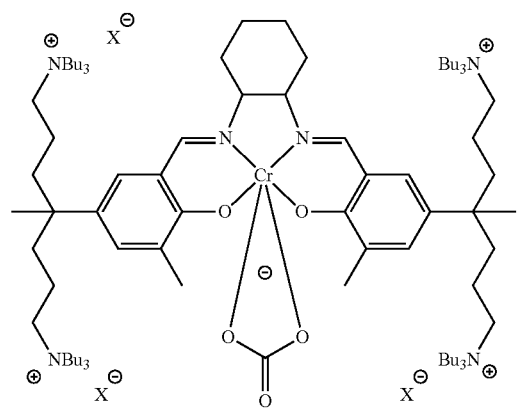
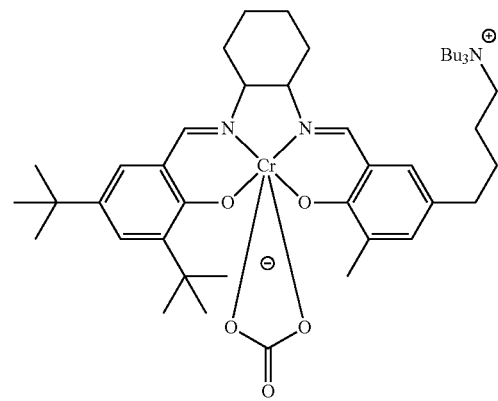
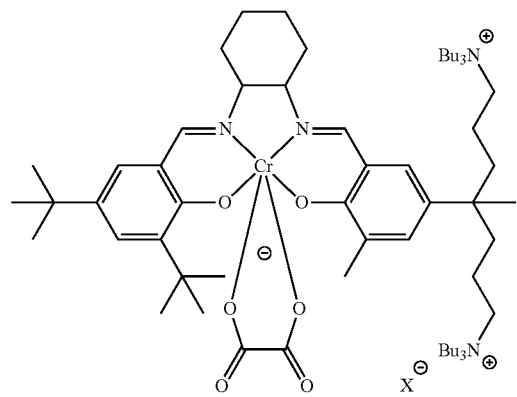

TABLE 1-continued
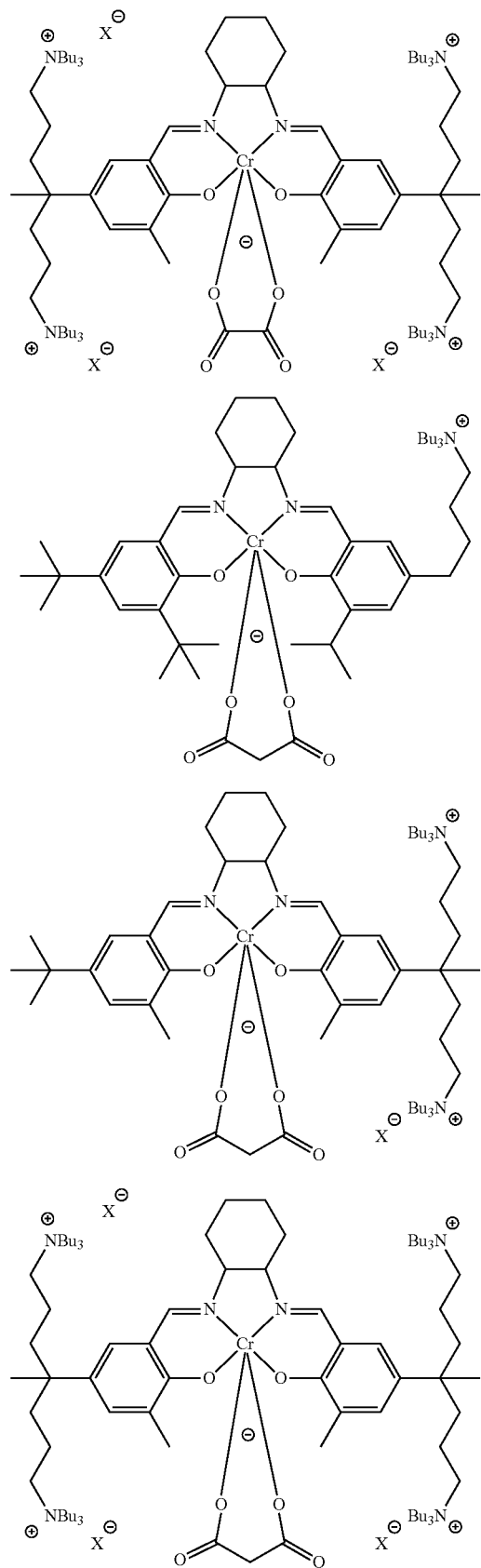

TABLE 1-continued
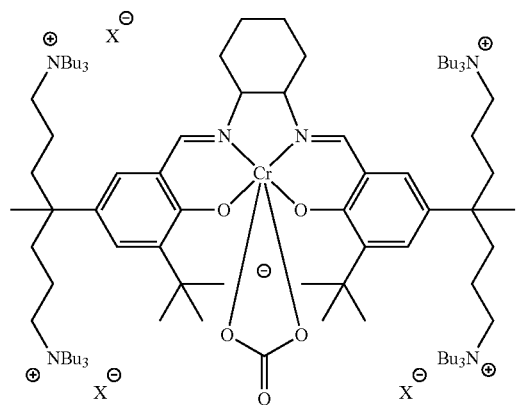
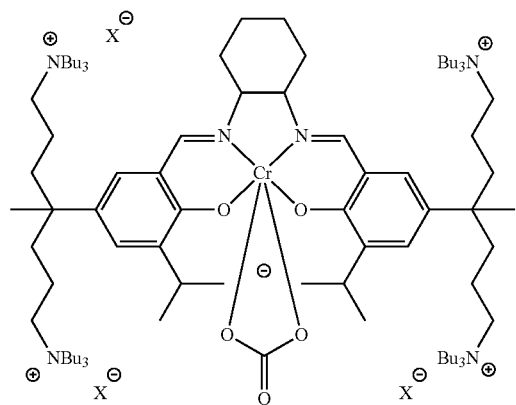
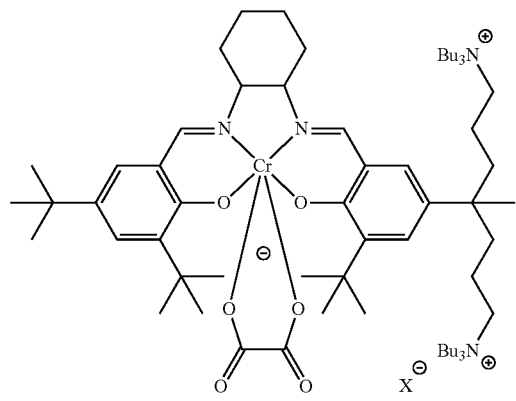
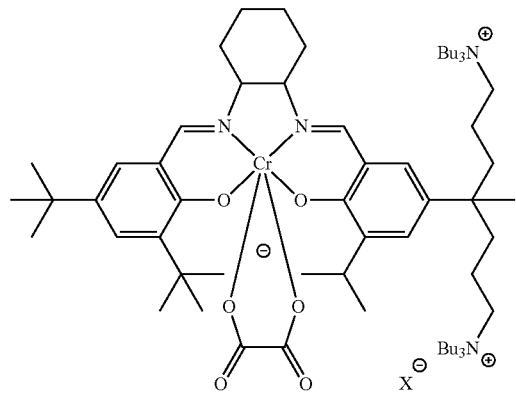

TABLE 1-continued
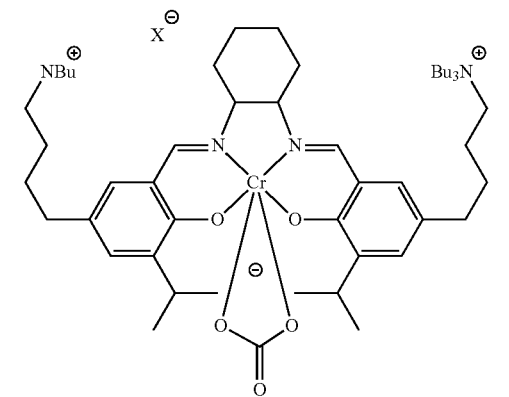
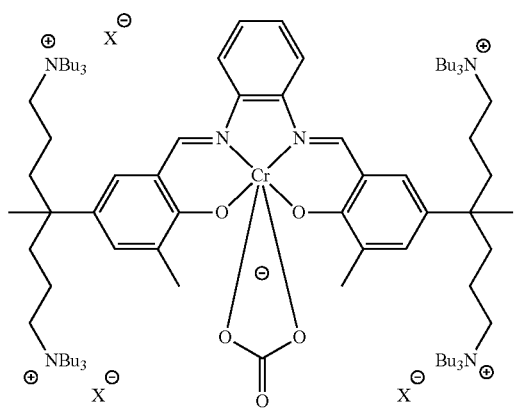
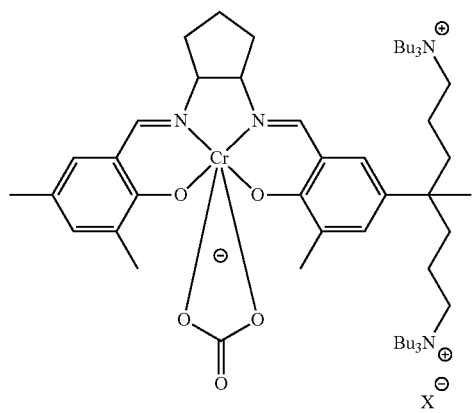
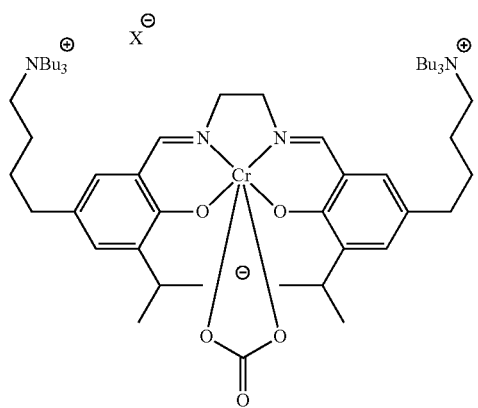

TABLE 1-continued
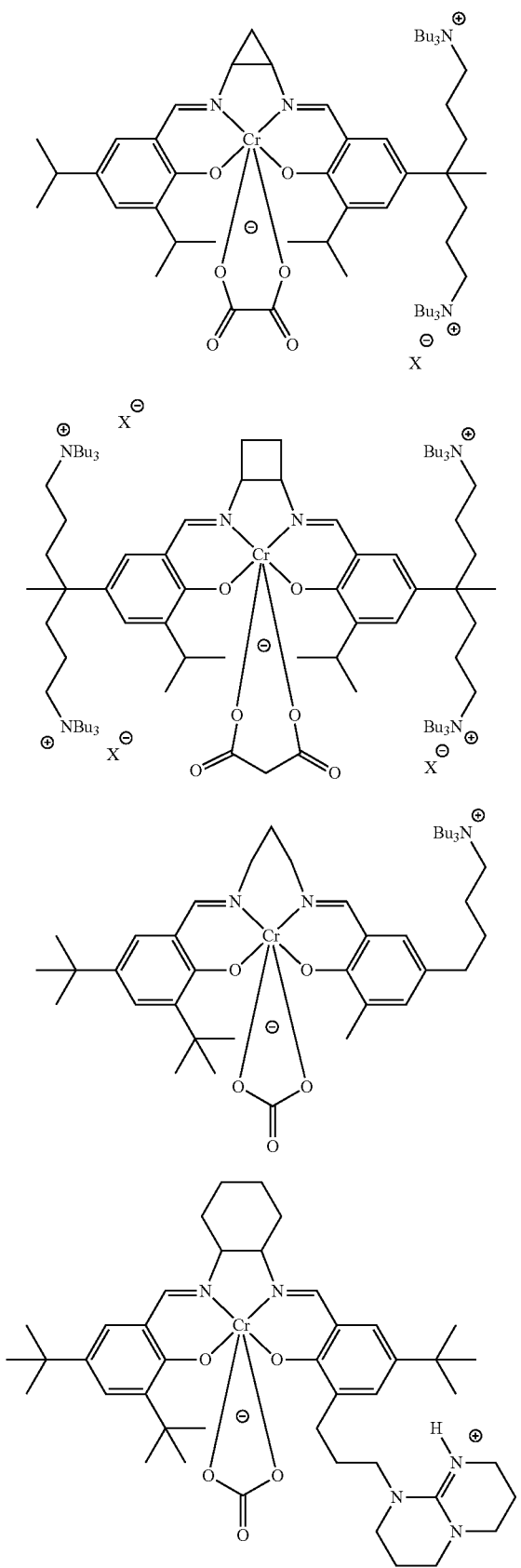

TABLE 1-continued
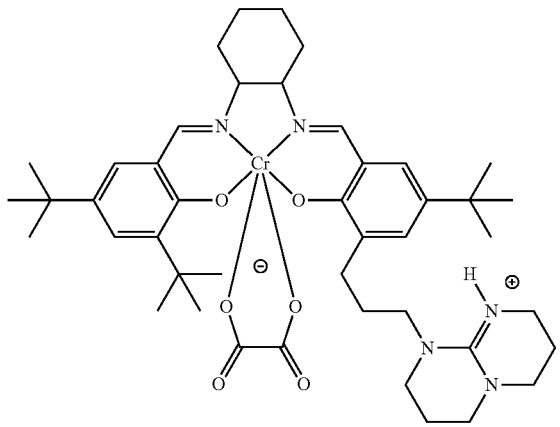
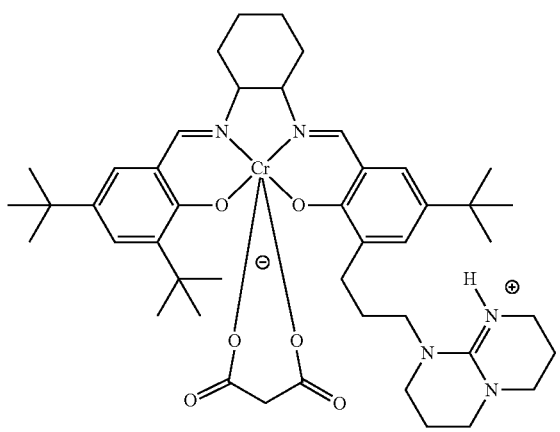
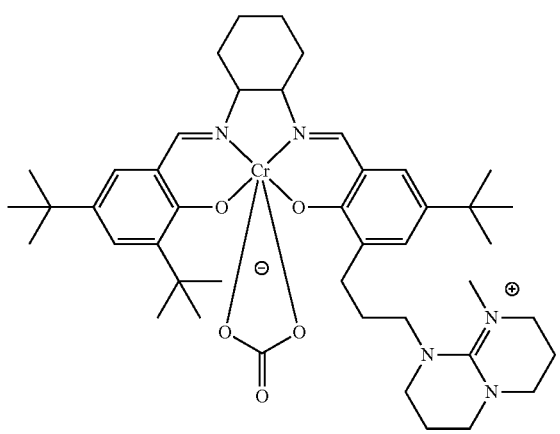

TABLE 1-continued
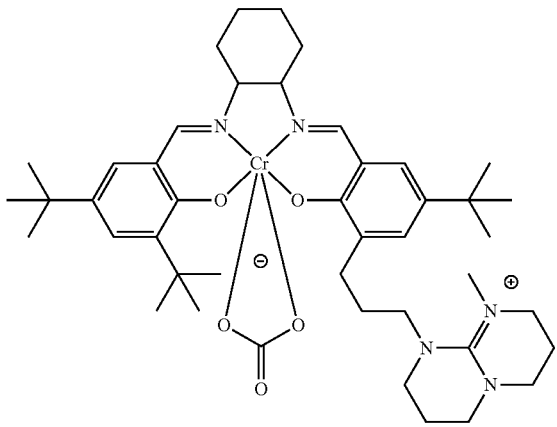
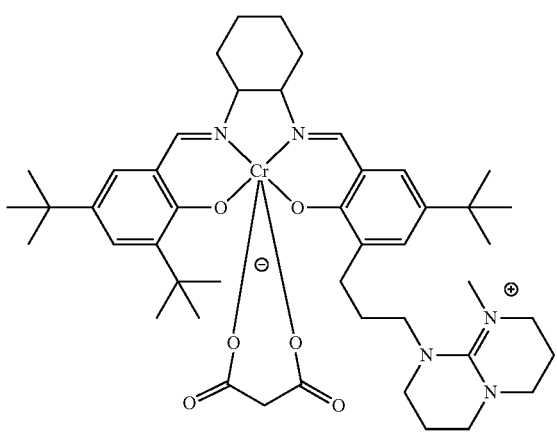
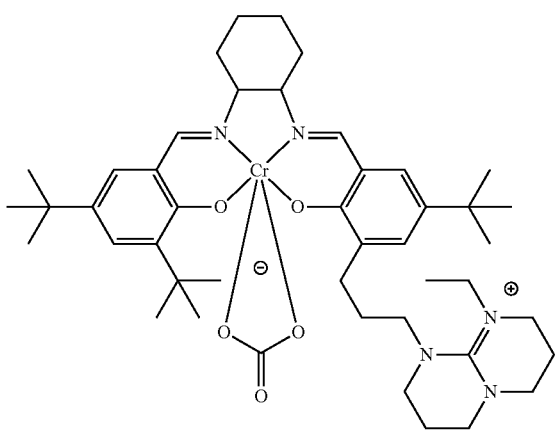

TABLE 1-continued
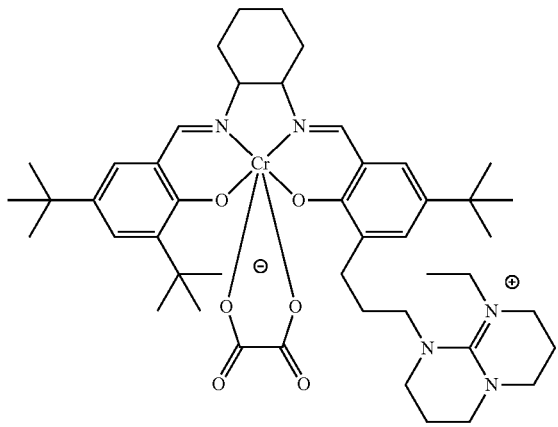
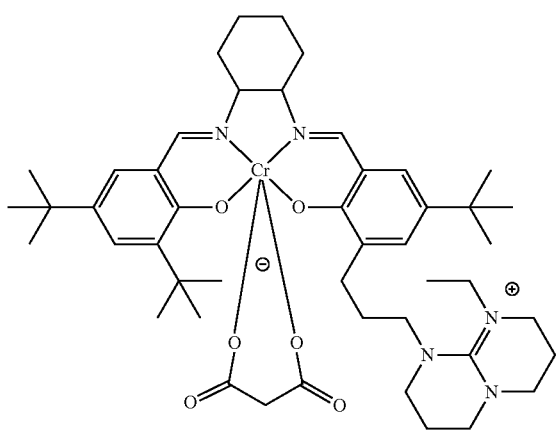
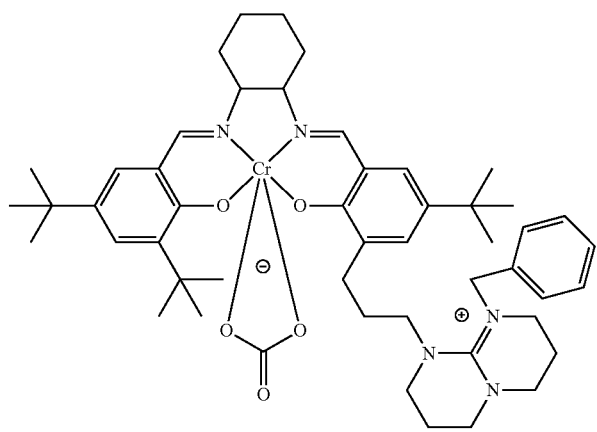

TABLE 1-continued
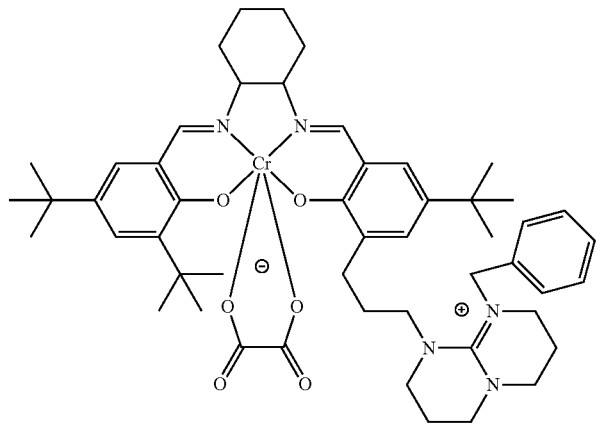
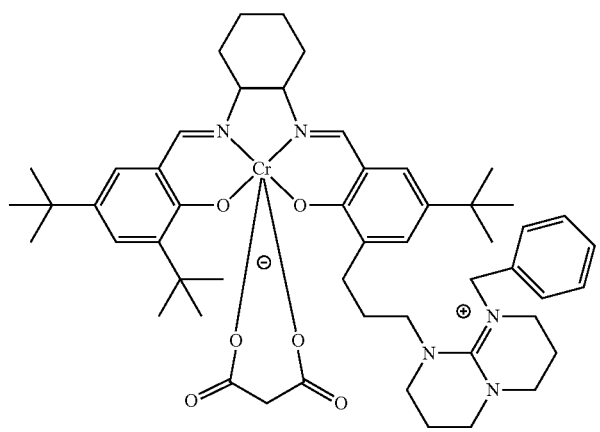
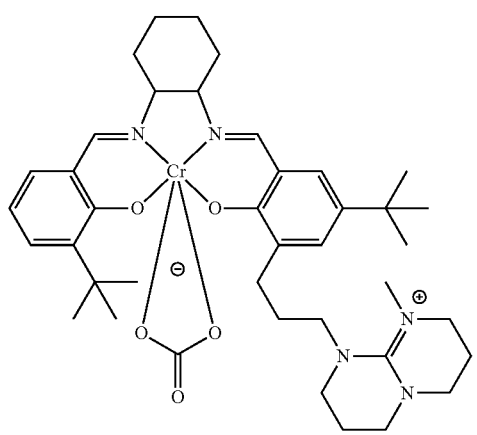

TABLE 1-continued
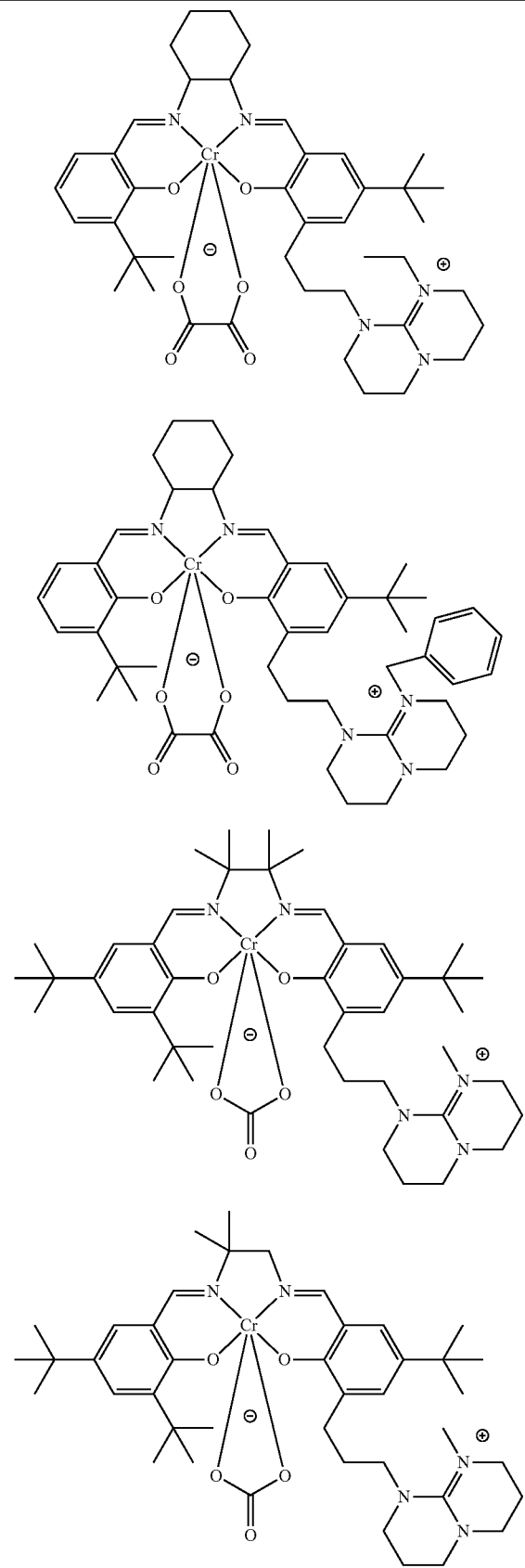

TABLE 1-continued
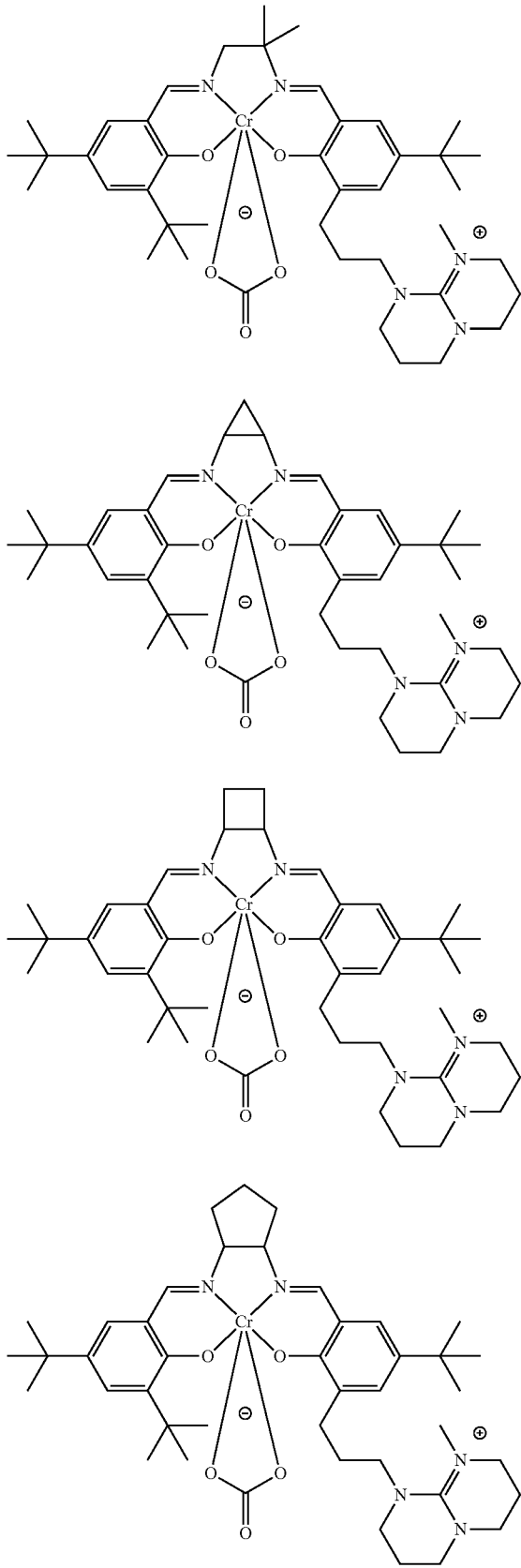

TABLE 1-continued
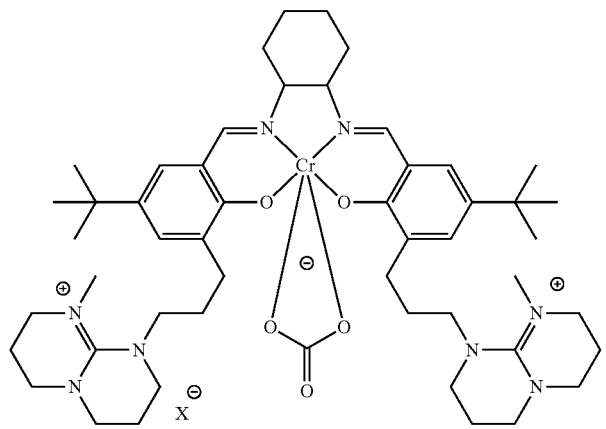
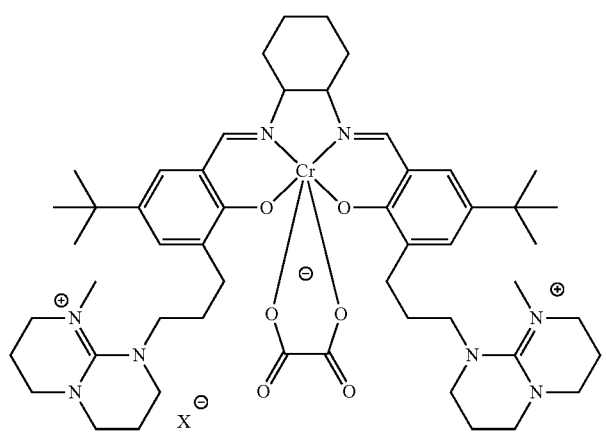
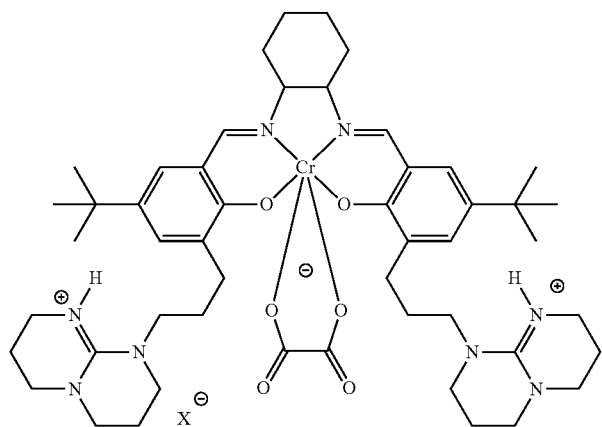

TABLE 1-continued
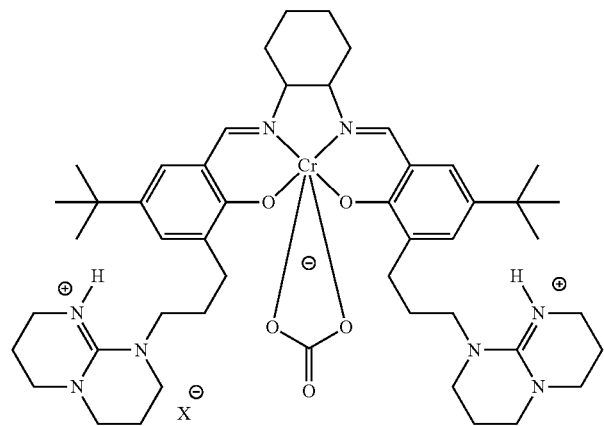
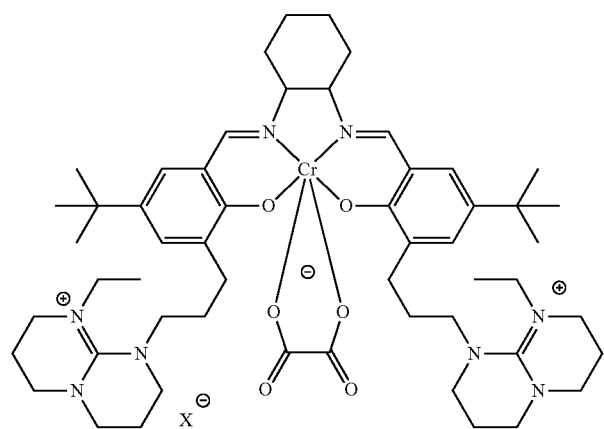
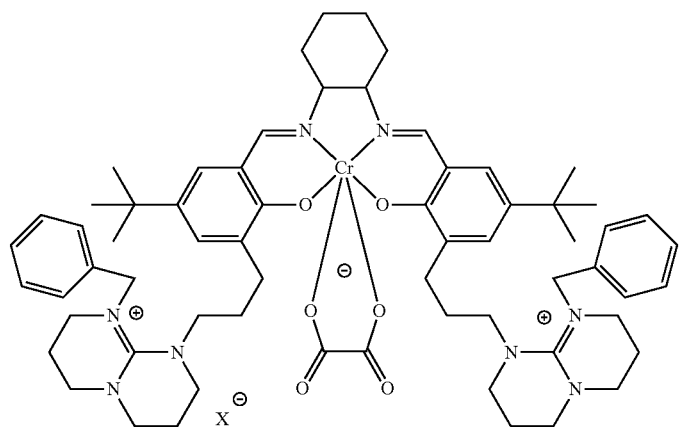

TABLE 1-continued
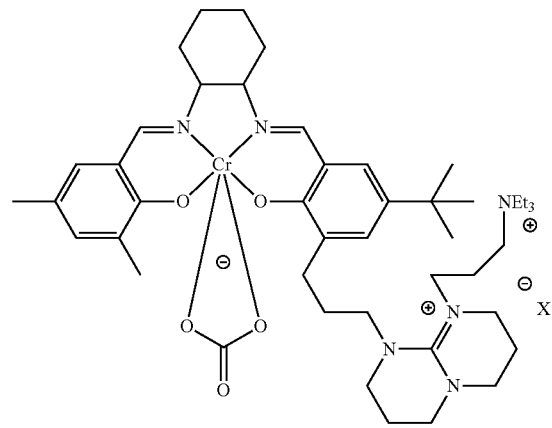
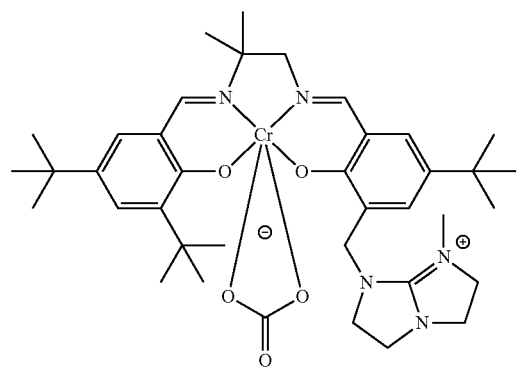
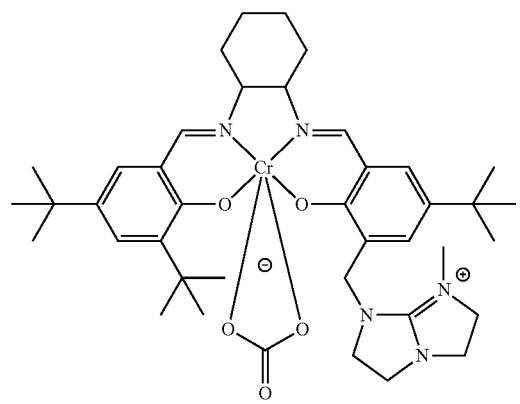
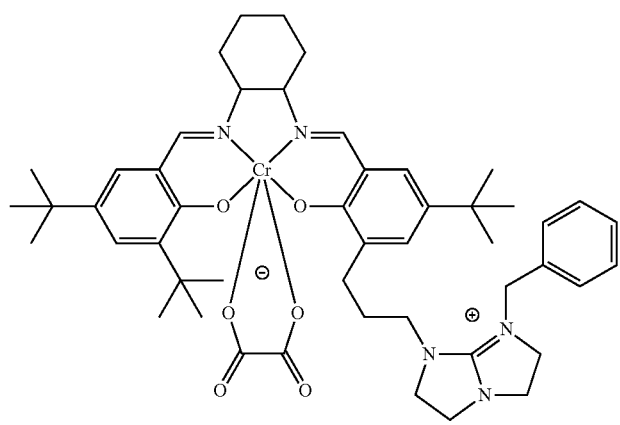

TABLE 1-continued
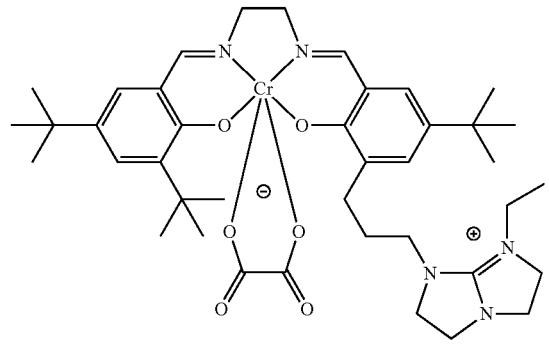
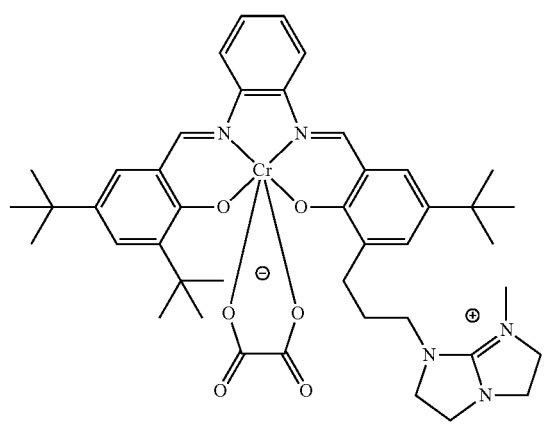
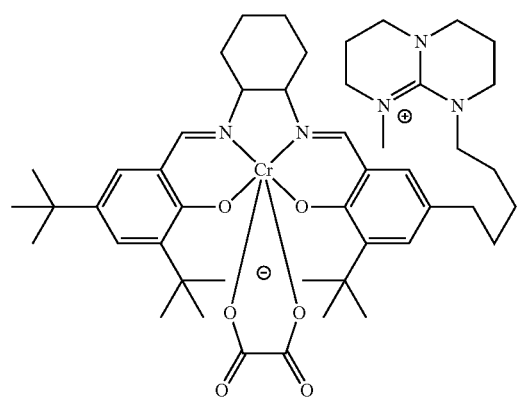
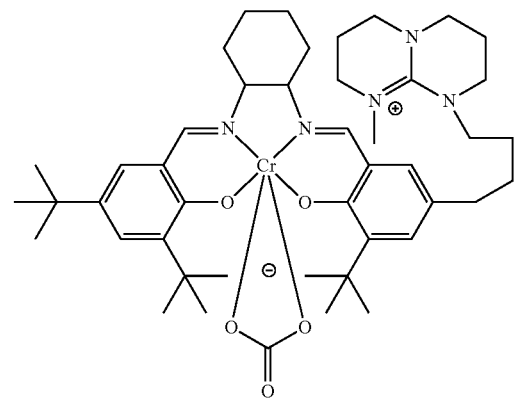

TABLE 1-continued
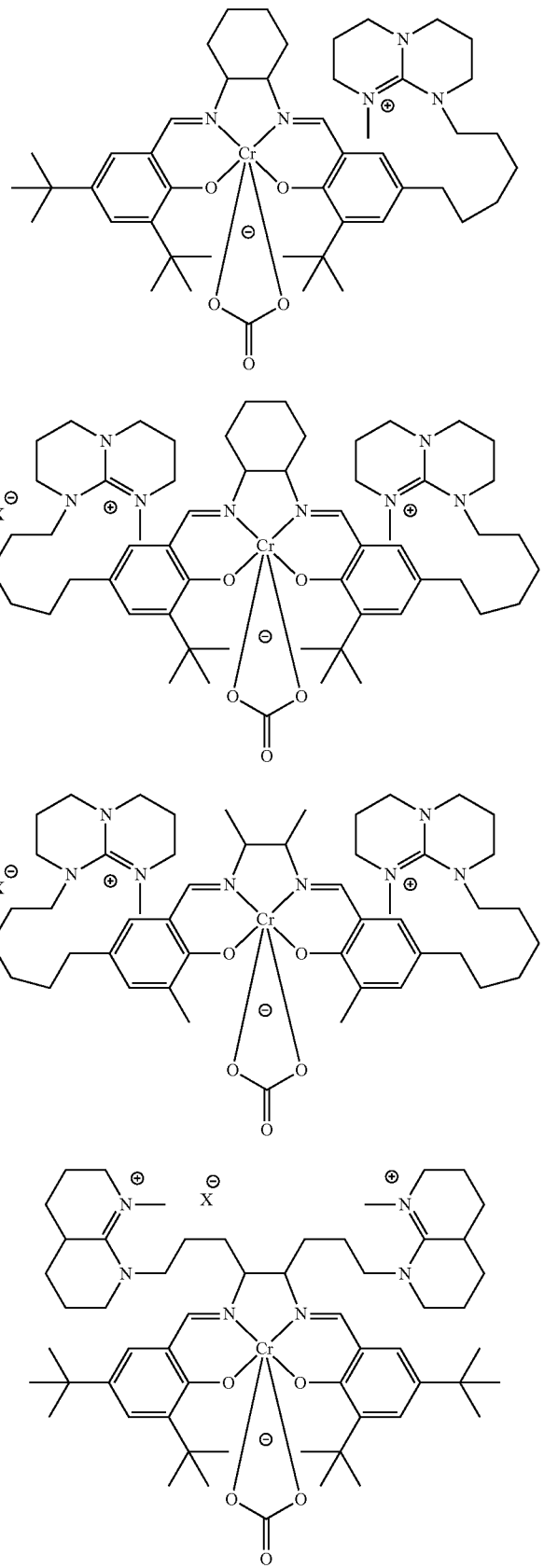

TABLE 1-continued
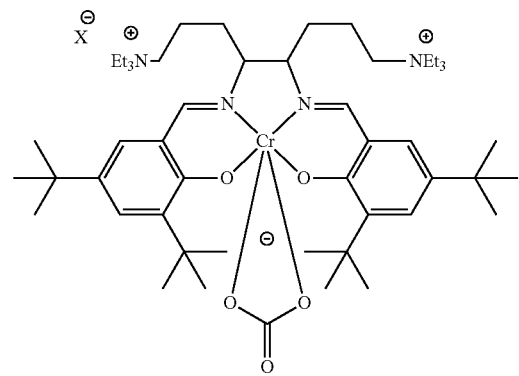
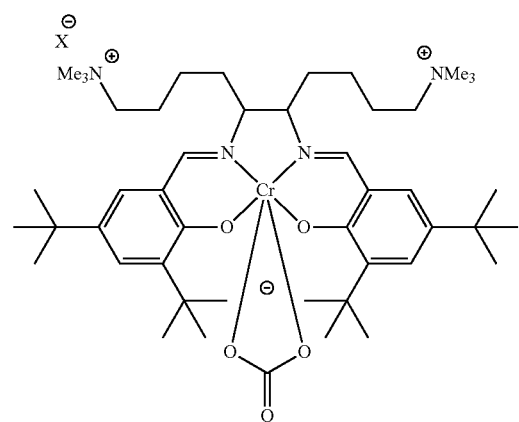
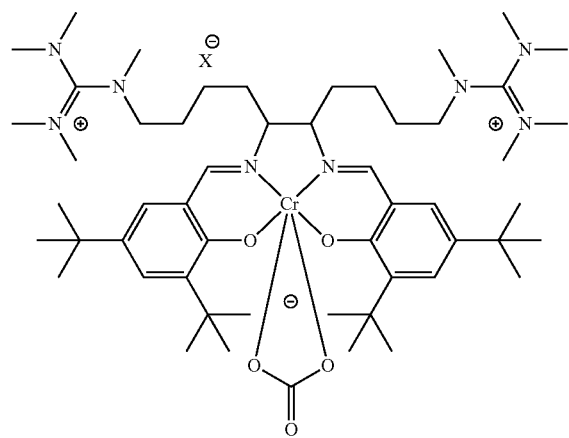

TABLE 1-continued
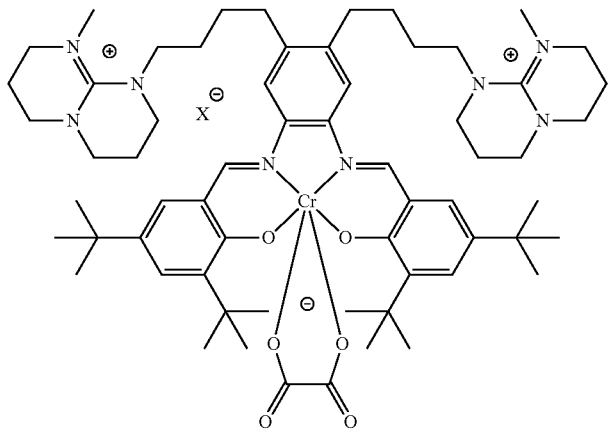
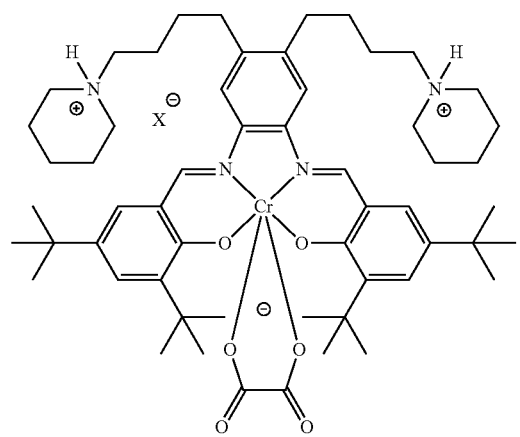
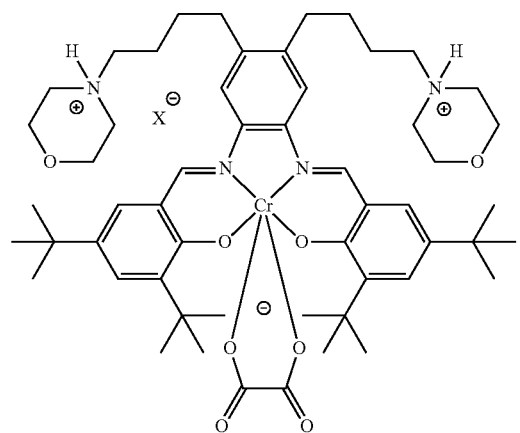

TABLE 1-continued
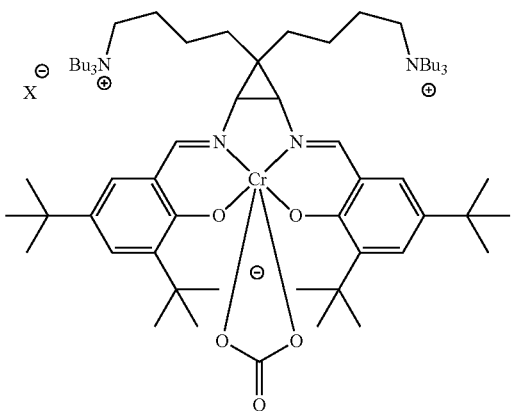
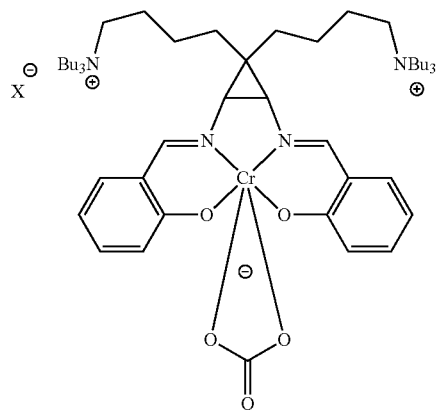
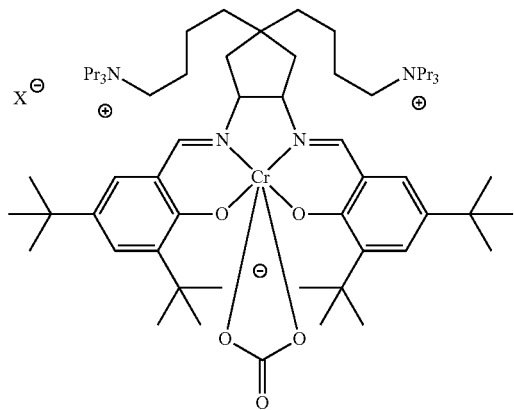
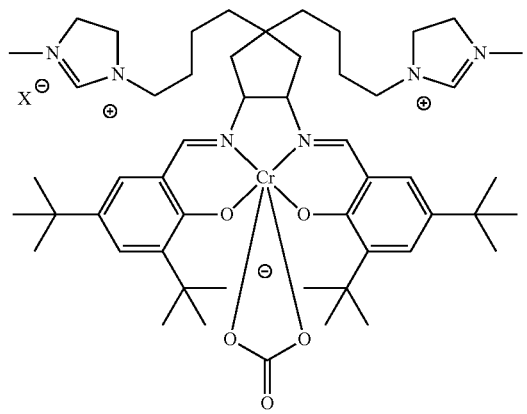

TABLE 1-continued
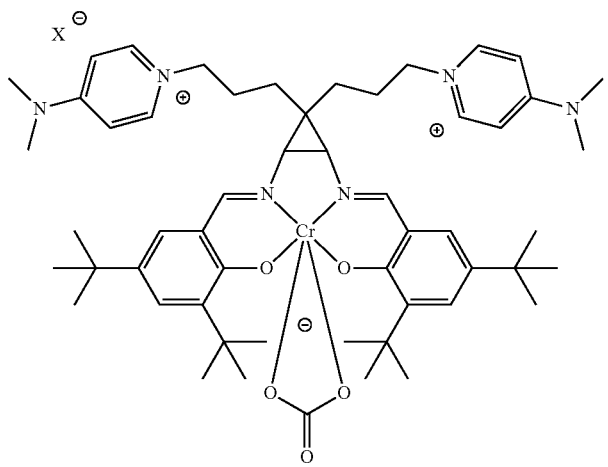
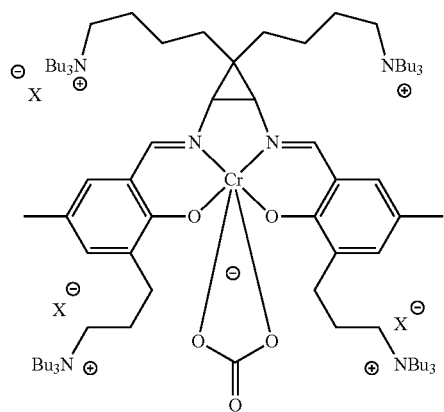
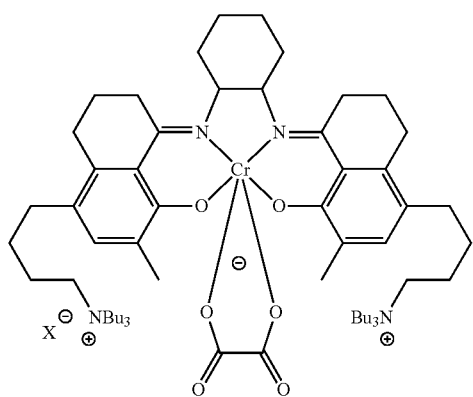

TABLE 1-continued
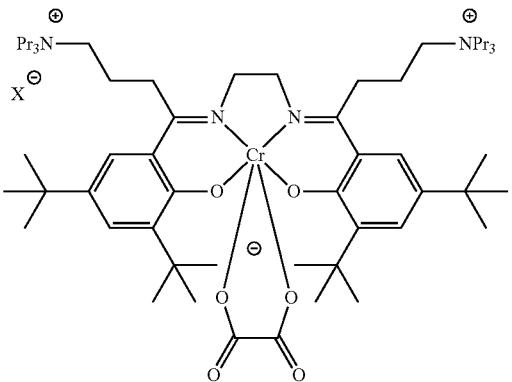
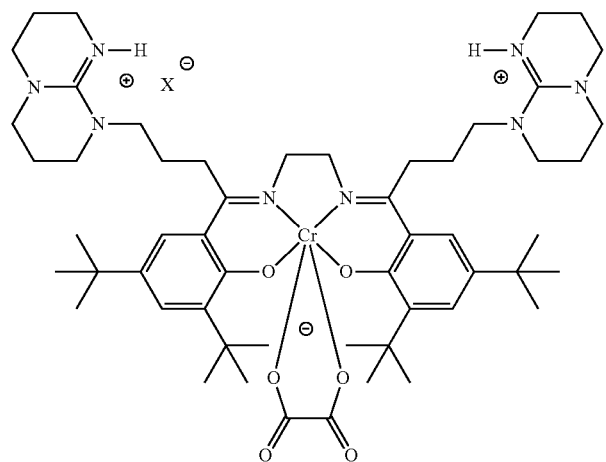
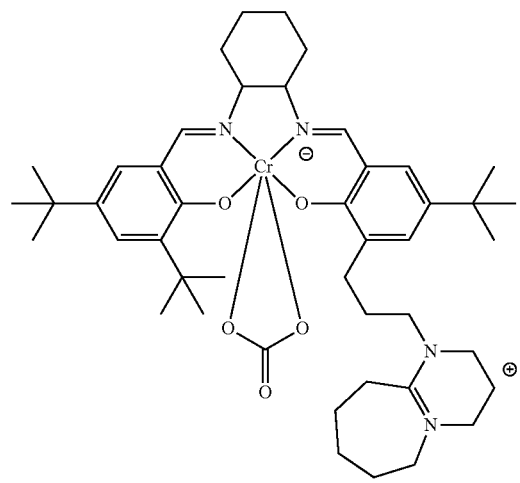

TABLE 1-continued
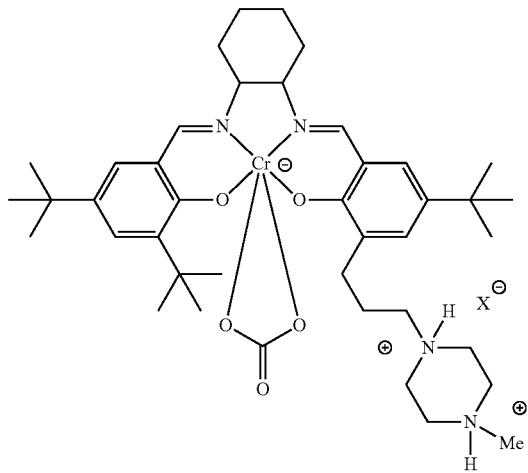
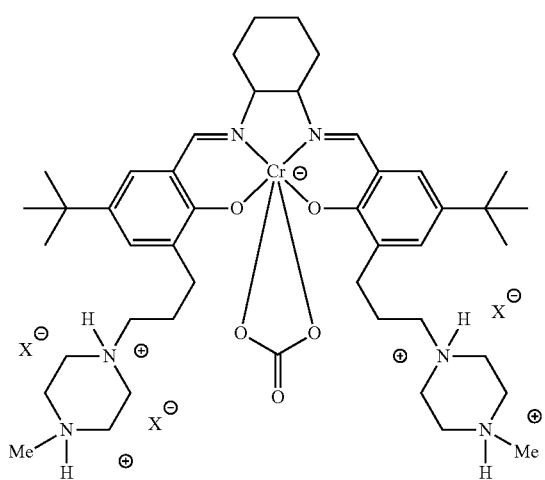
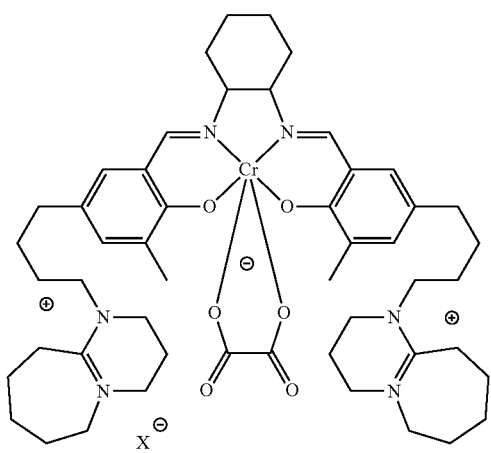

TABLE 1-continued
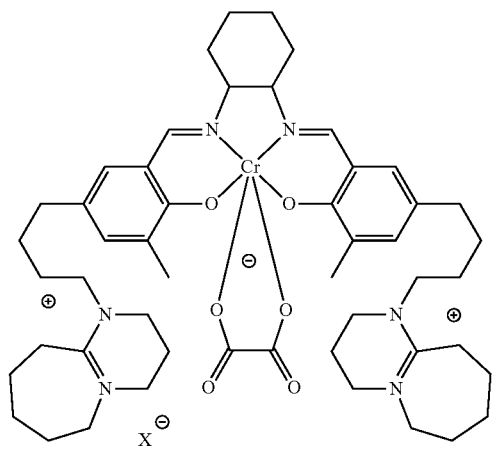
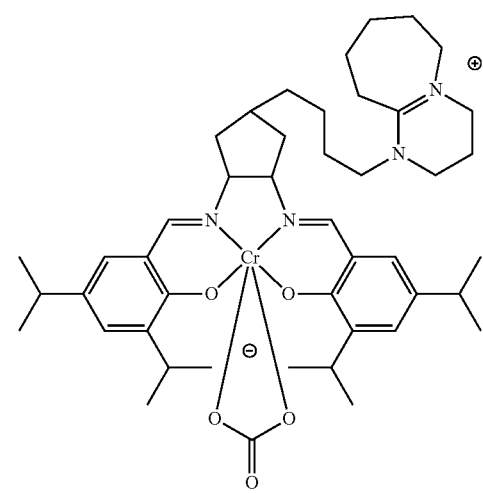
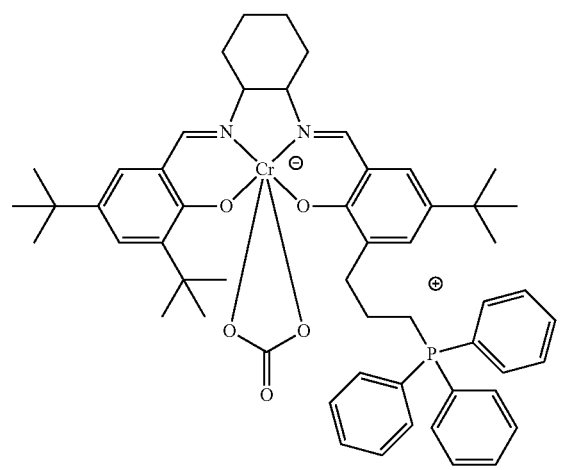

TABLE 1-continued
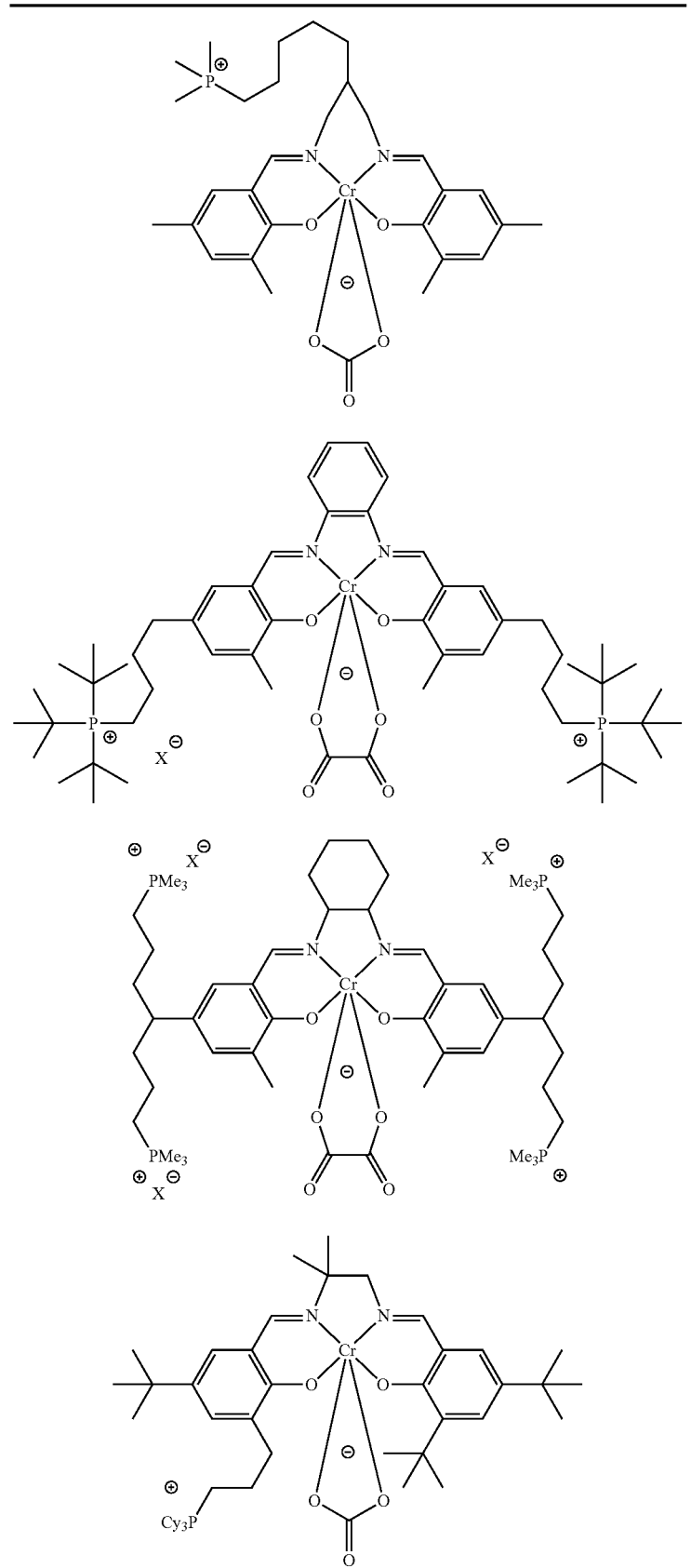

TABLE 1-continued
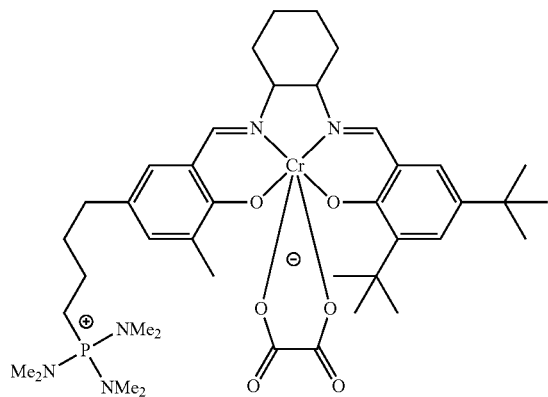
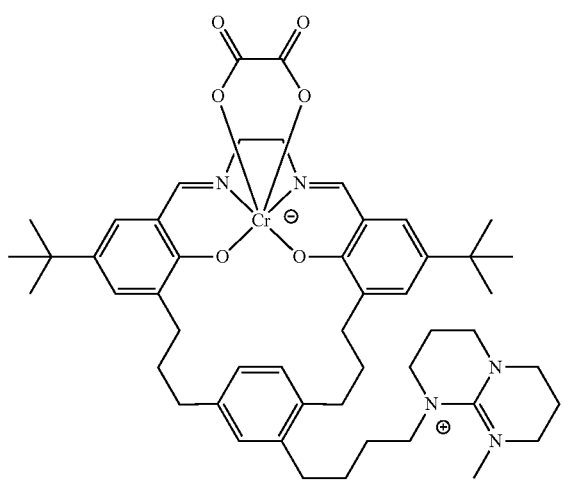
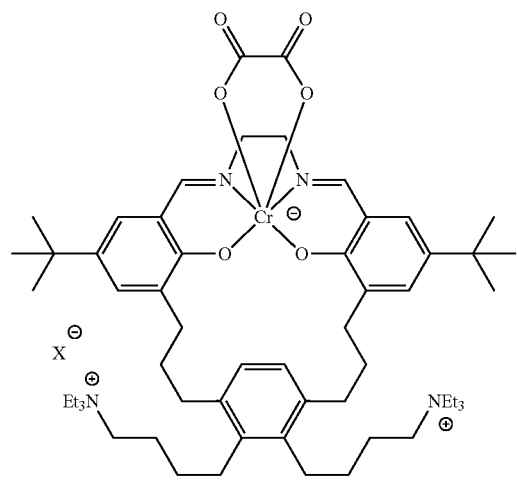

TABLE 1-continued
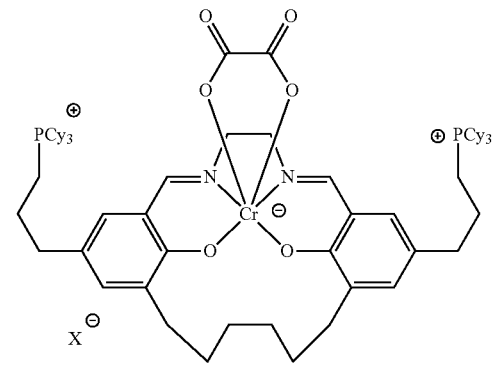
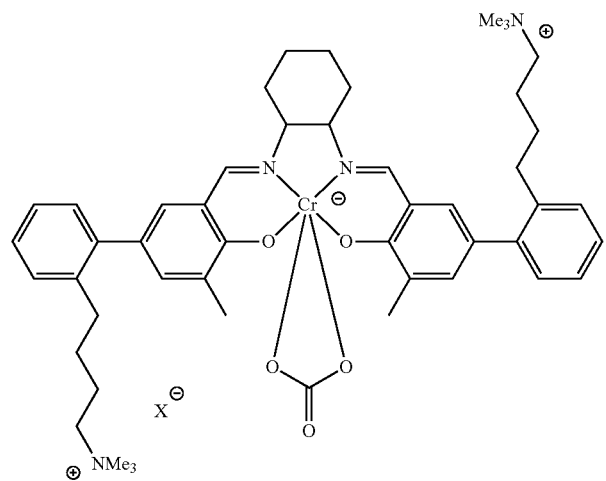
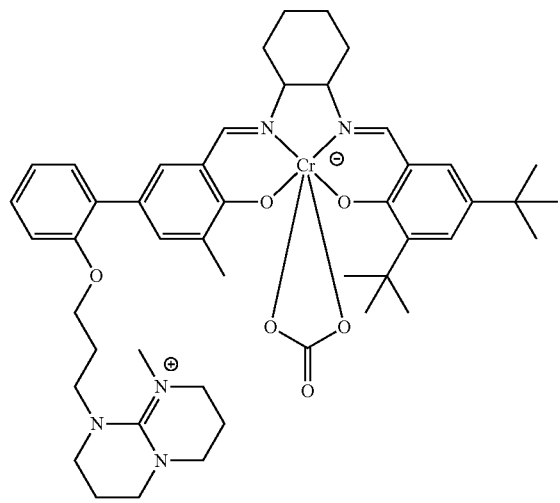

TABLE 1-continued
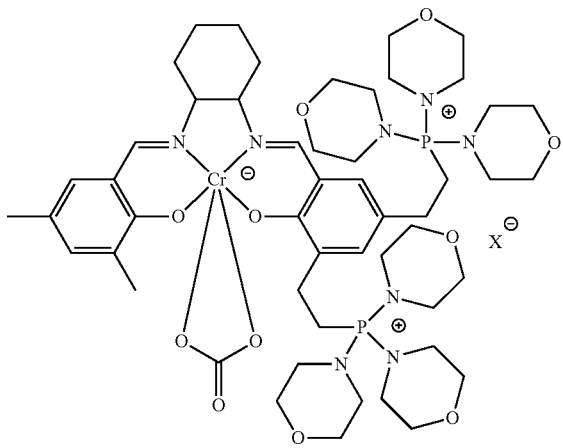
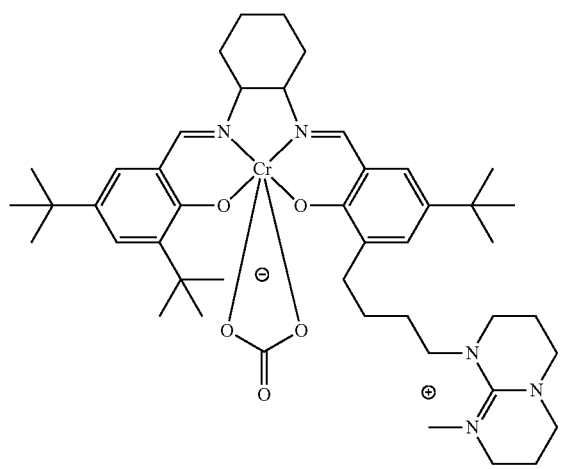
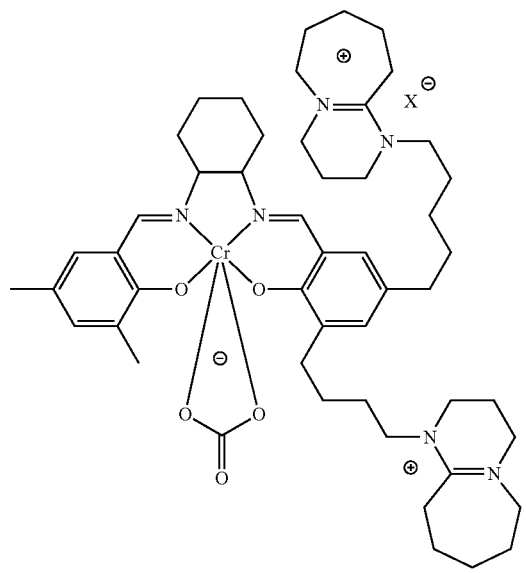

TABLE 1-continued
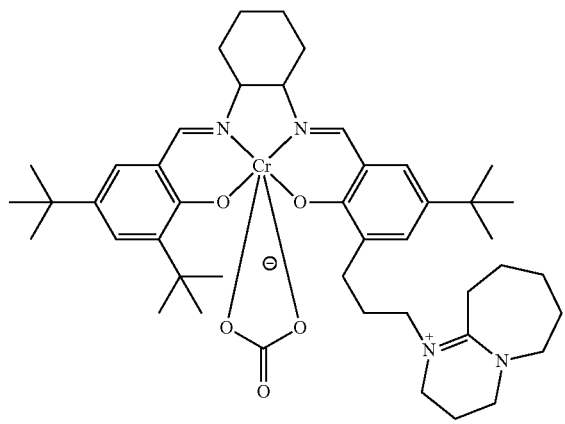
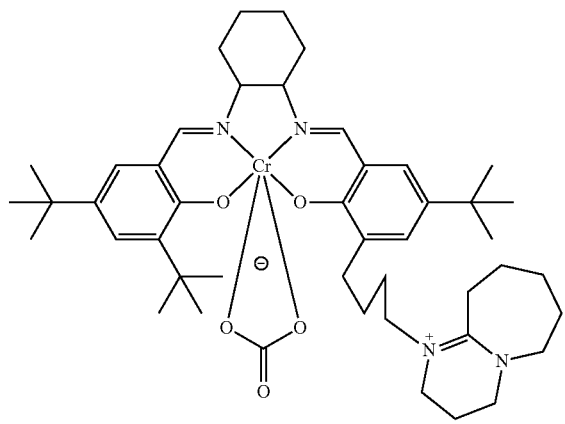
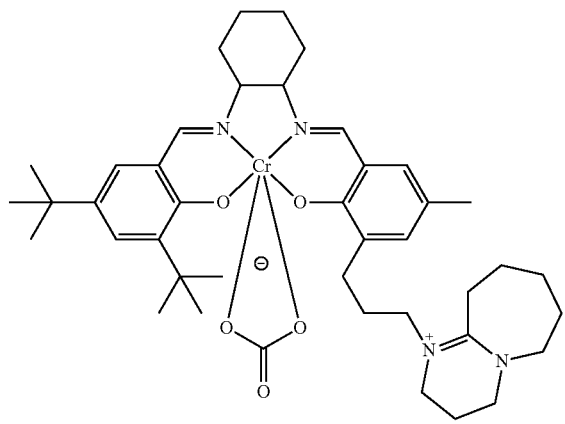
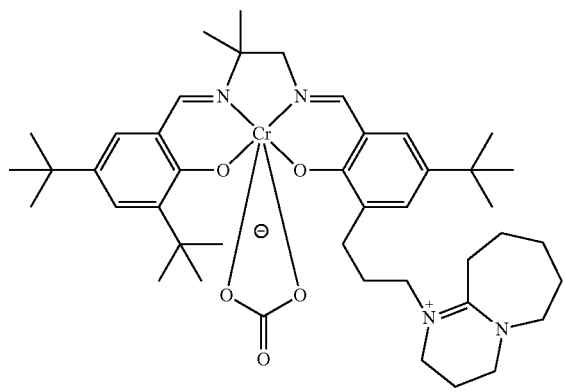

TABLE 1-continued
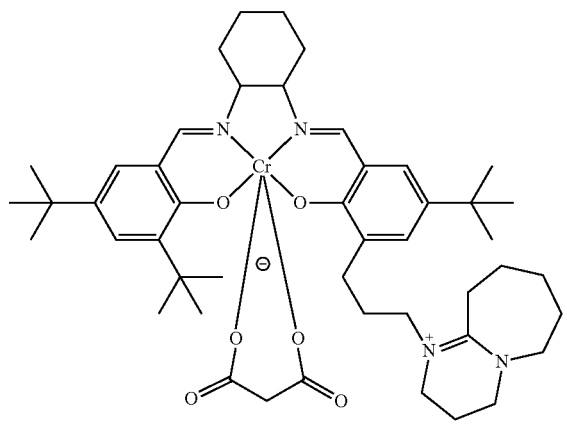
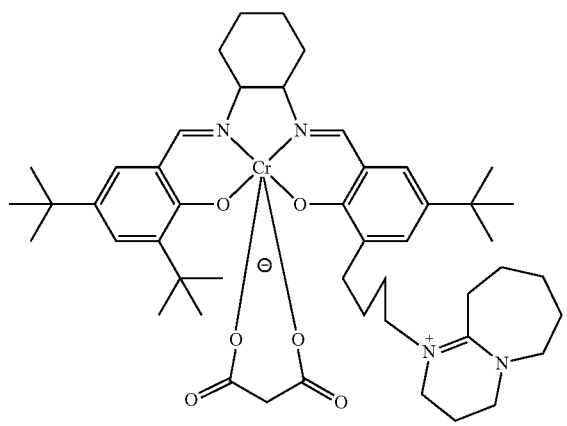
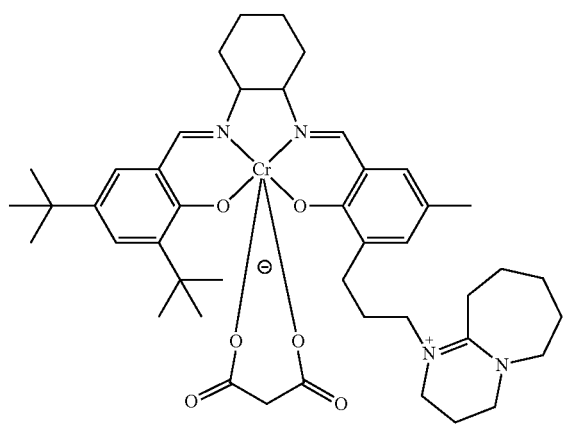

TABLE 1-continued

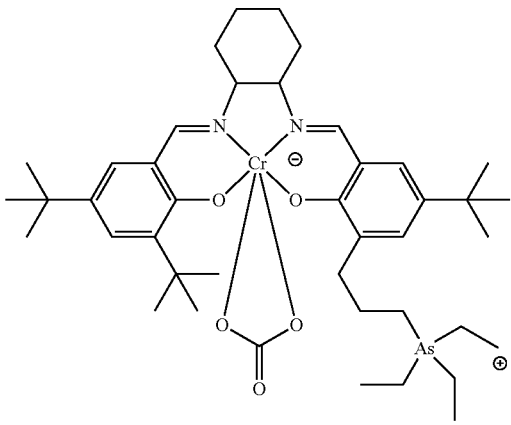

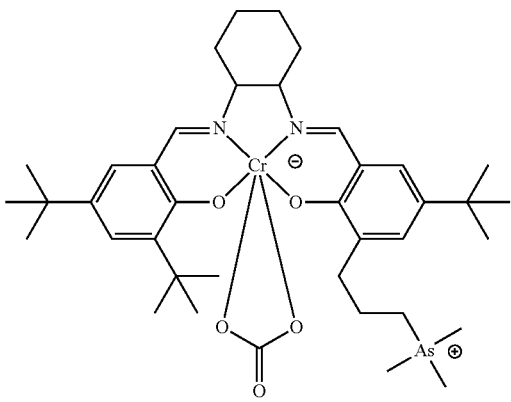

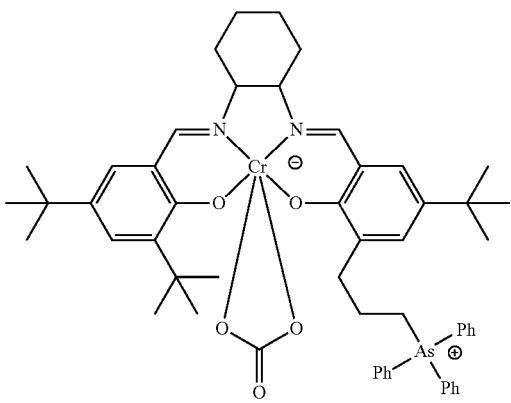

where X⁻ is independently at each occurrence any anion or a portion of any dianion Charge Balances As noted above, the chromium(III) and cobalt(III) salen complexes encompassed by the present invention comprise at least one dianion. In the certain embodiments, both negative charges of the dianion associate with metal atom, leaving it with a net −1 charge. This net charge will need to be balanced by a cation and this may occur in several ways. In certain embodiments described above, there are one or more cationic groups covalently tethered to the salen ligand. In certain embodiments encompassing these examples, the −1 charge on the metal can be balanced by the +1 charge of one of these tethered cations. In other embodiments, the −1 formal charge on the metal atom can be balanced by a cation not covalently bound to the complex, such cations may include any of the multitude known in the art including cationic metals, a proton, onium salts, and the like. Suitable metals include, but are not limited to sodium, lithium, potassium, zinc, magnesium, and transition metals. In certain embodiments, the positive charge necessary to balance the −1 charge, may come from a second molecule of a salen complex bearing a +1 charge on the metal. Such complexes may thus comprise one dianionic anion as described above, and two molecules of a cationic metal complex.

In some embodiments, particularly where there is another metal atom present, or where there are two or more cationic species covalently tethered to the salen ligand, the complex may comprise a number of additional cations or anions as required to provide an overall neutral molecule. For example, where there are two or more cationic species tethered to the ligand, one may serve to offset the −1 charge present on the chromium or cobalt atom associated with the dianion, while the other tethered cations may be associated with other anions. Likewise, as described above, in certain embodiments, there may be an additional metal atom present (to balance the formal −1 charge on the chromium or cobalt atom, for example). In cases where the additional metal has a 2+ (or higher) charge, additional anions may also be present to balance the charge(s) and provide a neutral compound. These other anions may comprise additional equivalents of the dianic species described herein, or they may be other anions unrelated to the dianion on the metal center. Examples of other anions that may be associated under such circumstances include halide, nitrate, tetrafluoroborate, carboxylate, phenolate, azide, and the like.

It is thus to be understood that while not explicitly shown in every structure or example, it is implied that the complexes described herein will be, in their isolated form, neutral compounds and that any number of additional ions (whether shown or not) may be present to balance charges shown or described in the complexes herein. For example, if a salen ligand is of formula Ia-6 and each $(Z)_m$ moiety comprises one quaternary ammonium salt, the net charge of the complex (denoted δ in the formula) will be 3+, the accounting that leads to this includes the net +1 charge on the metal atom, the 2− charge of the dianion —O—$R^J$—O—, and four +1 charges for the four ammonium salts. There must be anions present to balance these 3 cations, and as described above, these may be provided by additional dianionic groups, or by other anions such as halide, carboxylate and the like. If the +3 charge is balanced by the dianions, it may arise that an excess charge from more than one chromium salen complex is balanced by the same dianion—for example, two chromium(III) or cobalt(III) complexes each having four tethered cations might form a complex with 5 dianions —O—$R^J$—O—, to form a neutral complex.

Catalyst Purification Methods

In certain embodiments, a salen complex of Formula I having a dianionic counterion has the unexpected advantage of being easily isolated from solution by precipitation (or crystallization). Therefore, in another aspect, the present invention provides useful methods for the purification of cobalt salen or chromium salen complexes. In certain embodiments the methods comprise a step of converting a cobalt or chromium complex having one or more monoanioic counterions to a corresponding complex having one or more dianionic counterions. In certain embodiments, the methods comprise the additional step of isolating the complex comprising one or more dianionic counterions as a solid. In certain embodiments, the isolating step includes a substep of precipitating the metal complex from a solution. In certain embodiments, the precipitating step includes a substep of adding additional solvents to the solution. In certain embodiments, the precipitating step includes a substep of stripping a portion of the solvent from the solution. In certain embodiments, the precipitating step includes one or more substeps selected from the group consisting of: cooling, heating, or stirring the solution.

In certain embodiments, the solution from which the complex having one or more dianionic counterions is precipitated comprises one or more alcohols. In certain embodiments, the method comprises the step of precipitating the complex from a suitable alcohol solvent by addition of a suitable ether and/or ester. Suitable alcohol solvents are known to the skilled artisan and include, without limitation, $C_{1-4}$ alcohols. In some embodiments, a suitable alcohol is selected from MeOH, EtOH, iPrOH, nPrOH, nBuOH, sec-BuOH, t-BuOH and mixtures of any two or more of these. Suitable ethers are known to the skilled artisan and include, without limitation, diethyl ether, MTBE, THF, methyl cyclopentyl ether, diisopropyl ether, di-n-butyl ether, 1,4-dioxane, higher weight ethers, and mixtures of any two or more of these. Suitable esters are also known to the skilled artisan and include, without limitation, methyl acetate, ethyl acetate, isopropyl acetate, n-propyl acetate, n-butyl acetate, ethyl propionate, higher weight esters, and mixtures of any two or more of these.

In certain embodiments, a salen complex of Formula I with a dianionic counterion is precipitated from a mixture of a suitable alcohol solvent and a suitable alkyl ester solvent in any relative proportion by addition of a suitable ether or more ester solvent. Suitable alcohol solvents are known to the skilled artisan and include, without limitation, $C_{1-4}$ alcohols. In some embodiments, a suitable alcohol is selected MeOH, EtOH, iPrOH, nPrOH, nBuOH, sec-BuOH, t-BuOH and mixtures of any two or more of these. Suitable alkyl esters are known to the skilled artisan and include, without limitation, MeOAc, EtOAc, iPrOAc, nPrOAc, nBuOAc, sec-BuOAc, and mixtures of any two or more of these. Suitable ethers are known to the skilled artisan and include, without limitation, ether, MTBE, THF, methyl cyclopentyl ether, diisopropyl ether, di-n-butyl ether, 1,4-dioxane, higher weight ethers, and mixtures of any two or more of these.

In certain embodiments, a salen complex of Formula I with a dianionic counterion is precipitated from a mixture of a suitable alcohol solvent and toluene in any relative proportion by addition of a suitable ether. Suitable alcohol solvents are known to the skilled artisan and include, without limitation, $C_{1-4}$ alcohols. In some embodiments, a suitable alcohol is selected from MeOH, EtOH, iPrOH, nPrOH, nBuOH, and sec-BuOH. Suitable ethers are known to the skilled artisan and include, without limitation, MTBE, THF, methyl cyclopentyl ether, diisopropyl ether, di-n-butyl ether, 1,4-dioxane, and higher weight ethers.

In certain embodiments of compounds of Formula I, the precipitated metal salen catalyst with a dianionic counterion obtained by filtration is characterized in that it is green in color.

In certain embodiments of compounds of Formula I, the precipitated salen catalyst with dianionic counterion obtained by filtration has an absorption spectrum in the range of 195-700 nm with four maxima ($\lambda_{max}$). In some embodiments, ranges for the maxima are 195-205 nm ($\lambda_{max1}$), 225-245 nm ($\lambda_{max2}$), 255-270 nm ($\lambda_{max3}$), and 390-425 nm ($\lambda_{max4}$).

Polymer Compositions

One of the advantages of metal complex catalysts for epoxide $CO_2$ copolymerization (i.e. as opposed to hetergenous zinc-based catalysts or double metal cyanide catalysts) is that they provide polymers with a high percentage of carbonate linkages (i.e. few ether linkages) and narrow molecular weight distributions. However, it is well known in the art while that, even though the resulting polymers have narrow molecular weight distributions, the polymers invariably have a bimodal molecular weight distribution. It is also understood why this is so. The first step in epoxide $CO_2$ copolymerization with this class of catalysts consists of epoxide ring-opening by the anion associated with the metal atom of the catalytic complex. This anion is commonly referred to as a polymerization initiator. During polymerization the initiator opens an epoxide and is thereby covalently bound to the end of the polymer chain which then grows from the oxygen atom of the ring-opened epoxide, propagation continues in one direction to yield the final polymer chain.

It is also known that chain transfer agents can be added to epoxide $CO_2$ copolymerizations and that their presence results in the formation of more than one polymer chain per catalyst molecule with a corresponding decrease in the average molecular weight of the polymer chains formed. Chain transfer agents with more than one nucleophilic site result in polymer chains that propagate in two or more directions and which therefore gain molecular weight at a higher rate than the chains initiated with a monoanion. Since these are living polymerizations and water is can act as a chain transfer agent, the polymers contain a population of chains initiated by water which grow at approximately twice the rate of chains initiated by anions from the catalytic complexes. Without being bound by theory, or thereby limiting the scope of this invention, it is believed the the bimodal characteristics prior art aliphatic polycarbonate polymer compositions are explained by a mechanism such as that shown in Scheme 1 which depicts the copolymerization of propylene oxide and $CO_2$ by with a prior art catalyst having a mono-anionic initiator (acetate):

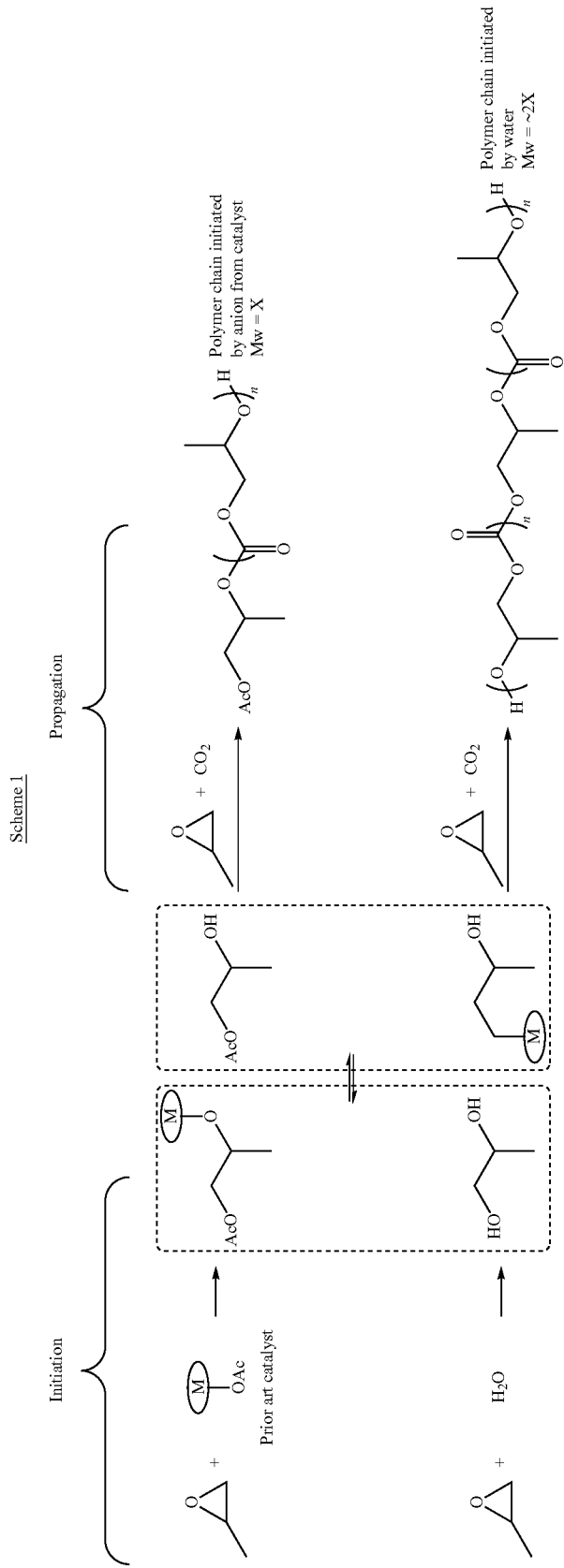

Figure 8A:
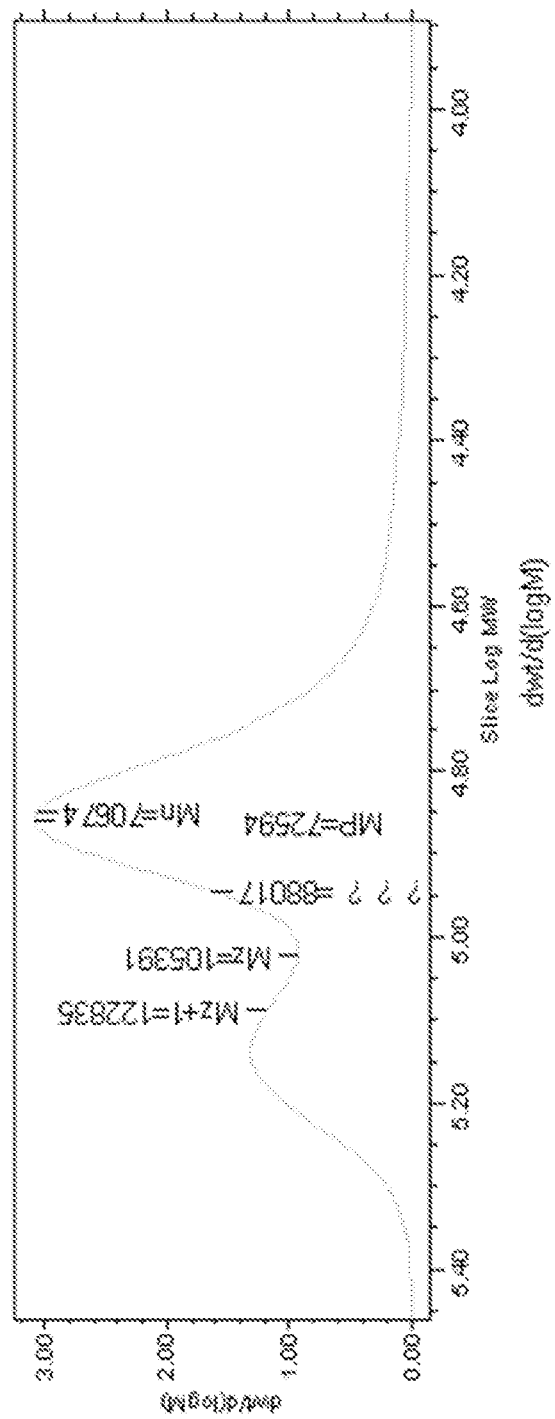
FIG. 8a-c shows GPC traces of prior art aliphatic polycarbonates (APCs).
Figure 8B:
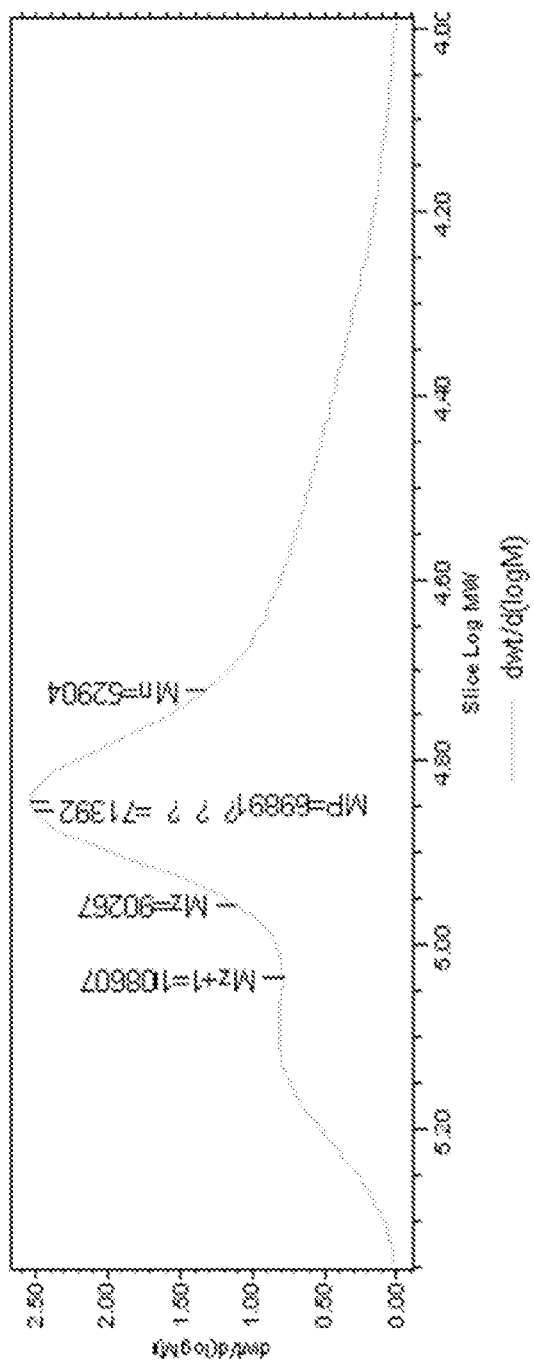
Figure 8C:
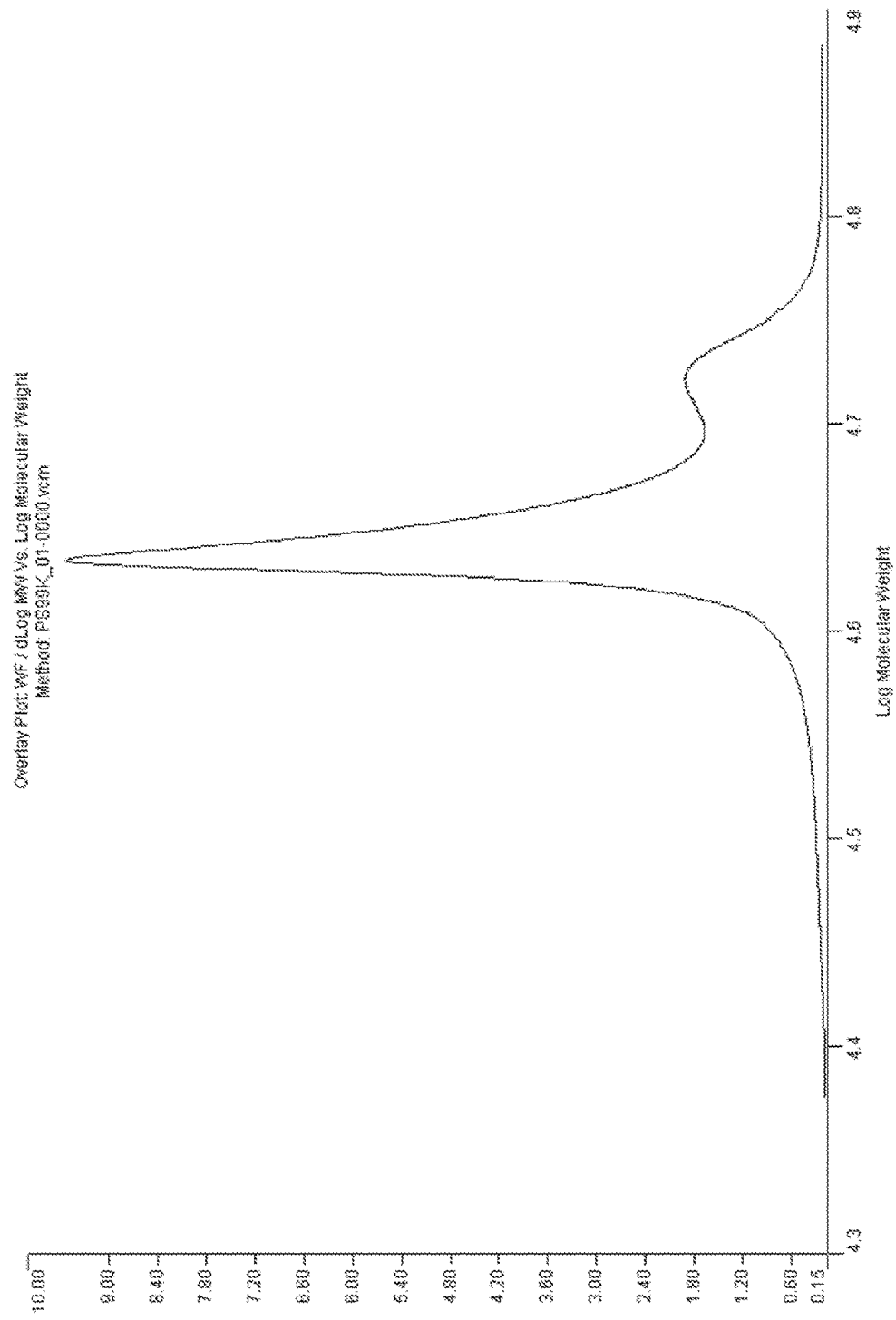

Since it is impossible to completely exclude water from epoxide $CO_2$ polymerization mixtures, the prior art aliphatic polycarbonates have had bimodal molecular weight distributions. For representative examples see for example (J. AM. CHEM. SOC. 2007, 129, 8082-8083, and supporting info.; and *Macromolecules,* 2010, 43 (3), pp 1396-1402 and supporting info) and the GPC traces of prior art polymers shown FIGS. 8a-8c. The GPC traces in FIGS. 8a and 8b show PPC made with a catalyst having multiple dinitrophenolate initiators. The polymers show the bimodality typical of this class of polymer and two molecular weight populations are clearly discernable in each chromatogram. The GPC trace in FIG. 8c shows PCHC (poly (cyclohexane carbonate) made with a similar catalyst. Again, the polymer is exhibits bimodality in its molecular weight distribution.

During epoxide $CO_2$ copolymerizations, water is invariably present in the reaction mixtures and it has therefore been impossible to obtain truly unimodal aliphatic polycarbonates using this class of catalyst. This is particularly true for high molecular weight polymers where the catalyst must be provided in a very small molar ratio relative to the epoxide (e.g. 1:10,000 or less) and where even low parts-per-million levels of water in the reaction mixture will lead to a significant population of higher molecular weight chains in the final polymer compositions. It is also known that previous classes of catalysts used for epoxide $CO_2$ copolymerizations such as those based on zinc carboxylates produce aliphatic polycarbonates having broad molecular weight distributions (i.e. high polydispersity indices PDIs) and/or relatively high proportions of ether linkages.

Therefore, polymer compositions made with the inventive catalysts described herein are different in key respects from any aliphatic polycarbonate compositions previously described. Without being bound by theory, or thereby limiting the scope of this invention, it is believed the unique monomodal characteristics of the inventive polymer compositions are explained by a mechanism such as that shown in Scheme 2.

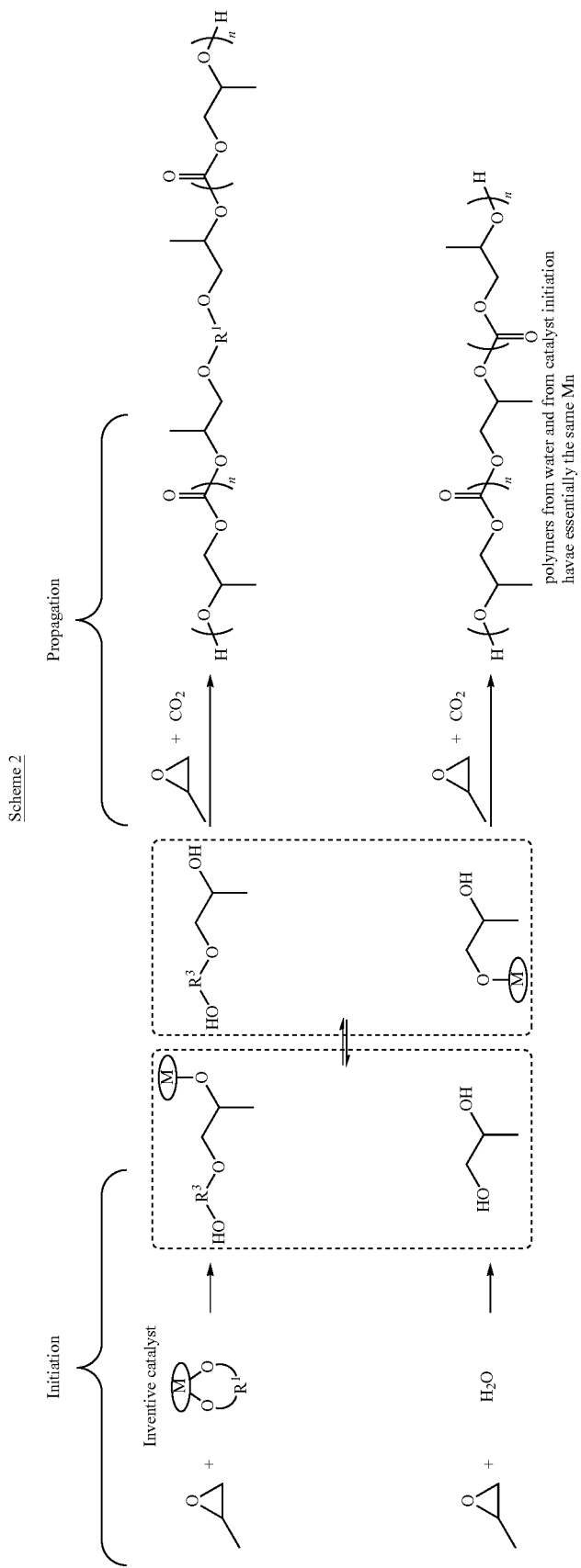

As shown in Scheme 2, using the inventive catalysts, the two populations of polymer have the same degree of polymerization and therefore essentially identical Mn. This leads to the observed monomodal molecular weight distribution.

Figure 9A:
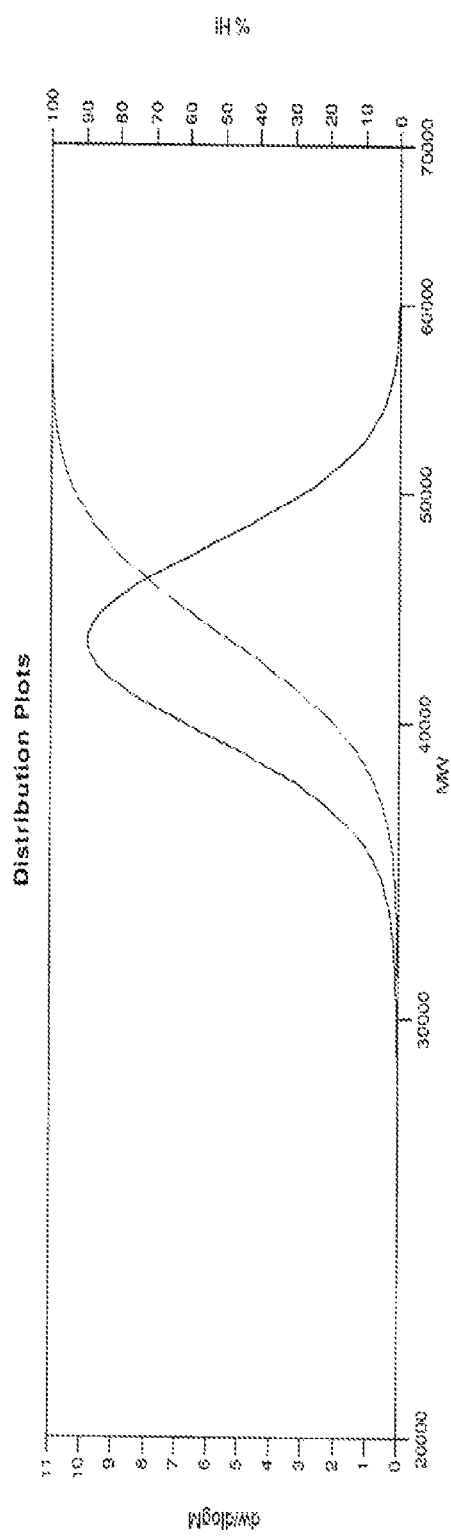
FIG. 9a-c shows GPC traces of monomodal APCs of the present invention along with a comparative polymer made according to the prior art.
Figure 9B:
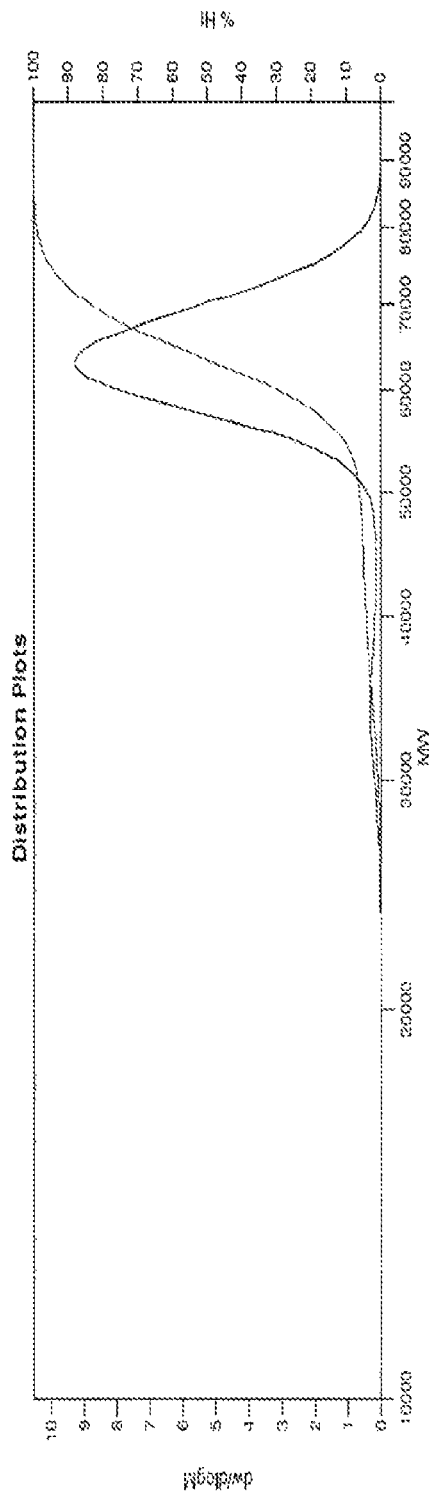
Figure 9C:
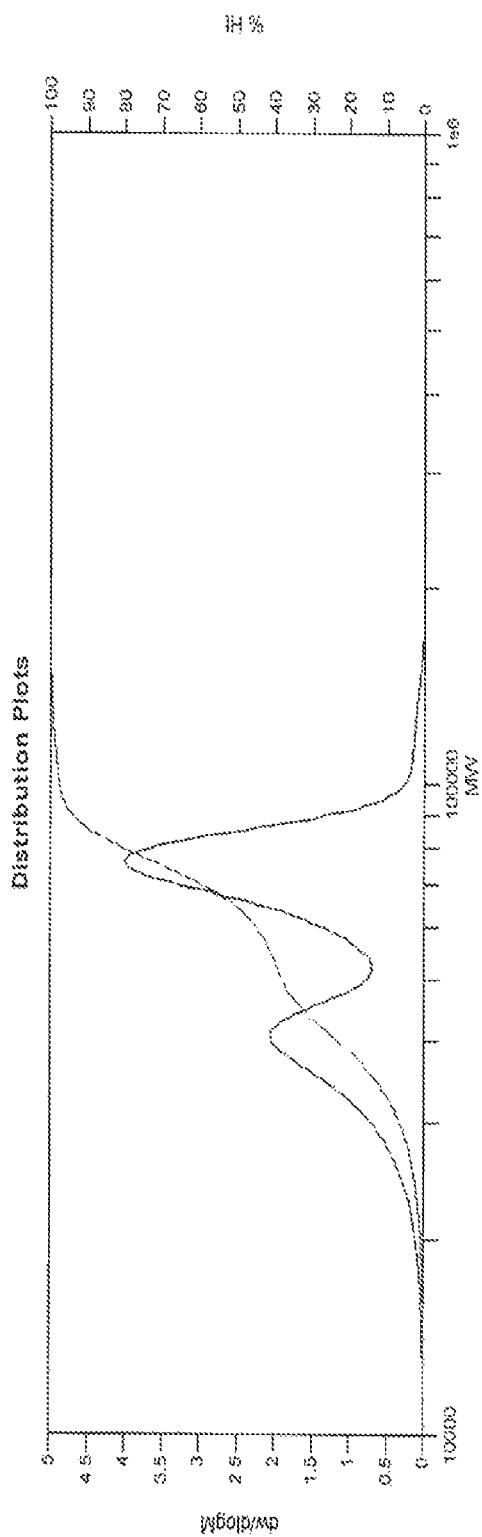

FIGS. 9a and 9b show GPC traces for samples of poly (propylene carbonate) made with a catalyst of the present invention having a carbonate counterion. FIG. 9c shows a similar PPC composition made with an otherwise identical catalyst that had a nitrate initiator. The GPC of the polymer composition from the inventive carbonate catalyst is substantially monomodal, while the polymer composition from the nitrate catalyst shows the bimodal distribution typical of prior art polymer compositions.

The polymers of the present invention are useful since a bimodal Mn distribution in a polymer composition can be undesirable. For example, it is known that differences in the molecular weight distribution of polymers can affect their processing characteristics and physical properties. Furthermore, since it is impractical to precisely control the water content of reaction mixtures between polymerization batches in a commercial process, it is very difficult to make aliphatic polycarbonate products with consistent molecular weight profiles from batch to batch. This variability is not desirable since the differences in the molecular weight distributions between batches may lead to corresponding inconsistencies in processing characteristics or product performance.

It should be noted that, because of the way the polydispersity is defined, some prior art polymers with bimodal molecular weight distributions still have very low polydisperisty indices (PDIs). It is understood in the art that low polydispersity does not equate to a mono-modal molecular weight distribution. It is also noted that while it is possible to separate monodisperse polymer fractions using methods such as gel permeation chromatography (GPC), this is only practical for small analytical samples and has no utility at commercial scale. Nonetheless, in certain embodiments, the inventive polymer compositions of the present invention are further characterized in that they have not been fractionated or otherwise treated in a post-polymerization step to substantially change their molecular weight distribution.

Therefore, in certain embodiments, the present invention provides aliphatic polycarbonate compositions characterized in that they have narrow and monomodal molecular weight distributions.

In certain embodiments, the narrow molecular weight distribution is such that the PDI of the composition is less than 1.7. In certain embodiments, the PDI of the composition is less than 1.6, less than 1.5, less than 1.4, less than 1.3, less than 1.25, less than 1.2, less than 1.15, or less than 1.1.

In certain embodiments, the inventive aliphatic polycarbonate compositions of the present invention are characterized in that they conform to the PDI limitations just described and are also characterized in that, when the Mn is measure by GPC, at least 90% of the polymer chains belong to a single molecular weight population. In certain embodiments, aliphatic polycarbonate compositions of the present invention are characterized in that at least 92.5%, at least 95%, at least 95%, at least 97%, at least 97.5%, at least 98%, at least 98.5%, at least 99%, or at least 99.5% of the polymer chains belong to a single molecular weight population. In certain embodiments, essentially all of the chains belong to a single molecular weight population.

In certain embodiments, the inventive aliphatic polycarbonate compositions of the present invention are characterized in that they conform to the PDI limitations just described and are also characterized in that, when the Mn is measure by GPC, less than 10% of the polymer belongs to a lower molecular weight population with an Mn of approximately one half of the molecular weight of the predominate molecular weight population. In certain embodiments, less than 8%, less than 7.5%, less than 6%, less than 5%, less than 4%, less than 3%, less than 2% or less than 1% of the polymer belongs to a lower molecular weight population with an Mn of approximately one half of the molecular weight of the predominate molecular weight population.

In certain embodiments, the inventive aliphatic polycarbonate compositions are further characterized in that they have high molecular weights. In certain embodiments, the aliphatic polycarbonate compositions have an Mn above about 40,000 g/mol. In certain embodiments, the aliphatic polycarbonate compositions have an Mn of at least 50,000 g/mol, at least 75,000 g/mol, at least 100,000 g/mol, at least 125,000 g/mol, at least 150,000 g/mol, at least 175,000 g/mol, at least 200,000 g/mol, or at least at least 250,000 g/mol.

In certain embodiments, the inventive aliphatic polycarbonate compositions comprise copolymers of $CO_2$ and one or more epoxides wherein the PDI less than 1.5, less than 1.3, less than 1.2 or less than 1.1 and the Mn is above 50,000 g/mol, above 75,000 g/mol, above 100,000 g/mol, or above 150,000 g/mol; characterized in that a GPC of the composition shows a unimodal molecular weight distribution. In certain embodiments, the unimodal molecular weight distribution is characterized in that more than 95%, more than 98%, or more than 99% of the polymer chains belong to a single molecular weight population. In certain embodiments, the epoxide $CO_2$ copolymers are further characterized in that at least 95% of the linkages between adjacent enchained epoxides are carbonate linkages. In certain embodiments, such aliphatic polycarbonate compositions are further characterized in that, if there is a minor secondary population of polymer chains belonging to a different molecular weight population present, the polymer chains in the minor population have a lower Mn than the predominate molecular weight population. In certain embodiments, the lower Mn population has an Mn approximately one half the Mn of the predominate molecular weight population.

In certain embodiments, the inventive aliphatic polycarbonates comprise poly(propylene carbonate) (PPC) wherein the PDI less than 1.5, less than 1.3, less than 1.2 or less than 1.1 and the Mn is above 50,000 g/mol, above 75,000 g/mol, above 100,000 g/mol, or above 150,000 g/mol; characterized in that a GPC of the composition shows a unimodal molecular weight distribution. In certain embodiments, the unimodal molecular weight distribution is characterized in that more than 95%, more than 98%, or more than 99% of the polymer chains belong to a single molecular weight population. In certain embodiments, the PPC compositions are further characterized in that at least 95% of the linkages between adjacent enchained propylene oxide units are carbonate linkages. In certain embodiments, such PPC compositions are further characterized in that, if there is a minor secondary population of polymer chains belonging to a different molecular weight population present, the polymer chains in the minor population have a lower Mn than the predominate molecular weight population. In certain embodiments, the lower Mn population has an Mn approximately one half the Mn of the predominate molecular weight population.

In certain embodiments, the inventive aliphatic polycarbonates comprise poly(ethylene carbonate) (PEC) wherein the PDI is less than 1.5, less than 1.3, less than 1.2 or less than 1.1 and the Mn is above 50,000 g/mol, above 75,000 g/mol, above 100,000 g/mol, or above 150,000 g/mol; characterized in that a GPC of the composition shows a unimodal molecular weight distribution. In certain embodiments, the unimodal molecular weight distribution is characterized in that more than 90%, more than 95%, more than 98%, or more than 99% of the polymer chains belong to a single molecular weight population. In certain embodiments, the PEC compositions are further characterized in that at least 95% of the linkages between adjacent enchained propylene oxide units are carbonate linkages. In certain embodiments, such PEC compositions are further characterized in that, if there is a minor secondary population of polymer chains belonging to a different molecular weight population, the polymer chains in the minor population have a lower Mn than the predominate molecular weight population. In certain embodiments, the lower Mn population has an Mn approximately one half the Mn of the predominate molecular weight population.

In certain embodiments, the inventive aliphatic polycarbonates comprise poly(butylene carbonate) (PBC) wherein the PDI less than 1.5, less than 1.3, less than 1.2 or less than 1.1 and the Mn is above 50,000 g/mol, above 75,000 g/mol, above 100,000 g/mol, or above 150,000 g/mol; characterized in that a GPC of the composition shows a unimodal molecular weight distribution. In certain embodiments, the unimodal molecular weight distribution is characterized in that more than 90%, more than 95%, more than 98%, or more than 99% of the polymer chains belong to a single molecular weight population. In certain embodiments, such PBC compositions are further characterized in that, if there is a minor secondary population of polymer chains belonging to a different molecular weight population, the polymer chains in the minor population have a lower Mn than the predominate molecular weight population. In certain embodiments, the lower Mn population has an Mn approximately one half the Mn of the predominate molecular weight population.

Certain catalysts of the present invention provide novel polymer products that have narrow and unimodal molecular weight distributions. For example, when a catalyst with only dianionic counterions as described above is used for epoxide $CO_2$ copolymerization, the polymer compositions arising from the copolymerization of $CO_2$ and epoxides using the catalyst exhibit only one peak in the GPC. Therefore, in another aspect, the present invention comprises a method for the synthesis of aliphatic polycarbonates having narrow and monomodal molecular weight distributions. In certain embodiments, the methods comprise the step of contacting a mixture of one or more epoxides and $CO_2$ with any of the metal complexes described hereinabove characterized in that they comprise dianionic counterions.

EXAMPLES

Example 1: Preparation of Compound N, a Cobalt(III)Salen Complex with an Oxalate Counterion

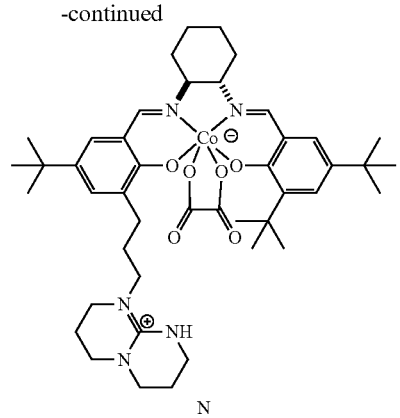

A sample of the nitrate complex M (1 g, 1.2 mmol) was dissolved in isopropanol (7 mL) and isopropyl acetate (7 mL). A solution of sodium oxalate (7.4 g, 55 mmol) in water (80 mL) was prepared. The solution of nitrate complex M was washed with the aqueous oxalate solution (2×10 mL) and then water (2×10 mL). The organic solution was stripped to a minimal volume and diluted with isopropyl ether. The green precipitate that formed was collected by filtration to provide oxalate complex N (0.67 g, 68%) as a mixture of two isomers observed by NMR in approximately a 10:1 ratio in $d_6$-DMSO. $^1$H NMR (400 MHz, $d_6$-DMSO): δ 1.0-1.25 (m, 27H), 1.25-2.40 (m, 14H), 2.7-3.2 (m, 13H), 3.94 (t, J=11 Hz, 1H), 6.88 (d, J=2.4 Hz, 0.1H), 6.95 (d, J=2.5 Hz, 0.9H), 7.08 (d, J=2.5 Hz, 0.9H), 7.12 (d, J=2.5 Hz, 0.9H), 7.14 (t, J=2.5 Hz, 0.2H), 7.19 (d, J=2.6 Hz, 1H), 7.45 (s, 0.9H), 7.47 (s, 0.1H), 7.74 (broad s, 1H), 7.90 (s, 0.1H), 7.91 (s, 0.9H). The UV-vis absorption spectrum of this compound shows absorption maxima centered at 200, 232, 263, and 406 nm.

Example 2: Preparation of Compound O, a Cobalt(III)Salen Complex with a Malonate Counterion

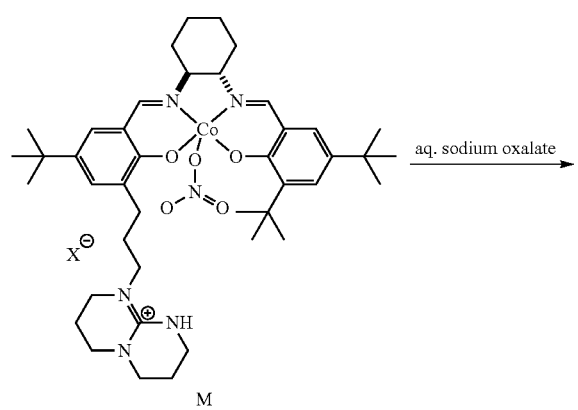

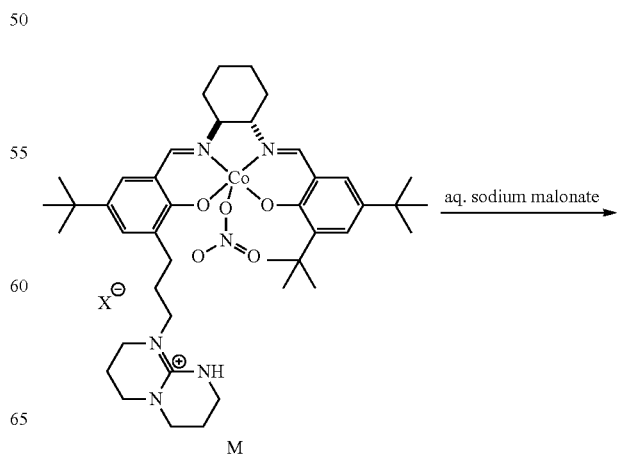

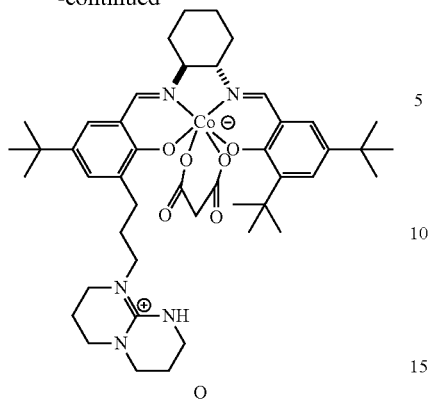

O

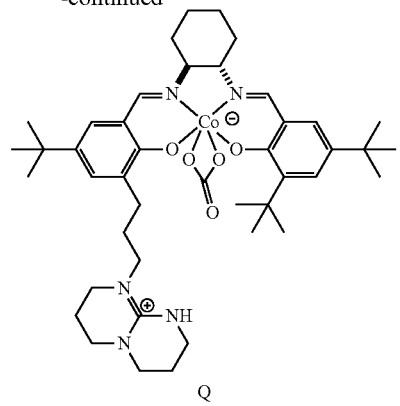

Q

A sample of the nitrate complex M (1 g, 1.2 mmol) was dissolved in isopropanol (7 mL) and isopropyl acetate (7 mL). A solution of sodium malonate (8.15 g, 55 mmol) in water (50 mL) was prepared. The solution of nitrate complex M was washed with the aqueous oxalate solution (2×10 mL) and then water (2×10 mL). The organic solution was stripped to dryness and the resulting solid was re-dissolved in a minimal volume of isopropanol and methanol. Isopropyl ether was added and the green precipitate that formed was collected by filtration to provide malonate complex O (0.57 g, 57%) as a mixture of two isomers observed by NMR in approximately a 6:1 ratio in $d_6$-DMSO. $^1$H NMR (300 MHz, $d_6$-DMSO): δ 1.17-1.40 (m, 27H), 1.40-2.05 (m, 14H), 2.8-3.6 (m, 15H), 4.48 (t, J=10 Hz, 1H), 6.84 (d, J=2.5 Hz, 0.15H), 6.90 (d, J=2.5 Hz, 0.85H), 7.09-7.22 (m, 3H), 7.33 (s, 0.85H), 7.38 (s, 0.15H), 7.68 (broad s, 1H), 7.72 (s, 0.15H), 7.74 (s, 0.85H). The UV-vis absorption spectrum of this compound shows absorption maxima centered at 199, 235, 264, and 402 nm.

A toluene and isopropyl alcohol solution (30 mL each) of the salen cobalt(III) complex M' (10.3 mmol, X=OAc, Cl, Br) was washed with saturated sodium bicarbonate (1×50 mL, 1×25 mL). The dark solution was then stripped (~27 mL solvent) and polish filtered; approximately 20 mL isopropanol was used in the transfer and washing of the filter cake. Another 40 mL of solvent was stripped and the concentrated solution was diluted with isopropyl acetate (60 mL). A green precipitate formed and was collected by filtration. After oven drying at 40° C. (100 mBar) overnight, the salen cobalt(III) carbonate complex was obtained as a green powder in 69% yield (5.75 g). Proton NMR shows a mixture of two isomers in approximately a 2:1 ratio in $d_6$-DMSO. $^1$H NMR (400 MHz, $d_6$-DMSO): δ1.16-1.33 (m, 27H), 1.34-2.43 (m, 14H), 2.56-3.3 (m, 13H), 3.74 (m, 1H), 6.87 (d, J=2.5 Hz, 0.35H), 6.94 (d, J=2.5 Hz, 0.65H), 7.03-7.20 (m, 3H), 7.42 (s, 0.65H), 7.46 (s, 0.35H), 7.78 (broad s, 1H), 7.96 (s, 0.35H), 7.98 (s, 0.65H). The UV-vis absorption spectrum of this compound shows absorption maxima centered at 199, 238, 263, and 410 nm.

Example 3: Preparation of Compound Q, a Cobalt(III)Salen Complex with a Carbonate Counterion Example 4: Preparation of Compound R, a Cobalt(III)Salen Complex with a Carbonate Counterion

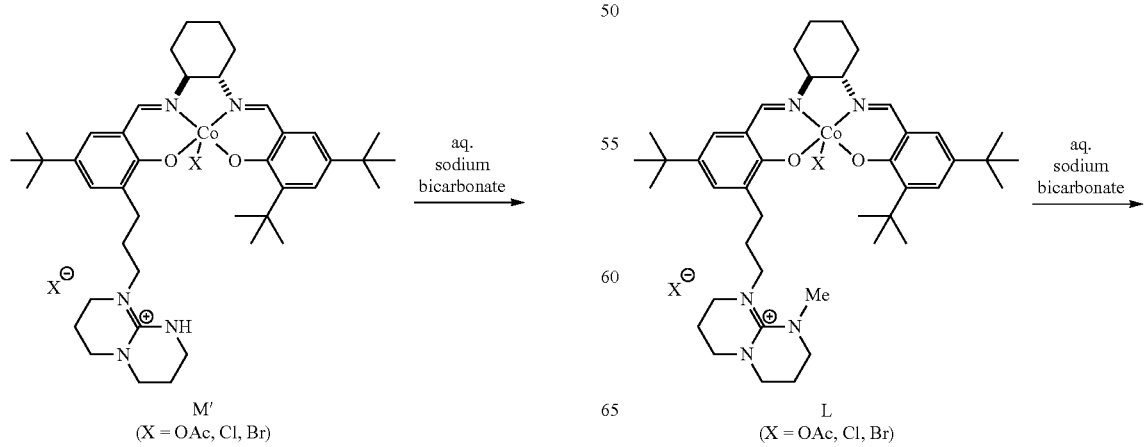

M'
(X = OAc, Cl, Br)

L
(X = OAc, Cl, Br)

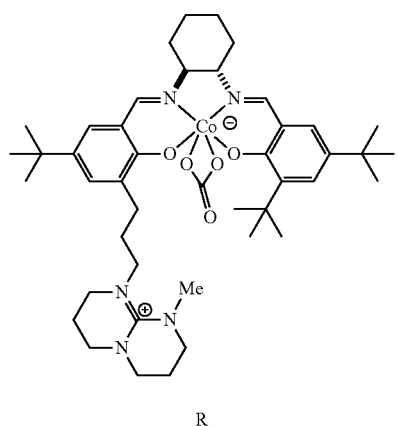

R

A propanol and butyl acetate solution (50 mL each) of the salen cobalt(III) complex L (17.2 mmol, X=OAc, Cl, Br) was washed with saturated sodium bicarbonate (1×100 mL, 1×50 mL). The dark solution was then stripped (~70 mL solvent). Approximately 10 mL isopropanol was added along with more butyl acetate (50 mL). The dark solution was stripped further and then diluted with MTBE (120 mL). The resulting suspension was cooled to ca. 10° C. and the product R was collected by filtration. The filter cake was washed with MTBE (2×75 mL) and then dried overnight in a vacuum oven at 30° C. (100 mBar). The salen cobalt(III) carbonate complex R was obtained as a green powder in 68% yield (9.4 g) after correcting for volatiles. Proton NMR shows a mixture of two isomers in approximately a 2:1 ratio. $^1$H NMR (400 MHz, d$_6$-DMSO): δ 1.16-1.37 (m, 27H), 1.37-1.95 (m, 12H), 2.20-2.42 (m, 2H), 2.56 (s, 1H), 2.59 (s, 2H), 2.77-3.36 (m, 13H), 3.79 (m, 1H), 6.89 (d, J=2.5 Hz, 0.35H), 6.95 (d, J=2.5 Hz, 0.65H), 7.05-7.15 (m, 3H), 7.36 (s, 0.65H), 7.44 (s, 0.35H), 8.03 (s, 0.35H), 8.04 (s, 0.65H). NOV-067-235. R (Gen2b CO3): The UV-vis absorption spectrum of this compound shows absorption maxima centered at 199, 235, 265, and 416 nm.

Example 5: Preparation of Compound T, a Chromium(III) Salen Complex with an Oxalate Counterion

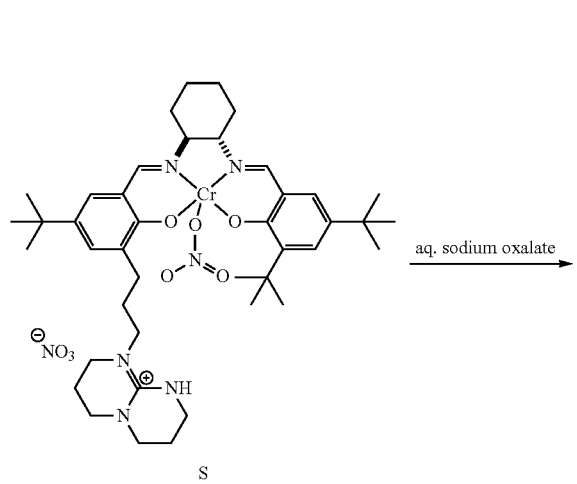

S

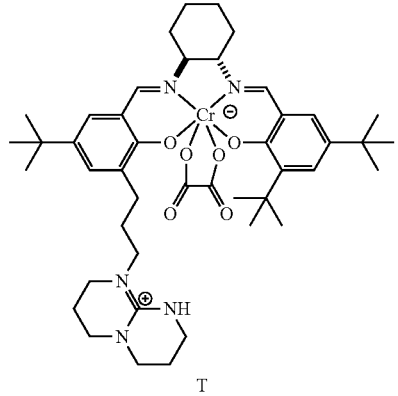

T

A sample of the nitrate complex S (1.2 mmol) is dissolved in isopropanol (7 mL) and isopropyl acetate (7 mL). A solution of sodium oxalate (7.4 g, 55 mmol) in water (80 mL) is prepared. The solution of nitrate complex S is washed with the aqueous oxalate solution (2×10 mL) and then water (2×10 mL). The organic solution is stripped to a minimal volume and diluted with isopropyl ether. The precipitate formed is collected by filtration to provide oxalate complex T as a green solid.

Example 6: Preparation of Compound U, a Chromium(III)Salen Complex with a Malonate Counterion

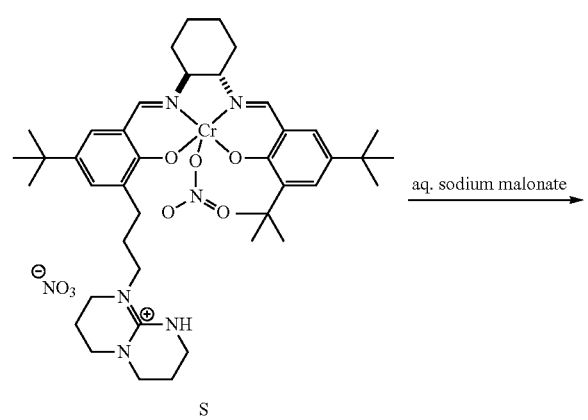

S

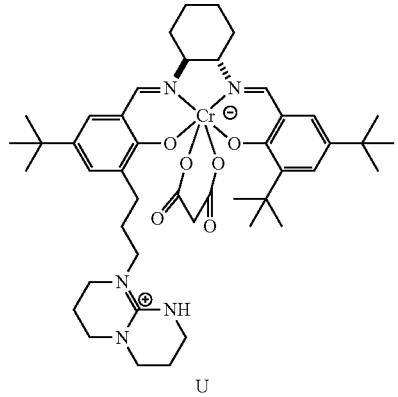

U

A sample of the nitrate complex S (1.2 mmol) is dissolved in isopropanol (7 mL) and isopropyl acetate (7 mL). A solution of sodium malonate (8.15 g, 55 mmol) in water (50 mL) is prepared. The solution of nitrate complex S is washed with the aqueous oxalate solution (2×10 mL) and then water (2×10 mL). The organic solution is stripped to dryness and the resulting solid is re-dissolved in a minimal volume of isopropanol and methanol. Isopropyl ether is added and the precipitate formed is collected by filtration to provide malonate complex U.

Example 7: Preparation of Compound Q, a Chromium(III)Salen Complex with a Carbonate Counterion

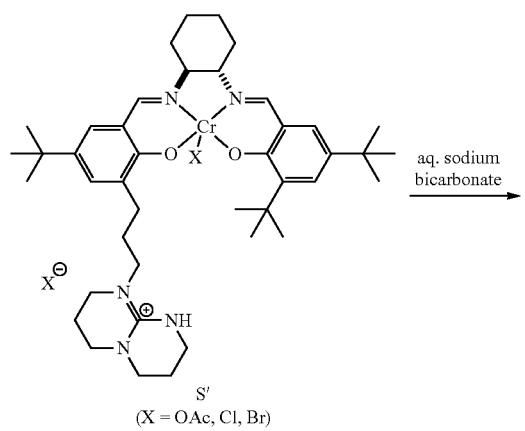

S'
(X = OAc, Cl, Br)

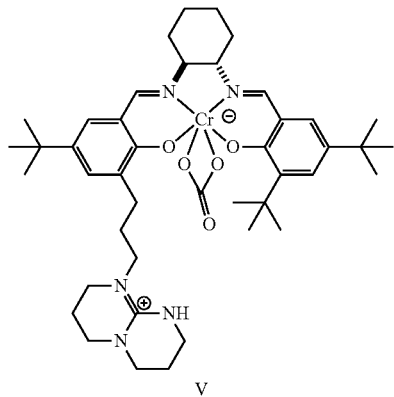

V

A toluene and isopropyl alcohol solution (30 mL each) of the salen chromium(III) complex S' (10.3 mmol, X=OAc, Cl, Br) is washed with saturated sodium bicarbonate (1×50 mL, 1×25 mL). The dark solution is then stripped and polish filtered; isopropanol is used in the transfer and washing of the filter cake. Another 40 mL of solvent is stripped and the concentrated solution is diluted with isopropyl acetate (60 mL). A precipitate forms and is collected by filtration. After oven drying at 40° C. (100 mBar) overnight, the salen chromium(III) carbonate complex V is obtained.

Example 8: Preparation of Compound Y, a Chromium(III)Salen Complex with a Carbonate Counterion

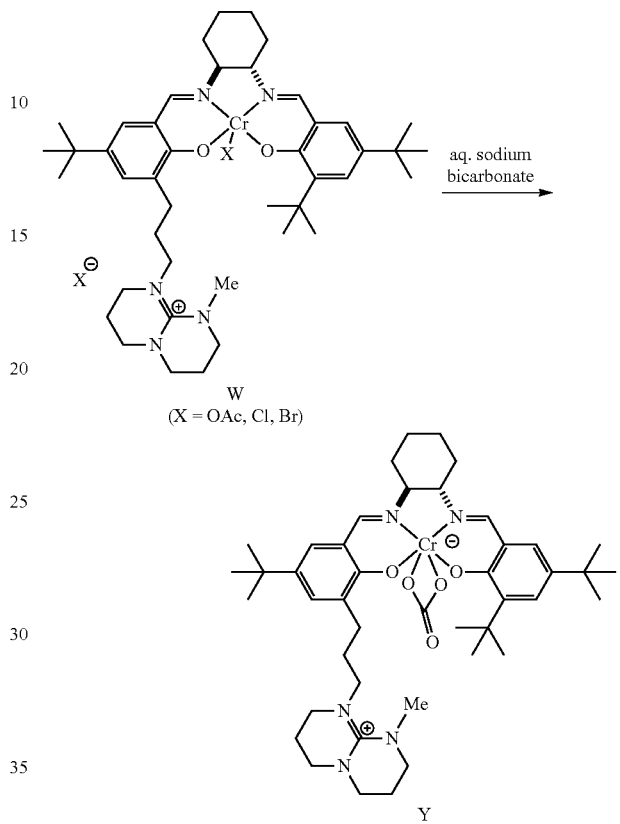

A propanol and butyl acetate solution (50 mL each) of the salen chromium(III) complex W (17.2 mmol, X=OAc, Cl, Br) is washed with saturated sodium bicarbonate (1×100 mL, 1×50 mL). The solution is then stripped (~70 mL solvent). Approximately 10 mL isopropanol is added along with more butyl acetate (50 mL). The solution is stripped further and then diluted with MTBE (120 mL). The resulting suspension is cooled to ca. 10° C. and the product Y is collected by filtration. The filter cake is washed with MTBE (2×75 mL) and then dried overnight in a vacuum oven at 30° C. (100 mBar). The salen chromium(III) carbonate complex Y is obtained as a powder.

Other Embodiments

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

APPENDIX A

This appendix describes in more detail the compositions and connectivity of the tethered activating groups mentioned above.

In some embodiments, the moiety —ᶥ—(Z)$_m$ in compounds described hereinabove, (also referred to as "an activating functional group") is selected from those described below in this appendix. In certain embodiments, an activating functional group is selected from the group consisting of neutral nitrogen-containing functional groups, cationic moieties, phosphorous-containing functional groups, and combinations of two or more of these.

A.1. Tether Moieties

In certain embodiments, each activating moiety —ᶥ—(Z)$_m$ comprises a tether "—ᶥ—" coupled to at least one activating functional group Z as described above, with m denoting the number of activating functional groups present on a single Z-linker moiety.

In some embodiments, there is one or more activating moieties —ᶥ—(Z)$_m$ tethered to a given metal complex; similarly, each activating moiety itself may contain more than one activating functional group Z. In certain embodiments, each activating moiety contains only one activating functional group (i.e. m=1). In some embodiments, each activating moiety contains more than one activating functional groups (i.e. m>1). In certain embodiments, an activating moiety contains two activating functional groups (i.e. m=2). In certain embodiments, an activating moiety contains three activating functional groups (i.e. m=3). In certain embodiments, an activating moiety contains four activating functional groups (i.e. m=4). In certain embodiments where more than one activating functional group is present on an activating moiety, the activating functional groups are the same. In some embodiments where more than one activating functional group is present on an activating moiety, two or more of the activating functional groups are different.

In certain embodiments, each tether (or "Z-linker") moiety —ᶥ— contains 1-30 atoms including at least one carbon atom, and optionally one or more atoms selected from the group consisting of N, O, S, Si, B, and P.

In certain embodiments, a Z-linker is a bivalent, optionally substituted $C_{2-30}$ aliphatic group wherein one or more carbons are optionally and independently replaced by —Cy—, —NR—, —N(R)C(O)—, —C(O)N(R)—, —O—, —C(O)—, —OC(O)—, —C(O)O—, —S—, —SO—, —SO$_2$—, —C(=S)—, —C(=NR)—, or —N=N—, wherein:

each —Cy— is independently an optionally substituted 5- to 8-membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and R is as defined above.

In certain embodiments, a Z-linker moiety is a $C_4$-$C_{12}$ aliphatic group substituted with one or more moieties selected from the group consisting of halogen, —NO$_2$, —CN, —SR, —S(O)R, —S(O)$_2$R, —NRC(O)R, —OC(O)R, —CO$_2$R, —NCO, —N$_3$, —OR$^4$, —OC(O)N(R)$_2$, —N(R)$_2$, —NRC(O)R, and —NRC(O)OR, where each R and R$^4$ is independently as defined herein and described in classes and subclasses herein.

In certain embodiments, a Z-linker moiety is an optionally substituted $C_3$-$C_{30}$ aliphatic group. In certain embodiments, a Z-linker is an optionally substituted $C_{4-24}$ aliphatic group. In certain embodiments, a Z-linker moiety is an optionally substituted $C_4$-$C_{20}$ aliphatic group. In certain embodiments, a Z-linker moiety is an optionally substituted $C_4$-$C_{12}$ aliphatic group. In certain embodiments, a Z-linker is an optionally substituted $C_{4-10}$ aliphatic group. In certain embodiments, a Z-linker is an optionally substituted $C_{4-8}$ aliphatic group. In certain embodiments, a Z-linker moiety is an optionally substituted $C_4$-$C_6$ aliphatic group. In certain embodiments, a Z-linker moiety is an optionally substituted $C_6$-$C_{12}$ aliphatic group. In certain embodiments, a Z-linker moiety is an optionally substituted $C_8$ aliphatic group. In certain embodiments, a Z-linker moiety is an optionally substituted $C_7$ aliphatic group. In certain embodiments, a Z-linker moiety is an optionally substituted $C_6$ aliphatic group. In certain embodiments, a Z-linker moiety is an optionally substituted $C_5$ aliphatic group. In certain embodiments, a Z-linker moiety is an optionally substituted $C_4$ aliphatic group. In certain embodiments, a Z-linker moiety is an optionally substituted $C_3$ aliphatic group. In certain embodiments, a aliphatic group in the Z-linker moiety is an optionally substituted straight alkyl chain. In certain embodiments, the aliphatic group is an optionally substituted branched alkyl chain. In some embodiments, a Z-linker moiety is a $C_4$ to $C_{20}$ alkyl group having one or more methylene groups replaced by —C(R°)$_2$— wherein R° is as defined above. In certain embodiments, a Z-linker moiety consists of a bivalent aliphatic group having 4 to 30 carbons including one or more $C_{1-4}$ alkyl substituted carbon atoms. In certain embodiments, a Z-linker moiety consists of a bivalent aliphatic group having 4 to 30 carbons including one or more gem-dimethyl substituted carbon atoms.

In certain embodiments, a Z-linker moiety includes one or more optionally substituted cyclic groups selected from the group consisting of saturated or partially unsaturated carbocyclic, aryl, heterocyclic, or heteroaryl. In certain embodiments, a Z-linker moiety consists of a substituted cyclic group. In some embodiments a cyclic group is part of a Z-linker, wherein one or more non-ring heteroatoms or optionally substituted aliphatic groups comprise other parts of the Z-linker moiety.

In some embodiments, a Z-linker moiety is of sufficient length to allow one or more activating functional groups to be positioned near a metal atom of a metal complex. In certain embodiments, structural constraints are built into a Z-linker moiety to control the disposition and orientation of one or more activating functional groups near a metal center of a metal complex. In certain embodiments, such structural constraints are selected from the group consisting of cyclic moieties, bicyclic moieties, bridged cyclic moieties and tricyclic moieties. In some embodiments, such structural constraints are the result of acyclic steric interactions. In certain embodiments, steric interactions due to syn-pentane, gauche-butane, and/or allylic strain in a Z-linker moiety, bring about structural constraints that affect the orientation of a Z-linker and one or more activating groups. In certain embodiments, structural constraints are selected from the group consisting of cis double bonds, trans double bonds, cis allenes, trans allenes, and triple bonds. In some embodiments, structural constraints are selected from the group consisting of substituted carbons including geminally disubstituted groups such as sprirocyclic rings, gem dimethyl groups, gem diethyl groups and gem diphenyl groups. In certain embodiments, structural constraints are selected from the group consisting of heteratom-containing functional groups such as sulfoxides, amides, and oximes.

In certain embodiments, Z-linker moieties are selected from the group consisting of:

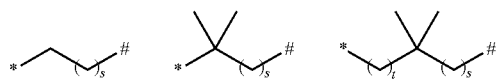

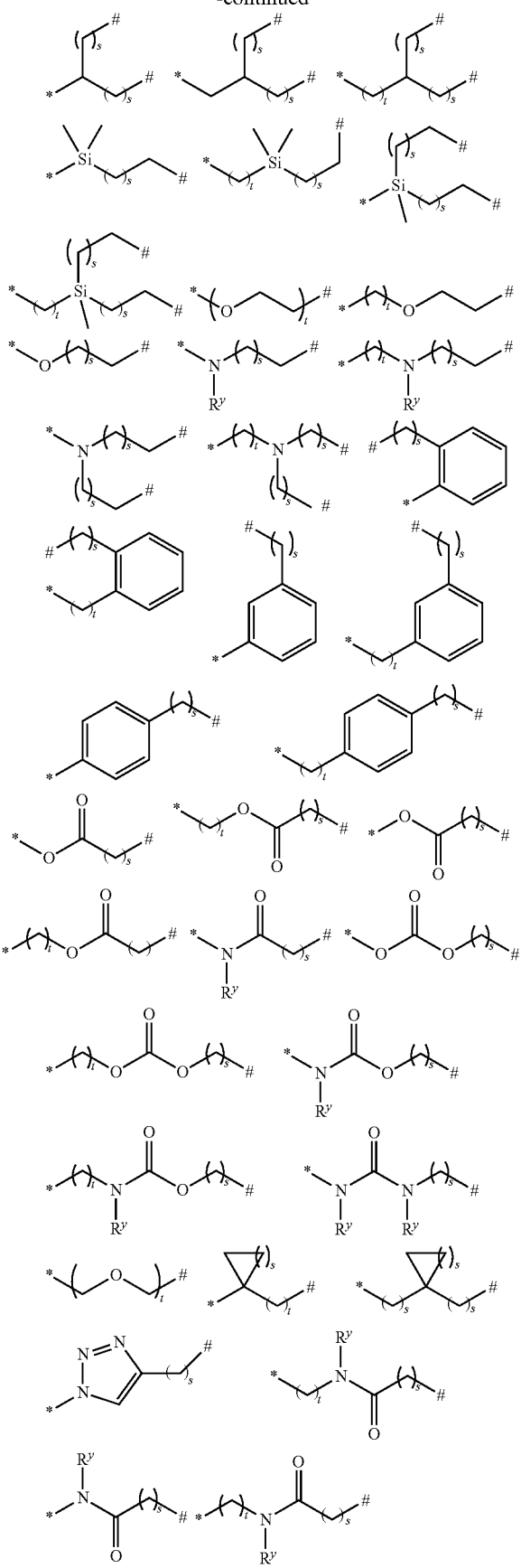
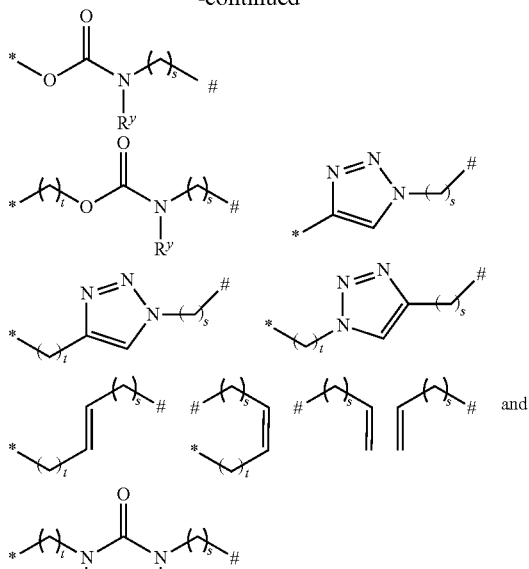

wherein each s is independently 0-6, t is 0-4, $R^y$ as defined above and described in classes and subclasses herein, * represents the site of attachment to a ligand, and each # represents a site of attachment of an activating functional group.

In some embodiments, s is 0. In some embodiments, s is 1. In some embodiments, s is 2. In some embodiments, s is 3. In some embodiments, s is 4. In some embodiments, s is 5. In some embodiments, s is 6.

In some embodiments, t is 1. In some embodiments, t is 2. In some embodiments, t is 3. In some embodiments, t is 4.

A.2. Neutral Nitrogen-Containing Activating Groups

In some embodiments, one or more tethered activating functional groups (i.e., Z) on provided metal complexes are neutral nitrogen-containing moieties. In certain embodiments, one or more Z group is independently a neutral functional group selected from the group consisting of amines, phosphines, guanidines, bis-guanidines, amidines, and nitrogen-containing heterocycles.

In some embodiments, such Z moieties are selected from one or more of the structures in Table Z-1:

TABLE Z-1

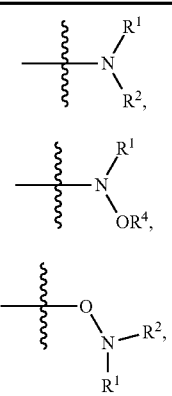

TABLE Z-1-continued

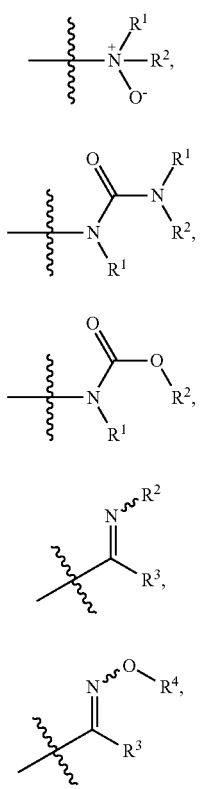

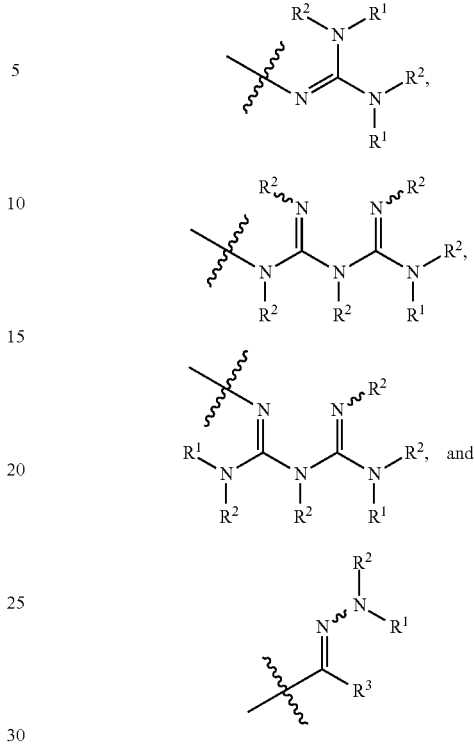

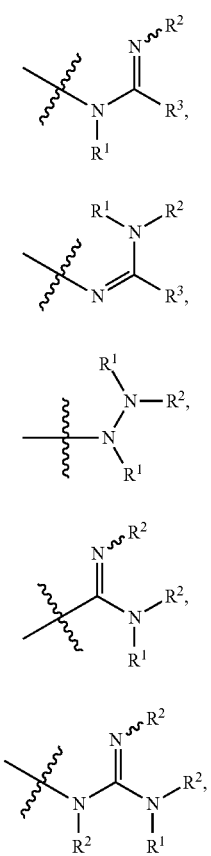

or a combination of two or more of these, wherein:

each $R^1$ and $R^2$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein $R^1$ and $R^2$ can be taken together with intervening atoms to form one or more optionally substituted rings optionally containing one or more additional heteroatoms;

each $R^3$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an $R^3$ group can be taken with an $R^1$ or $R^2$ group to form one or more optionally substituted rings; and each $R^4$ is independently hydrogen, a hydroxyl protecting group, or an optionally substituted radical selected from the group consisting of $C_{1-20}$ acyl; $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring.

In certain embodiments, each $R^1$ group is the same. In other embodiments, $R^1$ groups are different. In certain embodiments, $R^1$ is hydrogen. In some embodiments, $R^1$ is an optionally substituted radical selected from the group consisting of $C_{1-20}$ aliphatic; $C_{1-20}$ heteroaliphatic, 5- to 14-membered heteroaryl, phenyl, 8- to 10-membered aryl and 3- to 7-membered heterocyclic. In some embodiments, $R^1$ is an optionally substituted radical selected from the group consisting of a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring.

In certain embodiments, $R^1$ is an optionally substituted radical selected from the group consisting of $C_{1-12}$ aliphatic and $C_{1-12}$ heteroaliphatic. In some embodiments, $R^1$ is optionally substituted $C_{1-20}$ aliphatic. In some embodiments, $R^1$ is optionally substituted $C_{1-12}$ aliphatic. In some embodiments, $R^1$ is optionally substituted $C_{1-6}$ aliphatic. In some embodiments, $R^1$ is optionally substituted $C_{1-20}$ heteroaliphatic. In some embodiments, $R^1$ is optionally substituted $C_{1-12}$ heteroaliphatic. In some embodiments, $R^1$ is optionally substituted phenyl. In some embodiments, $R^1$ is optionally substituted 8- to 10-membered aryl. In some embodiments, $R^1$ is an optionally substituted 5- to 6-membered heteroaryl group. In some embodiments, $R^1$ is an optionally substituted 8- to 14-membered polycyclic heteroaryl group. In some embodiments, $R^1$ is optionally substituted 3- to 8-membered heterocyclic.

In certain embodiments, each $R^1$ is independently hydrogen, methyl, ethyl, propyl, butyl, pentyl, hexyl, heptyl, octyl, optionally substituted phenyl, or optionally substituted benzyl. In certain embodiments, $R^1$ is methyl, ethyl, propyl, butyl, pentyl, hexyl, heptyl, octyl, phenyl or benzyl. In some embodiments, $R^1$ is butyl. In some embodiments, $R^1$ is isopropyl. In some embodiments, $R^1$ is neopentyl. In some embodiments, $R^1$ is perfluoro. In some embodiments, $R^1$ is $-CF_2CF_3$. In some embodiments, $R^1$ is phenyl. In some embodiments, $R^1$ is benzyl.

In certain embodiments, each $R^2$ group is the same. In other embodiments, $R^2$ groups are different. In certain embodiments, $R^2$ is hydrogen. In some embodiments, $R^2$ is an optionally substituted radical selected from the group consisting of $C_{1-20}$ aliphatic; $C_{1-20}$ heteroaliphatic, 5- to 14-membered heteroaryl, phenyl, 8- to 10-membered aryl and 3- to 7-membered heterocyclic. In some embodiments, $R^2$ is an optionally substituted radical selected from the group consisting of a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring.

In certain embodiments, $R^2$ is an optionally substituted radical selected from the group consisting of $C_{1-12}$ aliphatic and $C_{1-12}$ heteroaliphatic. In some embodiments, $R^2$ is optionally substituted $C_{1-20}$ aliphatic. In some embodiments, $R^2$ is optionally substituted $C_{1-12}$ aliphatic. In some embodiments, $R^2$ is optionally substituted $C_{1-6}$ aliphatic. In some embodiments, $R^2$ is optionally substituted $C_{1-20}$ heteroaliphatic. In some embodiments, $R^2$ is optionally substituted $C_{1-12}$ heteroaliphatic. In some embodiments, $R^2$ is optionally substituted phenyl. In some embodiments, $R^2$ is optionally substituted 8- to 10-membered aryl. In some embodiments, $R^2$ is an optionally substituted 5- to 6-membered heteroaryl group. In some embodiments, $R^2$ is an optionally substituted 8- to 14-membered polycyclic heteroaryl group. In some embodiments, $R^2$ is optionally substituted 3- to 8-membered heterocyclic.

In certain embodiments, each $R^2$ is independently hydrogen, methyl, ethyl, propyl, butyl, pentyl, hexyl, heptyl, octyl, optionally substituted phenyl, or optionally substituted benzyl. In certain embodiments, $R^2$ is methyl, ethyl, propyl, butyl, pentyl, hexyl, heptyl, octyl, phenyl or benzyl. In some embodiments, $R^2$ is butyl. In some embodiments, $R^2$ is isopropyl. In some embodiments, $R^2$ is neopentyl. In some embodiments, $R^2$ is perfluoro. In some embodiments, $R^2$ is $-CF_2CF_3$. In some embodiments, $R^2$ is phenyl. In some embodiments, $R^2$ is benzyl.

In certain embodiments, each $R^1$ and $R^2$ are hydrogen. In some embodiments, each $R^1$ is hydrogen each and each $R^2$ is other than hydrogen. In some embodiments, each $R^2$ is hydrogen each and each $R^1$ is other than hydrogen.

In certain embodiments, $R^1$ and $R^2$ are both methyl, ethyl, propyl, butyl, pentyl, hexyl, heptyl, octyl, phenyl or benzyl. In some embodiments, $R^1$ and $R^2$ are each butyl. In some embodiments, $R^1$ and $R^2$ are each isopropyl. In some embodiments, $R^1$ and $R^2$ are each perfluoro. In some embodiments, $R^1$ and $R^2$ are —$CF_2CF_3$. In some embodiments, $R^1$ and $R^2$ are each phenyl. In some embodiments, $R^1$ and $R^2$ are each benzyl.

In some embodiments, $R^1$ and $R^2$ are taken together with intervening atoms to form one or more optionally substituted carbocyclic, heterocyclic, aryl, or heteroaryl rings. In certain embodiments, $R^1$ and $R^2$ are taken together to form a ring fragment selected from the group consisting of: —$C(R^y)_2$—, —$C(R^y)_2C(R^y)_2$—, —$C(R^y)_2C(R^y)_2C(R^y)_2$—, —$C(R^y)_2OC(R^y)_2$—, and —$C(R^y)_2NR^yC(R^y)_2$—, wherein $R^y$ is as defined above. In certain embodiments, $R^1$ and $R^2$ are taken together to form a ring fragment selected from the group consisting of: —$CH_2$—, —$CH_2CH_2$—, —$CH_2CH_2CH_2$—, —$CH_2OCH_2$—, and —$CH_2NR^yCH_2$—. In some embodiments, $R^1$ and $R^2$ are taken together to form an unsaturated linker moiety optionally containing one or more additional heteroatoms. In some embodiments, the resulting nitrogen-containing ring is partially unsaturated. In certain embodiments, the resulting nitrogen-containing ring comprises a fused polycyclic heterocycle.

In certain embodiments, $R^3$ is H. In certain embodiments, $R^3$ is optionally $C_{1-20}$ aliphatic; $C_{1-20}$ heteroaliphatic, 5- to 14-membered heteroaryl, phenyl, 8- to 10-membered aryl or 3- to 7-membered heterocyclic. In some embodiments, $R^3$ is an optionally substituted radical selected from the group consisting of a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring. In certain embodiments, $R^3$ is optionally substituted $C_{1-12}$ aliphatic. In some embodiments, $R^3$ is optionally substituted $C_{1-6}$ aliphatic. In certain embodiments, $R^3$ is optionally substituted phenyl.

In certain embodiments, $R^3$ is methyl, ethyl, propyl, butyl, pentyl, hexyl, heptyl, octyl, phenyl or benzyl. In some embodiments, $R^3$ is butyl. In some embodiments, $R^3$ is isopropyl. In some embodiments, $R^3$ is perfluoro. In some embodiments, $R^3$ is —$CF_2CF_3$.

In some embodiments, one or more $R^1$ or $R^2$ groups are taken together with $R^3$ and intervening atoms to form an optionally substituted heterocyclic or heteroaryl ring. In certain embodiments, $R^1$ and $R^3$ are taken together to form an optionally substituted 5- or 6-membered ring. In some embodiments, $R^2$ and $R^3$ are taken together to form an optionally substituted 5- or 6-membered ring optionally containing one or more additional heteroatoms. In some embodiments, $R^1$, $R^2$ and $R^3$ are taken together to form an optionally substituted fused ring system. In some embodiments, such rings formed by combinations of any of $R^1$, $R^2$ and $R^3$ are partially unsaturated or aromatic.

In certain embodiments, $R^4$ is hydrogen. In some embodiments, $R^4$ is an optionally substituted radical selected from the group consisting of $C_{1-12}$ aliphatic, phenyl, 8- to 10-membered aryl, and 3- to 8-membered heterocyclic. In certain embodiments, $R^4$ is a $C_{1-12}$ aliphatic. In certain embodiments, $R^4$ is a $C_{1-6}$ aliphatic. In some embodiments, $R^4$ is an optionally substituted 8- to 10-membered aryl group. In certain embodiments, $R^4$ is optionally substituted $C_{1-12}$ acyl or in some embodiments, optionally substituted $C_{1-6}$ acyl. In certain embodiments, $R^4$ is optionally substituted phenyl. In some embodiments, $R^4$ is a hydroxyl protecting group. In some embodiments, $R^4$ is a silyl protecting group. In some embodiments, $R^4$ is methyl, ethyl, propyl, butyl, pentyl, hexyl, heptyl, octyl, allyl, phenyl or benzyl.

In certain embodiments, $R^1$ and $R^4$ are taken together with intervening atoms to form one or more optionally substituted heterocyclic or heteroaryl rings optionally containing one or more additional heteroatoms.

In some embodiments, an activating functional group is an N-linked amino group:

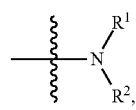

wherein $R^1$ and $R^2$ are as defined above and described in classes and subclasses herein.

In some embodiments, an N-linked amino activating functional group is selected from the group consisting of:

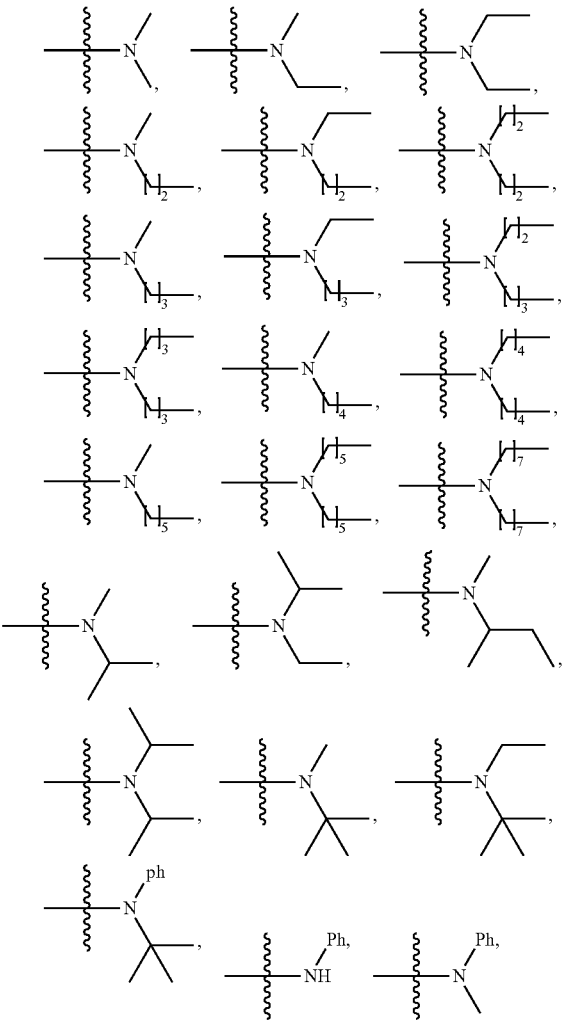

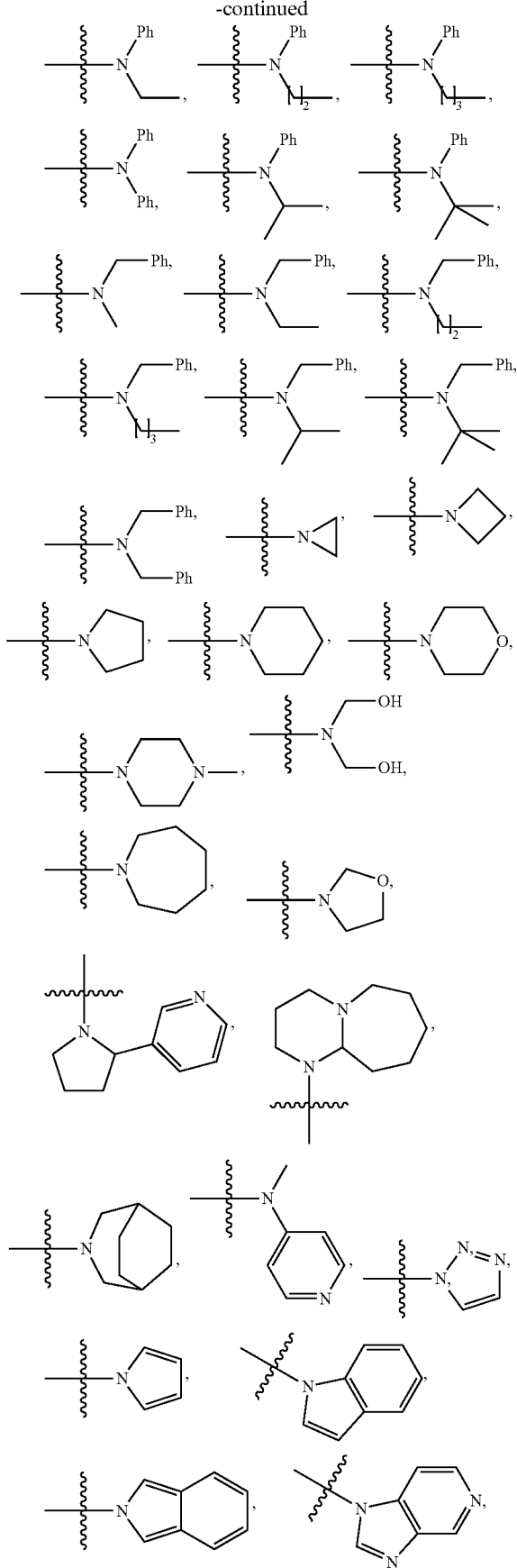
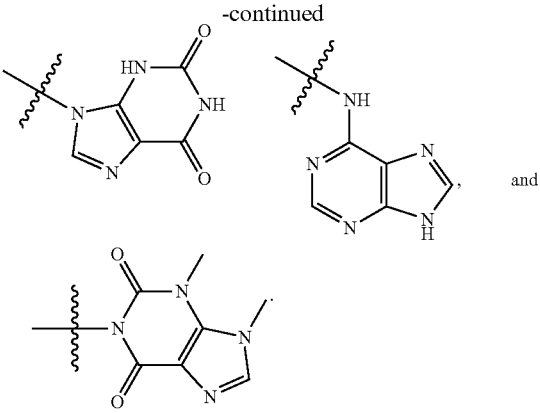
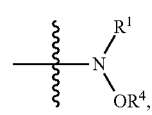
In some embodiments, one or more activating functional groups is an N-linked hydroxyl amine derivative:
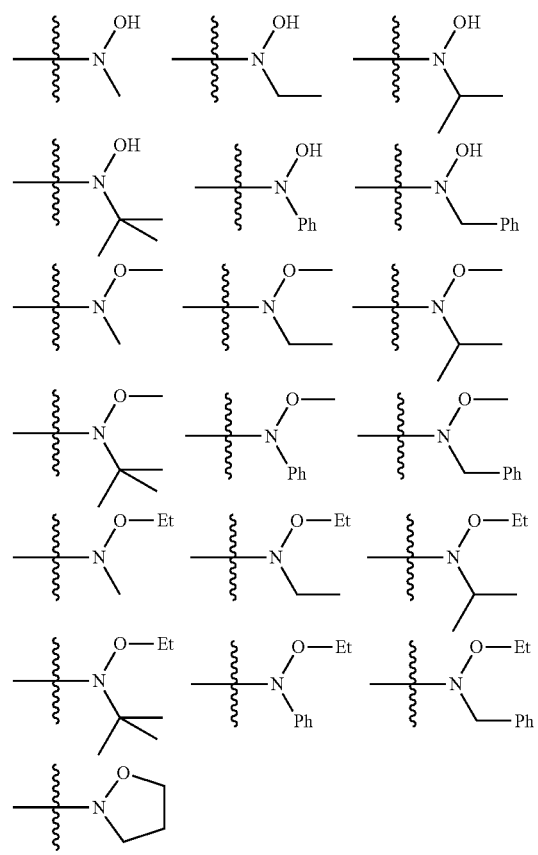
wherein $R^1$ and $R^4$ are as defined above and described in classes and subclasses herein.
In certain embodiments, one or more N-linked hydroxyl amine activating functional groups are selected from the group consisting of:

In some embodiments, an activating functional group in a provided metal complex is an amidine. In certain embodiments, such amidine activating functional groups are selected from

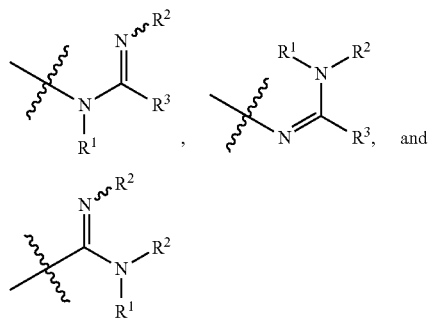

wherein each of $R^1$, $R^2$, and $R^3$ is as defined above and described in classes and subclasses herein.

In certain embodiments, an activating functional group is an N-linked amidine:

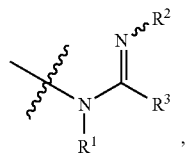

wherein each of $R^1$, $R^2$, and $R^3$ is as defined above and described in classes and subclasses herein. In certain embodiments, such N-linked amidine groups are selected from the group consisting of:

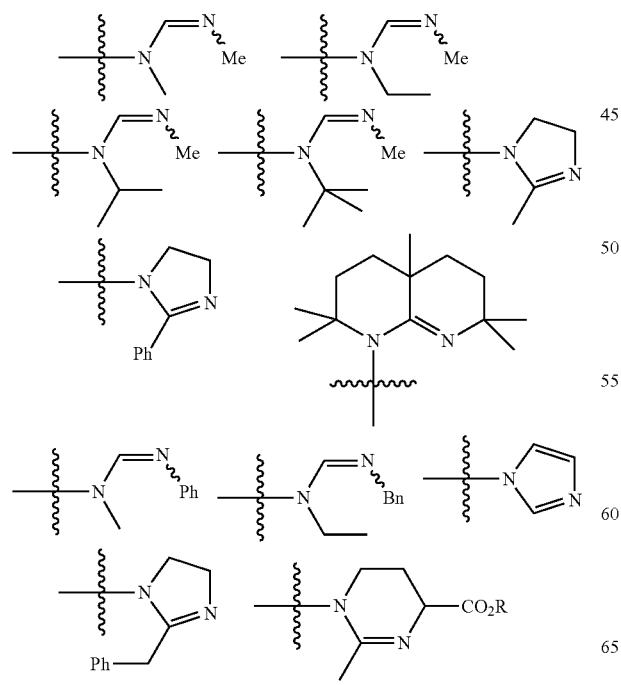

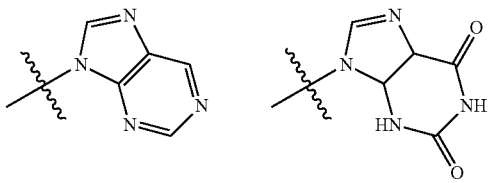

In certain embodiments, activating functional groups are amidine moieties linked through the imine nitrogen:

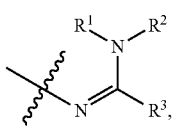

wherein each of $R^1$, $R^2$, and $R^3$ is as defined above and described in classes and subclasses herein. In certain embodiments, such imine-linked amidine activating functional groups are selected from the group consisting of:

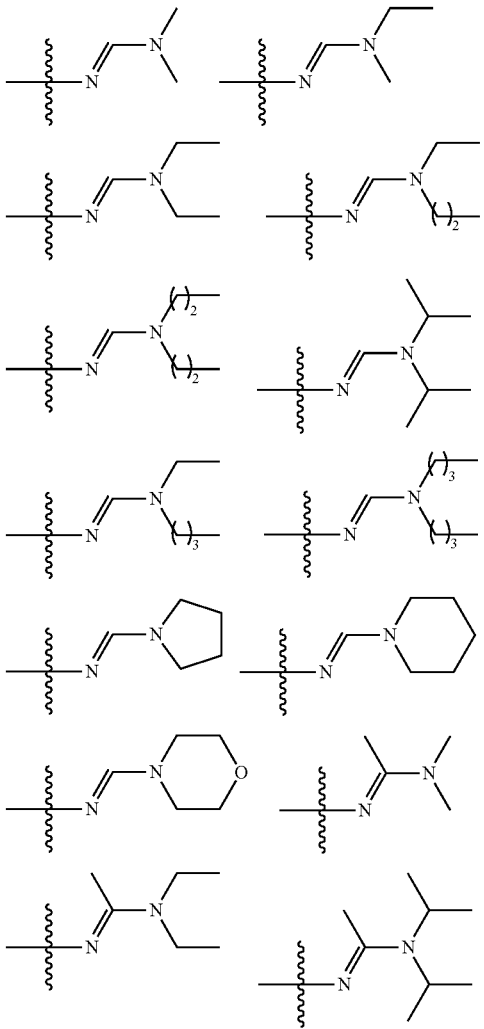

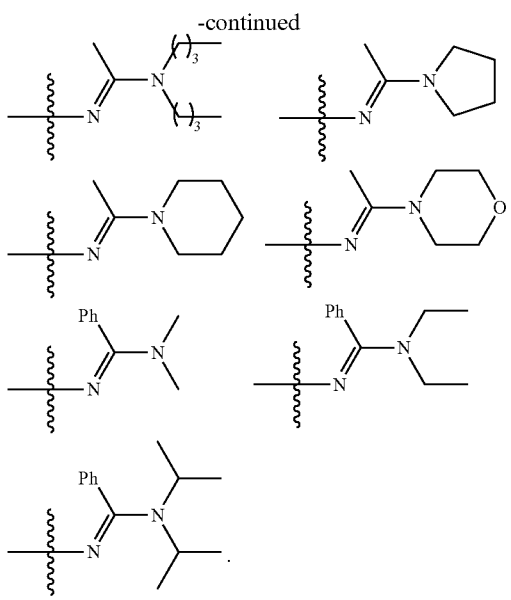
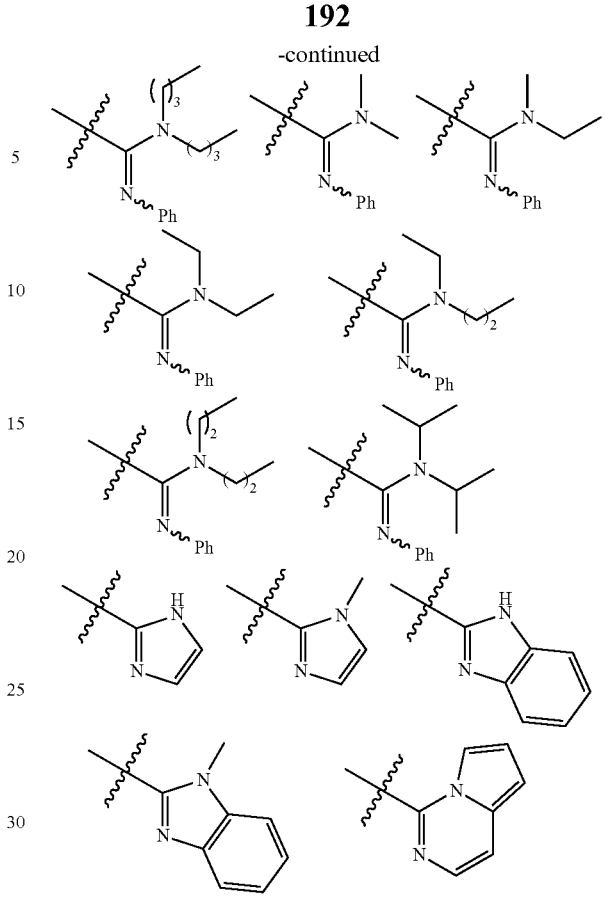

In certain embodiments, activating functional groups are amidine moieties linked through a carbon atom:

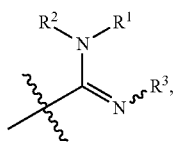

wherein each of $R^1$, $R^2$, and $R^3$ is as defined above and described in classes and subclasses herein. In certain embodiments, such carbon-linked amidine activating groups are selected from the group consisting of:

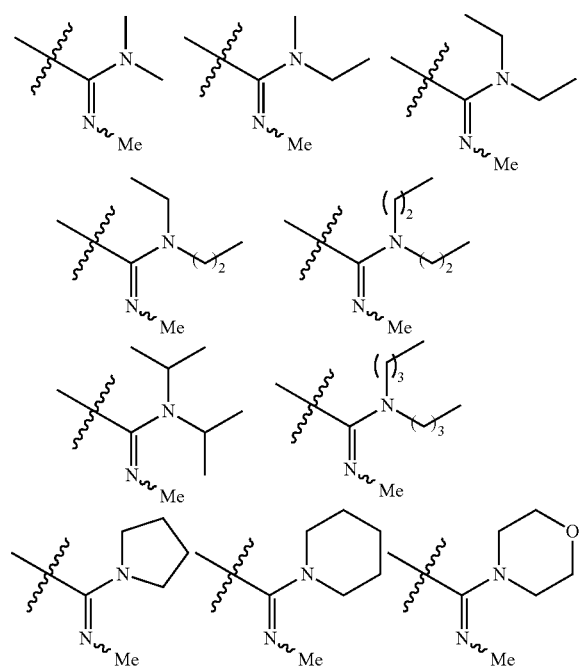

In some embodiments, one or more activating functional groups is a carbamate. In certain embodiments, a carbamate is N-linked:

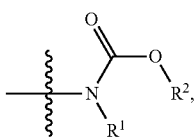

wherein each of $R^1$ and $R^2$ is as defined above and described in classes and subclasses herein. In some embodiments, a carbamate is O-linked:

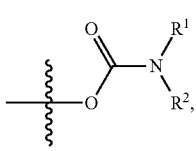

wherein each of $R^1$ and $R^2$ is as defined above and described in classes and subclasses herein.

In some embodiments, $R^2$ is selected from the group consisting of: methyl, t-butyl, t-amyl, benzyl, adamantyl, allyl, 4-methoxycarbonylphenyl, 2-(methylsulfonyl)ethyl, 2-(4-biphenylyl)-prop-2-yl, 2-(trimethylsilyl)ethyl, 2-bromoethyl, and 9-fluorenylmethyl.

In some embodiments, at least one activating functional group is a guanidine or bis-guanidine group:

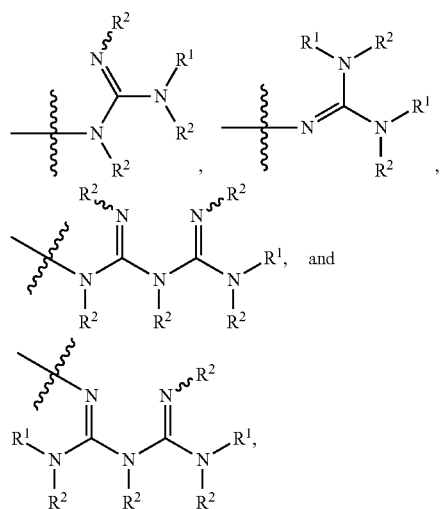

wherein each $R^1$ and $R^2$ is as defined above and described in classes and subclasses herein.

In some embodiments, each $R^1$ and $R^2$ is independently hydrogen or optionally substituted $C_{1-20}$ aliphatic. In some embodiments, each $R^1$ and $R^2$ is independently hydrogen or optionally substituted $C_{1-10}$ aliphatic. In some embodiments, any two or more $R^1$ or $R^2$ groups are taken together with intervening atoms to form one or more optionally substituted carbocyclic, heterocyclic, aryl, or heteroaryl rings. In certain embodiments, $R^1$ and $R^2$ groups are taken together to form an optionally substituted 5- or 6-membered ring. In some embodiments, three or more $R^1$ and/or $R^2$ groups are taken together to form an optionally substituted fused ring system.

In certain embodiments, where an activating functional group is a guanidine or bis guanidine moiety, it is selected from the group consisting of:

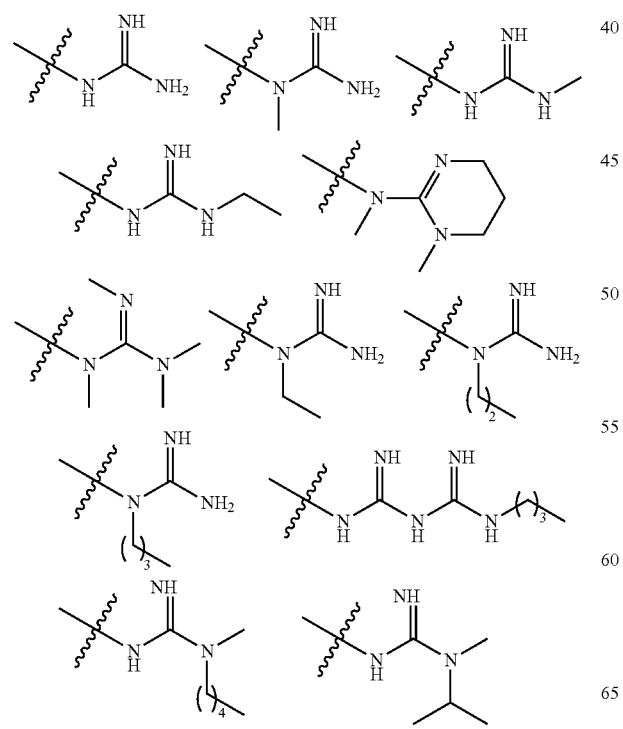

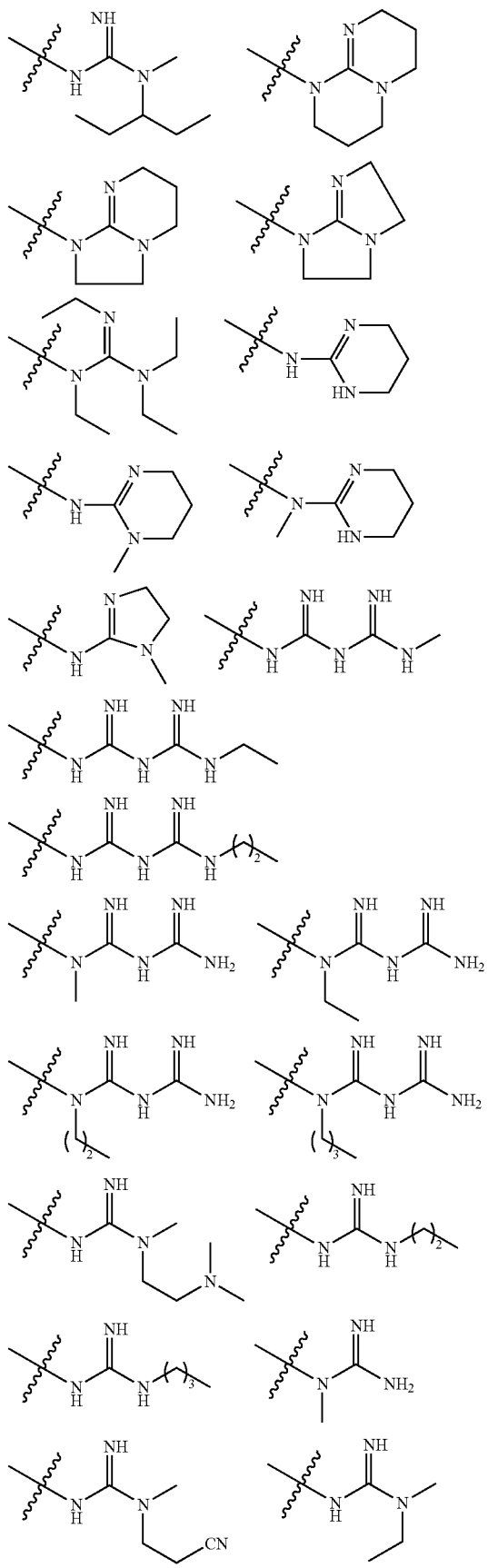

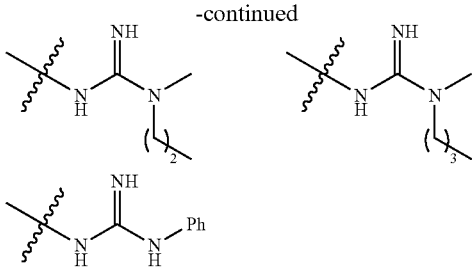

In some embodiments, an activating functional group is a urea:

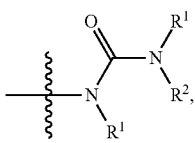

wherein each $R^1$ and $R^2$ is independently as defined above and described in classes and subclasses herein.

In certain embodiments, activating functional groups are oxime or hydrazone groups:

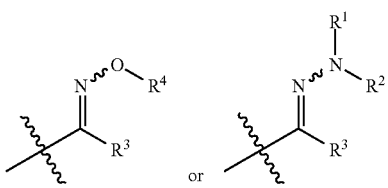

wherein each of $R^1$, $R^2$, $R^3$, and $R^4$ is as defined above and described in classes and subclasses herein.

In some embodiments, an activating functional group is an N-oxide derivative:

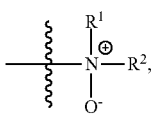

wherein each of $R^1$ and $R^2$ is as defined above and described in classes and subclasses herein.

In certain embodiments, an N-oxide activating functional group is selected from the group consisting of:

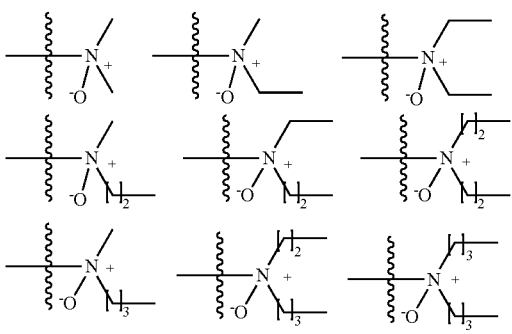
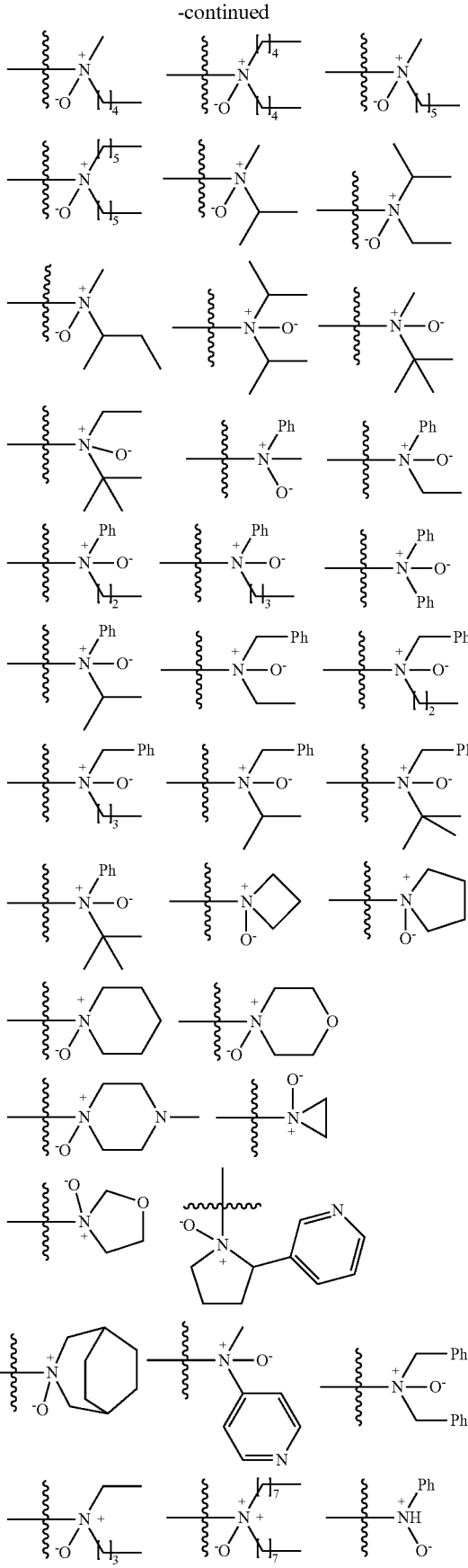

-continued

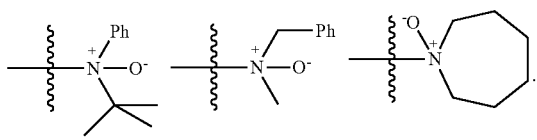

A.3. Cationic Activating Groups

In some embodiments, one or more tethered activating functional groups on provided metal complexes comprise a cationic moiety. In certain embodiments, one or more Z groups is independently a cationic functional group selected from the group consisting of quaternary amines, guanidines, bis-guanidines, amidines, and nitrogen-containing heterocycles.

In some embodiments, Z moieties are selected from one or more of the selected from a structure in Table Z-2:

TABLE Z2

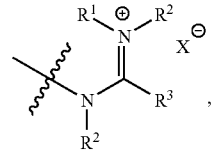

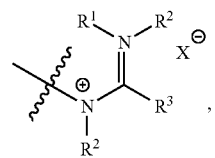

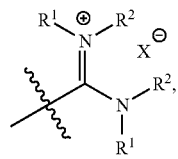

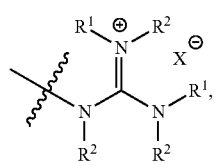

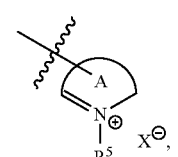

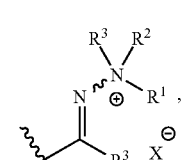

TABLE Z2-continued

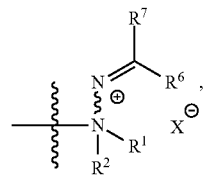

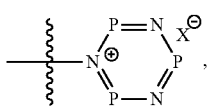

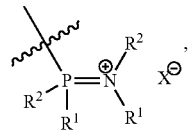

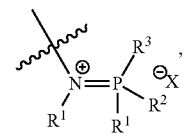

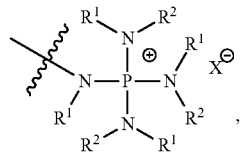

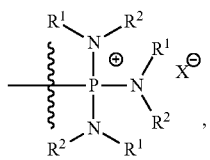

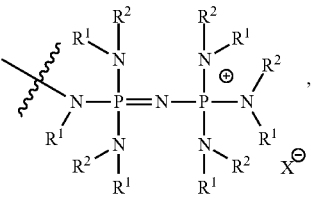

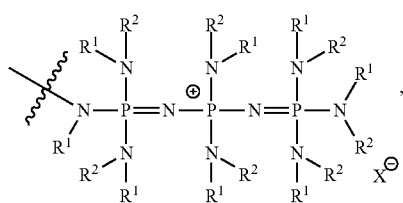

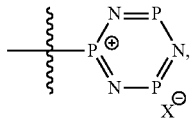

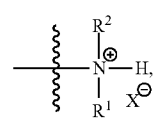

TABLE Z2-continued

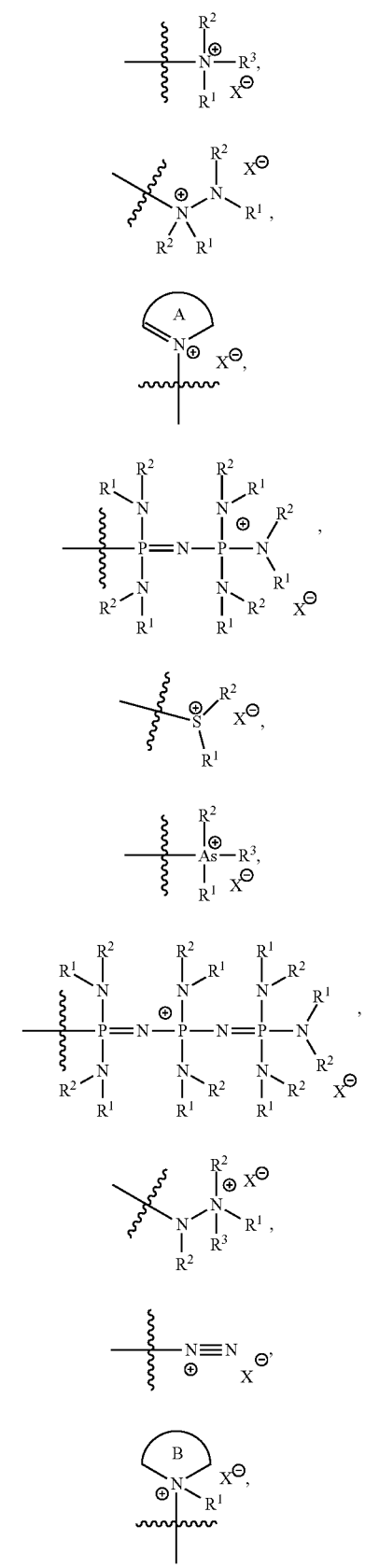

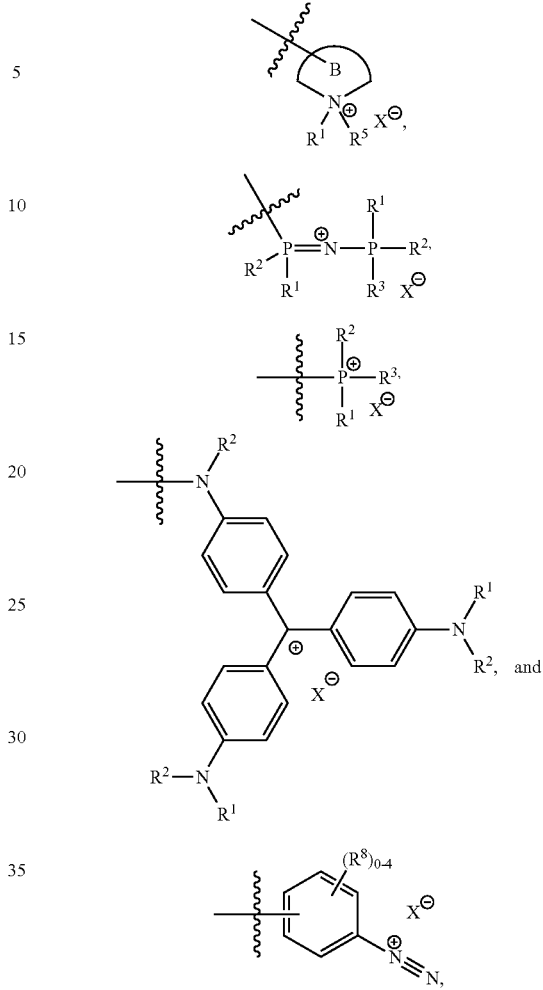

or a combination of two or more of these, wherein:
each of $R^1$, $R^2$, and $R^3$ is independently as defined above and described in classes and subclasses herein, both singly and in combination;
$R^5$ is $R^2$ or hydroxyl; wherein $R^1$ and $R^5$ can be taken together with intervening atoms to form one or more optionally substituted carbocyclic, heterocyclic, aryl, or heteroaryl rings;
each $R^6$ and $R^7$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein $R^6$ and $R^7$ can be taken together with intervening atoms to form one or more optionally substituted rings optionally containing one or more heteroatoms, and an $R^6$ and $R^7$ group can be taken with an $R^1$ or $R^2$ group to form one or more optionally substituted rings;

each occurrence of $R^8$ is independently selected from the group consisting of: halogen, $-NO_2$, $-CN$, $-SR^y$, $-S(O)R^y$, $-S(O)_2R^y$, $-NR^yC(O)R^y$, $-OC(O)R^y$, $-CO_2R^y$, $-NCO$, $-N_3$, $-OR^7$, $-OC(O)N(R^y)_2$, $-N(R^y)_2$, $-NR^yC(O)R^y$, $-NR^yC(O)OR^y$; or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein each $R^y$ is independently as defined above and described in classes and subclasses herein, and where two or more adjacent $R^8$ groups can be taken together to form an optionally substituted saturated, partially unsaturated, or aromatic 5- to 12-membered ring containing 0 to 4 heteroatoms;

Ring A is an optionally substituted, 5- to 10-membered heteroaryl group; and

Ring B is an optionally substituted, 3- to 8-membered saturated or partially unsaturated monocyclic heterocyclic ring having 0-2 heteroatoms in addition to the depicted ring nitrogen atom independently selected from nitrogen, oxygen, or sulfur.

In certain embodiments, a cationic activating functional group is a protonated amine:

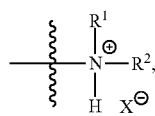

where each of $R^1$ and $R^2$ is as defined above and described in classes and subclasses herein.

In specific embodiments, a protonated amine activating functional group is selected from the group consisting of:

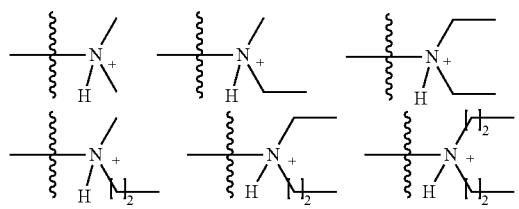

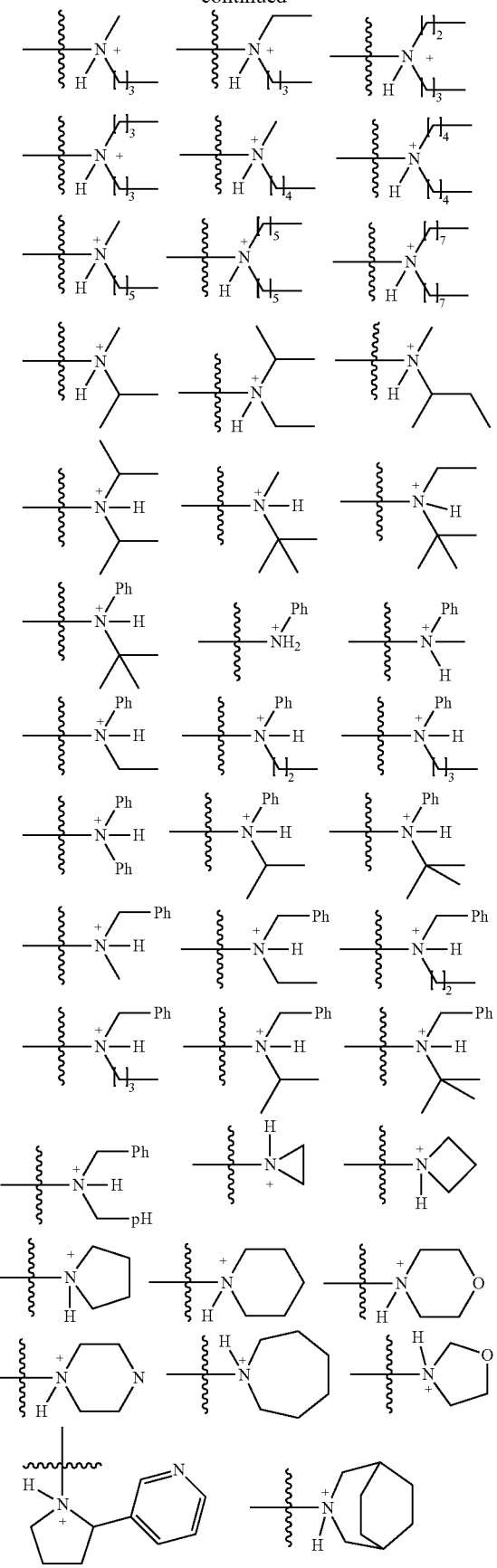

-continued

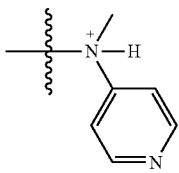

In certain embodiments, an activating functional group is a guanidinium group:

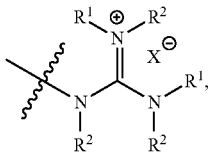

wherein each $R^1$ and $R^2$ is independently as defined above and described in classes and subclasses herein. In some embodiments, each $R^1$ and $R^2$ is independently hydrogen or optionally substituted $C_{1-20}$ aliphatic. In some embodiments, each $R^1$ and $R^2$ is independently hydrogen or optionally substituted $C_{1-10}$ aliphatic. In some embodiments, each $R^1$ and $R^2$ is independently hydrogen or $C_{1-12}$ aliphatic. In some embodiments, each $R^1$ and $R^2$ is independently hydrogen or $C_{1-20}$ heteroaliphatic. In some embodiments, each $R^1$ and $R^2$ is independently hydrogen or phenyl. In some embodiments, each $R^1$ and $R^2$ is independently hydrogen or 8- to 10-membered aryl. In some embodiments, each $R^1$ and $R^2$ is independently hydrogen or 5- to 10-membered heteroaryl. In some embodiments, each $R^1$ and $R^2$ is independently hydrogen or 3- to 7-membered heterocyclic. In some embodiments, one or more of $R^1$ and $R^2$ is optionally substituted $C_{1-12}$ aliphatic.

In some embodiments, any two or more $R^1$ or $R^2$ groups are taken together with intervening atoms to form one or more optionally substituted carbocyclic, heterocyclic, aryl, or heteroaryl rings. In certain embodiments, $R^1$ and $R^2$ groups are taken together to form an optionally substituted 5- or 6-membered ring. In some embodiments, three or more $R^1$ and/or $R^2$ groups are taken together to form an optionally substituted fused ring system.

In certain embodiments, a $R^1$ and $R^2$ group are taken together with intervening atoms to form a compound selected from:

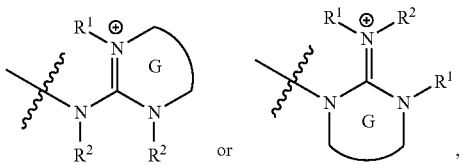

wherein each $R^1$ and $R^2$ is independently as defined above and described in classes and subclasses herein, and Ring G is an optionally substituted 5- to 7-membered saturated or partially unsaturated heterocyclic ring.

It will be appreciated that when a guanidinium cation is depicted as

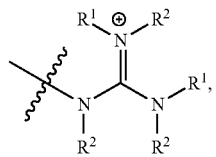

all such resonance forms are contemplated and encompassed by the present disclosure. For example, such groups can also be depicted as

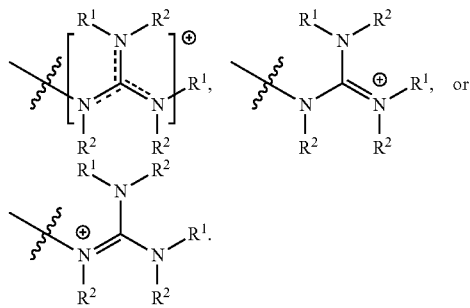

In specific embodiments, a guanidinium activating functional group is selected from the group consisting of:

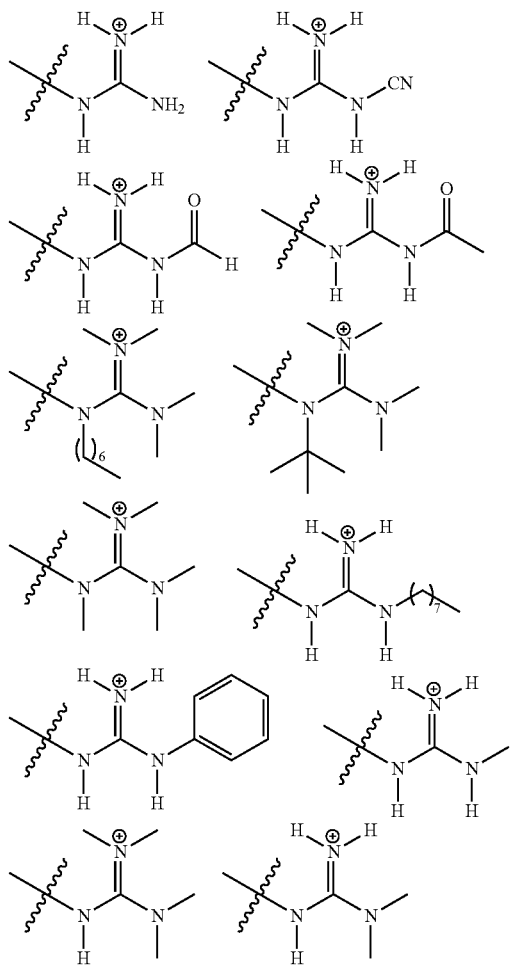

-continued

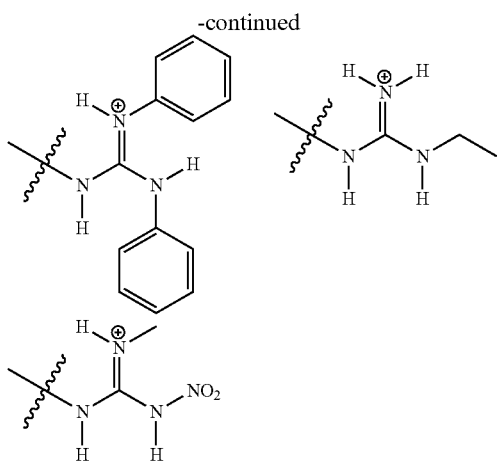

In some embodiments, an activating functional group is a sulfonium group or an arsonium group:

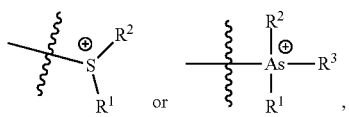

wherein each of R¹, R², and R³ are as defined above and described in classes and subclasses herein.

In specific embodiments, an arsonium activating functional group is selected from the group consisting of:

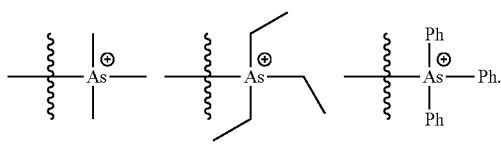

In some embodiments, an activating functional group is an optionally substituted nitrogen-containing heterocycle. In certain embodiments, the nitrogen-containing heterocycle is an aromatic heterocycle. In certain embodiments, the optionally substituted nitrogen-containing heterocycle is selected from the group consisting of: pyridine, imidazole, pyrrolidine, pyrazole, quinoline, thiazole, dithiazole, oxazole, triazole, pyrazolem, isoxazole, isothiazole, tetrazole, pyrazine, thiazine, and triazine.

In some embodiments, a nitrogen-containing heterocycle includes a quaternarized nitrogen atom. In certain embodiments, a nitrogen-containing heterocycle includes an iminium moiety such as

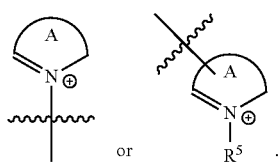

In certain embodiments, the optionally substituted nitrogen-containing heterocycle is selected from the group consisting of pyridinium, imidazolium, pyrrolidinium, pyrazolium, quinolinium, thiazolium, dithiazolium, oxazolium, triazolium, isoxazolium, isothiazolium, tetrazolium, pyrazinium, thiazinium, and triazinium.

In certain embodiments, a nitrogen-containing heterocycle is linked to a metal complex via a ring nitrogen atom. In some embodiments, a ring nitrogen to which the attachment is made is thereby quaternized, and in some embodiments, linkage to a metal complex takes the place of an N—H bond and the nitrogen atom thereby remains neutral. In certain embodiments, an optionally substituted N-linked nitrogen-containing heterocycle is a pyridinium derivative. In certain embodiments, optionally substituted N-linked nitrogen-containing heterocycle is an imidazolium derivative. In certain embodiments, optionally substituted N-linked nitrogen-containing heterocycle is a thiazolium derivative. In certain embodiments, optionally substituted N-linked nitrogen-containing heterocycle is a pyridinium derivative.

In some embodiments, an activating functional group is

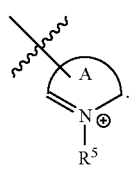

In certain embodiments, ring A is an optionally substituted, 5- to 10-membered heteroaryl group. In some embodiments, Ring A is an optionally substituted, 6-membered heteroaryl group. In some embodiments, Ring A is a ring of a fused heterocycle. In some embodiments, Ring A is an optionally substituted pyridyl group.

In some embodiments, when Z is

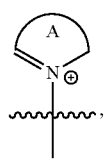

ring A is other than an imidazole, an oxazole, or a thiazole.

In specific embodiments, a nitrogen-containing heterocycle activating functional group is selected from the group consisting of:

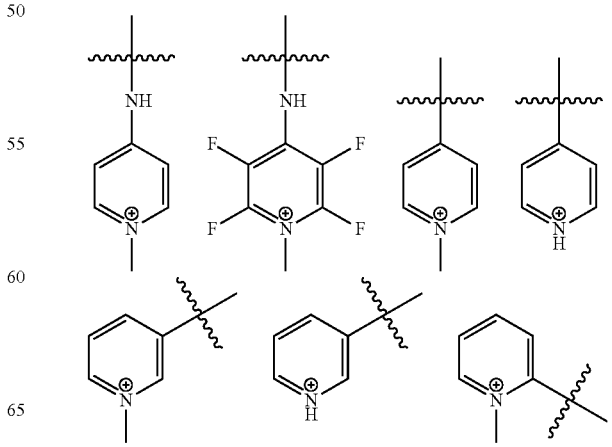

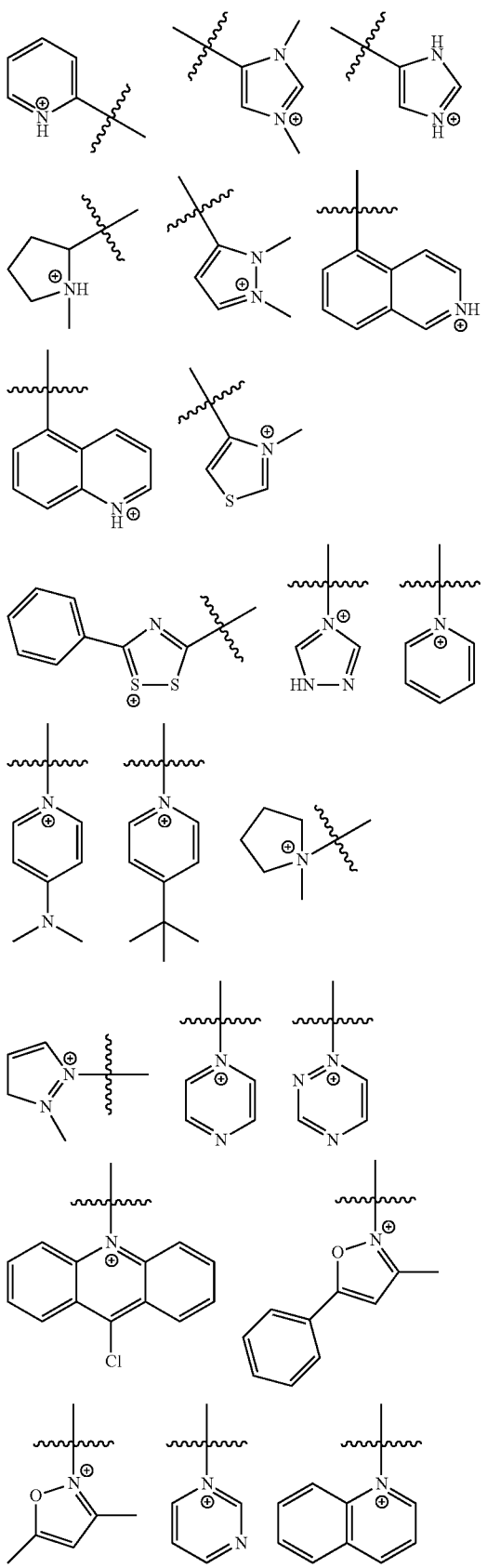

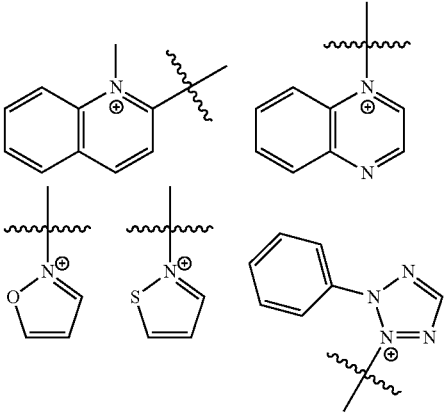

In certain embodiments, Ring A is a 5-membered saturated or partially unsaturated monocyclic heterocyclic ring. In certain embodiments, Ring A is a 6-membered saturated or partially unsaturated heterocycle. In certain embodiments, Ring A is a 7-membered saturated or partially unsaturated heterocycle. In certain embodiments, Ring A is tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. In some embodiments, Ring A is piperidinyl.

In some embodiments, an activating functional group is

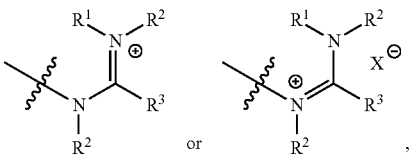

where each $R^1$, $R^2$, and $R^3$ is independently as defined above and described in classes and subclasses herein.

In some embodiments, an activating functional group is

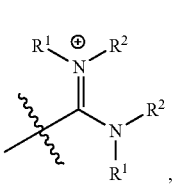

wherein each $R^1$ and $R^2$ is independently as defined above and described in classes and subclasses herein.

In some embodiments, an activating functional group is

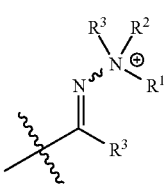

wherein each $R^1$, $R^2$, and $R^3$ is independently as defined above and described in classes and subclasses herein.

In some embodiments, an activating functional group is

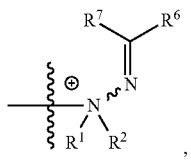

wherein each of $R^1$, $R^2$, $R^6$, and $R^7$ is as defined above and described in classes and subclasses herein.

In certain embodiments, $R^6$ and $R^7$ are each independently an optionally substituted group selected from the group consisting of $C_{1-20}$ aliphatic; $C_{1-20}$ heteroaliphatic; phenyl, and 8-10-membered aryl. In some embodiments, $R^6$ and $R^7$ are each independently an optionally substituted $C_{1-20}$ aliphatic. In some embodiments, $R^6$ and $R^7$ are each independently an optionally substituted $C_{1-20}$ heteroaliphatic having. In some embodiments, $R^6$ and $R^7$ are each independently an optionally substituted phenyl or 8-10-membered aryl. In some embodiments, $R^6$ and $R^7$ are each independently an optionally substituted 5- to 10-membered heteroaryl. In some embodiments, $R^6$ and $R^7$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In some embodiments, $R^6$ and $R^7$ are each independently an optionally substituted $C_{1-6}$ aliphatic. In some embodiments, each occurrence of $R^6$ and $R^7$ is independently methyl, ethyl, propyl, butyl, pentyl, hexyl, heptyl, octyl, or benzyl. In some embodiments, each occurrence of $R^6$ and $R^7$ is independently perfluoro. In some embodiments, each occurrence of $R^6$ and $R^7$ is independently —$CF_2CF_3$.

In some embodiments, an activating functional group is

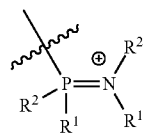

wherein each $R^1$ and $R^2$ is independently as defined above and described in classes and subclasses herein, both singly and in combination.

In some embodiments, an activating functional group is

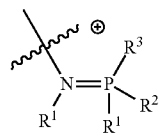

wherein each $R^1$, $R^2$, and $R^3$ is independently as defined above and described in classes and subclasses herein.

In some embodiments, an activating functional group is

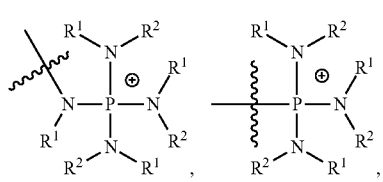

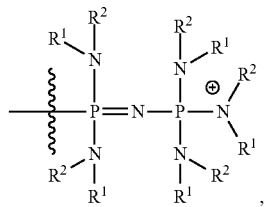

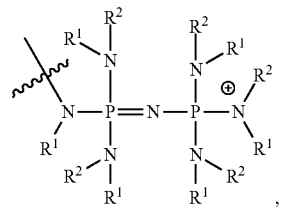

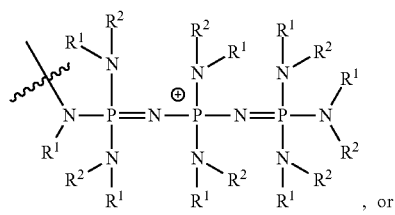

, or

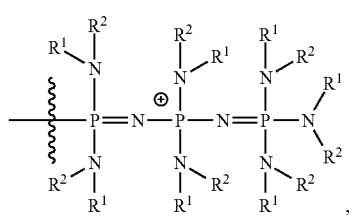

wherein each $R^1$ and $R^2$ is independently as defined above and described in classes and subclasses herein.

In some embodiments, an activating functional group is

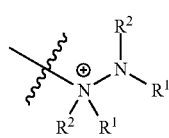

wherein each $R^1$ and $R^2$ is independently as defined above and described in classes and subclasses herein.

In some embodiments, an activating functional group is

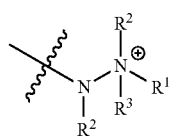

wherein each $R^1$, $R^2$, and $R^3$ is independently as defined above and described in classes and subclasses herein.

In some embodiments, an activating functional group is

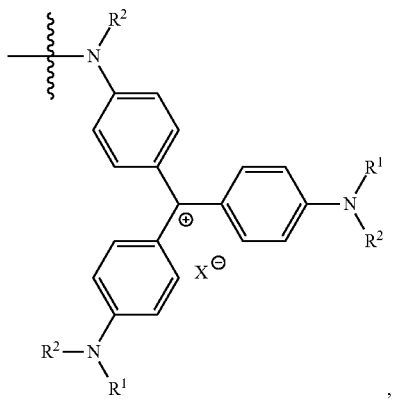

wherein each $R^1$ and $R^2$ is independently as defined above and described in classes and subclasses herein.

A.4. Phosphorus-Containing Activating Groups

In some embodiments, activating functional groups Z are phosphorous containing groups.

In certain embodiments, a phosphorous-containing functional group is chosen from the group consisting of: phosphines (—$PR^y_2$); Phosphine oxides —$P(O)R^y_2$; phosphinites $P(OR^4)R^y_2$; phosphonites $P(OR^4)_2R^y$; phosphites $P(OR^4)_3$; phosphinates $OP(OR^4)R^y_2$; phosphonates; $OP(OR^4)_2R^y$; phosphates —$OP(OR^4)_3$; phosponium salts ($[—PR^y_3]^+$) where a phosphorous-containing functional group may be linked to a metal complex through any available position (e.g. direct linkage via the phosphorous atom, or in some cases via an oxygen atom).

In certain embodiments, a phosphorous-containing functional group is chosen from the group consisting of:

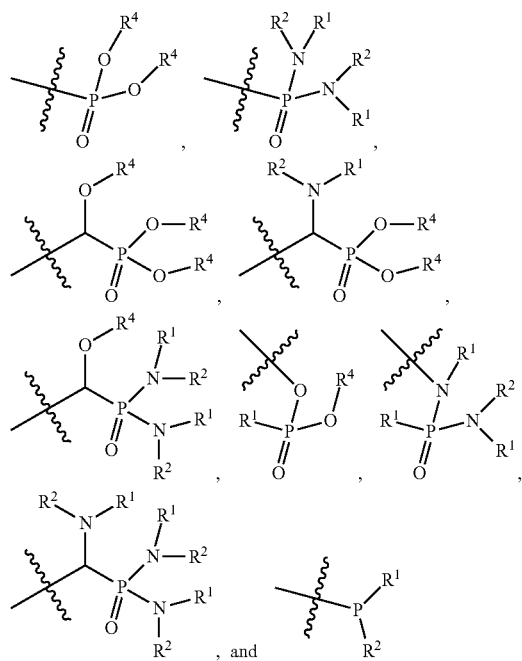

or a combination of two or more of these
wherein each $R^1$, $R^2$, and $R^4$ is as defined above and described in classes and subclasses herein, both singly and in combination; and where two $R^4$ groups can be taken together with intervening atoms to form an optionally substituted ring optionally containing one or more heteroatoms, or an $R^4$ group can be taken with an $R^1$ or $R^2$ group to an optionally substituted carbocyclic, heterocyclic, heteroaryl, or aryl ring.

In some embodiments, phosphorous containing functional groups include those disclosed in *The Chemistry of Organophosphorus Compounds. Volume 4. Ter- and Quinquevalent Phosphorus Acids and their Derivatives*. The Chemistry of Functional Group Series Edited by Frank R. Hartley (Cranfield University, Cranfield, U.K.). Wiley: New York. 1996. ISBN 0-471-95706-2, the entirety of which is hereby incorporated herein by reference.

In certain embodiments, phosphorous containing functional groups have the formula:

V is —O—, —N=, or —NR$^z$—,
b is 1 or 0,
each of $R^9$, $R^{10}$ and $R^{11}$ are independently present or absent and, if present, are independently selected from the group consisting of optionally substituted $C_1$-$C_{20}$ aliphatic, optionally substituted phenyl, optionally substituted $C_8$-$C_{14}$ aryl, optionally substituted 3- to 14-membered heterocyclic, optionally substituted 5- to 14-membered heteroaryl, halogen, =O, —OR$^z$, =NR$^z$, and N(R$^z$)$_2$ where R$^z$ is hydrogen, or an optionally substituted $C_1$-$C_{20}$ aliphatic, optionally substituted phenyl, optionally substituted 8- to 14-membered aryl, optionally substituted 3- to 14-membered heterocyclic, or optionally substituted 5- to 14-membered heteroaryl,
W is any anion, and
n' is from 1 to 4, inclusive.

In some embodiments, an activating functional group is a phosphonate group:

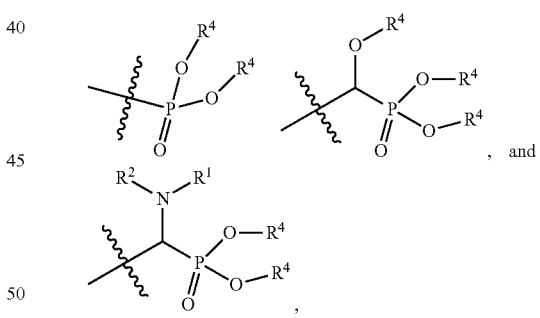

wherein each $R^1$, $R^2$, and $R^4$ is independently as defined above and described in classes and subclasses herein, both singly and in combination.

In specific embodiments, a phosphonate activating functional group is selected from the group consisting of:

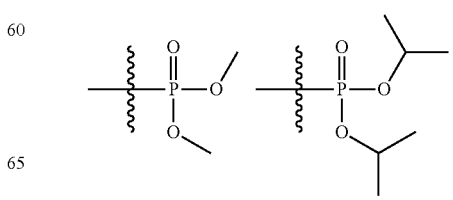

-continued

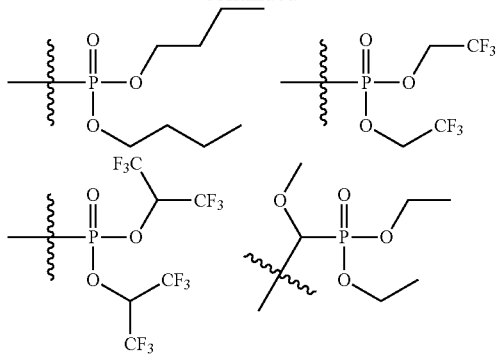

In some embodiments, an activating functional group is a phosphonic diamide group:

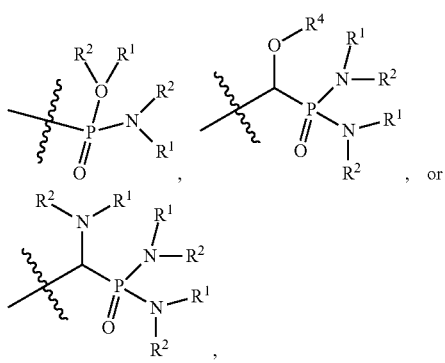

wherein each $R^1$, $R^2$, and $R^4$ is independently as defined above and described in classes and subclasses herein. In certain embodiments, each $R^1$ and $R^2$ group in a phosphonic diamide is methyl.

In some embodiments, an activating functional group is a phosphine group:

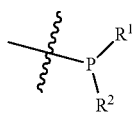

wherein $R^1$, and $R^2$ are as defined above and described in classes and subclasses herein, both singly and in combination.

In specific embodiments, a phosphine activating functional group is selected from the group consisting of:

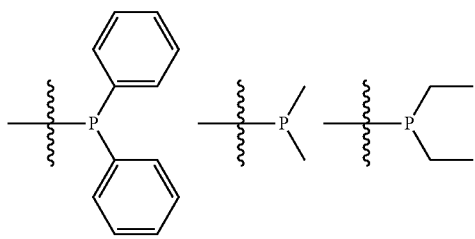

-continued

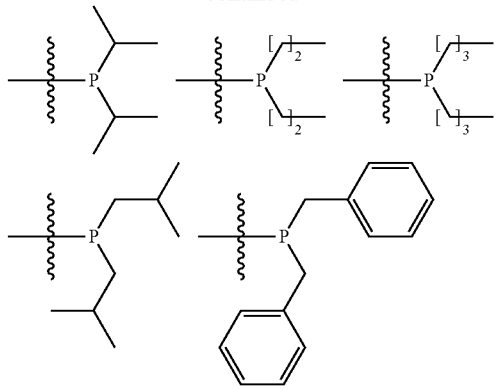

What is claimed is:

1. A metal salen complex comprising:
    a metal atom selected from cobalt and chromium;
    a salen ligand, wherein the salen ligand includes at least one tethered moiety that is either cationic, or capable of being protonated to form a cation; and
    a dianionic counterion associated with the metal atom.

2. The metal salen complex of claim 1, wherein the metal atom is cobalt.

3. The metal salen complex of claim 1, wherein the complex has a formula:

$$\left[ \begin{array}{c} \text{structure with } R^G, R^{1a'}, R^{1a}, R^{2a'}, R^{2a}, R^{3a'}, R^{3a}, M, R^{J} \end{array} \right]^{\delta}$$

wherein:
M is the metal atom selected from cobalt or chromium,
$R^{1a}$, $R^{1a'}$, $R^{2a}$, $R^{2a'}$, $R^{3a}$, and $R^{3a'}$ are independently a $\sim(Z)_m$ group, hydrogen, R, halogen, —OR, —NR$_2$, —SR, —CN, —NO$_2$, —SO$_2$R, —SOR, —SO$_2$NR$_2$, —CNO, —NRSO$_2$R, —NCO, —N$_3$, —SiR$_3$, —C(O)R, —NRC(O)R, —OC(O)R, —CO$_2$R, —OC(O)N(R)$_2$, —C(O)NR$_2$, —NRC(O)NR—, —NRC(O)OR, or an optionally substituted radical selected from the group consisting of C$_{1-20}$ aliphatic, C$_{1-20}$ heteroaliphatic, phenyl, a 3- to 8-membered saturated or partially unsaturated monocyclic carbocycle, a 7- to 14-membered saturated, partially unsaturated or aromatic polycyclic carbocycle, a 5- to 6-membered monocyclic heteroaryl ring having 1-4 heteroatoms independently selected from nitrogen, oxygen, and sulfur, a 3- to 8-membered monocyclic saturated or partially unsaturated heterocyclic ring having 1-3 heteroatoms independently selected from nitrogen, oxygen, and sulfur, a 6- to 12-membered polycyclic saturated or partially unsaturated heterocycle having 1-5 heteroatoms independently selected from nitrogen, oxygen, and sulfur, and an 8- to 10-membered bicyclic heteroaryl ring having 1-5 heteroatoms independently selected from nitrogen, oxygen, and sulfur;

each R is independently hydrogen or an optionally substituted radical selected from the group consisting of: acyl, carbamoyl, arylalkyl, phenyl, $C_{1-12}$ aliphatic, $C_{1-12}$ heteroaliphatic, a 3- to 8-membered saturated or partially unsaturated monocyclic carbocycle, a 7- to 14-membered saturated, partially unsaturated or aromatic polycyclic carbocycle, a 5- to 6-membered monocyclic heteroaryl ring having 1-4 heteroatoms independently selected from nitrogen, oxygen, and sulfur, a 3- to 8-membered monocyclic saturated or partially unsaturated heterocyclic ring having 1-3 heteroatoms independently selected from nitrogen, oxygen, and sulfur, and an 8- to 10-membered bicyclic heteroaryl ring having 1-5 heteroatoms independently selected from nitrogen, oxygen, sulfur, an oxygen protecting group, or a nitrogen protecting group, or two R on the same nitrogen atom are taken with the nitrogen to form a 3- to 7-membered heterocyclic ring; wherein any of [$R^{2a'}$ and $R^{3a'}$], [$R^{2a}$ and $R^{3a}$], [$R^{1a}$ and $R^{2a}$], and [$R^{1a'}$ and $R^{2a'}$] may optionally be taken together with the carbon atoms to which they are attached to form one or more rings which may in turn be substituted with —$(Z)_m$ or one or more $R^d$ groups;

$R^G$ is selected from the group consisting of:

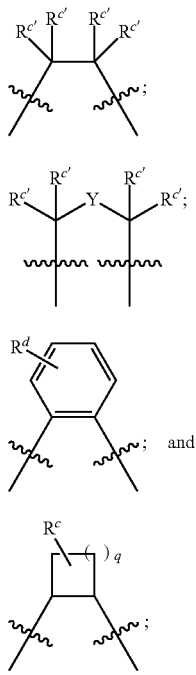

$R^J$ is a bivalent linker selected from the group consisting of: —C(O)—, —C(O)C(O)—, —C(O)—$R^H$—C(O)—, —SO—, —SO$_2$—, —P(O)(OR$^{J1}$)—, —P(O)R$^{J1}$—, —R$^{J1}$C=N—, —C(O)—$R^H$—P(O)(OR$^{J1}$)—, —C(O)—$R^H$—S(O)—, —C(O)—$R^H$—S(O)$_2$—, —SO$_2$—$R^H$—P(O)(OR$^{J1}$)—, —SO—$R^H$—P(O)(OR$^{J1}$)—, and —C(O)R$^H$—;

each $R^c$ is optionally present, and if present is, independently at each occurrence, a —$(Z)_m$ group, halogen, —OR, —NR$_2$, —SR, —CN, —NO$_2$, —SO$_2$R, —SOR, —SO$_2$NR$_2$, —CNO, —NRSO$_2$R, —NCO, —N$_3$, —SiR$_3$, —C(O)R, —NRC(O)R, —OC(O)R, —CO$_2$R, —OC(O)N(R)$_2$, —C(O)NR$_2$, —NRC(O)NR—, —NRC(O)OR, or an optionally substituted radical selected from the group consisting of arylalkyl, phenyl, $C_{1-20}$ aliphatic, $C_{1-20}$ heteroaliphatic, a 3- to 8-membered saturated or partially unsaturated monocyclic carbocycle, a 7- to 14-membered saturated, partially unsaturated or aromatic polycyclic carbocycle, a 5- to 6-membered monocyclic heteroaryl ring having 1-4 heteroatoms independently selected from nitrogen, oxygen, and sulfur, a 3- to 8-membered monocyclic saturated or partially unsaturated heterocyclic ring having 1-3 heteroatoms independently selected from nitrogen, oxygen, and sulfur, and an 8- to 10-membered bicyclic heteroaryl ring having 1-5 heteroatoms independently selected from nitrogen, oxygen, and sulfur, where two or more $R^c$ groups may be taken together with the carbon atoms to which they are attached and any intervening atoms to form one or more optionally substituted rings; and when two $R^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine, and an optionally substituted alkene;

each $R^{c'}$ is, independently at each occurrence, H or $R^c$;

Y is a bivalent linker selected from the group consisting of: —(CR$^{c'}_2$)$_{q'}$—, —NR—, —N(R)C(O)—, —C(O)NR—, —O—, —C(O)—, —OC(O)—, —C(R)$_2$—, —C(O)O—, —S—, —SO—, —SO$_2$—, —C(=S)—, —C(=NR)—, or —N=N—, a polyether, $C_{1-6}$ aliphatic, a $C_3$ to $C_8$ substituted or unsubstituted carbocycle, and a 3- to 8-membered substituted or unsubstituted heterocycle;

each $R^d$ is, independently at each occurrence, a —$(Z)_m$ group, halogen, R, —OR, —NR$_2$, —SR, —CN, —NO$_2$, —SO$_2$R, —SOR, —SO$_2$NR$_2$, —CNO, —NRSO$_2$R, —NCO, —N$_3$, —SiR$_3$, —C(O)R, —NRC(O)R, —OC(O)R, —CO$_2$R, —OC(O)N(R)$_2$, —C(O)NR$_2$, —NRC(O)NR—, —NRC(O)OR, or an optionally substituted group selected from the group consisting of $C_{1-20}$ aliphatic, $C_{1-20}$ heteroaliphatic having 1-4 heteroatoms independently selected from the group consisting of nitrogen, oxygen, and sulfur, 6-10-membered aryl, 5-10-membered heteroaryl having 1-4 heteroatoms independently selected from nitrogen, oxygen, and sulfur, and 4-7-membered heterocyclic having 1-2 heteroatoms independently selected from the group consisting of nitrogen, oxygen, and sulfur;

where two or more $R^d$ groups may be taken together with the carbon atoms to which they are attached and any intervening atoms to form one or more optionally substituted rings optionally containing one or more heteroatoms;

$R^H$ is selected from the group consisting of $R^G$ and —(CR$^{c'}_2$)$_{q'}$, $R^{J1}$ is, independently at each occurrence, selected from the group consisting of:
hydrogen, a metal atom, and an optionally substituted radical selected from the group consisting of acyl carbamoyl, arylalkyl, phenyl, $C_{1-12}$ aliphatic, $C_{1-12}$ heteroaliphatic, 4- to 7-membered heterocyclyl, a 5- to 6-membered monocyclic heteroaryl ring having 1-4 heteroatoms independently selected from nitrogen, oxygen, and sulfur, and an oxygen protecting group;

q' is an integer from 1 to 6, inclusive;

q is an integer from 0 to 5, inclusive;

x is 0, 1, or 2;

δ represents the net charge of the metal salen complex exclusive of any non-covalently bound counterions and may be any number between −1 and +5; and ⸺(Z)$_m$ represents one or more activating moieties attached to the metal salen complex, where ⸺ is a linker moiety covalently coupled to the metal salen complex;

each Z is an activating functional group; and m is an integer from 1 to 4, inclusive, representing the number of Z groups present on the linker moiety.

4. The metal salen complex of claim 3, wherein at least one of [$R^{2a}$ and $R^{3a}$] and [$R^{2a'}$ and $R^{3a'}$] are taken together to form an optionally substituted ring.

5. The metal salen complex of claim 4 having the formula:

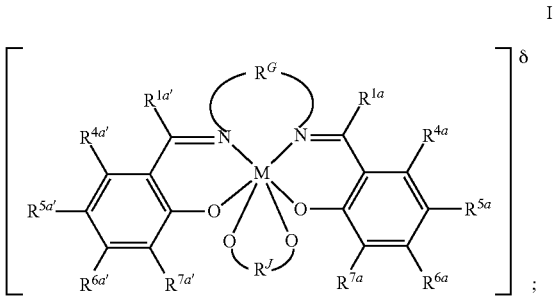

Ia

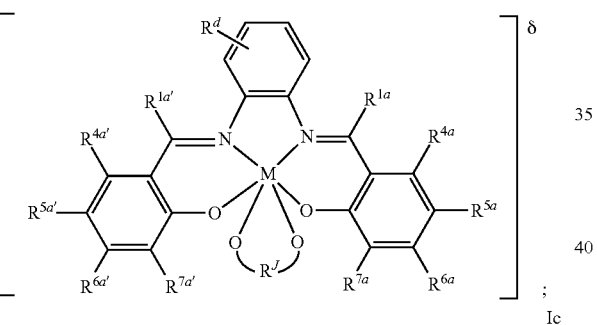

Ib

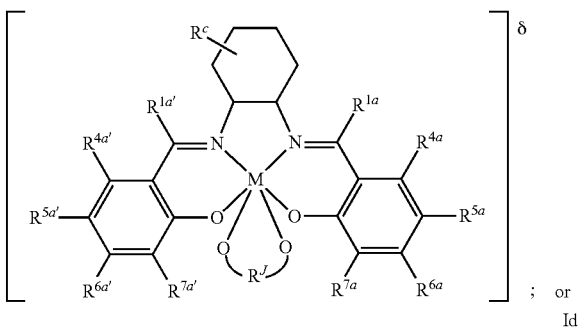

Ic

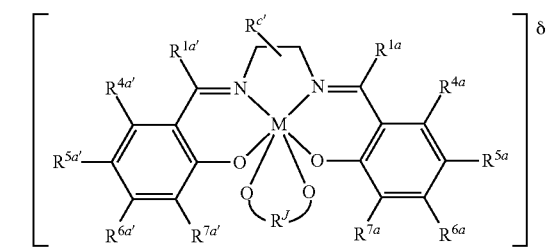

; or

Id wherein:

$R^{4a}$, $R^{4a'}$, $R^{5a}$, $R^{5a'}$, $R^{6a}$, $R^{6a'}$, $R^{7a}$, and $R^{7a'}$ are each independently hydrogen or an $R^d$ group; and wherein [$R^{1a}$ and $R^{4a}$], [$R^{1a'}$ and $R^{4a'}$] and any two adjacent $R^{4a}$, $R^{4a'}$, $R^{5a}$, $R^{5a'}$, $R^{6a}$, $R^{6a'}$, $R^{7a}$, and $R^{7a'}$ groups can be taken together with intervening atoms to form one or more optionally substituted rings.

6. The metal salen complex of claim 5, wherein one or more of $R^{1a}$, $R^{1a'}$, $R^{4a}$, $R^{4a'}$, $R^{5a}$, $R^{5a'}$, $R^{6a}$, $R^{6a'}$, $R^{7a}$, or $R^{7a'}$ are independently a ⸺(Z)$_m$ group.

7. The metal salen complex of claim 4, wherein the salen complex is selected from the group consisting of:

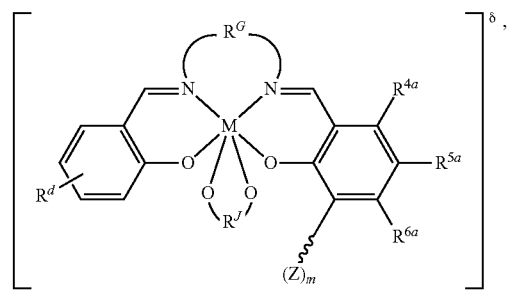

Ia-1

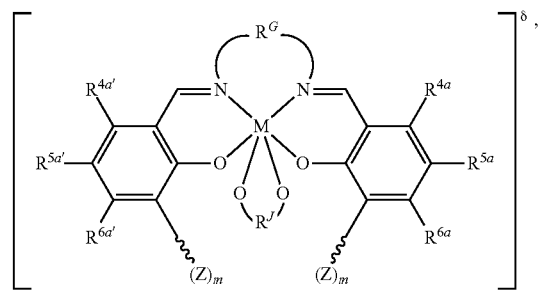

Ia-2

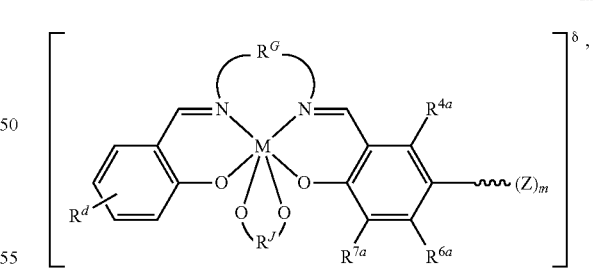

Ia-3

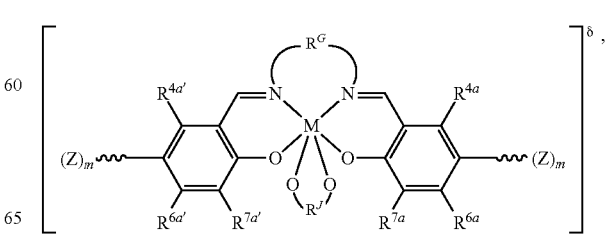

Ia-4 wherein:
$R^{4a}$, $R^{4a'}$, $R^{5a}$, $R^{5a'}$, $R^{6a}$, $R^{6a'}$, $R^{7a}$, and $R^{7a'}$ are each independently hydrogen or an $R^d$ group;
wherein [$R^{1a}$ and $R^{4a}$], [$R^{1a'}$ and $R^{4a'}$] and any two adjacent $R^{4a}$, $R^{4a'}$, $R^{5a}$, $R^{5a'}$, $R^{6a}$, $R^{6a'}$, $R^{7a}$, and $R^{7a'}$ groups can be taken together with intervening atoms to form one or more optionally substituted rings.

8. The metal salen complex of claim 7, wherein is selected from the group:

9. The metal salen complex of claim 7, wherein is selected from the group:

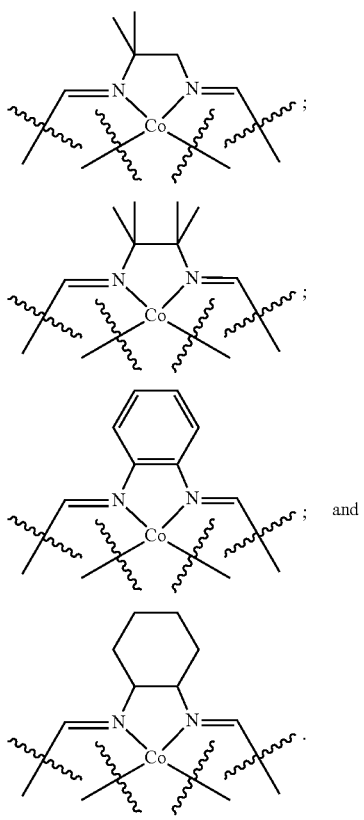

10. The metal salen complex of claim 7, wherein

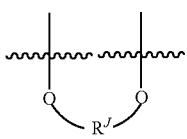

is oxalate, malonate, maleate, fumurate, succinate, glutarate or phthalate.

11. The metal salen complex of claim 7, wherein Z is selected from the following:

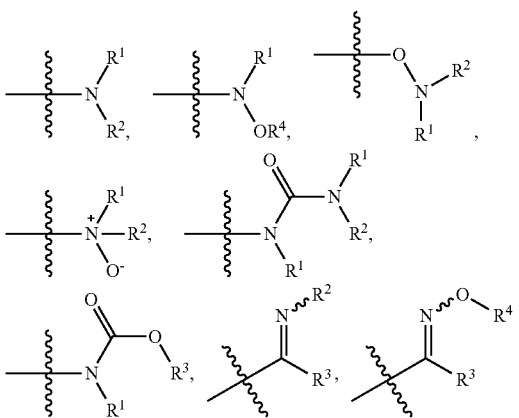

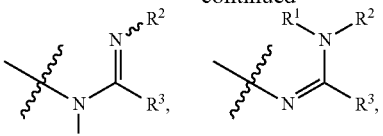
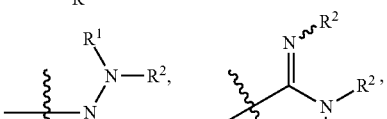
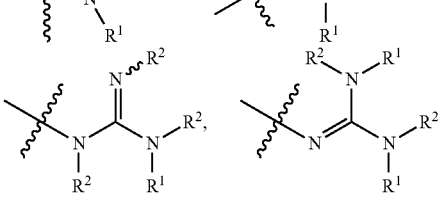
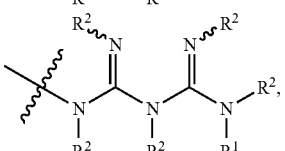
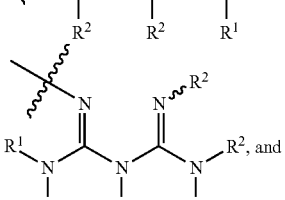
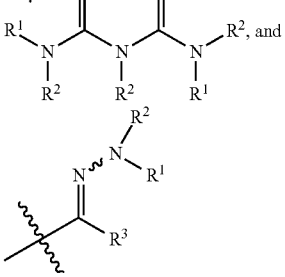
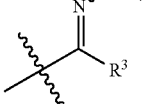

or a combination of two or more of these, wherein:

each $R^1$ and $R^2$ is independently hydrogen or an optionally substituted radical selected from the group consisting of $C_{1-20}$ aliphatic, $C_{1-20}$ heteroaliphatic, a 3- to 8-membered saturated or partially unsaturated monocyclic carbocycle, a 7- to 14-membered saturated or partially unsaturated polycyclic carbocycle, a 5- to 6-membered monocyclic heteroaryl ring having 1-4 heteroatoms independently selected from nitrogen, oxygen, and sulfur, an 8- to 14-membered polycyclic heteroaryl ring having 1-5 heteroatoms independently selected from nitrogen, oxygen, and sulfur, a 3- to 8-membered saturated or partially unsaturated monocyclic heterocyclic ring having 1-3 heteroatoms independently selected from nitrogen, oxygen, and sulfur, a 6- to 14-membered saturated or partially unsaturated polycyclic heterocycle having 1-5 heteroatoms independently selected from nitrogen, oxygen, and sulfur, phenyl, and an 8- to 14-membered polycyclic aryl ring; wherein $R^1$ and $R^2$ can be taken together with intervening atoms to form one or more optionally substituted rings optionally containing one or more additional heteroatoms;

each $R^3$ is independently hydrogen or an optionally substituted radical selected from the group consisting of $C_{1-20}$ aliphatic $C_{1-20}$ heteroaliphatic, a 3- to 8-membered saturated or partially unsaturated monocyclic carbocycle, a 7- to 14-membered saturated or partially unsaturated polycyclic carbocycle, a 5- to 6-membered monocyclic heteroaryl ring having 1-4 heteroatoms independently selected from nitrogen, oxygen, and sulfur, an 8- to 14-membered polycyclic heteroaryl ring having 1-5 heteroatoms independently selected from nitrogen, oxygen, and sulfur, a 3- to 8-membered saturated or partially unsaturated monocyclic heterocyclic ring having 1-3 heteroatoms independently selected from nitrogen, oxygen, and sulfur, a 6- to 14-membered saturated or partially unsaturated polycyclic heterocycle having 1-5 heteroatoms independently selected from nitrogen, oxygen, and sulfur, phenyl, and an 8- to 14-membered polycyclic aryl ring;

wherein an $R^3$ group can be taken with an $R^1$ or $R^2$ group to form one or more optionally substituted rings; and each $R^4$ is independently hydrogen, a hydroxyl protecting group, or an optionally substituted radical selected from the group consisting of $C_{1-20}$ acyl, $C_{1-20}$ aliphatic, $C_{1-20}$ heteroaliphatic, a 3- to 8-membered saturated or partially unsaturated monocyclic carbocycle, a 7- to 14-membered saturated or partially unsaturated polycyclic carbocycle, a 5- to 6-membered monocyclic heteroaryl ring having 1-4 heteroatoms independently selected from nitrogen, oxygen, and sulfur, an 8- to 14-membered polycyclic heteroaryl ring having 1-5 heteroatoms independently selected from nitrogen, oxygen, and sulfur, a 3- to 8-membered saturated or partially unsaturated monocyclic heterocyclic ring having 1-3 heteroatoms independently selected from nitrogen, oxygen, and sulfur, a 6- to 14-membered saturated or partially unsaturated polycyclic heterocycle having 1-5 heteroatoms independently selected from nitrogen, oxygen, and sulfur, phenyl, and an 8- to 14-membered polycyclic aryl ring.

12. The metal salen complex of claim 7, wherein Z is selected from the following:

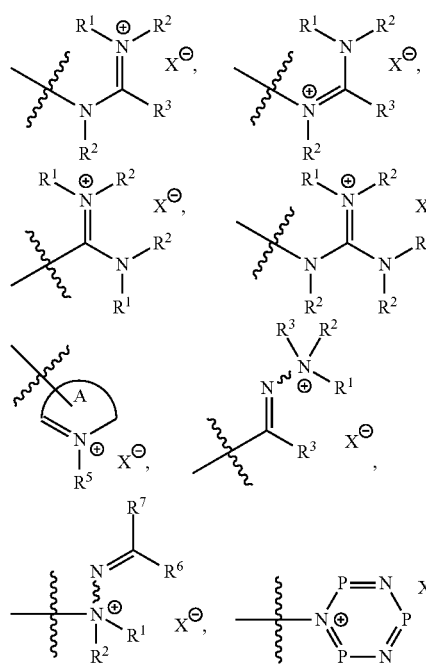

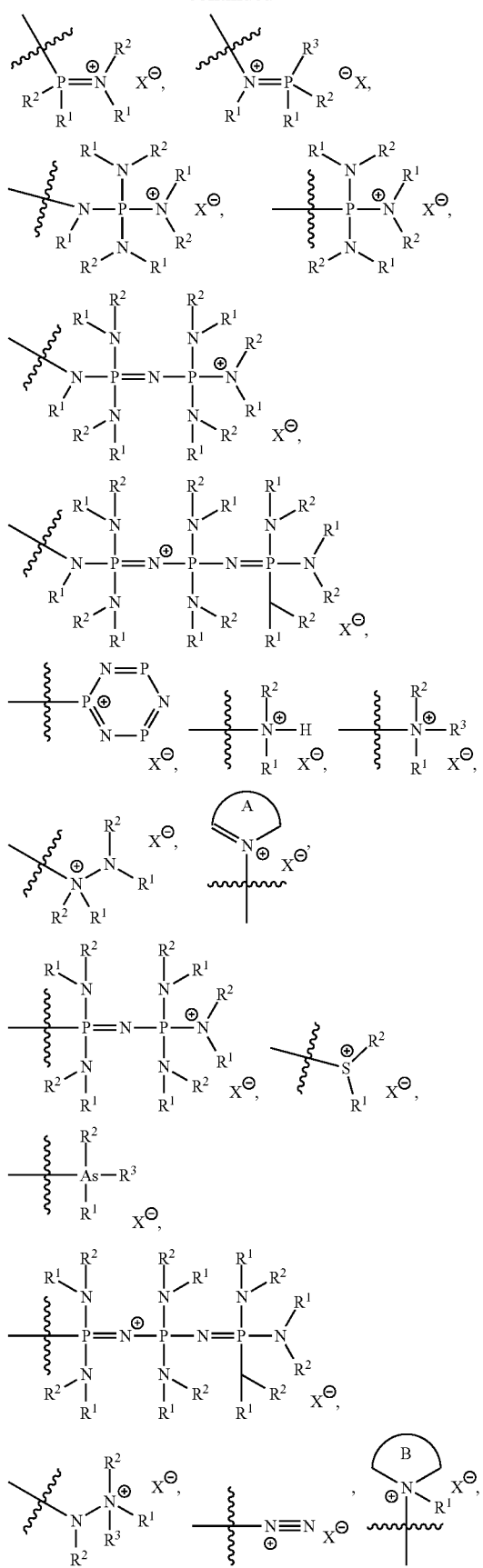

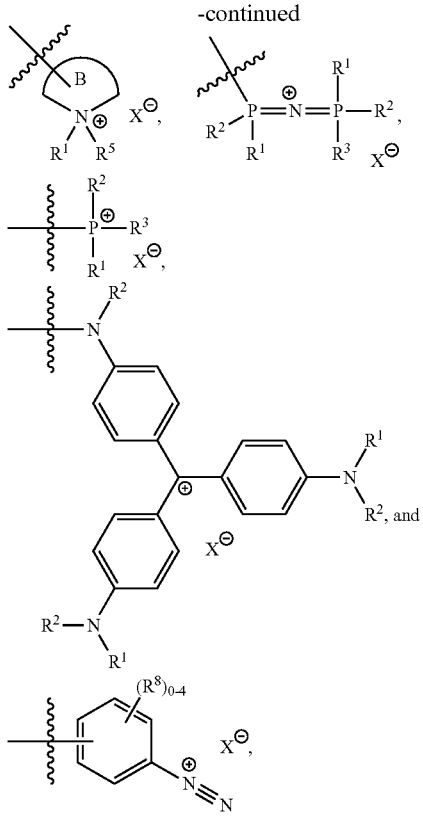

or a combination of two or more of these,
wherein:
X is an anion;
each $R^1$ and $R^2$ is independently hydrogen or an optionally substituted radical selected from the group consisting of $C_{1-20}$ aliphatic, $C_{1-20}$ heteroaliphatic, a 3- to 8-membered saturated or partially unsaturated monocyclic carbocycle, a 7- to 14-membered saturated or partially unsaturated polycyclic carbocycle, a 5- to 6-membered monocyclic heteroaryl ring having 1-4 heteroatoms independently selected from nitrogen, oxygen, and sulfur, an 8- to 14-membered polycyclic heteroaryl ring having 1-5 heteroatoms independently selected from nitrogen, oxygen, and sulfur, a 3- to 8-membered saturated or partially unsaturated monocyclic heterocyclic ring having 1-3 heteroatoms independently selected from nitrogen, oxygen, and sulfur, a 6- to 14-membered saturated or partially unsaturated polycyclic heterocycle having 1-5 heteroatoms independently selected from nitrogen, oxygen, and sulfur, phenyl, and an 8- to 14-membered polycyclic aryl ring; wherein $R^1$ and $R^2$ can be taken together with intervening atoms to form one or more optionally substituted rings optionally containing one or more additional heteroatoms;

each $R^3$ is independently hydrogen or an optionally substituted radical selected from the group consisting of $C_{1-20}$ aliphatic, $C_{1-20}$ heteroaliphatic, a 3- to 8-membered saturated or partially unsaturated monocyclic carbocycle, a 7- to 14-membered saturated or partially unsaturated polycyclic carbocycle, a 5- to 6-membered monocyclic heteroaryl ring having 1-4 heteroatoms independently selected from nitrogen, oxygen, and sulfur, an 8- to 14-membered polycyclic heteroaryl ring having 1-5 heteroatoms independently selected from nitrogen, oxygen, and sulfur, a 3- to 8-membered saturated or partially unsaturated monocyclic heterocyclic ring having 1-3 heteroatoms independently selected from nitrogen, oxygen, and sulfur, a 6- to 14-membered saturated or partially unsaturated polycyclic heterocycle having 1-5 heteroatoms independently selected from nitrogen, oxygen, and sulfur, phenyl; and an 8- to 14-membered polycyclic aryl ring; wherein an $R^3$ group can be taken with an $R^1$ or $R^2$ group to form one or more optionally substituted rings;

$R^5$ is $R^2$ or hydroxyl;
wherein $R^1$ and $R^5$ can be taken together with intervening atoms to form one or more optionally substituted carbocyclic, heterocyclic, aryl, or heteroaryl rings;

each $R^6$ and $R^7$ is independently hydrogen or an optionally substituted radical selected from the group consisting of $C_{1-20}$ aliphatic, $C_{1-20}$ heteroaliphatic, a 3- to 8-membered saturated or partially unsaturated monocyclic carbocycle, a 7- to 14-membered saturated or partially unsaturated polycyclic carbocycle, a 5- to 6-membered monocyclic heteroaryl ring having 1-4 heteroatoms independently selected from nitrogen, oxygen, and sulfur, an 8- to 14-membered polycyclic heteroaryl ring having 1-5 heteroatoms independently selected from nitrogen, oxygen, and sulfur, a 3- to 8-membered saturated or partially unsaturated monocyclic heterocyclic ring having 1-3 heteroatoms independently selected from nitrogen, oxygen, and sulfur, a 6- to 14-membered saturated or partially unsaturated polycyclic heterocycle having 1-5 heteroatoms independently selected from nitrogen, oxygen, and sulfur, phenyl, and an 8- to 14-membered polycyclic aryl ring; wherein $R^6$ and $R^7$ can be taken together with intervening atoms to form one or more optionally substituted rings optionally containing one or more heteroatoms, and an $R^6$ and $R^7$ group can be taken with an $R^1$ or $R^2$ group to form one or more optionally substituted rings;

each occurrence of $R^8$ is independently selected from: halogen, —$NO_2$, —CN, —NCO, —$N_3$, and an optionally substituted radical selected from the group consisting of $C_{1-20}$ aliphatic, $C_{1-20}$ heteroaliphatic, a 3- to 8-membered saturated or partially unsaturated monocyclic carbocycle, a 7- to 14-membered saturated or partially unsaturated polycyclic carbocycle, a 5- to 6-membered monocyclic heteroaryl ring having 1-4 heteroatoms independently selected from nitrogen, oxygen, and sulfur, an 8- to 14-membered polycyclic heteroaryl ring having 1-5 heteroatoms independently selected from nitrogen, oxygen, and sulfur, a 3- to 8-membered saturated or partially unsaturated monocyclic heterocyclic ring having 1-3 heteroatoms independently selected from nitrogen, oxygen, and sulfur, a 6- to 14-membered saturated or partially unsaturated polycyclic heterocycle having 1-5 heteroatoms independently selected from nitrogen, oxygen, and sulfur, phenyl, and an 8- to 14-membered polycyclic aryl ring; where two or more adjacent $R^8$ groups can be taken together to form an optionally substituted saturated, partially unsaturated, or aromatic 5- to 12-membered ring containing 0 to 4 heteroatoms;

Ring A is an optionally substituted 5- to 10-membered heteroaryl group; and

Ring B is an optionally substituted 3- to 8-membered saturated or partially unsaturated monocyclic heterocyclic ring having 0-2 heteroatoms in addition to the depicted ring nitrogen atom independently selected from nitrogen, oxygen, and sulfur.
13. The metal salen complex of claim 1, wherein the complex is selected from:
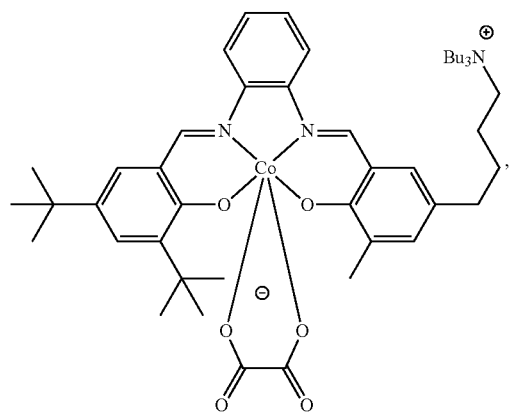
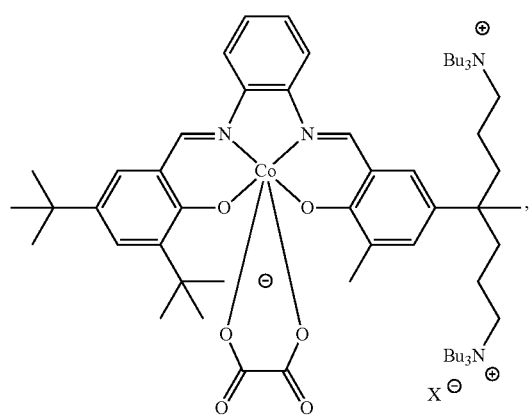
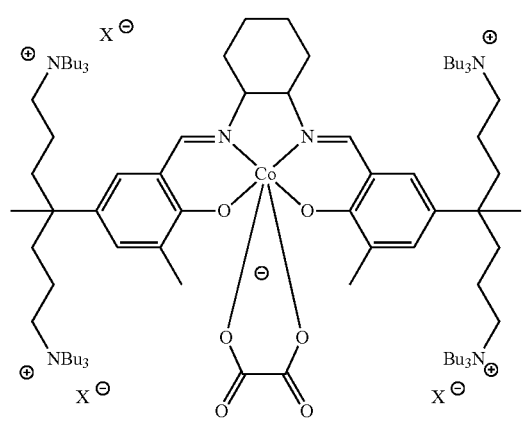
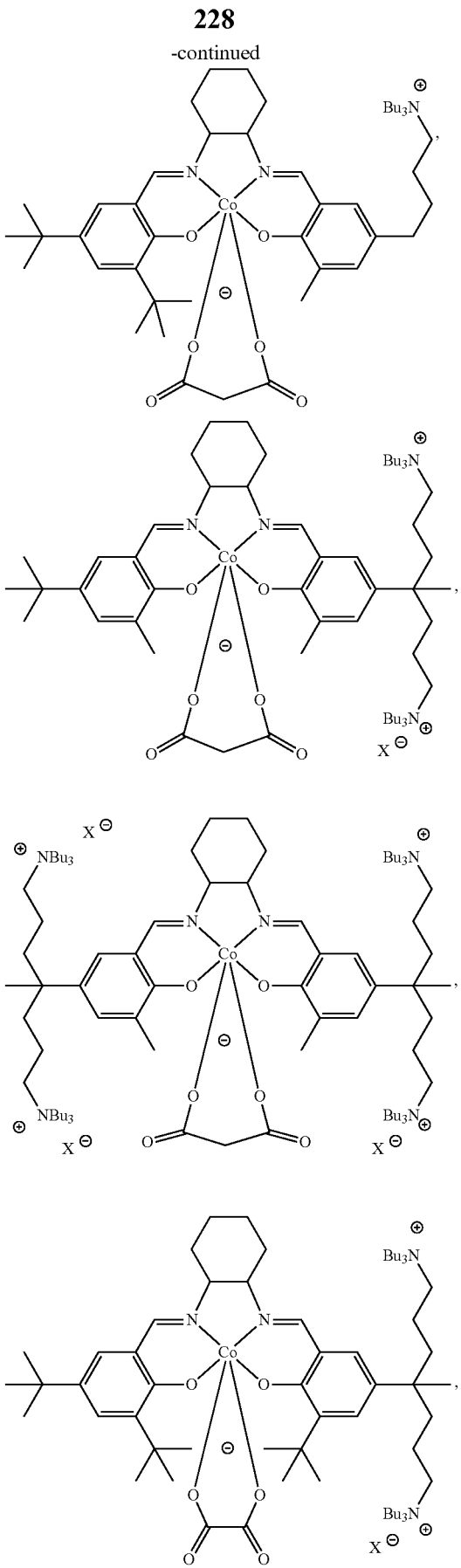

| 229 -continued | 230 -continued |
|---|---|
| 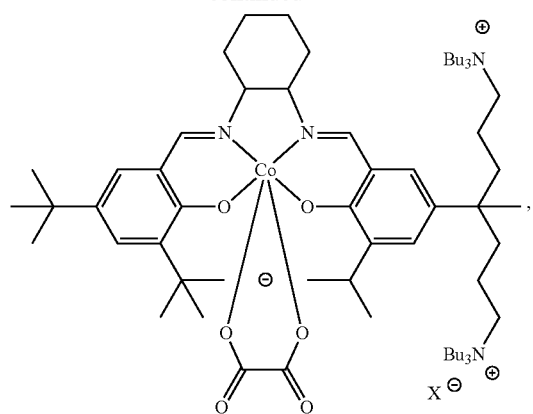 | 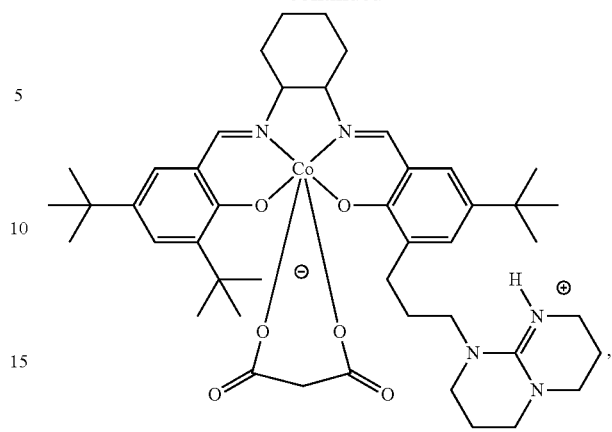 |
| 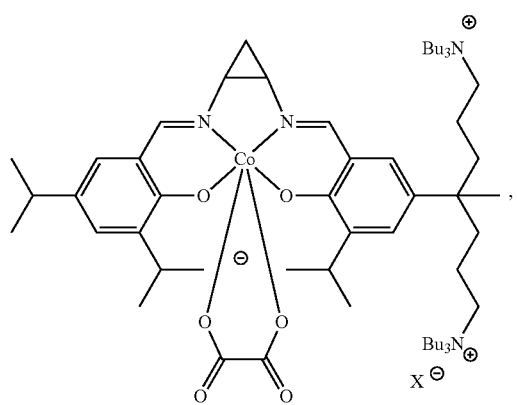 | 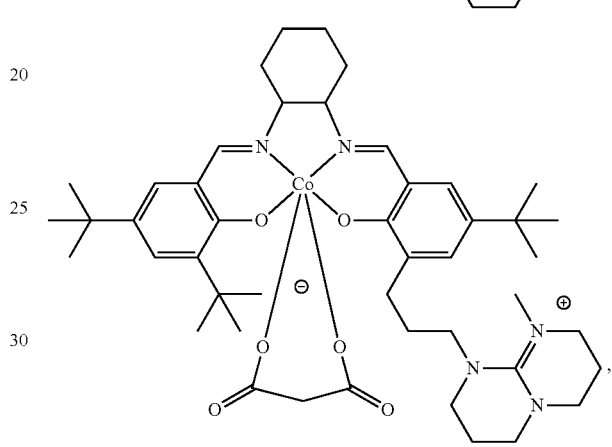 |
| 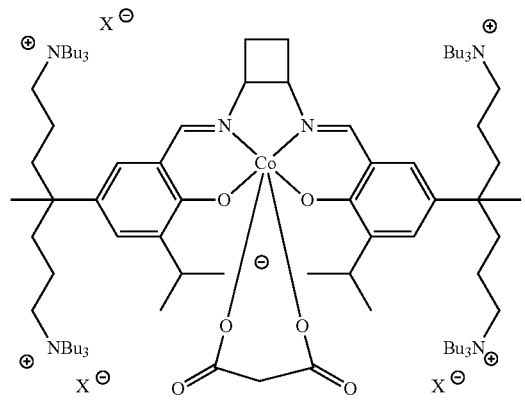 | 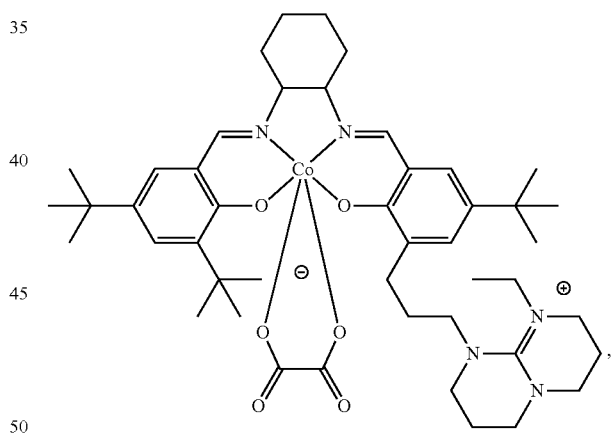 |
| 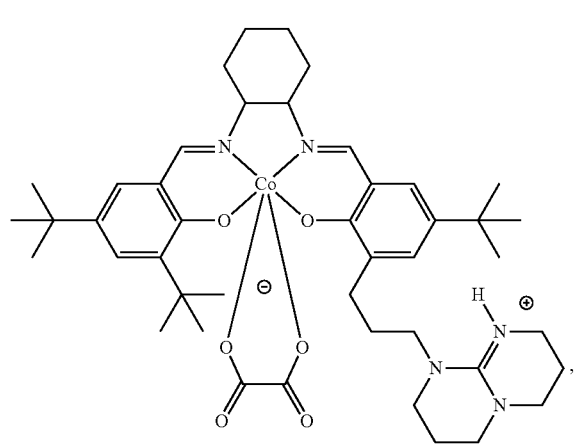 | |

231
-continued
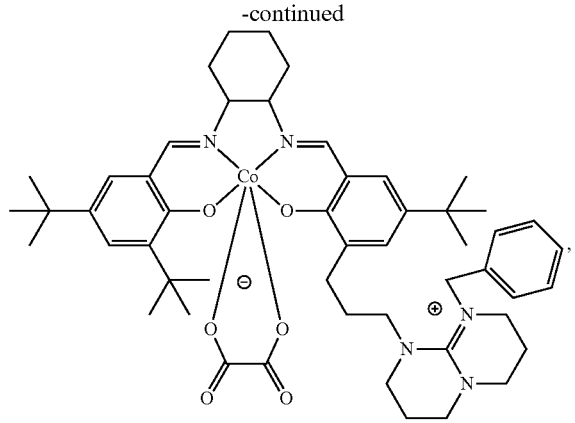
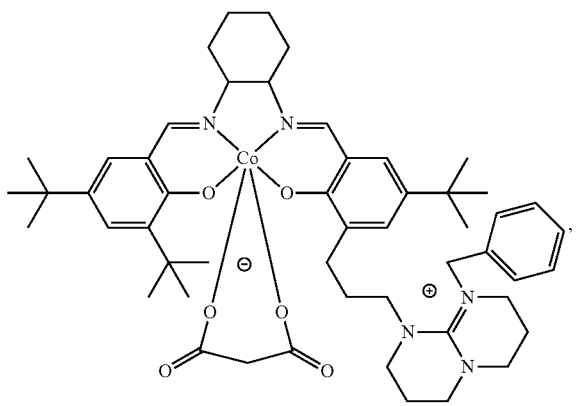
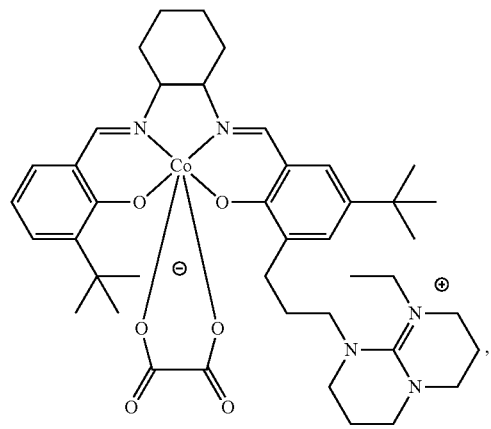
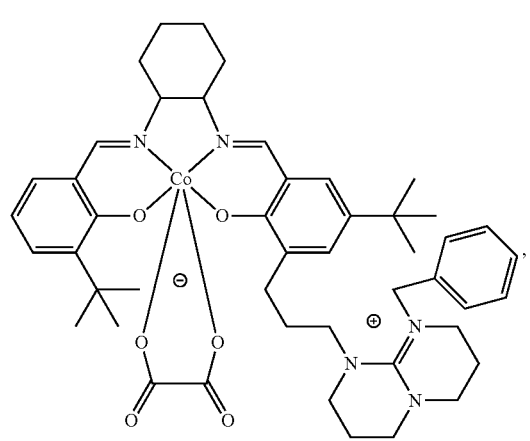
232
-continued
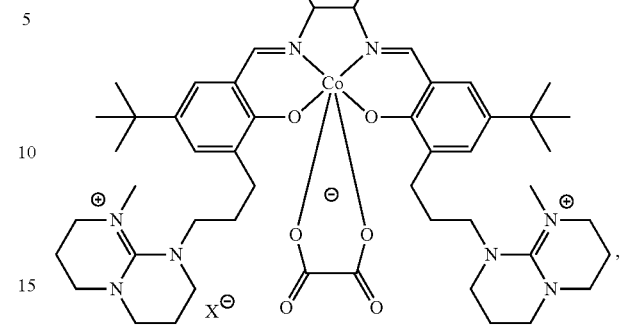
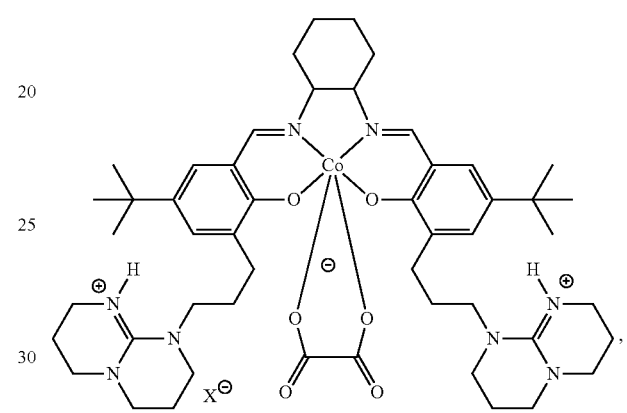
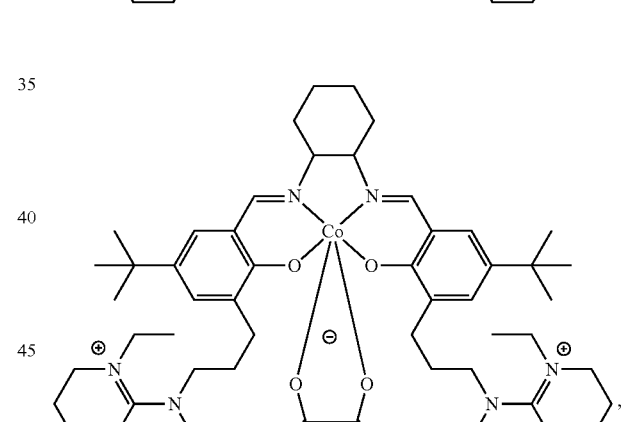
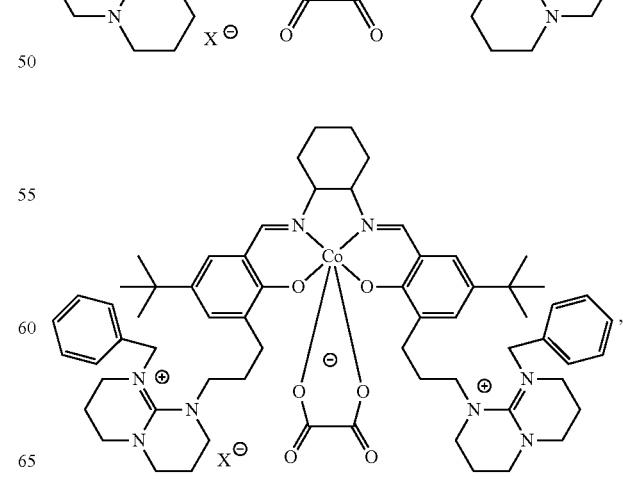

233
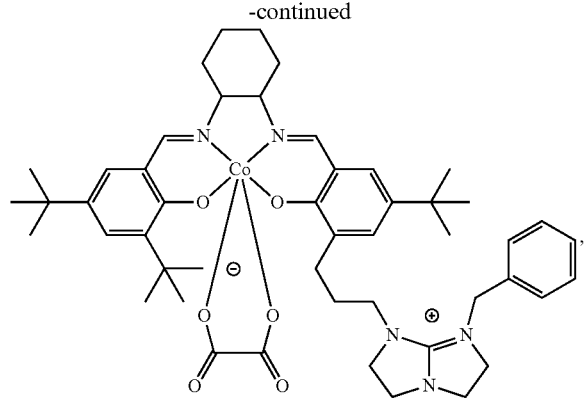
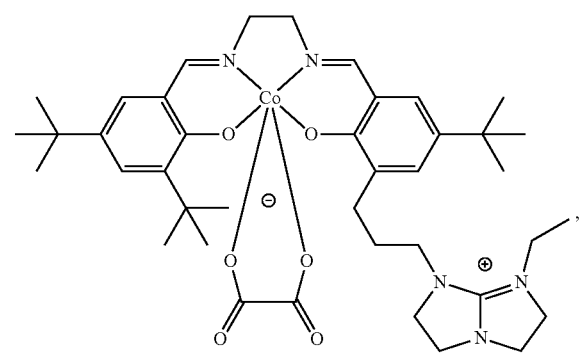
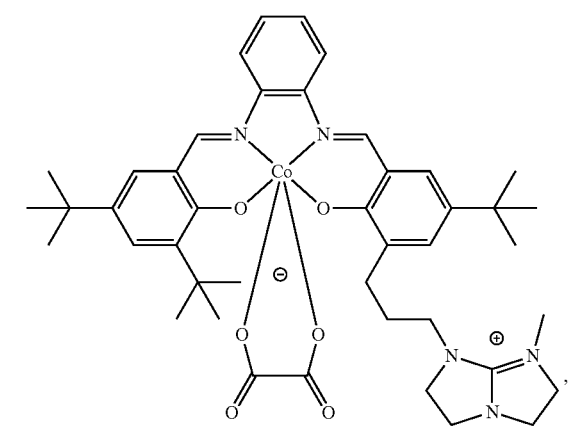
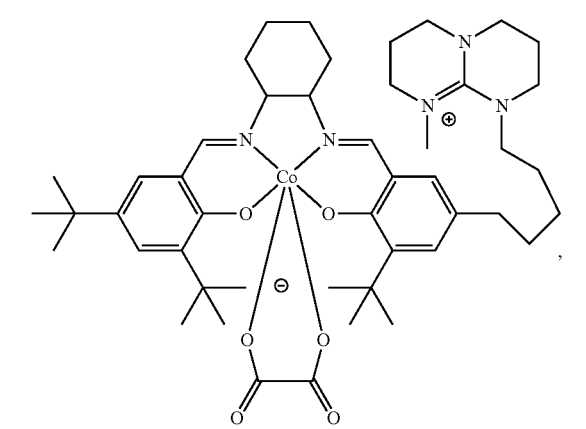
234
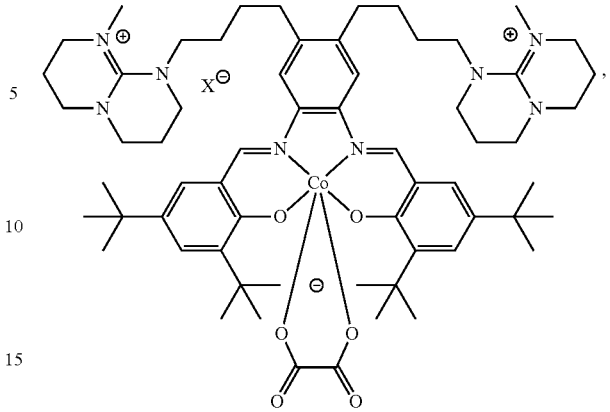
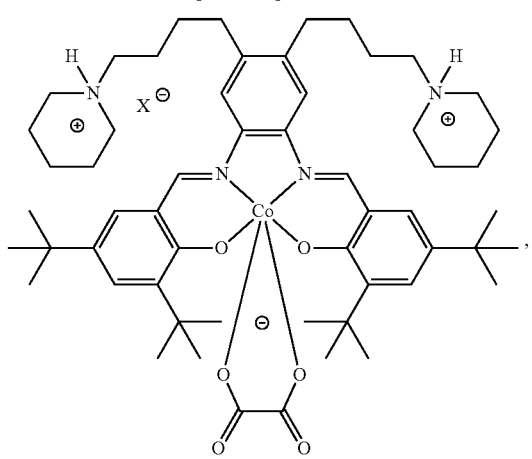
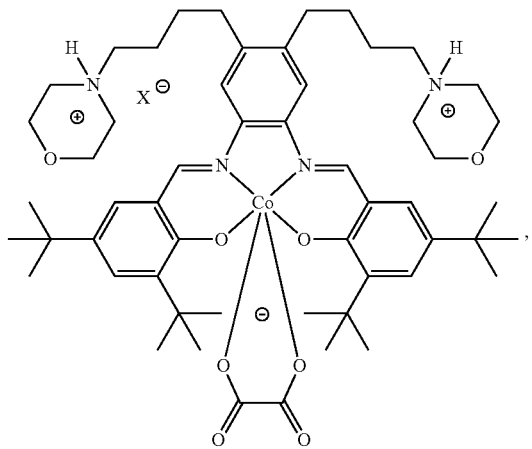
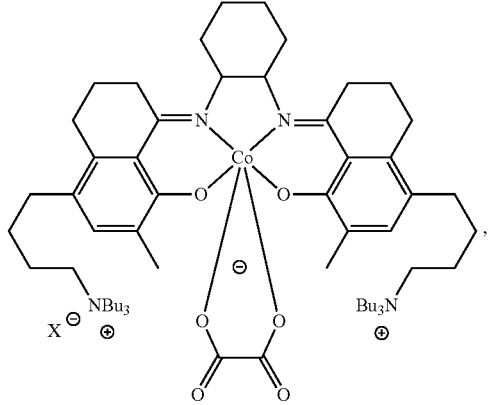

235
-continued
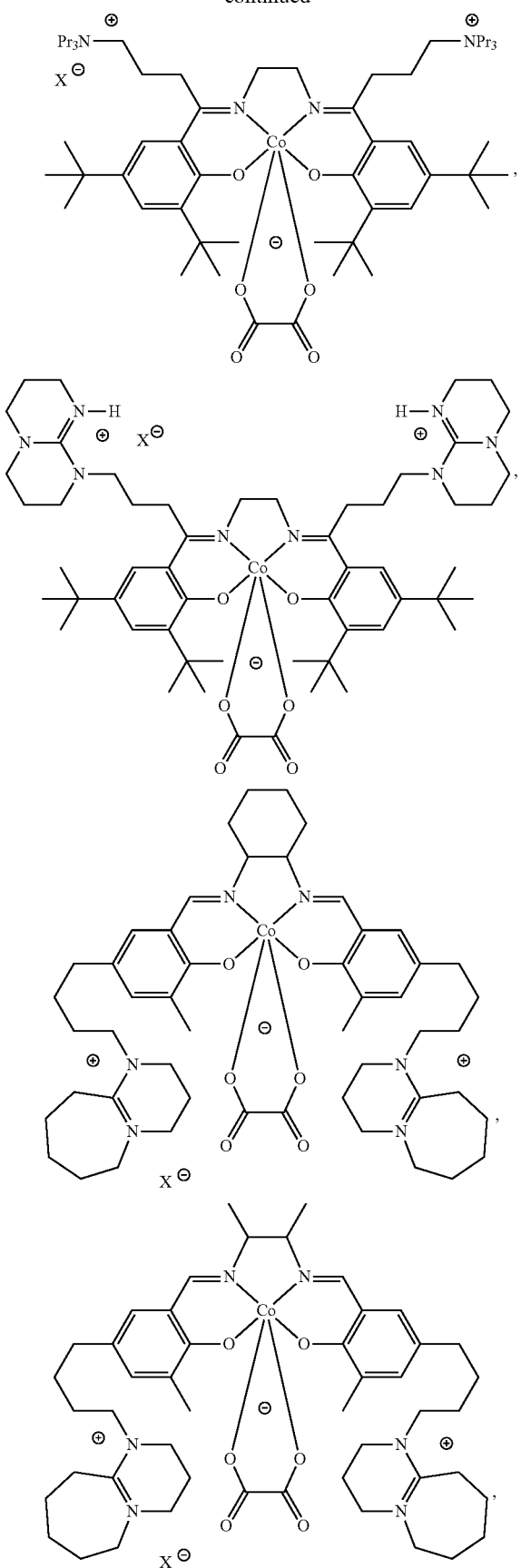
236
-continued
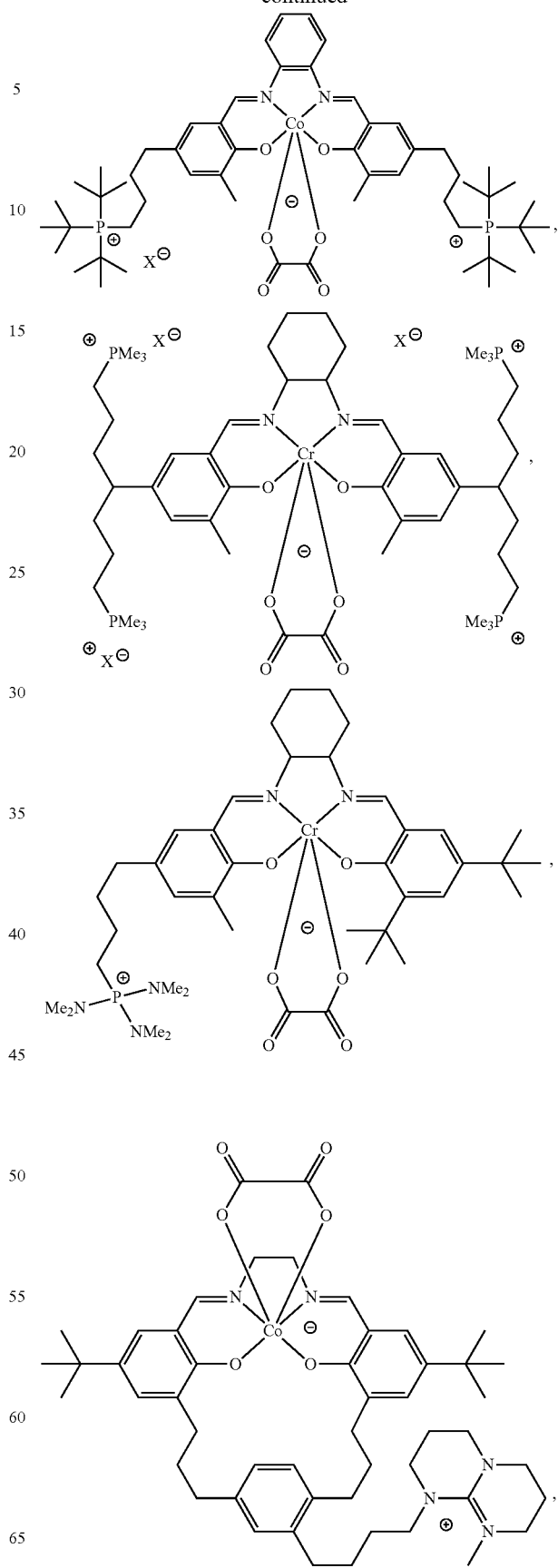

237
-continued
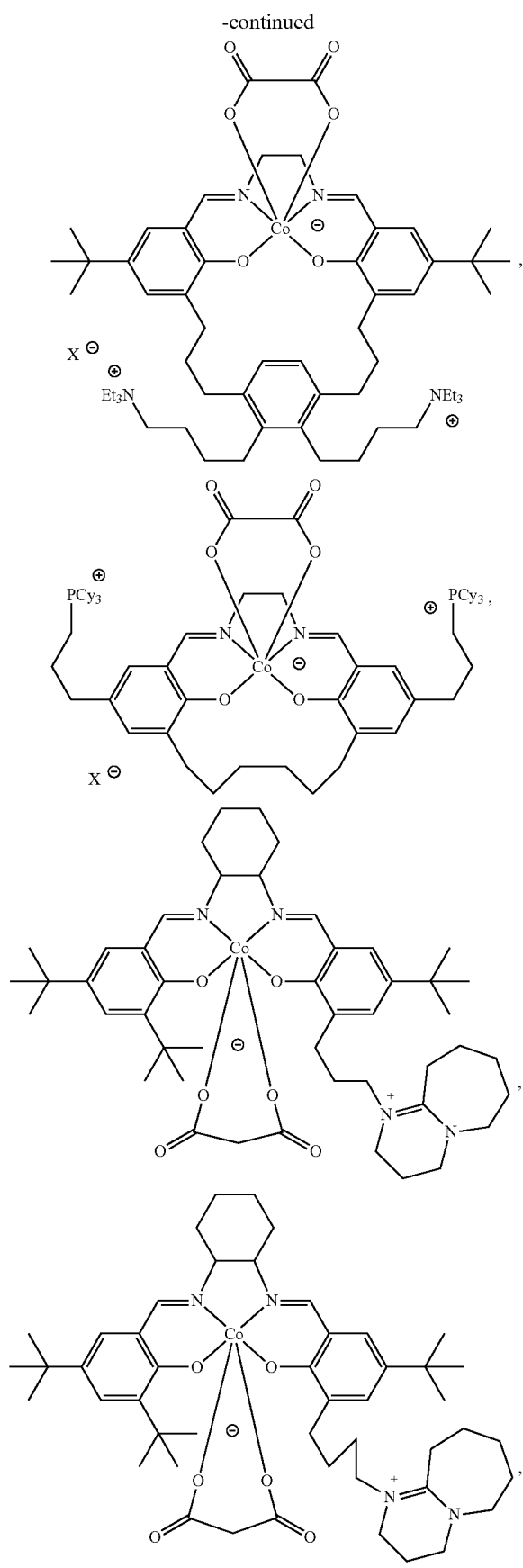
238
-continued
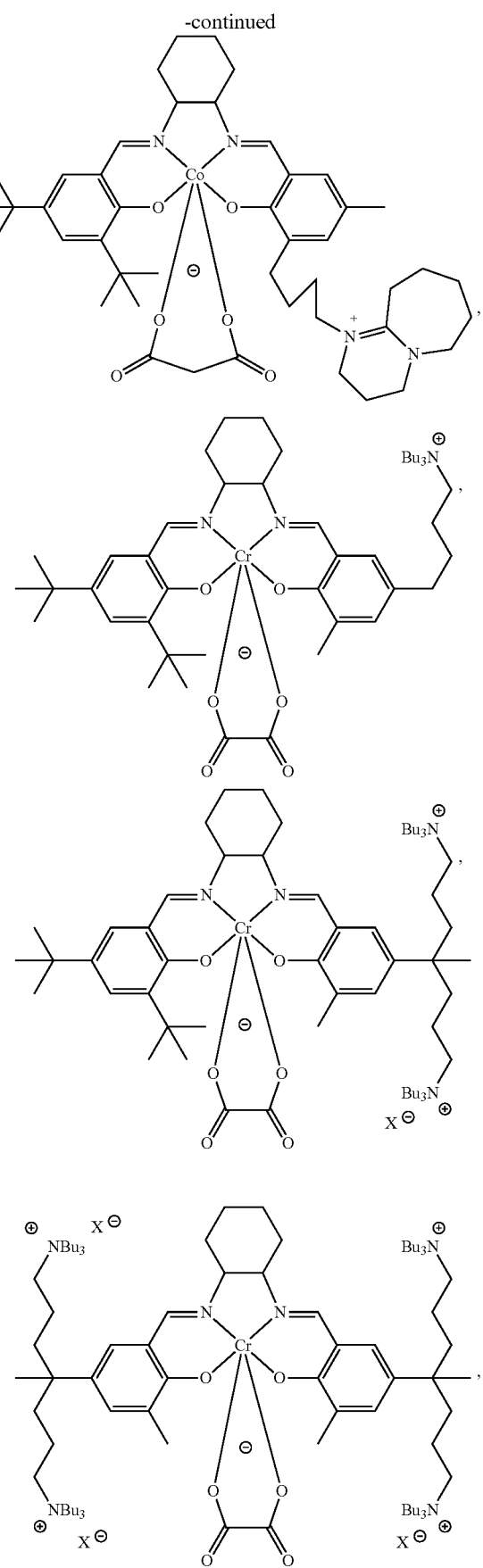

239
-continued
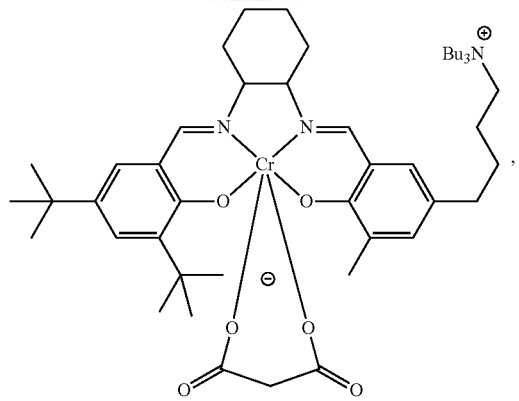
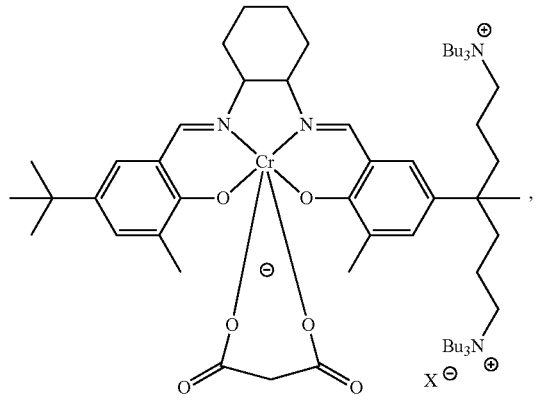
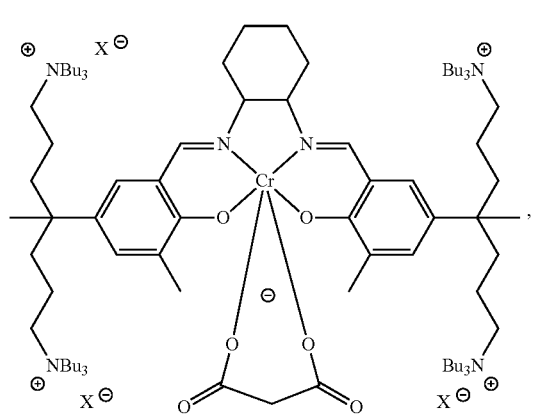
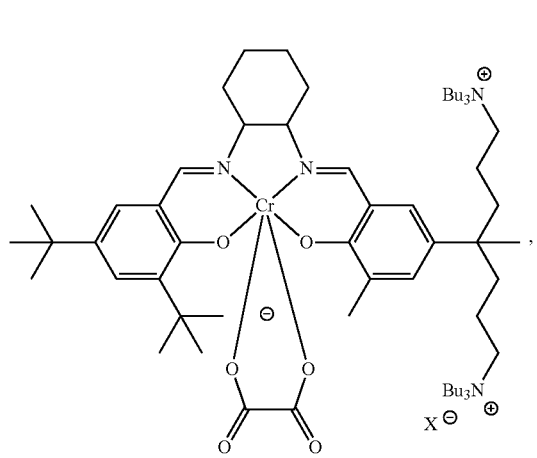
240
-continued
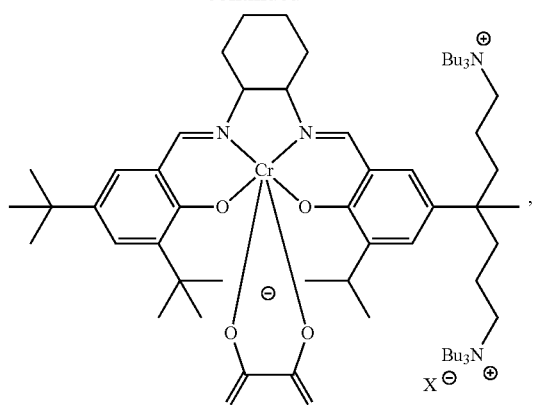
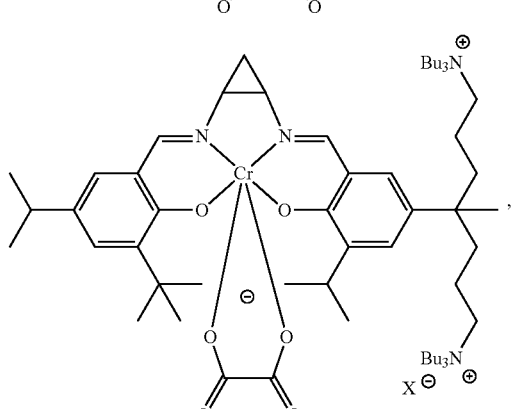
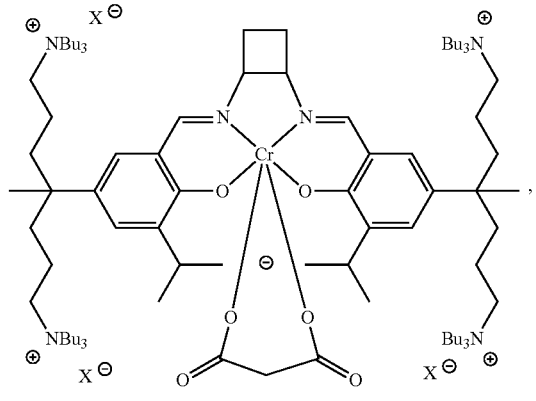
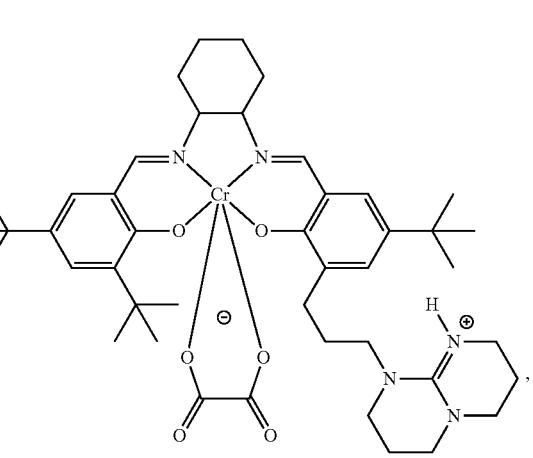

241
-continued
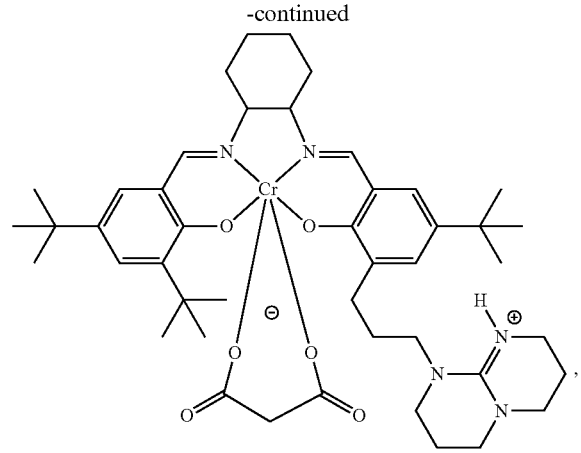
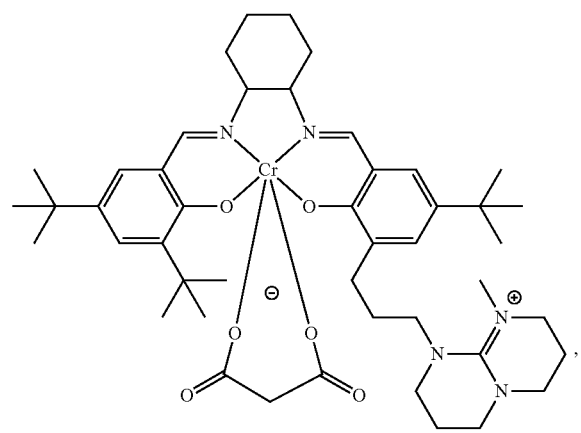
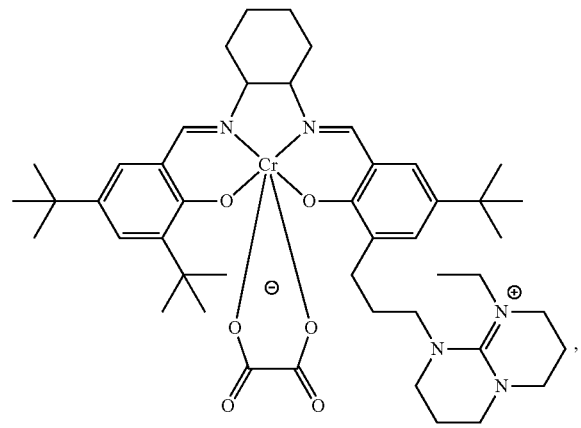
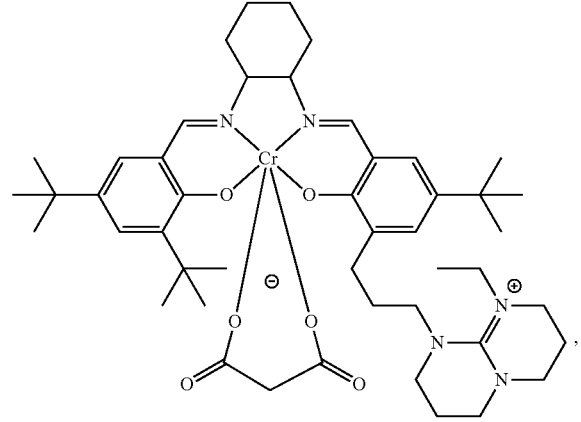
242
-continued
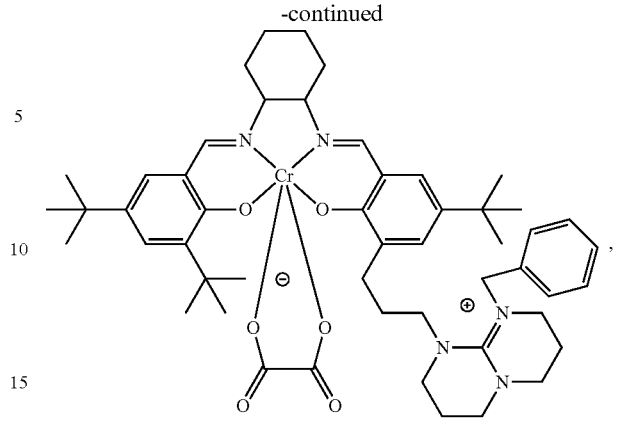
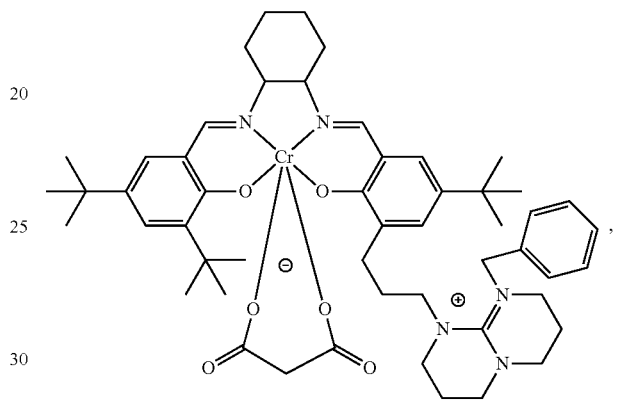
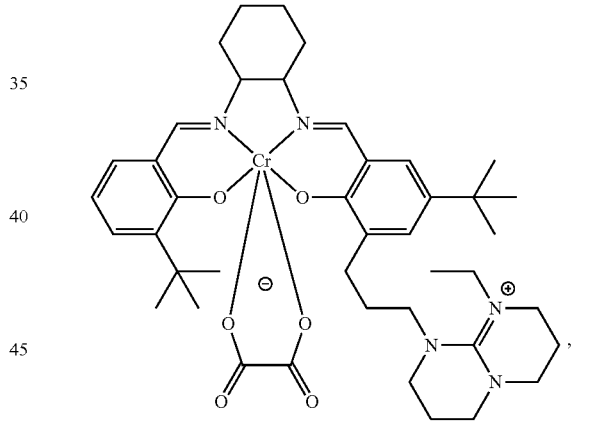
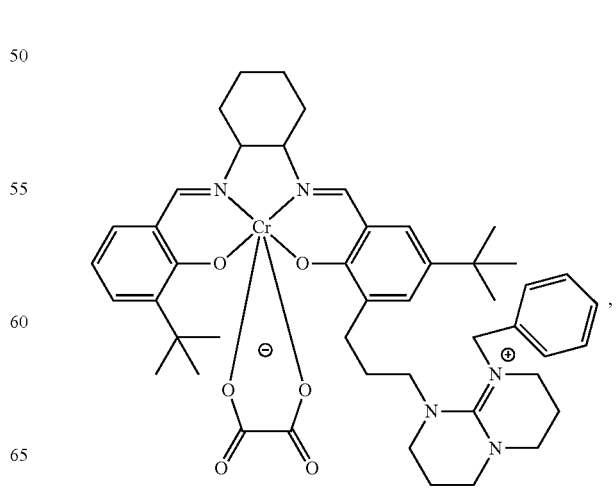

243
-continued
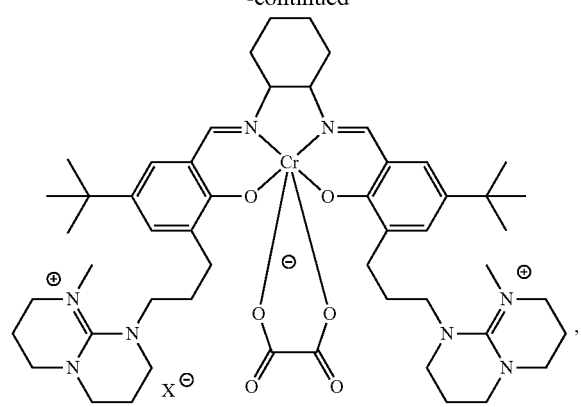
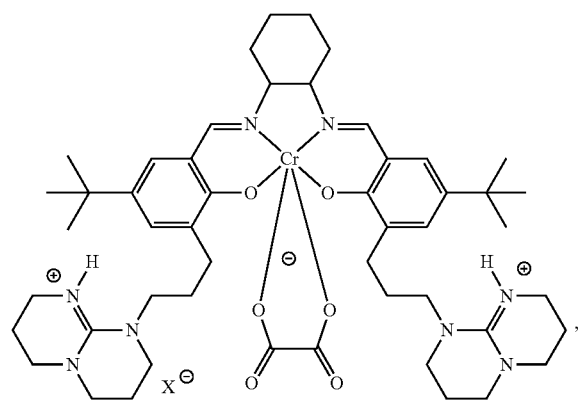
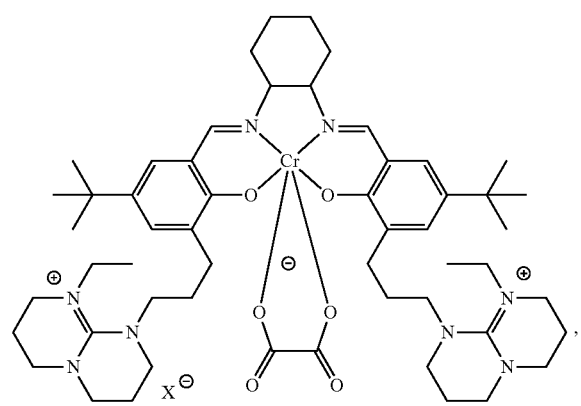
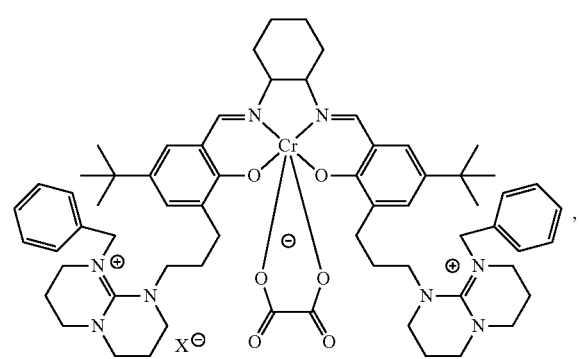
244
-continued
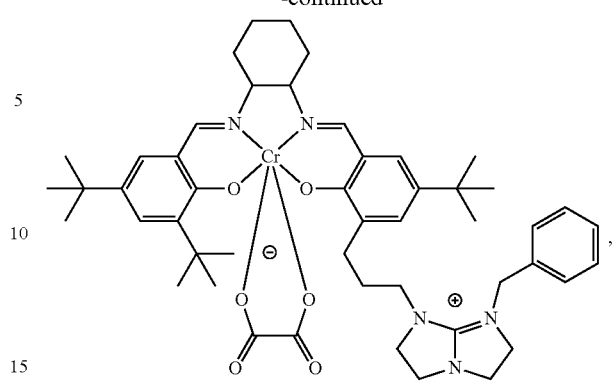
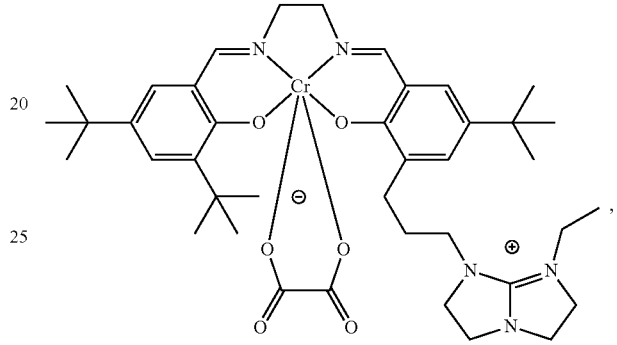
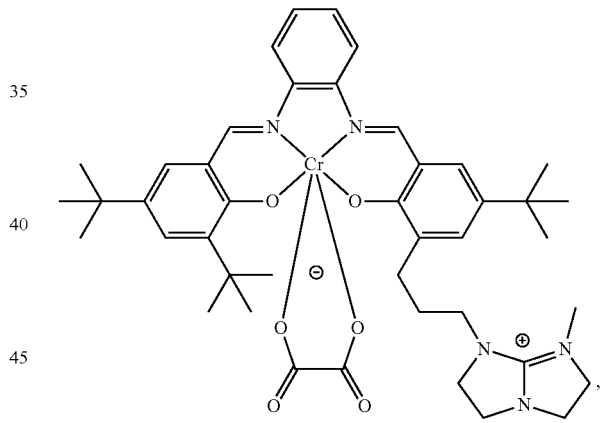
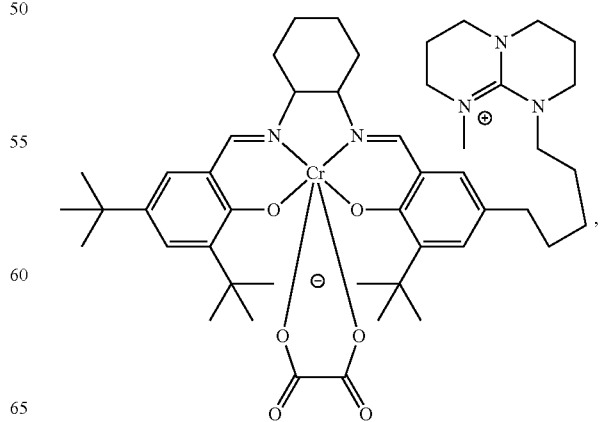

245
-continued
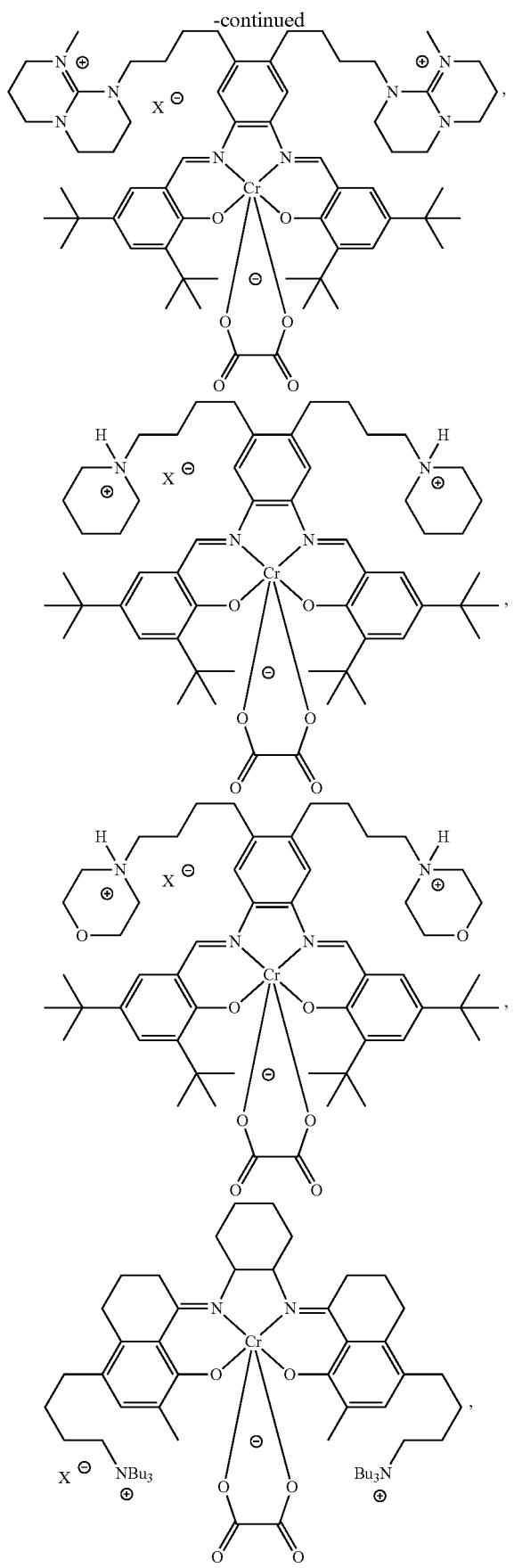
246
-continued
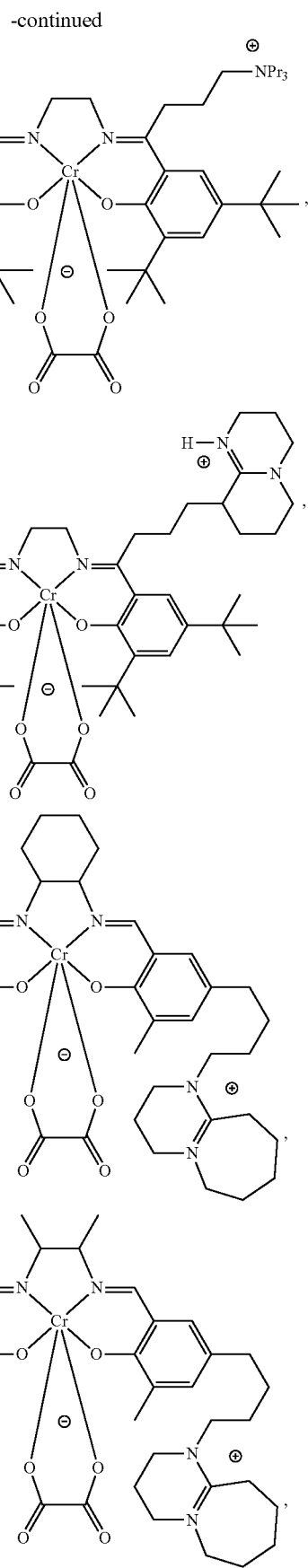

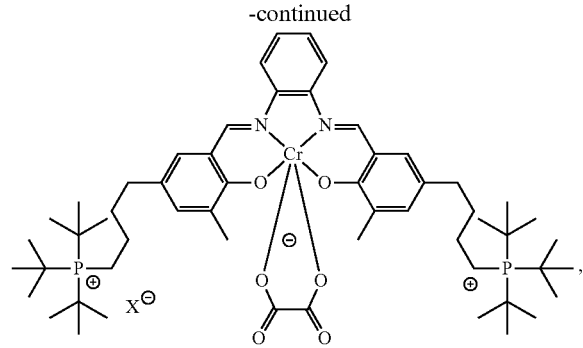
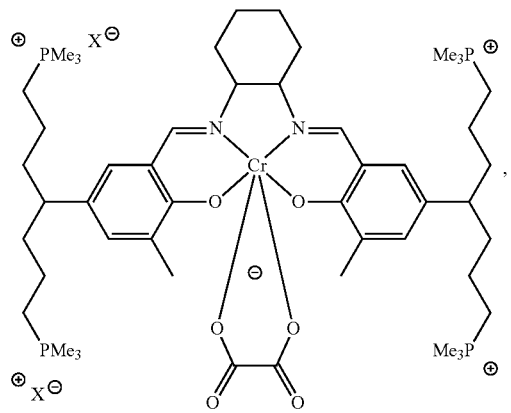
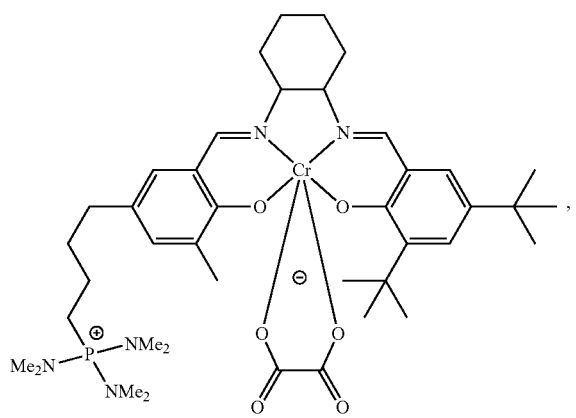
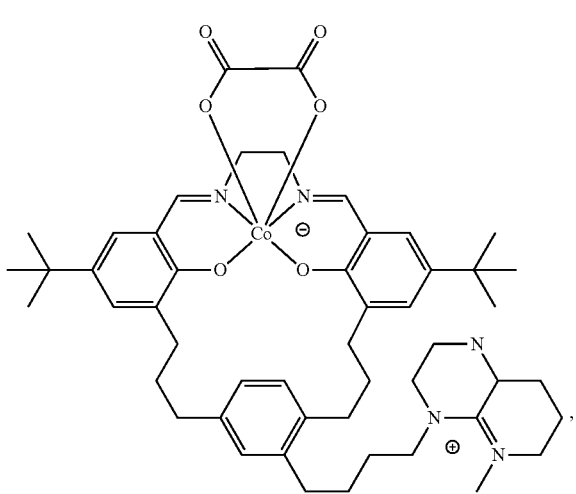
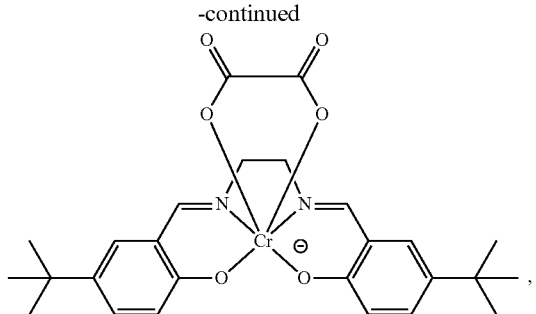
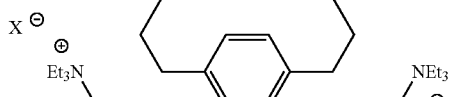
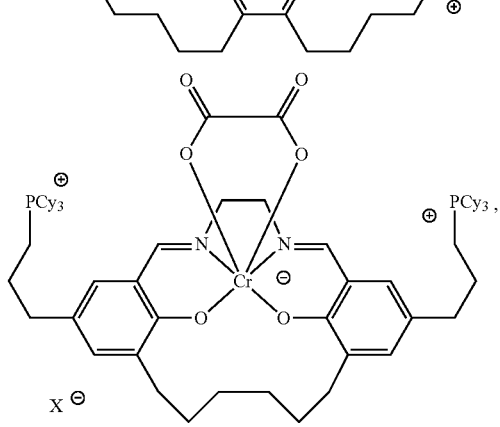
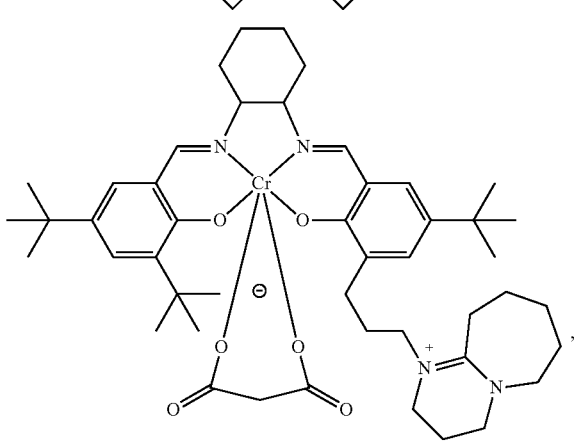
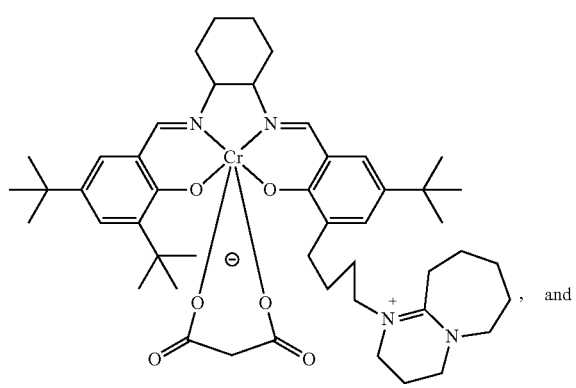

-continued
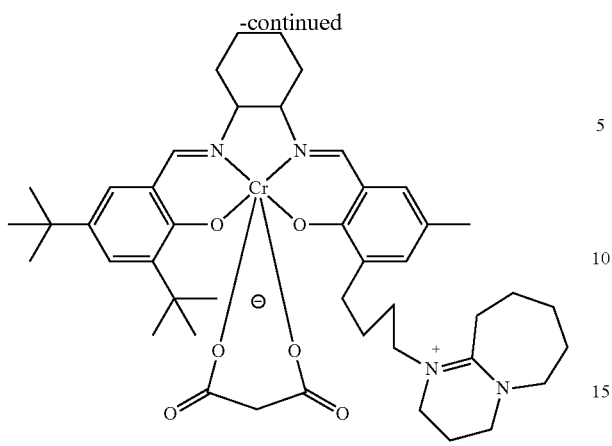
wherein X⁻ is, independently at each occurrence, an anion or dianion.
* * * * *

UNITED STATES PATENT AND TRADEMARK OFFICE
CERTIFICATE OF CORRECTION

PATENT NO. : 10,464,960 B2
APPLICATION NO. : 15/222502
DATED : November 5, 2019
INVENTOR(S) : Gabriel E. Job et al.

It is certified that error appears in the above-identified patent and that said Letters Patent is hereby corrected as shown below:

In the Claims

Claim 3, Column 215, Line 35: Please replace the structure

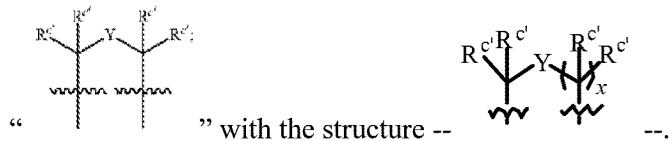

" with the structure -- --.

Claim 11, Column 221, Line 65: Please replace the structure

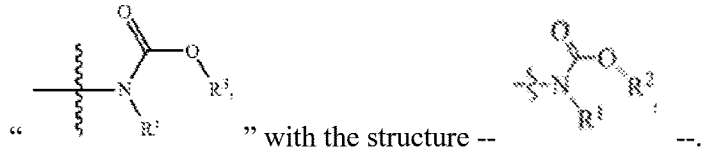

" with the structure -- --.

Claim 11, Column 222, Line 65: Please insert a --,-- after "$C_{1-20}$ aliphatic".

Claim 13, Column 227, Line 15: Please replace the structure

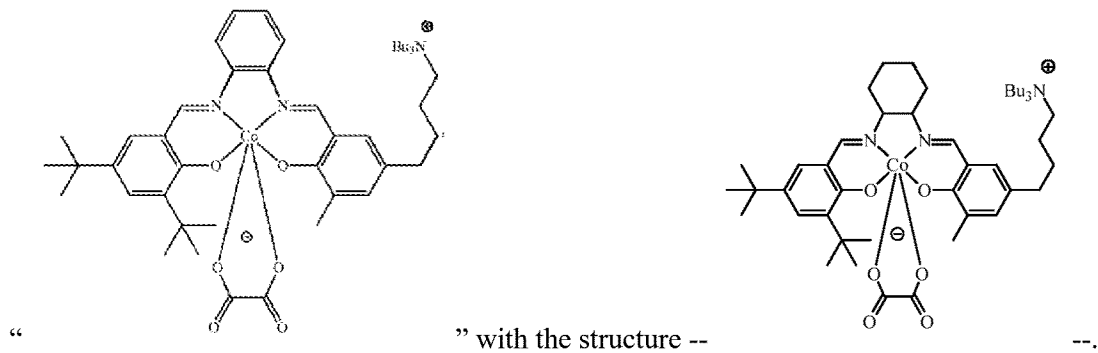

" with the structure -- --.

Signed and Sealed this
Fourth Day of February, 2020

Andrei Iancu
*Director of the United States Patent and Trademark Office*

Claim 13, Column 227, Line 35: Please replace the structure
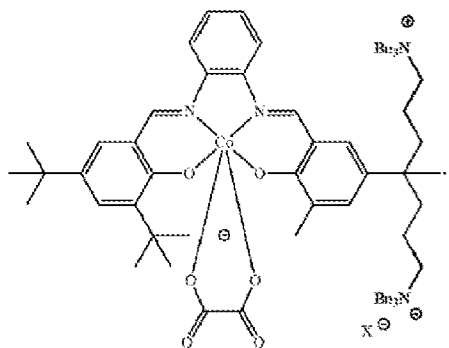 " with the structure -- 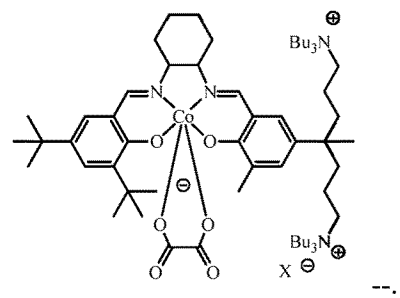 --.
Claim 13, Column 238, Line 1: Please replace the structure
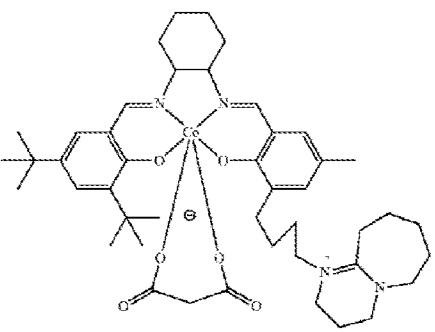 " with the structure -- 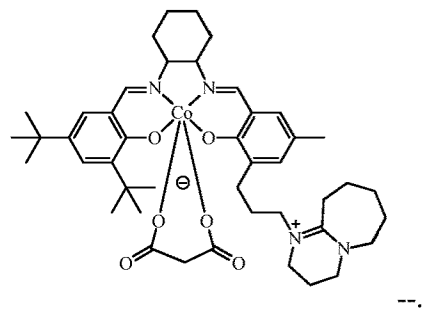 --.
Claim 13, Column 239, Line 55: Please replace the structure
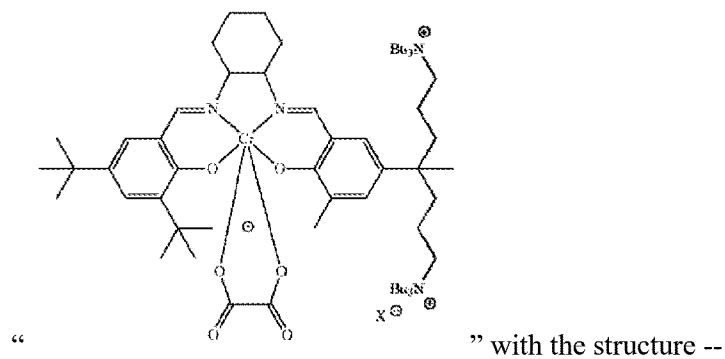 " with the structure -- 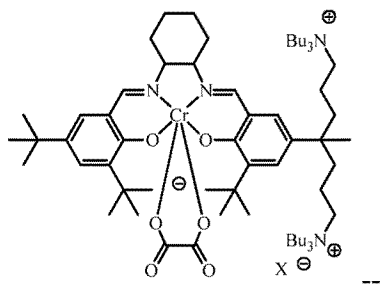 --.

CERTIFICATE OF CORRECTION (continued)

Claim 13, Column 240, Line 40: Please replace the structure

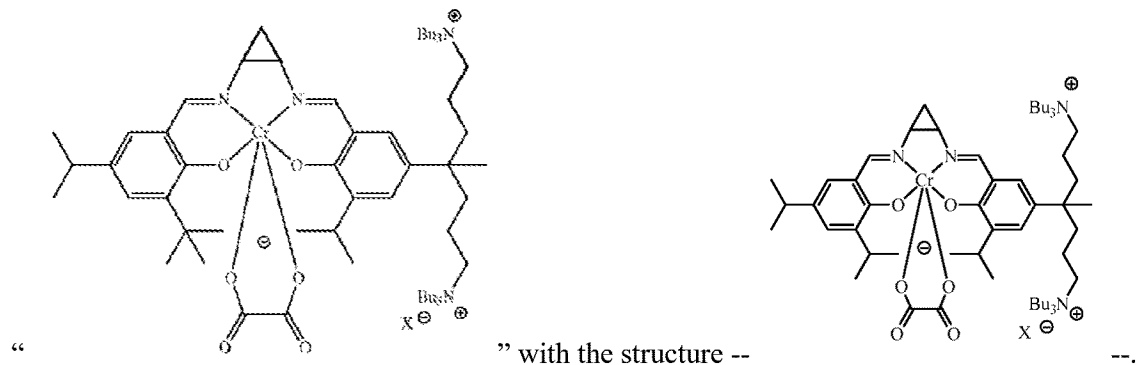

" with the structure -- --.

Claim 13, Column 246, Line 25: Please replace the structure

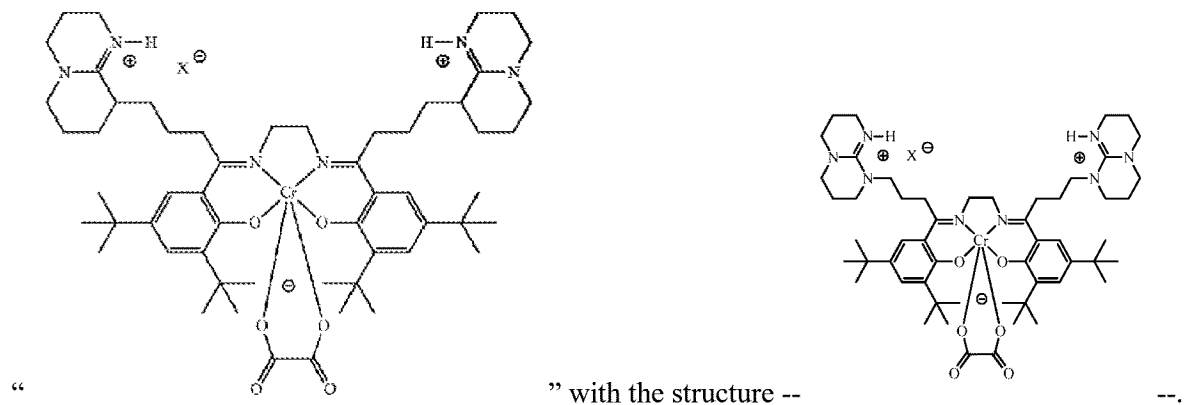

" with the structure -- --.

Claim 13, Column 246, Line 55: Please replace the structure

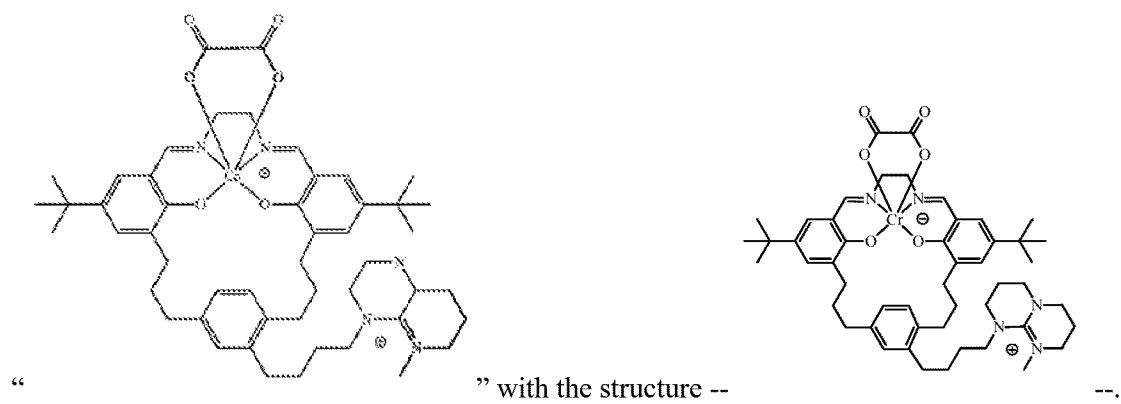

" with the structure -- --.

Claim 13, Column 249, Line 10: Please replace the structure

CERTIFICATE OF CORRECTION (continued)
U.S. Pat. No. 10,464,960 B2

" 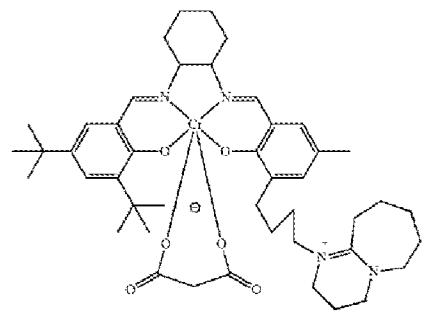 " with the structure -- 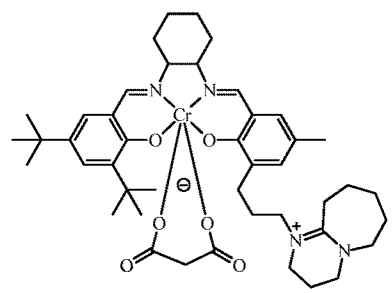 --.